(12) United States Patent
Nakazawa et al.

(10) Patent No.: US 8,198,256 B2
(45) Date of Patent: Jun. 12, 2012

(54) TREATMENT OF INFLUENZA

(75) Inventors: Misako Nakazawa, Nogi-machi (JP); Shin-etsu Kadowaki, Murayama (JP); Yoshiji Fujita, Tokyo (JP); Masato Miyake, Tokyo (JP); Takanori Ueda, Tokyo (JP); Tomohiro Yoshikawa, Tokyo (JP)

(73) Assignee: Kyorin Pharmaceutical Co., Ltd. (JP)

( * ) Notice: Subject to any disclaimer, the term of this patent is extended or adjusted under 35 U.S.C. 154(b) by 133 days.

(21) Appl. No.: 12/666,738

(22) PCT Filed: Jul. 2, 2008

(86) PCT No.: PCT/JP2008/062001
§ 371 (c)(1),
(2), (4) Date: Mar. 2, 2010

(87) PCT Pub. No.: WO2009/005095
PCT Pub. Date: Jan. 8, 2009

(65) Prior Publication Data
US 2010/0280096 A1    Nov. 4, 2010

(30) Foreign Application Priority Data
Jul. 3, 2007 (JP) ............................... P2007-175575

(51) Int. Cl.
*C12N 15/11* (2006.01)
*C07H 21/04* (2006.01)

(52) U.S. Cl. .................................. 514/44 A; 536/24.5
(58) Field of Classification Search ................ 514/44 A; 536/24.5
See application file for complete search history.

(56) References Cited

U.S. PATENT DOCUMENTS

| 2005/0159380 A1* | 7/2005 | Guerciolini et al. ............. 514/44 |
| 2005/0255487 A1* | 11/2005 | Khvorova et al. ................. 435/6 |
| 2006/0275265 A1 | 12/2006 | Pal et al. |
| 2007/0099858 A1* | 5/2007 | Jadhav et al. ..................... 514/44 |

FOREIGN PATENT DOCUMENTS

| WO | 99/32619 A1 | 7/1999 |
| WO | 01/75164 A2 | 10/2001 |
| WO | 03/070918 A2 | 8/2003 |

OTHER PUBLICATIONS

M. Nakazawa et al., "PA subunit of RNA polymerase as a promising target for anti-influenza virus agents", Antiviral Research, vol. 78, 2008, pp. 194-201.
Q. Ge et al., "Use of siRNAs to prevent and treat influenza virus infection", Virus Research, vol. 102, 2004, pp. 37-42.
N. Sugaya, "Treatment of influenza virus infection with anti-virals," Nippon Rinsho, Oct. 2006, pp. 1840-1844, vol. 64, No. 10.
Y. Gao, et al., "Rapid identification of small interfering RNA that can effectively inhibit the replication of multiple influenza B virus strains.," Antiviral Therapy, 2006, pp. 431-438, vol. 11, No. 4.
D. Spiro, et al, Database DDBJ/EMBL/GenBank [online], Accession No. CY018616, http://www.ncbi.nlm.nih.gov/entrez/viewer.fcqi?db=nuccore&id=119516346 ,Dec. 29, 2006, 1 page total, segment 5, complete sequence.
D. Spiro, et al, Database DDBJ/EMBL/GenBank [online], Accession No. CY018618, http://www.ncbi.nlm.nih.gov/entrez/viewer.fcgi?db=nuccore&id=119516351, Dec. 29, 2006, 1 page total, segment 3, complete sequence.
D. Spiro, et al, Database DDBJ/EMBL/GenBank [online], Accession No. CY018619, http://www.ncbi.nlm.nih.gov/entrez/viewer.fcgi?db=nuccore&id=119516353, Dec. 29, 2006, 1 page total, segment 1, complete sequence.
D. Spiro, et al, Database DDBJ/EMBL/GenBank [online], Accession No. CY018620, http://www.ncbi.nlm.nih.gov/entrez/viewer.fcgi?db=nuccore&id=119516355, Dec. 29, 2006, 1 page total, segment 2, complete sequence.
T. Yoshikawa, et al., Transfection microarray of human mesenchymal stem cells and on-chip siRNA gene knockdown., Journal of controlled release, 2004, pp. 227-232, vol. 96.
E. Uchimura, et al., "Advances in Transfection Microarray™-based studies of neuronal cell lines.,"Cyometry Research, 2004, pp. 39-44, vol. 14, No. 2.

* cited by examiner

*Primary Examiner* — Brian Whiteman
(74) *Attorney, Agent, or Firm* — Sughrue Mion, PLLC

(57) ABSTRACT

The present invention provides a double-stranded RNA which inhibits replication of influenza B viruses by RNA interference, in which the double-stranded RNA comprises an RNA having 19 to 25 nucleotides homologous with a part of an mRNA transcribed from a genomic RNA of the influenza B viruses and an antisense RNA thereof.

19 Claims, 4 Drawing Sheets

Fig.2
(A)
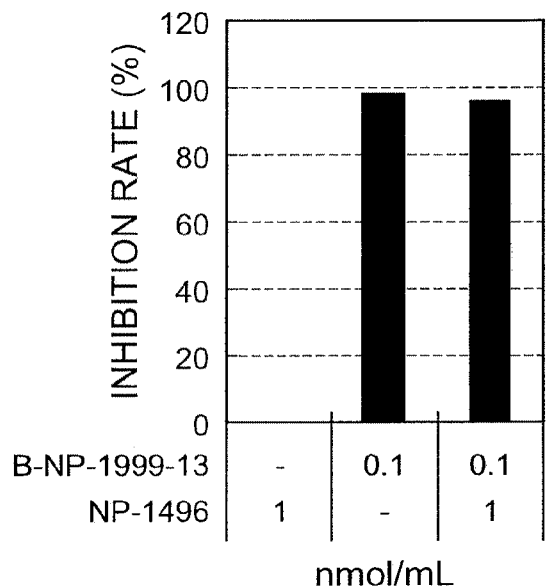
(B)
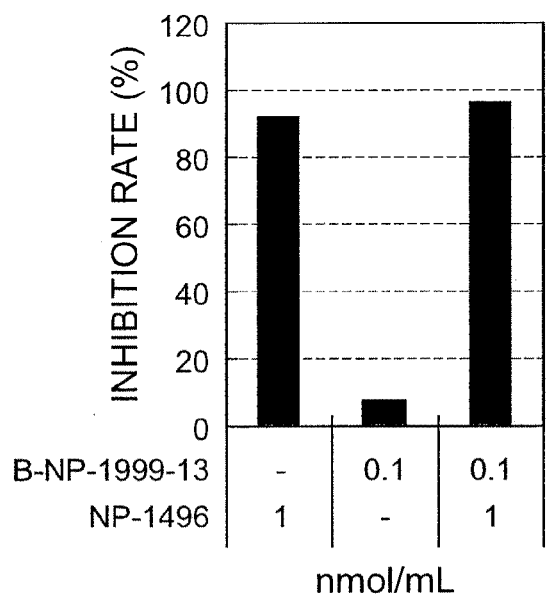

Fig.3
(A)
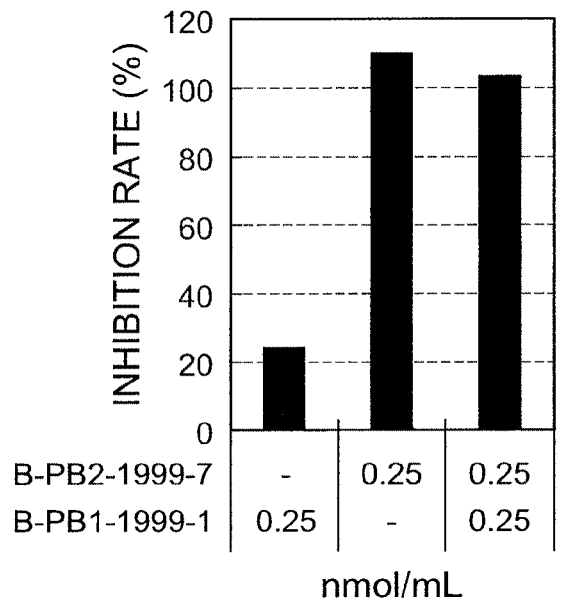
(B)
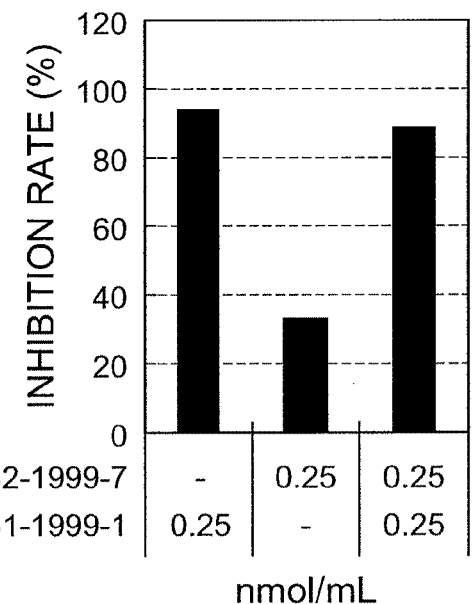

SEQUENCE LISTING

<160> NUMBER OF SEQ ID NOS: 2476

<210> SEQ ID NO 1
<211> LENGTH: 19
<212> TYPE: RNA
<213> ORGANISM: Influenza B virus

<400> SEQUENCE: 1
cgauuauuaa agcaacaaa                                                        19

<210> SEQ ID NO 2
<211> LENGTH: 19
<212> TYPE: RNA
<213> ORGANISM: Influenza B virus

<400> SEQUENCE: 2
gaagaaugcu gucaaugaa                                                        19

<210> SEQ ID NO 3
<211> LENGTH: 19
<212> TYPE: RNA
<213> ORGANISM: Influenza B virus

<400> SEQUENCE: 3
ccguugaaau uccaauuaa                                                        19

<210> SEQ ID NO 4
<211> LENGTH: 19
<212> TYPE: RNA
<213> ORGANISM: Influenza B virus

<400> SEQUENCE: 4
ggagggucug gccaaauaa                                                        19

<210> SEQ ID NO 5
<211> LENGTH: 19
<212> TYPE: RNA
<213> ORGANISM: Influenza B virus

<400> SEQUENCE: 5
gaugguaaga gaugauaaa                                                        19

<210> SEQ ID NO 6
<211> LENGTH: 19
<212> TYPE: RNA
<213> ORGANISM: Influenza B virus

<400> SEQUENCE: 6
ggcuauugag agacaucaa                                                        19

<210> SEQ ID NO 7
<211> LENGTH: 19
<212> TYPE: RNA
<213> ORGANISM: Influenza B virus

<400> SEQUENCE: 7
agaugguaag agaugauaa                                                        19

<210> SEQ ID NO 8
<211> LENGTH: 19
<212> TYPE: RNA
<213> ORGANISM: Influenza B virus

```
<400> SEQUENCE: 8
caaaggaggu ggaacuuua                                              19

<210> SEQ ID NO 9
<211> LENGTH: 19
<212> TYPE: RNA
<213> ORGANISM: Influenza B virus

<400> SEQUENCE: 9
cgauuuauag gaagagcaa                                              19

<210> SEQ ID NO 10
<211> LENGTH: 19
<212> TYPE: RNA
<213> ORGANISM: Influenza B virus

<400> SEQUENCE: 10
ggcacagaau ucaagccua                                              19

<210> SEQ ID NO 11
<211> LENGTH: 19
<212> TYPE: RNA
<213> ORGANISM: Influenza B virus

<400> SEQUENCE: 11
ggagagaaac cuaauccaa                                              19

<210> SEQ ID NO 12
<211> LENGTH: 19
<212> TYPE: RNA
<213> ORGANISM: Influenza B virus

<400> SEQUENCE: 12
gguguuuauu cuuauuaaa                                              19

<210> SEQ ID NO 13
<211> LENGTH: 19
<212> TYPE: RNA
<213> ORGANISM: Influenza B virus

<400> SEQUENCE: 13
ggguguuuau ucuuauuaa                                              19

<210> SEQ ID NO 14
<211> LENGTH: 19
<212> TYPE: RNA
<213> ORGANISM: Influenza B virus

<400> SEQUENCE: 14
agccuagauc agcauuaaa                                              19

<210> SEQ ID NO 15
<211> LENGTH: 19
<212> TYPE: RNA
<213> ORGANISM: Influenza B virus

<400> SEQUENCE: 15
gcaacaaacg aauccguaa                                              19

<210> SEQ ID NO 16
<211> LENGTH: 19
<212> TYPE: RNA
<213> ORGANISM: Influenza B virus
```

```
<400> SEQUENCE: 16
ggcugaauua agucugaaa                                                  19

<210> SEQ ID NO 17
<211> LENGTH: 19
<212> TYPE: RNA
<213> ORGANISM: Influenza B virus

<400> SEQUENCE: 17
caaauaagau ccaaaugaa                                                  19

<210> SEQ ID NO 18
<211> LENGTH: 19
<212> TYPE: RNA
<213> ORGANISM: Influenza B virus

<400> SEQUENCE: 18
ggaauagaag aauguauua                                                  19

<210> SEQ ID NO 19
<211> LENGTH: 19
<212> TYPE: RNA
<213> ORGANISM: Influenza B virus

<400> SEQUENCE: 19
gagugaaugg cacaaauaa                                                  19

<210> SEQ ID NO 20
<211> LENGTH: 19
<212> TYPE: RNA
<213> ORGANISM: Influenza B virus

<400> SEQUENCE: 20
ggaucaaacu gacccaaua                                                  19

<210> SEQ ID NO 21
<211> LENGTH: 19
<212> TYPE: RNA
<213> ORGANISM: Influenza B virus

<400> SEQUENCE: 21
gaaauacuuu guuaaugaa                                                  19

<210> SEQ ID NO 22
<211> LENGTH: 19
<212> TYPE: RNA
<213> ORGANISM: Influenza B virus

<400> SEQUENCE: 22
gcugggaaau agcauggaa                                                  19

<210> SEQ ID NO 23
<211> LENGTH: 19
<212> TYPE: RNA
<213> ORGANISM: Influenza B virus

<400> SEQUENCE: 23
caauagagua guaaaugaa                                                  19

<210> SEQ ID NO 24
<211> LENGTH: 19
<212> TYPE: RNA
<213> ORGANISM: Influenza B virus
```

```
<400> SEQUENCE: 24
gaaggaaaua cuuuguuaa                                          19

<210> SEQ ID NO 25
<211> LENGTH: 19
<212> TYPE: RNA
<213> ORGANISM: Influenza B virus

<400> SEQUENCE: 25
ggaagcaauu guugaacaa                                          19

<210> SEQ ID NO 26
<211> LENGTH: 19
<212> TYPE: RNA
<213> ORGANISM: Influenza B virus

<400> SEQUENCE: 26
gagggaaugu auucuggaa                                          19

<210> SEQ ID NO 27
<211> LENGTH: 19
<212> TYPE: RNA
<213> ORGANISM: Influenza B virus

<400> SEQUENCE: 27
ccaauagagu aguaaauga                                          19

<210> SEQ ID NO 28
<211> LENGTH: 19
<212> TYPE: RNA
<213> ORGANISM: Influenza B virus

<400> SEQUENCE: 28
ggaacagauc uauacuaaa                                          19

<210> SEQ ID NO 29
<211> LENGTH: 19
<212> TYPE: RNA
<213> ORGANISM: Influenza B virus

<400> SEQUENCE: 29
cggucuuguu cuccaauaa                                          19

<210> SEQ ID NO 30
<211> LENGTH: 19
<212> TYPE: RNA
<213> ORGANISM: Influenza B virus

<400> SEQUENCE: 30
gaaaggguuu ccucauaaa                                          19

<210> SEQ ID NO 31
<211> LENGTH: 19
<212> TYPE: RNA
<213> ORGANISM: Influenza B virus

<400> SEQUENCE: 31
ccuuuaagau gaauauaaa                                          19

<210> SEQ ID NO 32
<211> LENGTH: 19
<212> TYPE: RNA
<213> ORGANISM: Influenza B virus
```

-continued

```
<400> SEQUENCE: 32
gggaauguuu aauaugcua                                               19

<210> SEQ ID NO 33
<211> LENGTH: 19
<212> TYPE: RNA
<213> ORGANISM: Influenza B virus

<400> SEQUENCE: 33
ggucuuguuc uccaauaaa                                               19

<210> SEQ ID NO 34
<211> LENGTH: 19
<212> TYPE: RNA
<213> ORGANISM: Influenza B virus

<400> SEQUENCE: 34
ggaauguuug aauuuacaa                                               19

<210> SEQ ID NO 35
<211> LENGTH: 19
<212> TYPE: RNA
<213> ORGANISM: Influenza B virus

<400> SEQUENCE: 35
agauaucauu gauucauua                                               19

<210> SEQ ID NO 36
<211> LENGTH: 19
<212> TYPE: RNA
<213> ORGANISM: Influenza B virus

<400> SEQUENCE: 36
gagauggauu uguaucuaa                                               19

<210> SEQ ID NO 37
<211> LENGTH: 19
<212> TYPE: RNA
<213> ORGANISM: Influenza B virus

<400> SEQUENCE: 37
caguaaagaa uauaaagaa                                               19

<210> SEQ ID NO 38
<211> LENGTH: 19
<212> TYPE: RNA
<213> ORGANISM: Influenza B virus

<400> SEQUENCE: 38
ggauauccag aguggaaua                                               19

<210> SEQ ID NO 39
<211> LENGTH: 19
<212> TYPE: RNA
<213> ORGANISM: Influenza B virus

<400> SEQUENCE: 39
ggcuaugacu gaaagaaua                                               19

<210> SEQ ID NO 40
<211> LENGTH: 19
<212> TYPE: RNA
<213> ORGANISM: Influenza B virus
```

```
<400> SEQUENCE: 40
gcauaccauu agaaagaua                                              19

<210> SEQ ID NO 41
<211> LENGTH: 19
<212> TYPE: RNA
<213> ORGANISM: Influenza B virus

<400> SEQUENCE: 41
guauugaagu acaaucuaa                                              19

<210> SEQ ID NO 42
<211> LENGTH: 19
<212> TYPE: RNA
<213> ORGANISM: Influenza B virus

<400> SEQUENCE: 42
ugacaauaau aaagaacaa                                              19

<210> SEQ ID NO 43
<211> LENGTH: 19
<212> TYPE: RNA
<213> ORGANISM: Influenza B virus

<400> SEQUENCE: 43
guaaauuauu gggaauaaa                                              19

<210> SEQ ID NO 44
<211> LENGTH: 19
<212> TYPE: RNA
<213> ORGANISM: Influenza B virus

<400> SEQUENCE: 44
caugauucuu gaggaacaa                                              19

<210> SEQ ID NO 45
<211> LENGTH: 19
<212> TYPE: RNA
<213> ORGANISM: Influenza B virus

<400> SEQUENCE: 45
caguugaaag aguaagaaa                                              19

<210> SEQ ID NO 46
<211> LENGTH: 19
<212> TYPE: RNA
<213> ORGANISM: Influenza B virus

<400> SEQUENCE: 46
gcaguuaccu gguggaaua                                              19

<210> SEQ ID NO 47
<211> LENGTH: 19
<212> TYPE: RNA
<213> ORGANISM: Influenza B virus

<400> SEQUENCE: 47
caagggaaua caacuuaaa                                              19

<210> SEQ ID NO 48
<211> LENGTH: 19
<212> TYPE: RNA
<213> ORGANISM: Influenza B virus
```

```
<400> SEQUENCE: 48
gaucaauagu cgcaucaaa                                              19

<210> SEQ ID NO 49
<211> LENGTH: 19
<212> TYPE: RNA
<213> ORGANISM: Influenza B virus

<400> SEQUENCE: 49
gacugugaua gauacugaa                                              19

<210> SEQ ID NO 50
<211> LENGTH: 19
<212> TYPE: RNA
<213> ORGANISM: Influenza B virus

<400> SEQUENCE: 50
gcccguuaaa guaguuaaa                                              19

<210> SEQ ID NO 51
<211> LENGTH: 19
<212> TYPE: RNA
<213> ORGANISM: Influenza B virus

<400> SEQUENCE: 51
aauauaacau aauaagaaa                                              19

<210> SEQ ID NO 52
<211> LENGTH: 19
<212> TYPE: RNA
<213> ORGANISM: Influenza B virus

<400> SEQUENCE: 52 ggaaucaag ggaauacaa                                               19

<210> SEQ ID NO 53
<211> LENGTH: 19
<212> TYPE: RNA
<213> ORGANISM: Influenza B virus

<400> SEQUENCE: 53
ggaagacaug aaagauuua                                              19

<210> SEQ ID NO 54
<211> LENGTH: 19
<212> TYPE: RNA
<213> ORGANISM: Influenza B virus

<400> SEQUENCE: 54
ggauaaauga auuaaugaa                                              19

<210> SEQ ID NO 55
<211> LENGTH: 19
<212> TYPE: RNA
<213> ORGANISM: Influenza B virus

<400> SEQUENCE: 55
agaugaauau aaauccuua                                              19

<210> SEQ ID NO 56
<211> LENGTH: 19
<212> TYPE: RNA
<213> ORGANISM: Influenza B virus
```

```
<400> SEQUENCE: 56
acaaaugauu gaaaugaaa                                          19

<210> SEQ ID NO 57
<211> LENGTH: 19
<212> TYPE: RNA
<213> ORGANISM: Influenza B virus

<400> SEQUENCE: 57
gcggagccuu uaagaugaa                                          19

<210> SEQ ID NO 58
<211> LENGTH: 19
<212> TYPE: RNA
<213> ORGANISM: Influenza B virus

<400> SEQUENCE: 58
gaugucauua aaagggaaa                                          19

<210> SEQ ID NO 59
<211> LENGTH: 21
<212> TYPE: RNA
<213> ORGANISM: Influenza B virus

<400> SEQUENCE: 59
uacacugcuu acaaggugaa a                                       21

<210> SEQ ID NO 60
<211> LENGTH: 23
<212> TYPE: RNA
<213> ORGANISM: Influenza B virus

<400> SEQUENCE: 60
aggggagaaa uaaauuuucu uaa                                     23

<210> SEQ ID NO 61
<211> LENGTH: 19
<212> TYPE: RNA
<213> ORGANISM: Influenza B virus

<400> SEQUENCE: 61
cuggugcaaa acaccuauc                                          19

<210> SEQ ID NO 62
<211> LENGTH: 21
<212> TYPE: RNA
<213> ORGANISM: Influenza B virus

<400> SEQUENCE: 62
caaucgauga uuguggcuug u                                       21

<210> SEQ ID NO 63
<211> LENGTH: 21
<212> TYPE: RNA
<213> ORGANISM: Influenza B virus

<400> SEQUENCE: 63
uugaagcauu ugaaagcaua a                                       21

<210> SEQ ID NO 64
<211> LENGTH: 19
<212> TYPE: RNA
<213> ORGANISM: Influenza B virus
```

```
<400> SEQUENCE: 64
gcauuugaag cauuugaaa                                              19

<210> SEQ ID NO 65
<211> LENGTH: 21
<212> TYPE: RNA
<213> ORGANISM: Influenza B virus

<400> SEQUENCE: 65
aaaacaaaug cugaagacau a                                           21

<210> SEQ ID NO 66
<211> LENGTH: 19
<212> TYPE: RNA
<213> ORGANISM: Influenza B virus

<400> SEQUENCE: 66
gaaguaacga ucucuuuga                                              19

<210> SEQ ID NO 67
<211> LENGTH: 19
<212> TYPE: RNA
<213> ORGANISM: Influenza B virus

<400> SEQUENCE: 67
accaaagaac uggugcaaa                                              19

<210> SEQ ID NO 68
<211> LENGTH: 19
<212> TYPE: RNA
<213> ORGANISM: Influenza B virus

<400> SEQUENCE: 68
gagaccaaga ggucaugaa                                              19

<210> SEQ ID NO 69
<211> LENGTH: 21
<212> TYPE: RNA
<213> ORGANISM: Influenza B virus

<400> SEQUENCE: 69
aacaguagau caauauaaca u                                           21

<210> SEQ ID NO 70
<211> LENGTH: 21
<212> TYPE: RNA
<213> ORGANISM: Influenza B virus

<400> SEQUENCE: 70
aagaggaguu ccauguaaga u                                           21

<210> SEQ ID NO 71
<211> LENGTH: 19
<212> TYPE: RNA
<213> ORGANISM: Influenza B virus

<400> SEQUENCE: 71
gcaugguauu uucucaaga                                              19

<210> SEQ ID NO 72
<211> LENGTH: 21
<212> TYPE: RNA
<213> ORGANISM: Influenza B virus
```

```
<400> SEQUENCE: 72
aacccauugg agcuagcugu a                                          21

<210> SEQ ID NO 73
<211> LENGTH: 19
<212> TYPE: RNA
<213> ORGANISM: Influenza B virus

<400> SEQUENCE: 73
cuaucaaugg gugcugaaa                                             19

<210> SEQ ID NO 74
<211> LENGTH: 19
<212> TYPE: RNA
<213> ORGANISM: Influenza B virus

<400> SEQUENCE: 74
acuggugcaa aacaccuau                                             19

<210> SEQ ID NO 75
<211> LENGTH: 19
<212> TYPE: RNA
<213> ORGANISM: Influenza B virus

<400> SEQUENCE: 75
gcaaguauga cccagaucu                                             19

<210> SEQ ID NO 76
<211> LENGTH: 21
<212> TYPE: RNA
<213> ORGANISM: Influenza B virus

<400> SEQUENCE: 76
ucuaggucuc aaucgaugau u                                          21

<210> SEQ ID NO 77
<211> LENGTH: 19
<212> TYPE: RNA
<213> ORGANISM: Influenza B virus

<400> SEQUENCE: 77
guaugaggaa ucacccaaa                                             19

<210> SEQ ID NO 78
<211> LENGTH: 23
<212> TYPE: RNA
<213> ORGANISM: Influenza B virus

<400> SEQUENCE: 78
gagaaauaaa uuuucuuaau aga                                        23

<210> SEQ ID NO 79
<211> LENGTH: 21
<212> TYPE: RNA
<213> ORGANISM: Influenza B virus

<400> SEQUENCE: 79
aagagcugca uuaggacuaa a                                          21

<210> SEQ ID NO 80
<211> LENGTH: 21
<212> TYPE: RNA
<213> ORGANISM: Influenza B virus
```

```
<400> SEQUENCE: 80
gugaugucgc cugugacaua a                                              21

<210> SEQ ID NO 81
<211> LENGTH: 19
<212> TYPE: RNA
<213> ORGANISM: Influenza B virus

<400> SEQUENCE: 81
ccaaugggau gcauuugaa                                                 19

<210> SEQ ID NO 82
<211> LENGTH: 21
<212> TYPE: RNA
<213> ORGANISM: Influenza B virus

<400> SEQUENCE: 82
aaacaaauga gagaccaaga g                                              21

<210> SEQ ID NO 83
<211> LENGTH: 19
<212> TYPE: RNA
<213> ORGANISM: Influenza B virus

<400> SEQUENCE: 83
agaccaagag gucaugaaa                                                 19

<210> SEQ ID NO 84
<211> LENGTH: 21
<212> TYPE: RNA
<213> ORGANISM: Influenza B virus

<400> SEQUENCE: 84
cggcagaaug augucauuaa a                                              21

<210> SEQ ID NO 85
<211> LENGTH: 21
<212> TYPE: RNA
<213> ORGANISM: Influenza B virus

<400> SEQUENCE: 85
cuuggaauac aagggaauac a                                              21

<210> SEQ ID NO 86
<211> LENGTH: 21
<212> TYPE: RNA
<213> ORGANISM: Influenza B virus

<400> SEQUENCE: 86
cagaaagaug agacuugaca a                                              21

<210> SEQ ID NO 87
<211> LENGTH: 21
<212> TYPE: RNA
<213> ORGANISM: Influenza B virus

<400> SEQUENCE: 87
ugaugucgcc ugugacauaa u                                              21

<210> SEQ ID NO 88
<211> LENGTH: 21
<212> TYPE: RNA
<213> ORGANISM: Influenza B virus
```

```
<400> SEQUENCE: 88
aggccaacuu uuaucuccaa u                                              21

<210> SEQ ID NO 89
<211> LENGTH: 19
<212> TYPE: RNA
<213> ORGANISM: Influenza B virus

<400> SEQUENCE: 89
ccuaucaaug ggugcugaa                                                 19

<210> SEQ ID NO 90
<211> LENGTH: 19
<212> TYPE: RNA
<213> ORGANISM: Influenza B virus

<400> SEQUENCE: 90
agccauagac ggaggugau                                                 19

<210> SEQ ID NO 91
<211> LENGTH: 19
<212> TYPE: RNA
<213> ORGANISM: Influenza B virus

<400> SEQUENCE: 91
agccaaugac guaagugaa                                                 19

<210> SEQ ID NO 92
<211> LENGTH: 21
<212> TYPE: RNA
<213> ORGANISM: Influenza B virus

<400> SEQUENCE: 92
cuaucaaugg gugcugaaaa a                                              21

<210> SEQ ID NO 93
<211> LENGTH: 21
<212> TYPE: RNA
<213> ORGANISM: Influenza B virus

<400> SEQUENCE: 93
aauuguuaaa acaacuguua a                                              21

<210> SEQ ID NO 94
<211> LENGTH: 21
<212> TYPE: RNA
<213> ORGANISM: Influenza B virus

<400> SEQUENCE: 94
auuggagcua gcuguagaaa u                                              21

<210> SEQ ID NO 95
<211> LENGTH: 21
<212> TYPE: RNA
<213> ORGANISM: Influenza B virus

<400> SEQUENCE: 95
aaugcagugu uggcggguuu u                                              21

<210> SEQ ID NO 96
<211> LENGTH: 21
<212> TYPE: RNA
<213> ORGANISM: Influenza B virus
```

```
<400> SEQUENCE: 96
aagugggcaa uguguucuaa u                                              21

<210> SEQ ID NO 97
<211> LENGTH: 21
<212> TYPE: RNA
<213> ORGANISM: Influenza B virus

<400> SEQUENCE: 97
aaaaagucua cgaaagcuuu u                                              21

<210> SEQ ID NO 98
<211> LENGTH: 21
<212> TYPE: RNA
<213> ORGANISM: Influenza B virus

<400> SEQUENCE: 98
cacaagcuca gcuaaugaua a                                              21

<210> SEQ ID NO 99
<211> LENGTH: 19
<212> TYPE: RNA
<213> ORGANISM: Influenza B virus

<400> SEQUENCE: 99
ggaauaaacu aacugaauc                                                 19

<210> SEQ ID NO 100
<211> LENGTH: 19
<212> TYPE: RNA
<213> ORGANISM: Influenza B virus

<400> SEQUENCE: 100
agcucagcua augauaaca                                                 19

<210> SEQ ID NO 101
<211> LENGTH: 21
<212> TYPE: RNA
<213> ORGANISM: Influenza B virus

<400> SEQUENCE: 101
acccuucauu aaggaugaag u                                              21

<210> SEQ ID NO 102
<211> LENGTH: 21
<212> TYPE: RNA
<213> ORGANISM: Influenza B virus

<400> SEQUENCE: 102
aauguguucu aauuuucccu u                                              21

<210> SEQ ID NO 103
<211> LENGTH: 21
<212> TYPE: RNA
<213> ORGANISM: Influenza B virus

<400> SEQUENCE: 103
aaaaaaucuu aguuuaauaa a                                              21

<210> SEQ ID NO 104
<211> LENGTH: 21
<212> TYPE: RNA
<213> ORGANISM: Influenza B virus
```

-continued

```
<400> SEQUENCE: 104
aaaugaugaa gaaauauuaa u                                        21

<210> SEQ ID NO 105
<211> LENGTH: 21
<212> TYPE: RNA
<213> ORGANISM: Influenza B virus

<400> SEQUENCE: 105
aaggaaaggg ucuccucuau u                                        21

<210> SEQ ID NO 106
<211> LENGTH: 19
<212> TYPE: RNA
<213> ORGANISM: Influenza B virus

<400> SEQUENCE: 106
gaugaagugg gcaaugugu                                           19

<210> SEQ ID NO 107
<211> LENGTH: 19
<212> TYPE: RNA
<213> ORGANISM: Influenza B virus

<400> SEQUENCE: 107
cuuggauaca uagggaacu                                           19

<210> SEQ ID NO 108
<211> LENGTH: 19
<212> TYPE: RNA
<213> ORGANISM: Influenza B virus

<400> SEQUENCE: 108
gccaaaacag uauugaaac                                           19

<210> SEQ ID NO 109
<211> LENGTH: 21
<212> TYPE: RNA
<213> ORGANISM: Influenza B virus

<400> SEQUENCE: 109
aacaacuguu aagggacaau g                                        21

<210> SEQ ID NO 110
<211> LENGTH: 21
<212> TYPE: RNA
<213> ORGANISM: Influenza B virus

<400> SEQUENCE: 110
auugaaggga ggaggagaaa a                                        21

<210> SEQ ID NO 111
<211> LENGTH: 23
<212> TYPE: RNA
<213> ORGANISM: Influenza B virus

<400> SEQUENCE: 111
uccaaagaua uuuuuugaau aga                                      23

<210> SEQ ID NO 112
<211> LENGTH: 21
<212> TYPE: RNA
<213> ORGANISM: Influenza B virus
```

```
<400> SEQUENCE: 112
uuaaucggga acggaacaau a                                              21

<210> SEQ ID NO 113
<211> LENGTH: 21
<212> TYPE: RNA
<213> ORGANISM: Influenza B virus

<400> SEQUENCE: 113
aacuuaaaac aaaugcugaa g                                              21

<210> SEQ ID NO 114
<211> LENGTH: 21
<212> TYPE: RNA
<213> ORGANISM: Influenza B virus

<400> SEQUENCE: 114
uuguggcuug uagaaagaua a                                              21

<210> SEQ ID NO 115
<211> LENGTH: 19
<212> TYPE: RNA
<213> ORGANISM: Influenza B virus

<400> SEQUENCE: 115
gaugaagaaa ggaauagau                                                 19

<210> SEQ ID NO 116
<211> LENGTH: 21
<212> TYPE: RNA
<213> ORGANISM: Influenza B virus

<400> SEQUENCE: 116
aaucuuaguu uaauaaaaag g                                              21

<210> SEQ ID NO 117
<211> LENGTH: 19
<212> TYPE: RNA
<213> ORGANISM: Influenza B virus

<400> SEQUENCE: 117
cuaggaaaag aagacaugu                                                 19

<210> SEQ ID NO 118
<211> LENGTH: 21
<212> TYPE: RNA
<213> ORGANISM: Influenza B virus

<400> SEQUENCE: 118
aauaggagau acugaagguu u                                              21

<210> SEQ ID NO 119
<211> LENGTH: 19
<212> TYPE: RNA
<213> ORGANISM: Influenza B virus

<400> SEQUENCE: 119
cuccaaugua ucaacucca                                                 19

<210> SEQ ID NO 120
<211> LENGTH: 21
<212> TYPE: RNA
<213> ORGANISM: Influenza B virus
```

-continued

```
<400> SEQUENCE: 120
aauaucagga agaggauuca a                                              21

<210> SEQ ID NO 121
<211> LENGTH: 19
<212> TYPE: RNA
<213> ORGANISM: Influenza B virus

<400> SEQUENCE: 121
cgaugauugu ggcuuguag                                                 19

<210> SEQ ID NO 122
<211> LENGTH: 21
<212> TYPE: RNA
<213> ORGANISM: Influenza B virus

<400> SEQUENCE: 122
aaaagaagac auguuccaau g                                              21

<210> SEQ ID NO 123
<211> LENGTH: 21
<212> TYPE: RNA
<213> ORGANISM: Influenza B virus

<400> SEQUENCE: 123
aaacuacuaa uaaauucagc u                                              21

<210> SEQ ID NO 124
<211> LENGTH: 19
<212> TYPE: RNA
<213> ORGANISM: Influenza B virus

<400> SEQUENCE: 124
cucaguuucu ucuaggaaa                                                 19

<210> SEQ ID NO 125
<211> LENGTH: 21
<212> TYPE: RNA
<213> ORGANISM: Influenza B virus

<400> SEQUENCE: 125
aaggaauuaa gagacaaaga a                                              21

<210> SEQ ID NO 126
<211> LENGTH: 21
<212> TYPE: RNA
<213> ORGANISM: Influenza B virus

<400> SEQUENCE: 126
aauugaagau gaagaaagga a                                              21

<210> SEQ ID NO 127
<211> LENGTH: 21
<212> TYPE: RNA
<213> ORGANISM: Influenza B virus

<400> SEQUENCE: 127
uugaagggag gaggagaaaa u                                              21

<210> SEQ ID NO 128
<211> LENGTH: 19
<212> TYPE: RNA
<213> ORGANISM: Influenza B virus
```

```
<400> SEQUENCE: 128
caccuaagau gugggagau                                              19

<210> SEQ ID NO 129
<211> LENGTH: 21
<212> TYPE: RNA
<213> ORGANISM: Influenza B virus

<400> SEQUENCE: 129
aaauuuaucc auuaauucaa u                                           21

<210> SEQ ID NO 130
<211> LENGTH: 21
<212> TYPE: RNA
<213> ORGANISM: Influenza B virus

<400> SEQUENCE: 130
acgaugauaa cucccauugu a                                           21

<210> SEQ ID NO 131
<211> LENGTH: 19
<212> TYPE: RNA
<213> ORGANISM: Influenza B virus

<400> SEQUENCE: 131
aucugacuac acuuugaaa                                              19

<210> SEQ ID NO 132
<211> LENGTH: 18
<212> TYPE: RNA
<213> ORGANISM: Influenza B virus

<400> SEQUENCE: 132
cggagcguuu ucaagaug                                               18

<210> SEQ ID NO 133
<211> LENGTH: 21
<212> TYPE: RNA
<213> ORGANISM: Influenza B virus

<400> SEQUENCE: 133
aauauuaaaa aagagcaaaa u                                           21

<210> SEQ ID NO 134
<211> LENGTH: 21
<212> TYPE: RNA
<213> ORGANISM: Influenza B virus

<400> SEQUENCE: 134
agaacccuuc auuaaggaug a                                           21

<210> SEQ ID NO 135
<211> LENGTH: 19
<212> TYPE: RNA
<213> ORGANISM: Influenza B virus

<400> SEQUENCE: 135
cugaaucuag gucucaauc                                              19

<210> SEQ ID NO 136
<211> LENGTH: 21
<212> TYPE: RNA
<213> ORGANISM: Influenza B virus
```

-continued

```
<400> SEQUENCE: 136
aggugauguc gccugugaca u                                        21

<210> SEQ ID NO 137
<211> LENGTH: 21
<212> TYPE: RNA
<213> ORGANISM: Influenza B virus

<400> SEQUENCE: 137
aagagcaaaa ugagaaugga a                                        21

<210> SEQ ID NO 138
<211> LENGTH: 21
<212> TYPE: RNA
<213> ORGANISM: Influenza B virus

<400> SEQUENCE: 138
aacaaaugcu gaagacauag g                                        21

<210> SEQ ID NO 139
<211> LENGTH: 21
<212> TYPE: RNA
<213> ORGANISM: Influenza B virus

<400> SEQUENCE: 139
agaaucacaa gcucagcuaa u                                        21

<210> SEQ ID NO 140
<211> LENGTH: 19
<212> TYPE: RNA
<213> ORGANISM: Influenza B virus

<400> SEQUENCE: 140
gcaagagcag ugcucaaac                                           19

<210> SEQ ID NO 141
<211> LENGTH: 21
<212> TYPE: RNA
<213> ORGANISM: Influenza B virus

<400> SEQUENCE: 141
uaucacccgg gagggaauaa a                                        21

<210> SEQ ID NO 142
<211> LENGTH: 19
<212> TYPE: RNA
<213> ORGANISM: Influenza B virus

<400> SEQUENCE: 142
augacauuuc acaaggaau                                           19

<210> SEQ ID NO 143
<211> LENGTH: 21
<212> TYPE: RNA
<213> ORGANISM: Influenza B virus

<400> SEQUENCE: 143
aacuaaagag aauaucagga a                                        21

<210> SEQ ID NO 144
<211> LENGTH: 21
<212> TYPE: RNA
<213> ORGANISM: Influenza B virus
```

```
<400> SEQUENCE: 144
caaaggccaa augugcucaa u                                         21

<210> SEQ ID NO 145
<211> LENGTH: 19
<212> TYPE: RNA
<213> ORGANISM: Influenza B virus

<400> SEQUENCE: 145
ggaaaauuga agaugaaga                                            19

<210> SEQ ID NO 146
<211> LENGTH: 21
<212> TYPE: RNA
<213> ORGANISM: Influenza B virus

<400> SEQUENCE: 146
uggugcaaaa caccuaucaa u                                         21

<210> SEQ ID NO 147
<211> LENGTH: 21
<212> TYPE: RNA
<213> ORGANISM: Influenza B virus

<400> SEQUENCE: 147
ccaaggguga cauggcaaac a                                         21

<210> SEQ ID NO 148
<211> LENGTH: 21
<212> TYPE: RNA
<213> ORGANISM: Influenza B virus

<400> SEQUENCE: 148
ggaccaauag gagauacuga a                                         21

<210> SEQ ID NO 149
<211> LENGTH: 19
<212> TYPE: RNA
<213> ORGANISM: Influenza B virus

<400> SEQUENCE: 149
ggaauacaag ggaauacaa                                            19

<210> SEQ ID NO 150
<211> LENGTH: 21
<212> TYPE: RNA
<213> ORGANISM: Influenza B virus

<400> SEQUENCE: 150
ucaguucuug aggcuuguau u                                         21

<210> SEQ ID NO 151
<211> LENGTH: 19
<212> TYPE: RNA
<213> ORGANISM: Influenza B virus

<400> SEQUENCE: 151
ggggagccuu aucaguucu                                            19

<210> SEQ ID NO 152
<211> LENGTH: 21
<212> TYPE: RNA
<213> ORGANISM: Influenza B virus
```

```
<400> SEQUENCE: 152
ggagcagaag cggagcguuu u                                       21

<210> SEQ ID NO 153
<211> LENGTH: 23
<212> TYPE: RNA
<213> ORGANISM: Influenza B virus

<400> SEQUENCE: 153
aggagugagg ggagaaauaa auu                                     23

<210> SEQ ID NO 154
<211> LENGTH: 19
<212> TYPE: RNA
<213> ORGANISM: Influenza B virus

<400> SEQUENCE: 154
ggaguuccau guaagaugu                                          19

<210> SEQ ID NO 155
<211> LENGTH: 21
<212> TYPE: RNA
<213> ORGANISM: Influenza B virus

<400> SEQUENCE: 155
aagcauuuga aagcauaauc c                                       21

<210> SEQ ID NO 156
<211> LENGTH: 21
<212> TYPE: RNA
<213> ORGANISM: Influenza B virus

<400> SEQUENCE: 156
agcaacauca gcugaguuca u                                       21

<210> SEQ ID NO 157
<211> LENGTH: 21
<212> TYPE: RNA
<213> ORGANISM: Influenza B virus

<400> SEQUENCE: 157
aaagacaaag auuuggacga c                                       21

<210> SEQ ID NO 158
<211> LENGTH: 19
<212> TYPE: RNA
<213> ORGANISM: Influenza B virus

<400> SEQUENCE: 158
gacugugaua gauacugaa                                          19

<210> SEQ ID NO 159
<211> LENGTH: 19
<212> TYPE: RNA
<213> ORGANISM: Influenza B virus

<400> SEQUENCE: 159
acguaaguga auuagaauc                                          19

<210> SEQ ID NO 160
<211> LENGTH: 21
<212> TYPE: RNA
<213> ORGANISM: Influenza B virus
```

```
<400> SEQUENCE: 160
aagaaauauu aaucgggaac g                                            21

<210> SEQ ID NO 161
<211> LENGTH: 19
<212> TYPE: RNA
<213> ORGANISM: Influenza B virus

<400> SEQUENCE: 161
caccaaaguu aaggagaaa                                               19

<210> SEQ ID NO 162
<211> LENGTH: 19
<212> TYPE: RNA
<213> ORGANISM: Influenza B virus

<400> SEQUENCE: 162
ccacaaacag aaguccuaa                                               19

<210> SEQ ID NO 163
<211> LENGTH: 21
<212> TYPE: RNA
<213> ORGANISM: Influenza B virus

<400> SEQUENCE: 163
aauagagcag gccaacuuuu a                                            21

<210> SEQ ID NO 164
<211> LENGTH: 21
<212> TYPE: RNA
<213> ORGANISM: Influenza B virus

<400> SEQUENCE: 164
aauccacaaa cagaaguccu a                                            21

<210> SEQ ID NO 165
<211> LENGTH: 21
<212> TYPE: RNA
<213> ORGANISM: Influenza B virus

<400> SEQUENCE: 165
gugggcaaug uguucuaauu u                                            21

<210> SEQ ID NO 166
<211> LENGTH: 19
<212> TYPE: RNA
<213> ORGANISM: Influenza B virus

<400> SEQUENCE: 166
gagauacuga agguuucga                                               19

<210> SEQ ID NO 167
<211> LENGTH: 21
<212> TYPE: RNA
<213> ORGANISM: Influenza B virus

<400> SEQUENCE: 167
aauaaaaagg acuggggaag u                                            21

<210> SEQ ID NO 168
<211> LENGTH: 21
<212> TYPE: RNA
<213> ORGANISM: Influenza B virus
```

-continued

```
<400> SEQUENCE: 168
gagcagugcu caaacaaaug a                                              21

<210> SEQ ID NO 169
<211> LENGTH: 21
<212> TYPE: RNA
<213> ORGANISM: Influenza B virus

<400> SEQUENCE: 169
aucuaggucu caaucgauga u                                              21

<210> SEQ ID NO 170
<211> LENGTH: 19
<212> TYPE: RNA
<213> ORGANISM: Influenza B virus

<400> SEQUENCE: 170
caguucuuga ggcuuguau                                                 19

<210> SEQ ID NO 171
<211> LENGTH: 21
<212> TYPE: RNA
<213> ORGANISM: Influenza B virus

<400> SEQUENCE: 171
aaucgaugau uguggcuugu a                                              21

<210> SEQ ID NO 172
<211> LENGTH: 21
<212> TYPE: RNA
<213> ORGANISM: Influenza B virus

<400> SEQUENCE: 172
ucgaugauug uggcuuguag a                                              21

<210> SEQ ID NO 173
<211> LENGTH: 21
<212> TYPE: RNA
<213> ORGANISM: Influenza B virus

<400> SEQUENCE: 173
ugugcucaau agcagcaguu a                                              21

<210> SEQ ID NO 174
<211> LENGTH: 21
<212> TYPE: RNA
<213> ORGANISM: Influenza B virus

<400> SEQUENCE: 174
cauuggagcu agcuguagaa a                                              21

<210> SEQ ID NO 175
<211> LENGTH: 21
<212> TYPE: RNA
<213> ORGANISM: Influenza B virus

<400> SEQUENCE: 175
ugaagggagg aggagaaaau u                                              21

<210> SEQ ID NO 176
<211> LENGTH: 23
<212> TYPE: RNA
<213> ORGANISM: Influenza B virus
```

-continued

```
<400> SEQUENCE: 176
gagcuacaug ggauaaauga auu                                            23

<210> SEQ ID NO 177
<211> LENGTH: 21
<212> TYPE: RNA
<213> ORGANISM: Influenza B virus

<400> SEQUENCE: 177
uuggcggguu uucuuguuag u                                              21

<210> SEQ ID NO 178
<211> LENGTH: 19
<212> TYPE: RNA
<213> ORGANISM: Influenza B virus

<400> SEQUENCE: 178
gugcauggua uuuucucaa                                                 19

<210> SEQ ID NO 179
<211> LENGTH: 19
<212> TYPE: RNA
<213> ORGANISM: Influenza B virus

<400> SEQUENCE: 179
ggaauaccaa gagaaucua                                                 19

<210> SEQ ID NO 180
<211> LENGTH: 21
<212> TYPE: RNA
<213> ORGANISM: Influenza B virus

<400> SEQUENCE: 180
caguagauca auauaacaua a                                              21

<210> SEQ ID NO 181
<211> LENGTH: 19
<212> TYPE: RNA
<213> ORGANISM: Influenza B virus

<400> SEQUENCE: 181
ggaacggaac aauacagaa                                                 19

<210> SEQ ID NO 182
<211> LENGTH: 21
<212> TYPE: RNA
<213> ORGANISM: Influenza B virus

<400> SEQUENCE: 182
aaugauguca uuaaaaggga a                                              21

<210> SEQ ID NO 183
<211> LENGTH: 21
<212> TYPE: RNA
<213> ORGANISM: Influenza B virus

<400> SEQUENCE: 183
aauacaacuu aaaacaaaug c                                              21

<210> SEQ ID NO 184
<211> LENGTH: 21
<212> TYPE: RNA
<213> ORGANISM: Influenza B virus
```

```
<400> SEQUENCE: 184
aauacagaag auuggaauau g                                              21

<210> SEQ ID NO 185
<211> LENGTH: 23
<212> TYPE: RNA
<213> ORGANISM: Influenza B virus

<400> SEQUENCE: 185
aaguaacgau cucuuugauc aau                                            23

<210> SEQ ID NO 186
<211> LENGTH: 21
<212> TYPE: RNA
<213> ORGANISM: Influenza B virus

<400> SEQUENCE: 186
cccuuggaau acaagggaau a                                              21

<210> SEQ ID NO 187
<211> LENGTH: 21
<212> TYPE: RNA
<213> ORGANISM: Influenza B virus

<400> SEQUENCE: 187 uaggcucaa ucgaugauug u                                               21

<210> SEQ ID NO 188
<211> LENGTH: 19
<212> TYPE: RNA
<213> ORGANISM: Influenza B virus

<400> SEQUENCE: 188
gagcaggcca acuuuuauc                                                 19

<210> SEQ ID NO 189
<211> LENGTH: 23
<212> TYPE: RNA
<213> ORGANISM: Influenza B virus

<400> SEQUENCE: 189
aaggagugag gggagaaaua aau                                            23

<210> SEQ ID NO 190
<211> LENGTH: 19
<212> TYPE: RNA
<213> ORGANISM: Influenza B virus

<400> SEQUENCE: 190
cguaagugaa uuagaauca                                                 19

<210> SEQ ID NO 191
<211> LENGTH: 21
<212> TYPE: RNA
<213> ORGANISM: Influenza B virus

<400> SEQUENCE: 191
aaugaagcca aaacaguauu g                                              21

<210> SEQ ID NO 192
<211> LENGTH: 21
<212> TYPE: RNA
<213> ORGANISM: Influenza B virus
```

```
<400> SEQUENCE: 192
gugggccuug agcuaauaua a                                              21

<210> SEQ ID NO 193
<211> LENGTH: 21
<212> TYPE: RNA
<213> ORGANISM: Influenza B virus

<400> SEQUENCE: 193
aaucgggaac ggaacaauac a                                              21

<210> SEQ ID NO 194
<211> LENGTH: 21
<212> TYPE: RNA
<213> ORGANISM: Influenza B virus

<400> SEQUENCE: 194
acacugcuua caaggugaaa a                                              21

<210> SEQ ID NO 195
<211> LENGTH: 19
<212> TYPE: RNA
<213> ORGANISM: Influenza B virus

<400> SEQUENCE: 195
agagcagugc ucaaacaaa                                                 19

<210> SEQ ID NO 196
<211> LENGTH: 21
<212> TYPE: RNA
<213> ORGANISM: Influenza B virus

<400> SEQUENCE: 196
aaaauuucau cgaaguaagg a                                              21

<210> SEQ ID NO 197
<211> LENGTH: 21
<212> TYPE: RNA
<213> ORGANISM: Influenza B virus

<400> SEQUENCE: 197
aaagagaaua ucaggaagag g                                              21

<210> SEQ ID NO 198
<211> LENGTH: 21
<212> TYPE: RNA
<213> ORGANISM: Influenza B virus

<400> SEQUENCE: 198
aauggaaaaa cuacuaauaa a                                              21

<210> SEQ ID NO 199
<211> LENGTH: 21
<212> TYPE: RNA
<213> ORGANISM: Influenza B virus

<400> SEQUENCE: 199
aaugcagggg aauauuaaaa a                                              21

<210> SEQ ID NO 200
<211> LENGTH: 19
<212> TYPE: RNA
<213> ORGANISM: Influenza B virus
```

-continued

```
<400> SEQUENCE: 200
cugaguucau agaaaugcu                                              19

<210> SEQ ID NO 201
<211> LENGTH: 21
<212> TYPE: RNA
<213> ORGANISM: Influenza B virus

<400> SEQUENCE: 201
aaacaaacaa caguagauca a                                           21

<210> SEQ ID NO 202
<211> LENGTH: 21
<212> TYPE: RNA
<213> ORGANISM: Influenza B virus

<400> SEQUENCE: 202
aagaacccuu cauuaaggau g                                           21

<210> SEQ ID NO 203
<211> LENGTH: 19
<212> TYPE: RNA
<213> ORGANISM: Influenza B virus

<400> SEQUENCE: 203
gauacugaag guuucgaaa                                              19

<210> SEQ ID NO 204
<211> LENGTH: 21
<212> TYPE: RNA
<213> ORGANISM: Influenza B virus

<400> SEQUENCE: 204
aauauaaauu uauccauuaa u                                           21

<210> SEQ ID NO 205
<211> LENGTH: 21
<212> TYPE: RNA
<213> ORGANISM: Influenza B virus

<400> SEQUENCE: 205
agccaaugac guaagugaau u                                           21

<210> SEQ ID NO 206
<211> LENGTH: 19
<212> TYPE: RNA
<213> ORGANISM: Influenza B virus

<400> SEQUENCE: 206
gcaucugacu acacuuuga                                              19

<210> SEQ ID NO 207
<211> LENGTH: 21
<212> TYPE: RNA
<213> ORGANISM: Influenza B virus

<400> SEQUENCE: 207
cacccgggag ggaauaaacu a                                           21

<210> SEQ ID NO 208
<211> LENGTH: 19
<212> TYPE: RNA
<213> ORGANISM: Influenza B virus
```

```
<400> SEQUENCE: 208
guuccaugua agauguggu                                        19

<210> SEQ ID NO 209
<211> LENGTH: 21
<212> TYPE: RNA
<213> ORGANISM: Influenza B virus

<400> SEQUENCE: 209
agcagaagcg gagcguuuuc a                                     21

<210> SEQ ID NO 210
<211> LENGTH: 19
<212> TYPE: RNA
<213> ORGANISM: Influenza B virus

<400> SEQUENCE: 210
ggaggaggag aaaauuuca                                        19

<210> SEQ ID NO 211
<211> LENGTH: 21
<212> TYPE: RNA
<213> ORGANISM: Influenza B virus

<400> SEQUENCE: 211
ccuaucaaug ggugcugaaa a                                     21

<210> SEQ ID NO 212
<211> LENGTH: 21
<212> TYPE: RNA
<213> ORGANISM: Influenza B virus

<400> SEQUENCE: 212
aauucaauaa augcaauuga g                                     21

<210> SEQ ID NO 213
<211> LENGTH: 23
<212> TYPE: RNA
<213> ORGANISM: Influenza B virus

<400> SEQUENCE: 213
gugaggggag aaauaaauuu ucu                                   23

<210> SEQ ID NO 214
<211> LENGTH: 19
<212> TYPE: RNA
<213> ORGANISM: Influenza B virus

<400> SEQUENCE: 214
ccaauguauc aacuccaaa                                        19

<210> SEQ ID NO 215
<211> LENGTH: 21
<212> TYPE: RNA
<213> ORGANISM: Influenza B virus

<400> SEQUENCE: 215
auagagcagg ccaacuuuua u                                     21

<210> SEQ ID NO 216
<211> LENGTH: 21
<212> TYPE: RNA
<213> ORGANISM: Influenza B virus
```

```
<400> SEQUENCE: 216
aagugagcua caugggauaa a                                              21

<210> SEQ ID NO 217
<211> LENGTH: 21
<212> TYPE: RNA
<213> ORGANISM: Influenza B virus

<400> SEQUENCE: 217
uugcccuuuu guuucucacc a                                              21

<210> SEQ ID NO 218
<211> LENGTH: 19
<212> TYPE: RNA
<213> ORGANISM: Influenza B virus

<400> SEQUENCE: 218
augggagcca augacguaa                                                 19

<210> SEQ ID NO 219
<211> LENGTH: 21
<212> TYPE: RNA
<213> ORGANISM: Influenza B virus

<400> SEQUENCE: 219
aaaagaaccc uucauuaagg a                                              21

<210> SEQ ID NO 220
<211> LENGTH: 21
<212> TYPE: RNA
<213> ORGANISM: Influenza B virus

<400> SEQUENCE: 220
gcagcaguua ccugguggaa u                                              21

<210> SEQ ID NO 221
<211> LENGTH: 19
<212> TYPE: RNA
<213> ORGANISM: Influenza B virus

<400> SEQUENCE: 221
gagccuuauc aguucuuga                                                 19

<210> SEQ ID NO 222
<211> LENGTH: 21
<212> TYPE: RNA
<213> ORGANISM: Influenza B virus

<400> SEQUENCE: 222
aacgaugaua acucccauug u                                              21

<210> SEQ ID NO 223
<211> LENGTH: 21
<212> TYPE: RNA
<213> ORGANISM: Influenza B virus

<400> SEQUENCE: 223
aucaugucug acagccauag a                                              21

<210> SEQ ID NO 224
<211> LENGTH: 21
<212> TYPE: RNA
<213> ORGANISM: Influenza B virus
```

```
<400> SEQUENCE: 224
cuacacugcu uacaagguga a                                    21

<210> SEQ ID NO 225
<211> LENGTH: 19
<212> TYPE: RNA
<213> ORGANISM: Influenza B virus

<400> SEQUENCE: 225
gacauaauaa gagcugcau                                       19

<210> SEQ ID NO 226
<211> LENGTH: 19
<212> TYPE: RNA
<213> ORGANISM: Influenza B virus

<400> SEQUENCE: 226
gggaacggaa caauacaga                                       19

<210> SEQ ID NO 227
<211> LENGTH: 23
<212> TYPE: RNA
<213> ORGANISM: Influenza B virus

<400> SEQUENCE: 227
caguagauca auauaacaua aua                                  23

<210> SEQ ID NO 228
<211> LENGTH: 21
<212> TYPE: RNA
<213> ORGANISM: Influenza B virus

<400> SEQUENCE: 228
aaagaaugac aguugagucc a                                    21

<210> SEQ ID NO 229
<211> LENGTH: 21
<212> TYPE: RNA
<213> ORGANISM: Influenza B virus

<400> SEQUENCE: 229
aagaggauuc aaaaaugaug a                                    21

<210> SEQ ID NO 230
<211> LENGTH: 21
<212> TYPE: RNA
<213> ORGANISM: Influenza B virus

<400> SEQUENCE: 230
gaagcggagc guuuucaaga u                                    21

<210> SEQ ID NO 231
<211> LENGTH: 19
<212> TYPE: RNA
<213> ORGANISM: Influenza B virus

<400> SEQUENCE: 231
gcuacauggg auaaaugaa                                       19

<210> SEQ ID NO 232
<211> LENGTH: 21
<212> TYPE: RNA
<213> ORGANISM: Influenza B virus
```

```
<400> SEQUENCE: 232
ugcggcagaa ugaugucauu a                                              21

<210> SEQ ID NO 233
<211> LENGTH: 23
<212> TYPE: RNA
<213> ORGANISM: Influenza B virus

<400> SEQUENCE: 233
agcuacaugg gauaaaugaa uua                                            23

<210> SEQ ID NO 234
<211> LENGTH: 23
<212> TYPE: RNA
<213> ORGANISM: Influenza B virus

<400> SEQUENCE: 234
auguaucaac uccaaagaua uuu                                            23

<210> SEQ ID NO 235
<211> LENGTH: 21
<212> TYPE: RNA
<213> ORGANISM: Influenza B virus

<400> SEQUENCE: 235
augaagnggg caauguguuc u                                              21

<210> SEQ ID NO 236
<211> LENGTH: 19
<212> TYPE: RNA
<213> ORGANISM: Influenza B virus

<400> SEQUENCE: 236
ggaauacaua uggaccaau                                                 19

<210> SEQ ID NO 237
<211> LENGTH: 21
<212> TYPE: RNA
<213> ORGANISM: Influenza B virus

<400> SEQUENCE: 237
aaugauaaca uaugauacac c                                              21

<210> SEQ ID NO 238
<211> LENGTH: 19
<212> TYPE: RNA
<213> ORGANISM: Influenza B virus

<400> SEQUENCE: 238
ccaaggagug agggagaa                                                  19

<210> SEQ ID NO 239
<211> LENGTH: 21
<212> TYPE: RNA
<213> ORGANISM: Influenza B virus

<400> SEQUENCE: 239
aaagucuacg aaagcuuuuu u                                              21

<210> SEQ ID NO 240
<211> LENGTH: 19
<212> TYPE: RNA
<213> ORGANISM: Influenza B virus
```

```
<400> SEQUENCE: 240
gguauuuucu caagacacu                                               19

<210> SEQ ID NO 241
<211> LENGTH: 21
<212> TYPE: RNA
<213> ORGANISM: Influenza B virus

<400> SEQUENCE: 241
agcugcauua ggacuaaaga u                                            21

<210> SEQ ID NO 242
<211> LENGTH: 21
<212> TYPE: RNA
<213> ORGANISM: Influenza B virus

<400> SEQUENCE: 242
uaucaaggaa agcccguuaa a                                            21

<210> SEQ ID NO 243
<211> LENGTH: 21
<212> TYPE: RNA
<213> ORGANISM: Influenza B virus

<400> SEQUENCE: 243
aauugaaaag aacccuucau u                                            21

<210> SEQ ID NO 244
<211> LENGTH: 19
<212> TYPE: RNA
<213> ORGANISM: Influenza B virus

<400> SEQUENCE: 244
gaucaauagu cgcaucaaa                                               19

<210> SEQ ID NO 245
<211> LENGTH: 21
<212> TYPE: RNA
<213> ORGANISM: Influenza B virus

<400> SEQUENCE: 245
cuggugcaaa acaccuauca a                                            21

<210> SEQ ID NO 246
<211> LENGTH: 21
<212> TYPE: RNA
<213> ORGANISM: Influenza B virus

<400> SEQUENCE: 246
ggagcguuuu caagaugaca u                                            21

<210> SEQ ID NO 247
<211> LENGTH: 21
<212> TYPE: RNA
<213> ORGANISM: Influenza B virus

<400> SEQUENCE: 247
aaaauucaau acaucaagaa u                                            21

<210> SEQ ID NO 248
<211> LENGTH: 21
<212> TYPE: RNA
<213> ORGANISM: Influenza B virus
```

```
<400> SEQUENCE: 248
aaugacguaa gugaauuaga a                                          21

<210> SEQ ID NO 249
<211> LENGTH: 21
<212> TYPE: RNA
<213> ORGANISM: Influenza B virus

<400> SEQUENCE: 249
aauaaauuca gcuaaaagg a                                           21

<210> SEQ ID NO 250
<211> LENGTH: 21
<212> TYPE: RNA
<213> ORGANISM: Influenza B virus

<400> SEQUENCE: 250
aaaaaugcuc guguuucuac u                                          21

<210> SEQ ID NO 251
<211> LENGTH: 21
<212> TYPE: RNA
<213> ORGANISM: Influenza B virus

<400> SEQUENCE: 251
aaaggccaaa ugugcucaau a                                          21

<210> SEQ ID NO 252
<211> LENGTH: 21
<212> TYPE: RNA
<213> ORGANISM: Influenza B virus

<400> SEQUENCE: 252
aaaugcugaa gacauaggaa c                                          21

<210> SEQ ID NO 253
<211> LENGTH: 19
<212> TYPE: RNA
<213> ORGANISM: Influenza B virus

<400> SEQUENCE: 253
cagaucuugg agauuucaa                                             19

<210> SEQ ID NO 254
<211> LENGTH: 21
<212> TYPE: RNA
<213> ORGANISM: Influenza B virus

<400> SEQUENCE: 254
guuaccuggu ggaauacaua u                                          21

<210> SEQ ID NO 255
<211> LENGTH: 23
<212> TYPE: RNA
<213> ORGANISM: Influenza B virus

<400> SEQUENCE: 255
uugugcaugg uauuuucuca aga                                        23

<210> SEQ ID NO 256
<211> LENGTH: 23
<212> TYPE: RNA
<213> ORGANISM: Influenza B virus
```

-continued

```
<400> SEQUENCE: 256
gggagaaaua aauuucuua aua                                              23

<210> SEQ ID NO 257
<211> LENGTH: 21
<212> TYPE: RNA
<213> ORGANISM: Influenza B virus

<400> SEQUENCE: 257
caagugagcu acaugggaua a                                               21

<210> SEQ ID NO 258
<211> LENGTH: 19
<212> TYPE: RNA
<213> ORGANISM: Influenza B virus

<400> SEQUENCE: 258
gagaagagga guuccaugu                                                  19

<210> SEQ ID NO 259
<211> LENGTH: 19
<212> TYPE: RNA
<213> ORGANISM: Influenza B virus

<400> SEQUENCE: 259
cacuuugaaa ggguugua                                                   19

<210> SEQ ID NO 260
<211> LENGTH: 19
<212> TYPE: RNA
<213> ORGANISM: Influenza B virus

<400> SEQUENCE: 260
ugcaaacaag acugugaua                                                  19

<210> SEQ ID NO 261
<211> LENGTH: 21
<212> TYPE: RNA
<213> ORGANISM: Influenza B virus

<400> SEQUENCE: 261
aaaaaagagc aaaaugagaa u                                               21

<210> SEQ ID NO 262
<211> LENGTH: 21
<212> TYPE: RNA
<213> ORGANISM: Influenza B virus

<400> SEQUENCE: 262
uuaagggaca augaagccaa a                                               21

<210> SEQ ID NO 263
<211> LENGTH: 19
<212> TYPE: RNA
<213> ORGANISM: Influenza B virus

<400> SEQUENCE: 263
aggagaaaau uucaucgaa                                                  19

<210> SEQ ID NO 264
<211> LENGTH: 19
<212> TYPE: RNA
<213> ORGANISM: Influenza B virus
```

```
<400> SEQUENCE: 264
ccaguugaaa gaguaagaa                                                19

<210> SEQ ID NO 265
<211> LENGTH: 21
<212> TYPE: RNA
<213> ORGANISM: Influenza B virus

<400> SEQUENCE: 265
uuggacgacu ugaacuaaag a                                             21

<210> SEQ ID NO 266
<211> LENGTH: 21
<212> TYPE: RNA
<213> ORGANISM: Influenza B virus

<400> SEQUENCE: 266
aucagcugag uucauagaaa u                                             21

<210> SEQ ID NO 267
<211> LENGTH: 21
<212> TYPE: RNA
<213> ORGANISM: Influenza B virus

<400> SEQUENCE: 267
aaaaugagaa uggaaaaacu a                                             21

<210> SEQ ID NO 268
<211> LENGTH: 19
<212> TYPE: RNA
<213> ORGANISM: Influenza B virus

<400> SEQUENCE: 268
gugcucaaua gcagcaguu                                                19

<210> SEQ ID NO 269
<211> LENGTH: 21
<212> TYPE: RNA
<213> ORGANISM: Influenza B virus

<400> SEQUENCE: 269
uuaucaagga aagcccguua a                                             21

<210> SEQ ID NO 270
<211> LENGTH: 21
<212> TYPE: RNA
<213> ORGANISM: Influenza B virus

<400> SEQUENCE: 270
auaucacccg ggagggaaua a                                             21

<210> SEQ ID NO 271
<211> LENGTH: 21
<212> TYPE: RNA
<213> ORGANISM: Influenza B virus

<400> SEQUENCE: 271
aaacaacagu agaucaauau a                                             21

<210> SEQ ID NO 272
<211> LENGTH: 21
<212> TYPE: RNA
<213> ORGANISM: Influenza B virus
```

```
<400> SEQUENCE: 272
ucccauugua cuggcauaca u                                              21

<210> SEQ ID NO 273
<211> LENGTH: 21
<212> TYPE: RNA
<213> ORGANISM: Influenza B virus

<400> SEQUENCE: 273
ccuccagaug aagcaaguaa u                                              21

<210> SEQ ID NO 274
<211> LENGTH: 21
<212> TYPE: RNA
<213> ORGANISM: Influenza B virus

<400> SEQUENCE: 274
aaugggugcu gaaaaauuug g                                              21

<210> SEQ ID NO 275
<211> LENGTH: 21
<212> TYPE: RNA
<213> ORGANISM: Influenza B virus

<400> SEQUENCE: 275
uaagggacaa ugaagccaaa a                                              21

<210> SEQ ID NO 276
<211> LENGTH: 21
<212> TYPE: RNA
<213> ORGANISM: Influenza B virus

<400> SEQUENCE: 276
uacaccuaag augggggaga u                                              21

<210> SEQ ID NO 277
<211> LENGTH: 21
<212> TYPE: RNA
<213> ORGANISM: Influenza B virus

<400> SEQUENCE: 277
aacaucagcu gaguucauag a                                              21

<210> SEQ ID NO 278
<211> LENGTH: 21
<212> TYPE: RNA
<213> ORGANISM: Influenza B virus

<400> SEQUENCE: 278
aaaaaguauc uauaacaaaa a                                              21

<210> SEQ ID NO 279
<211> LENGTH: 19
<212> TYPE: RNA
<213> ORGANISM: Influenza B virus

<400> SEQUENCE: 279
ggaaucaccc aaagcaagu                                                 19

<210> SEQ ID NO 280
<211> LENGTH: 21
<212> TYPE: RNA
<213> ORGANISM: Influenza B virus
```

-continued

```
<400> SEQUENCE: 280
aaacagaauc cccuuggaau a                                        21

<210> SEQ ID NO 281
<211> LENGTH: 21
<212> TYPE: RNA
<213> ORGANISM: Influenza B virus

<400> SEQUENCE: 281
aaauauuaau cgggaacgga a                                        21

<210> SEQ ID NO 282
<211> LENGTH: 21
<212> TYPE: RNA
<213> ORGANISM: Influenza B virus

<400> SEQUENCE: 282
ugggagaugg gaacaaccaa a                                        21

<210> SEQ ID NO 283
<211> LENGTH: 19
<212> TYPE: RNA
<213> ORGANISM: Influenza B virus

<400> SEQUENCE: 283
ccauguaaga uguggugaa                                           19

<210> SEQ ID NO 284
<211> LENGTH: 21
<212> TYPE: RNA
<213> ORGANISM: Influenza B virus

<400> SEQUENCE: 284
agccauagac ggaggugaug u                                        21

<210> SEQ ID NO 285
<211> LENGTH: 21
<212> TYPE: RNA
<213> ORGANISM: Influenza B virus

<400> SEQUENCE: 285
ggagccaaug acguaaguga a                                        21

<210> SEQ ID NO 286
<211> LENGTH: 21
<212> TYPE: RNA
<213> ORGANISM: Influenza B virus

<400> SEQUENCE: 286
gagcguuuuc aagaugacau u                                        21

<210> SEQ ID NO 287
<211> LENGTH: 21
<212> TYPE: RNA
<213> ORGANISM: Influenza B virus

<400> SEQUENCE: 287
gaugggaaca accaaagaac u                                        21

<210> SEQ ID NO 288
<211> LENGTH: 21
<212> TYPE: RNA
<213> ORGANISM: Influenza B virus
```

```
<400> SEQUENCE: 288
aauacauaug gaccaauagg a                                             21

<210> SEQ ID NO 289
<211> LENGTH: 19
<212> TYPE: RNA
<213> ORGANISM: Influenza B virus

<400> SEQUENCE: 289
gggaugcauu ugaagcauu                                                19

<210> SEQ ID NO 290
<211> LENGTH: 19
<212> TYPE: RNA
<213> ORGANISM: Influenza B virus

<400> SEQUENCE: 290
gcugaagaca uaggaacca                                                19

<210> SEQ ID NO 291
<211> LENGTH: 21
<212> TYPE: RNA
<213> ORGANISM: Influenza B virus

<400> SEQUENCE: 291
agugagcuac augggauaaa u                                             21

<210> SEQ ID NO 292
<211> LENGTH: 19
<212> TYPE: RNA
<213> ORGANISM: Influenza B virus

<400> SEQUENCE: 292
agucauaaug ggagccaau                                                19

<210> SEQ ID NO 293
<211> LENGTH: 21
<212> TYPE: RNA
<213> ORGANISM: Influenza B virus

<400> SEQUENCE: 293
cgggaacgga acaauacaga a                                             21

<210> SEQ ID NO 294
<211> LENGTH: 21
<212> TYPE: RNA
<213> ORGANISM: Influenza B virus

<400> SEQUENCE: 294
ccagaagaug gcuggccaau a                                             21

<210> SEQ ID NO 295
<211> LENGTH: 21
<212> TYPE: RNA
<213> ORGANISM: Influenza B virus

<400> SEQUENCE: 295
aacauaauaa gaaaauucaa u                                             21

<210> SEQ ID NO 296
<211> LENGTH: 21
<212> TYPE: RNA
<213> ORGANISM: Influenza B virus
```

<400> SEQUENCE: 296
uguggcuugu agaaagauaa u                                   21

<210> SEQ ID NO 297
<211> LENGTH: 21
<212> TYPE: RNA
<213> ORGANISM: Influenza B virus

<400> SEQUENCE: 297
aauugaguga aaaaugcucg u                                   21

<210> SEQ ID NO 298
<211> LENGTH: 21
<212> TYPE: RNA
<213> ORGANISM: Influenza B virus

<400> SEQUENCE: 298
ugggcaaugu guucuaauuu u                                   21

<210> SEQ ID NO 299
<211> LENGTH: 19
<212> TYPE: RNA
<213> ORGANISM: Influenza B virus

<400> SEQUENCE: 299
gcggagcguu uucaagaug                                      19

<210> SEQ ID NO 300
<211> LENGTH: 19
<212> TYPE: RNA
<213> ORGANISM: Influenza B virus

<400> SEQUENCE: 300
gcccuuuugu uucucacca                                      19

<210> SEQ ID NO 301
<211> LENGTH: 23
<212> TYPE: RNA
<213> ORGANISM: Influenza B virus

<400> SEQUENCE: 301
aaggaagaca ugaaagauuu aau                                 23

<210> SEQ ID NO 302
<211> LENGTH: 19
<212> TYPE: RNA
<213> ORGANISM: Influenza B virus

<400> SEQUENCE: 302
gaagaaagga auagaucaa                                      19

<210> SEQ ID NO 303
<211> LENGTH: 19
<212> TYPE: RNA
<213> ORGANISM: Influenza B virus

<400> SEQUENCE: 303
cccauuggag cuagcugua                                      19

<210> SEQ ID NO 304
<211> LENGTH: 19
<212> TYPE: RNA
<213> ORGANISM: Influenza B virus

```
<400> SEQUENCE: 304
gagaaaauuu caucgaagu                                           19

<210> SEQ ID NO 305
<211> LENGTH: 21
<212> TYPE: RNA
<213> ORGANISM: Influenza B virus

<400> SEQUENCE: 305
aacaguauug aaacaaacaa c                                        21

<210> SEQ ID NO 306
<211> LENGTH: 19
<212> TYPE: RNA
<213> ORGANISM: Influenza B virus

<400> SEQUENCE: 306
augcaguguu ggcggguuu                                           19

<210> SEQ ID NO 307
<211> LENGTH: 21
<212> TYPE: RNA
<213> ORGANISM: Influenza B virus

<400> SEQUENCE: 307
aauacaaggg aauacaacuu a                                        21

<210> SEQ ID NO 308
<211> LENGTH: 19
<212> TYPE: RNA
<213> ORGANISM: Influenza B virus

<400> SEQUENCE: 308
caaggaauua agagacaaa                                           19

<210> SEQ ID NO 309
<211> LENGTH: 21
<212> TYPE: RNA
<213> ORGANISM: Influenza B virus

<400> SEQUENCE: 309
aaaagggaaa auugaagaug a                                        21

<210> SEQ ID NO 310
<211> LENGTH: 21
<212> TYPE: RNA
<213> ORGANISM: Influenza B virus

<400> SEQUENCE: 310
aauaagaaaa uucaauacau c                                        21

<210> SEQ ID NO 311
<211> LENGTH: 21
<212> TYPE: RNA
<213> ORGANISM: Influenza B virus

<400> SEQUENCE: 311
aaugggaugc auuugaagca u                                        21

<210> SEQ ID NO 312
<211> LENGTH: 21
<212> TYPE: RNA
<213> ORGANISM: Influenza B virus
```

```
<400> SEQUENCE: 312
aaaacaacug uuaagggaca a                                         21

<210> SEQ ID NO 313
<211> LENGTH: 21
<212> TYPE: RNA
<213> ORGANISM: Influenza B virus

<400> SEQUENCE: 313
aagagacaaa gaaugacagu u                                         21

<210> SEQ ID NO 314
<211> LENGTH: 21
<212> TYPE: RNA
<213> ORGANISM: Influenza B virus

<400> SEQUENCE: 314
aaaaaggaag acaugaaaga u                                         21

<210> SEQ ID NO 315
<211> LENGTH: 21
<212> TYPE: RNA
<213> ORGANISM: Influenza B virus

<400> SEQUENCE: 315
gaagugggca auguguucua a                                         21

<210> SEQ ID NO 316
<211> LENGTH: 23
<212> TYPE: RNA
<213> ORGANISM: Influenza B virus

<400> SEQUENCE: 316
gagugagggg agaaauaaau uuu                                       23

<210> SEQ ID NO 317
<211> LENGTH: 19
<212> TYPE: RNA
<213> ORGANISM: Influenza B virus

<400> SEQUENCE: 317
cuuggagauu ucaaaacua                                            19

<210> SEQ ID NO 318
<211> LENGTH: 19
<212> TYPE: RNA
<213> ORGANISM: Influenza B virus

<400> SEQUENCE: 318
agcaggccaa cuuuuaucu                                            19

<210> SEQ ID NO 319
<211> LENGTH: 21
<212> TYPE: RNA
<213> ORGANISM: Influenza B virus

<400> SEQUENCE: 319
aaaacugacc aguucauaaa g                                         21

<210> SEQ ID NO 320
<211> LENGTH: 23
<212> TYPE: RNA
<213> ORGANISM: Influenza B virus
```

```
<400> SEQUENCE: 320
uacaugggau aaaugaauua aug                                           23

<210> SEQ ID NO 321
<211> LENGTH: 21
<212> TYPE: RNA
<213> ORGANISM: Influenza B virus

<400> SEQUENCE: 321
gagccaauga cguaagugaa u                                             21

<210> SEQ ID NO 322
<211> LENGTH: 19
<212> TYPE: RNA
<213> ORGANISM: Influenza B virus

<400> SEQUENCE: 322
gaccaguuca uaaaguugu                                                19

<210> SEQ ID NO 323
<211> LENGTH: 21
<212> TYPE: RNA
<213> ORGANISM: Influenza B virus

<400> SEQUENCE: 323
gaccaagggu gacauggcaa a                                             21

<210> SEQ ID NO 324
<211> LENGTH: 21
<212> TYPE: RNA
<213> ORGANISM: Influenza B virus

<400> SEQUENCE: 324
gccaaugacg uaagugaauu a                                             21

<210> SEQ ID NO 325
<211> LENGTH: 19
<212> TYPE: RNA
<213> ORGANISM: Influenza B virus

<400> SEQUENCE: 325
cuggccaaua caguggauu                                                19

<210> SEQ ID NO 326
<211> LENGTH: 19
<212> TYPE: RNA
<213> ORGANISM: Influenza B virus

<400> SEQUENCE: 326
gggacggaga agaggaguu                                                19

<210> SEQ ID NO 327
<211> LENGTH: 21
<212> TYPE: RNA
<213> ORGANISM: Influenza B virus

<400> SEQUENCE: 327
acccgggagg gaauaaacua a                                             21

<210> SEQ ID NO 328
<211> LENGTH: 19
<212> TYPE: RNA
<213> ORGANISM: Influenza B virus
```

```
<400> SEQUENCE: 328
aacgaugaua acucccauu                                          19

<210> SEQ ID NO 329
<211> LENGTH: 19
<212> TYPE: RNA
<213> ORGANISM: Influenza B virus

<400> SEQUENCE: 329
ugggaacaac caaagaacu                                          19

<210> SEQ ID NO 330
<211> LENGTH: 21
<212> TYPE: RNA
<213> ORGANISM: Influenza B virus

<400> SEQUENCE: 330
uauaucaccc gggagggaau a                                       21

<210> SEQ ID NO 331
<211> LENGTH: 21
<212> TYPE: RNA
<213> ORGANISM: Influenza B virus

<400> SEQUENCE: 331
aaaaauuugg uaacacugaa g                                       21

<210> SEQ ID NO 332
<211> LENGTH: 21
<212> TYPE: RNA
<213> ORGANISM: Influenza B virus

<400> SEQUENCE: 332
ugggaugcau uugaagcauu u                                       21

<210> SEQ ID NO 333
<211> LENGTH: 19
<212> TYPE: RNA
<213> ORGANISM: Influenza B virus

<400> SEQUENCE: 333
cagaagcgga gcguuuuca                                          19

<210> SEQ ID NO 334
<211> LENGTH: 21
<212> TYPE: RNA
<213> ORGANISM: Influenza B virus

<400> SEQUENCE: 334
uagaucaaua uaacauaaua a                                       21

<210> SEQ ID NO 335
<211> LENGTH: 21
<212> TYPE: RNA
<213> ORGANISM: Influenza B virus

<400> SEQUENCE: 335
gggugcugaa aaauuuggua a                                       21

<210> SEQ ID NO 336
<211> LENGTH: 19
<212> TYPE: RNA
<213> ORGANISM: Influenza B virus
```

-continued

```
<400> SEQUENCE: 336
gauggcuggc caauacagu                                                19

<210> SEQ ID NO 337
<211> LENGTH: 21
<212> TYPE: RNA
<213> ORGANISM: Influenza B virus

<400> SEQUENCE: 337
aaaacaguau ugaaacaaac a                                             21

<210> SEQ ID NO 338
<211> LENGTH: 21
<212> TYPE: RNA
<213> ORGANISM: Influenza B virus

<400> SEQUENCE: 338
gacgacuuga acuaaagaga a                                             21

<210> SEQ ID NO 339
<211> LENGTH: 19
<212> TYPE: RNA
<213> ORGANISM: Influenza B virus

<400> SEQUENCE: 339
cacaaacaga aguccuaac                                                19

<210> SEQ ID NO 340
<211> LENGTH: 21
<212> TYPE: RNA
<213> ORGANISM: Influenza B virus

<400> SEQUENCE: 340
auguuccaau gggaugcauu u                                             21

<210> SEQ ID NO 341
<211> LENGTH: 21
<212> TYPE: RNA
<213> ORGANISM: Influenza B virus

<400> SEQUENCE: 341
gggugacaug gcaaacagaa u                                             21

<210> SEQ ID NO 342
<211> LENGTH: 21
<212> TYPE: RNA
<213> ORGANISM: Influenza B virus

<400> SEQUENCE: 342
aaaaaugaug aagaaauauu a                                             21

<210> SEQ ID NO 343
<211> LENGTH: 21
<212> TYPE: RNA
<213> ORGANISM: Influenza B virus

<400> SEQUENCE: 343
caaggugaaa auuggagaca a                                             21

<210> SEQ ID NO 344
<211> LENGTH: 21
<212> TYPE: RNA
<213> ORGANISM: Influenza B virus
```

```
<400> SEQUENCE: 344
aagagcagug cucaaacaaa u                                              21

<210> SEQ ID NO 345
<211> LENGTH: 21
<212> TYPE: RNA
<213> ORGANISM: Influenza B virus

<400> SEQUENCE: 345
aaaguuaagg agaaaugggg a                                              21

<210> SEQ ID NO 346
<211> LENGTH: 19
<212> TYPE: RNA
<213> ORGANISM: Influenza B virus

<400> SEQUENCE: 346
gaaacaaaca acaguagau                                                 19

<210> SEQ ID NO 347
<211> LENGTH: 21
<212> TYPE: RNA
<213> ORGANISM: Influenza B virus

<400> SEQUENCE: 347
aacggaacaa uacagaagau u                                              21

<210> SEQ ID NO 348
<211> LENGTH: 19
<212> TYPE: RNA
<213> ORGANISM: Influenza B virus

<400> SEQUENCE: 348
ggugcaaaac accuaucaa                                                 19

<210> SEQ ID NO 349
<211> LENGTH: 21
<212> TYPE: RNA
<213> ORGANISM: Influenza B virus

<400> SEQUENCE: 349
aacaauacag aagauuggaa u                                              21

<210> SEQ ID NO 350
<211> LENGTH: 19
<212> TYPE: RNA
<213> ORGANISM: Influenza B virus

<400> SEQUENCE: 350
gccaaaugug cucaauagc                                                 19

<210> SEQ ID NO 351
<211> LENGTH: 21
<212> TYPE: RNA
<213> ORGANISM: Influenza B virus

<400> SEQUENCE: 351
caccaccaaa guuaaggaga a                                              21

<210> SEQ ID NO 352
<211> LENGTH: 19
<212> TYPE: RNA
<213> ORGANISM: Influenza B virus
```

```
<400> SEQUENCE: 352
gagcguuuuc aagaugaca                                              19

<210> SEQ ID NO 353
<211> LENGTH: 23
<212> TYPE: RNA
<213> ORGANISM: Influenza B virus

<400> SEQUENCE: 353
cgggaacgga acaauacaga aga                                         23

<210> SEQ ID NO 354
<211> LENGTH: 19
<212> TYPE: RNA
<213> ORGANISM: Influenza B virus

<400> SEQUENCE: 354
gugauagaua cugaaccuu                                              19

<210> SEQ ID NO 355
<211> LENGTH: 21
<212> TYPE: RNA
<213> ORGANISM: Influenza B virus

<400> SEQUENCE: 355
aaauucagcu aaaaggaag a                                            21

<210> SEQ ID NO 356
<211> LENGTH: 19
<212> TYPE: RNA
<213> ORGANISM: Influenza B virus

<400> SEQUENCE: 356
caagacugug auagauacu                                              19

<210> SEQ ID NO 357
<211> LENGTH: 19
<212> TYPE: RNA
<213> ORGANISM: Influenza B virus

<400> SEQUENCE: 357
gcuggccaau acagggau                                               19

<210> SEQ ID NO 358
<211> LENGTH: 19
<212> TYPE: RNA
<213> ORGANISM: Influenza B virus

<400> SEQUENCE: 358
gccaacuuuu aucuccaau                                              19

<210> SEQ ID NO 359
<211> LENGTH: 19
<212> TYPE: RNA
<213> ORGANISM: Influenza B virus

<400> SEQUENCE: 359
gcauuaggac uaaagauca                                              19

<210> SEQ ID NO 360
<211> LENGTH: 23
<212> TYPE: RNA
<213> ORGANISM: Influenza B virus
```

-continued

```
<400> SEQUENCE: 360
ggggagaaau aaauuuucuu aau                                            23

<210> SEQ ID NO 361
<211> LENGTH: 19
<212> TYPE: RNA
<213> ORGANISM: Influenza B virus

<400> SEQUENCE: 361
caaggaguga ggggagaaa                                                 19

<210> SEQ ID NO 362
<211> LENGTH: 21
<212> TYPE: RNA
<213> ORGANISM: Influenza B virus

<400> SEQUENCE: 362
aaaagagcaa aaugagaaug g                                              21

<210> SEQ ID NO 363
<211> LENGTH: 21
<212> TYPE: RNA
<213> ORGANISM: Influenza B virus

<400> SEQUENCE: 363
augggacgga gaagaggagu u                                              21

<210> SEQ ID NO 364
<211> LENGTH: 21
<212> TYPE: RNA
<213> ORGANISM: Influenza B virus

<400> SEQUENCE: 364
aauacaucaa gaauugaaaa g                                              21

<210> SEQ ID NO 365
<211> LENGTH: 21
<212> TYPE: RNA
<213> ORGANISM: Influenza B virus

<400> SEQUENCE: 365
aauaaaugca auugagugaa a                                              21

<210> SEQ ID NO 366
<211> LENGTH: 21
<212> TYPE: RNA
<213> ORGANISM: Influenza B virus

<400> SEQUENCE: 366
aagaugaaga aaggaauaga u                                              21

<210> SEQ ID NO 367
<211> LENGTH: 21
<212> TYPE: RNA
<213> ORGANISM: Influenza B virus

<400> SEQUENCE: 367
guuucucacc accaaaguua a                                              21

<210> SEQ ID NO 368
<211> LENGTH: 23
<212> TYPE: RNA
<213> ORGANISM: Influenza B virus
```

-continued

```
<400> SEQUENCE: 368
ugggauaaau gaauuaauga aug                                           23

<210> SEQ ID NO 369
<211> LENGTH: 21
<212> TYPE: RNA
<213> ORGANISM: Influenza B virus

<400> SEQUENCE: 369
aaaugcaauu gagugaaaaa u                                             21

<210> SEQ ID NO 370
<211> LENGTH: 21
<212> TYPE: RNA
<213> ORGANISM: Influenza B virus

<400> SEQUENCE: 370
gcuagcugua gaaauugcaa a                                             21

<210> SEQ ID NO 371
<211> LENGTH: 19
<212> TYPE: RNA
<213> ORGANISM: Influenza B virus

<400> SEQUENCE: 371
ccagaucuug gagauuuca                                                19

<210> SEQ ID NO 372
<211> LENGTH: 23
<212> TYPE: RNA
<213> ORGANISM: Influenza B virus

<400> SEQUENCE: 372
cuccaaagau auuuuugaa uag                                            23

<210> SEQ ID NO 373
<211> LENGTH: 21
<212> TYPE: RNA
<213> ORGANISM: Influenza B virus

<400> SEQUENCE: 373
aagggaaaau ugaagaugaa g                                             21

<210> SEQ ID NO 374
<211> LENGTH: 21
<212> TYPE: RNA
<213> ORGANISM: Influenza B virus

<400> SEQUENCE: 374
aagcucagcu aaugauaaca u                                             21

<210> SEQ ID NO 375
<211> LENGTH: 21
<212> TYPE: RNA
<213> ORGANISM: Influenza B virus

<400> SEQUENCE: 375
aaaguaucua uaacaaaaaa u                                             21

<210> SEQ ID NO 376
<211> LENGTH: 21
<212> TYPE: RNA
<213> ORGANISM: Influenza B virus
```

```
<400> SEQUENCE: 376
augcggcaga augaugucau u                                              21

<210> SEQ ID NO 377
<211> LENGTH: 21
<212> TYPE: RNA
<213> ORGANISM: Influenza B virus

<400> SEQUENCE: 377
aaacagaagu ccuaacuaua u                                              21

<210> SEQ ID NO 378
<211> LENGTH: 21
<212> TYPE: RNA
<213> ORGANISM: Influenza B virus

<400> SEQUENCE: 378
aaaguuguug cccuuuuguu u                                              21

<210> SEQ ID NO 379
<211> LENGTH: 19
<212> TYPE: RNA
<213> ORGANISM: Influenza B virus

<400> SEQUENCE: 379
ccccuuggaa uacaaggga                                                 19

<210> SEQ ID NO 380
<211> LENGTH: 21
<212> TYPE: RNA
<213> ORGANISM: Influenza B virus

<400> SEQUENCE: 380
augggaugca uuugaagcau u                                              21

<210> SEQ ID NO 381
<211> LENGTH: 21
<212> TYPE: RNA
<213> ORGANISM: Influenza B virus

<400> SEQUENCE: 381
ggcuggccaa uacaguggau u                                              21

<210> SEQ ID NO 382
<211> LENGTH: 21
<212> TYPE: RNA
<213> ORGANISM: Influenza B virus

<400> SEQUENCE: 382
aagguuucga aaaagucuac g                                              21

<210> SEQ ID NO 383
<211> LENGTH: 19
<212> TYPE: RNA
<213> ORGANISM: Influenza B virus

<400> SEQUENCE: 383
cucagcuaau gauaacaua                                                 19

<210> SEQ ID NO 384
<211> LENGTH: 21
<212> TYPE: RNA
<213> ORGANISM: Influenza B virus
```

-continued

```
<400> SEQUENCE: 384
aaaauugaag augaagaaag g                                      21

<210> SEQ ID NO 385
<211> LENGTH: 19
<212> TYPE: RNA
<213> ORGANISM: Influenza B virus

<400> SEQUENCE: 385
ccucuauucu cuuacaauc                                         19

<210> SEQ ID NO 386
<211> LENGTH: 21
<212> TYPE: RNA
<213> ORGANISM: Influenza B virus

<400> SEQUENCE: 386
aauuagaauc acaagcucag c                                      21

<210> SEQ ID NO 387
<211> LENGTH: 19
<212> TYPE: RNA
<213> ORGANISM: Influenza B virus

<400> SEQUENCE: 387
gcucaauagc agcaguuac                                         19

<210> SEQ ID NO 388
<211> LENGTH: 21
<212> TYPE: RNA
<213> ORGANISM: Influenza B virus

<400> SEQUENCE: 388
gaacggaaca auacagaaga u                                      21

<210> SEQ ID NO 389
<211> LENGTH: 21
<212> TYPE: RNA
<213> ORGANISM: Influenza B virus

<400> SEQUENCE: 389
aacugaccag uucauaaagu u                                      21

<210> SEQ ID NO 390
<211> LENGTH: 23
<212> TYPE: RNA
<213> ORGANISM: Influenza B virus

<400> SEQUENCE: 390
uagaaguaac gaucucuuug auc                                    23

<210> SEQ ID NO 391
<211> LENGTH: 19
<212> TYPE: RNA
<213> ORGANISM: Influenza B virus

<400> SEQUENCE: 391
ccaccaaagu uaaggagaa                                         19

<210> SEQ ID NO 392
<211> LENGTH: 19
<212> TYPE: RNA
<213> ORGANISM: Influenza B virus
```

```
<400> SEQUENCE: 392
cgacuugaac uaaagagaa                                          19

<210> SEQ ID NO 393
<211> LENGTH: 23
<212> TYPE: RNA
<213> ORGANISM: Influenza B virus

<400> SEQUENCE: 393
aucaacucca aagauauuuu uug                                     23

<210> SEQ ID NO 394
<211> LENGTH: 21
<212> TYPE: RNA
<213> ORGANISM: Influenza B virus

<400> SEQUENCE: 394
caucagcuga guucauagaa a                                       21

<210> SEQ ID NO 395
<211> LENGTH: 19
<212> TYPE: RNA
<213> ORGANISM: Influenza B virus

<400> SEQUENCE: 395
ggcucaguuu cuucuagga                                          19

<210> SEQ ID NO 396
<211> LENGTH: 21
<212> TYPE: RNA
<213> ORGANISM: Influenza B virus

<400> SEQUENCE: 396
aaucacaagc ucagcuaaug a                                       21

<210> SEQ ID NO 397
<211> LENGTH: 19
<212> TYPE: RNA
<213> ORGANISM: Influenza B virus

<400> SEQUENCE: 397
cuccucuauu cucuuacaa                                          19

<210> SEQ ID NO 398
<211> LENGTH: 19
<212> TYPE: RNA
<213> ORGANISM: Influenza B virus

<400> SEQUENCE: 398
ggugacaugg caaacagaa                                          19

<210> SEQ ID NO 399
<211> LENGTH: 21
<212> TYPE: RNA
<213> ORGANISM: Influenza B virus

<400> SEQUENCE: 399
gaugucgccu gugacauaau a                                       21

<210> SEQ ID NO 400
<211> LENGTH: 21
<212> TYPE: RNA
<213> ORGANISM: Influenza B virus
```

```
<400> SEQUENCE: 400
uaauagagca ggccaacuuu u                                     21

<210> SEQ ID NO 401
<211> LENGTH: 21
<212> TYPE: RNA
<213> ORGANISM: Influenza B virus

<400> SEQUENCE: 401
aaaaucuuag uuuaauaaaa a                                     21

<210> SEQ ID NO 402
<211> LENGTH: 21
<212> TYPE: RNA
<213> ORGANISM: Influenza B virus

<400> SEQUENCE: 402
uaggaaccaa aggccaaaug u                                     21

<210> SEQ ID NO 403
<211> LENGTH: 21
<212> TYPE: RNA
<213> ORGANISM: Influenza B virus

<400> SEQUENCE: 403
aagugaauua gaaucacaag c                                     21

<210> SEQ ID NO 404
<211> LENGTH: 21
<212> TYPE: RNA
<213> ORGANISM: Influenza B virus

<400> SEQUENCE: 404
aacuauaugc ggcagaauga u                                     21

<210> SEQ ID NO 405
<211> LENGTH: 21
<212> TYPE: RNA
<213> ORGANISM: Influenza B virus

<400> SEQUENCE: 405
aauacagugg auuugcaaga g                                     21

<210> SEQ ID NO 406
<211> LENGTH: 21
<212> TYPE: RNA
<213> ORGANISM: Influenza B virus

<400> SEQUENCE: 406
uaaggaugaa gugggcaaug u                                     21

<210> SEQ ID NO 407
<211> LENGTH: 21
<212> TYPE: RNA
<213> ORGANISM: Influenza B virus

<400> SEQUENCE: 407
augggagcca augacguaag u                                     21

<210> SEQ ID NO 408
<211> LENGTH: 19
<212> TYPE: RNA
<213> ORGANISM: Influenza B virus
```

```
<400> SEQUENCE: 408
acccaaagca agugagcua                                              19

<210> SEQ ID NO 409
<211> LENGTH: 21
<212> TYPE: RNA
<213> ORGANISM: Influenza B virus

<400> SEQUENCE: 409
uuggauacau agggaacuga u                                           21

<210> SEQ ID NO 410
<211> LENGTH: 19
<212> TYPE: RNA
<213> ORGANISM: Influenza B virus

<400> SEQUENCE: 410
gaagaggagu uccauguaa                                              19

<210> SEQ ID NO 411
<211> LENGTH: 21
<212> TYPE: RNA
<213> ORGANISM: Influenza B virus

<400> SEQUENCE: 411
caggccaacu uuuaucucca a                                           21

<210> SEQ ID NO 412
<211> LENGTH: 21
<212> TYPE: RNA
<213> ORGANISM: Influenza B virus

<400> SEQUENCE: 412
aagccaaaac aguauugaaa c                                           21

<210> SEQ ID NO 413
<211> LENGTH: 21
<212> TYPE: RNA
<213> ORGANISM: Influenza B virus

<400> SEQUENCE: 413
gagcugcauu aggacuaaag a                                           21

<210> SEQ ID NO 414
<211> LENGTH: 21
<212> TYPE: RNA
<213> ORGANISM: Influenza B virus

<400> SEQUENCE: 414
aaauuuggua acacugaagg c                                           21

<210> SEQ ID NO 415
<211> LENGTH: 21
<212> TYPE: RNA
<213> ORGANISM: Influenza B virus

<400> SEQUENCE: 415
aacaaaaaau cuuaguuuaa u                                           21

<210> SEQ ID NO 416
<211> LENGTH: 21
<212> TYPE: RNA
<213> ORGANISM: Influenza B virus
```

```
<400> SEQUENCE: 416
guggaauaca uauggaccaa u                                          21

<210> SEQ ID NO 417
<211> LENGTH: 21
<212> TYPE: RNA
<213> ORGANISM: Influenza B virus

<400> SEQUENCE: 417
ugggccuuga gcuaauauaa a                                          21

<210> SEQ ID NO 418
<211> LENGTH: 21
<212> TYPE: RNA
<213> ORGANISM: Influenza B virus

<400> SEQUENCE: 418
acagccauag acggagguga u                                          21

<210> SEQ ID NO 419
<211> LENGTH: 19
<212> TYPE: RNA
<213> ORGANISM: Influenza B virus

<400> SEQUENCE: 419
ggagaaaauu ucaucgaag                                             19

<210> SEQ ID NO 420
<211> LENGTH: 23
<212> TYPE: RNA
<213> ORGANISM: Influenza B virus

<400> SEQUENCE: 420
aacuccaaag auauuuuuug aau                                        23

<210> SEQ ID NO 421
<211> LENGTH: 19
<212> TYPE: RNA
<213> ORGANISM: Influenza B virus

<400> SEQUENCE: 421
agcaaaauga gaauggaaa                                             19

<210> SEQ ID NO 422
<211> LENGTH: 23
<212> TYPE: RNA
<213> ORGANISM: Influenza B virus

<400> SEQUENCE: 422
aagugagcua caugggauaa aug                                        23

<210> SEQ ID NO 423
<211> LENGTH: 21
<212> TYPE: RNA
<213> ORGANISM: Influenza B virus

<400> SEQUENCE: 423
uauggaccaa uaggagauac u                                          21

<210> SEQ ID NO 424
<211> LENGTH: 21
<212> TYPE: RNA
<213> ORGANISM: Influenza B virus
```

```
<400> SEQUENCE: 424
aaaggaagac augaaagauu u                                        21

<210> SEQ ID NO 425
<211> LENGTH: 21
<212> TYPE: RNA
<213> ORGANISM: Influenza B virus

<400> SEQUENCE: 425
agggacaaug aagccaaaac a                                        21

<210> SEQ ID NO 426
<211> LENGTH: 21
<212> TYPE: RNA
<213> ORGANISM: Influenza B virus

<400> SEQUENCE: 426
aauucaauac aucaagaauu g                                        21

<210> SEQ ID NO 427
<211> LENGTH: 21
<212> TYPE: RNA
<213> ORGANISM: Influenza B virus

<400> SEQUENCE: 427
aacuguuaag ggacaaugaa g                                        21

<210> SEQ ID NO 428
<211> LENGTH: 23
<212> TYPE: RNA
<213> ORGANISM: Influenza B virus

<400> SEQUENCE: 428
gaggggagaa auaaauuuuc uua                                      23

<210> SEQ ID NO 429
<211> LENGTH: 21
<212> TYPE: RNA
<213> ORGANISM: Influenza B virus

<400> SEQUENCE: 429
aagaauugaa aagaacccuu c                                        21

<210> SEQ ID NO 430
<211> LENGTH: 21
<212> TYPE: RNA
<213> ORGANISM: Influenza B virus

<400> SEQUENCE: 430
gucgccugug acauaauaag a                                        21

<210> SEQ ID NO 431
<211> LENGTH: 21
<212> TYPE: RNA
<213> ORGANISM: Influenza B virus

<400> SEQUENCE: 431
gagcaacauc agcugaguuc a                                        21

<210> SEQ ID NO 432
<211> LENGTH: 21
<212> TYPE: RNA
<213> ORGANISM: Influenza B virus
```

```
<400> SEQUENCE: 432
agaagcggag cguuuucaag a                                          21

<210> SEQ ID NO 433
<211> LENGTH: 21
<212> TYPE: RNA
<213> ORGANISM: Influenza B virus

<400> SEQUENCE: 433
agugggcaau guguucuaau u                                          21

<210> SEQ ID NO 434
<211> LENGTH: 21
<212> TYPE: RNA
<213> ORGANISM: Influenza B virus

<400> SEQUENCE: 434
aacauaugau acaccuaaga u                                          21

<210> SEQ ID NO 435
<211> LENGTH: 21
<212> TYPE: RNA
<213> ORGANISM: Influenza B virus

<400> SEQUENCE: 435
cacaaggaau uaagagacaa a                                          21

<210> SEQ ID NO 436
<211> LENGTH: 21
<212> TYPE: RNA
<213> ORGANISM: Influenza B virus

<400> SEQUENCE: 436
aaacagaaaa aguaucuaua a                                          21

<210> SEQ ID NO 437
<211> LENGTH: 21
<212> TYPE: RNA
<213> ORGANISM: Influenza B virus

<400> SEQUENCE: 437
aaccaaagaa cuggugcaaa a                                          21

<210> SEQ ID NO 438
<211> LENGTH: 21
<212> TYPE: RNA
<213> ORGANISM: Influenza B virus

<400> SEQUENCE: 438
ccaccaaagu uaaggagaaa u                                          21

<210> SEQ ID NO 439
<211> LENGTH: 19
<212> TYPE: RNA
<213> ORGANISM: Influenza B virus

<400> SEQUENCE: 439
agcguuuuca agaugacau                                             19

<210> SEQ ID NO 440
<211> LENGTH: 21
<212> TYPE: RNA
<213> ORGANISM: Influenza B virus
```

```
<400> SEQUENCE: 440
caacuguuaa gggacaauga a                                    21

<210> SEQ ID NO 441
<211> LENGTH: 19
<212> TYPE: RNA
<213> ORGANISM: Influenza B virus

<400> SEQUENCE: 441
cgccugugac auaauaaga                                       19

<210> SEQ ID NO 442
<211> LENGTH: 21
<212> TYPE: RNA
<213> ORGANISM: Influenza B virus

<400> SEQUENCE: 442
aaugagaaug gaaaaacuac u                                    21

<210> SEQ ID NO 443
<211> LENGTH: 19
<212> TYPE: RNA
<213> ORGANISM: Influenza B virus

<400> SEQUENCE: 443
gacaaagaau gacaguuga                                       19

<210> SEQ ID NO 444
<211> LENGTH: 19
<212> TYPE: RNA
<213> ORGANISM: Influenza B virus

<400> SEQUENCE: 444
ggaauuaaga gacaaagaa                                       19

<210> SEQ ID NO 445
<211> LENGTH: 21
<212> TYPE: RNA
<213> ORGANISM: Influenza B virus

<400> SEQUENCE: 445
aauuucaucg aaguaaggaa a                                    21

<210> SEQ ID NO 446
<211> LENGTH: 21
<212> TYPE: RNA
<213> ORGANISM: Influenza B virus

<400> SEQUENCE: 446
aaagauuugg acgacuugaa c                                    21

<210> SEQ ID NO 447
<211> LENGTH: 21
<212> TYPE: RNA
<213> ORGANISM: Influenza B virus

<400> SEQUENCE: 447
aagacaugaa agauuuaaua a                                    21

<210> SEQ ID NO 448
<211> LENGTH: 19
<212> TYPE: RNA
<213> ORGANISM: Influenza B virus
```

<400> SEQUENCE: 448
gcagugcuca aacaaauga                                          19

<210> SEQ ID NO 449
<211> LENGTH: 19
<212> TYPE: RNA
<213> ORGANISM: Influenza B virus

<400> SEQUENCE: 449
ggccaacuuu uaucuccaa                                          19

<210> SEQ ID NO 450
<211> LENGTH: 21
<212> TYPE: RNA
<213> ORGANISM: Influenza B virus

<400> SEQUENCE: 450
agcggagcgu uuucaagaug a                                       21

<210> SEQ ID NO 451
<211> LENGTH: 21
<212> TYPE: RNA
<213> ORGANISM: Influenza B virus

<400> SEQUENCE: 451
ggaacgauga uaacucccau u                                       21

<210> SEQ ID NO 452
<211> LENGTH: 21
<212> TYPE: RNA
<213> ORGANISM: Influenza B virus

<400> SEQUENCE: 452
cugaccaguu cauaaaguug u                                       21

<210> SEQ ID NO 453
<211> LENGTH: 21
<212> TYPE: RNA
<213> ORGANISM: Influenza B virus

<400> SEQUENCE: 453
aauauaacau aauaagaaaa u                                       21

<210> SEQ ID NO 454
<211> LENGTH: 23
<212> TYPE: RNA
<213> ORGANISM: Influenza B virus

<400> SEQUENCE: 454
augaggaauc acccaaagca agu                                     23

<210> SEQ ID NO 455
<211> LENGTH: 21
<212> TYPE: RNA
<213> ORGANISM: Influenza B virus

<400> SEQUENCE: 455
aaaaacuacu aauaaauuca g                                       21

<210> SEQ ID NO 456
<211> LENGTH: 21
<212> TYPE: RNA
<213> ORGANISM: Influenza B virus

```
<400> SEQUENCE: 456
aaagcuuuuu ucucagaaag a                                              21

<210> SEQ ID NO 457
<211> LENGTH: 21
<212> TYPE: RNA
<213> ORGANISM: Influenza B virus

<400> SEQUENCE: 457
aagggaauac aacuuaaaac a                                              21

<210> SEQ ID NO 458
<211> LENGTH: 19
<212> TYPE: RNA
<213> ORGANISM: Influenza B virus

<400> SEQUENCE: 458
gucuccucua uucucuuac                                                 19

<210> SEQ ID NO 459
<211> LENGTH: 21
<212> TYPE: RNA
<213> ORGANISM: Influenza B virus

<400> SEQUENCE: 459
aagaaaauuc aauacaucaa g                                              21

<210> SEQ ID NO 460
<211> LENGTH: 21
<212> TYPE: RNA
<213> ORGANISM: Influenza B virus

<400> SEQUENCE: 460
uggagcagaa gcggagcguu u                                              21

<210> SEQ ID NO 461
<211> LENGTH: 21
<212> TYPE: RNA
<213> ORGANISM: Influenza B virus

<400> SEQUENCE: 461
cauaggaacc aaaggccaaa u                                              21

<210> SEQ ID NO 462
<211> LENGTH: 19
<212> TYPE: RNA
<213> ORGANISM: Influenza B virus

<400> SEQUENCE: 462
gagcaaaaug agaauggaa                                                 19

<210> SEQ ID NO 463
<211> LENGTH: 21
<212> TYPE: RNA
<213> ORGANISM: Influenza B virus

<400> SEQUENCE: 463
ggugagauug gguacacaua a                                              21

<210> SEQ ID NO 464
<211> LENGTH: 21
<212> TYPE: RNA
<213> ORGANISM: Influenza B virus
```

```
<400> SEQUENCE: 464
caccaggagg gaucagcaug a                                              21

<210> SEQ ID NO 465
<211> LENGTH: 21
<212> TYPE: RNA
<213> ORGANISM: Influenza B virus

<400> SEQUENCE: 465
agugccuaug cacaauuaga u                                              21

<210> SEQ ID NO 466
<211> LENGTH: 21
<212> TYPE: RNA
<213> ORGANISM: Influenza B virus

<400> SEQUENCE: 466
gauuccaaag uggaaggaaa a                                              21

<210> SEQ ID NO 467
<211> LENGTH: 21
<212> TYPE: RNA
<213> ORGANISM: Influenza B virus

<400> SEQUENCE: 467
aagagacaug uauggaagga a                                              21

<210> SEQ ID NO 468
<211> LENGTH: 23
<212> TYPE: RNA
<213> ORGANISM: Influenza B virus

<400> SEQUENCE: 468
auguauggaa ggaauaaacg acu                                            23

<210> SEQ ID NO 469
<211> LENGTH: 21
<212> TYPE: RNA
<213> ORGANISM: Influenza B virus

<400> SEQUENCE: 469
aaaaucuaga acaaaguggu u                                              21

<210> SEQ ID NO 470
<211> LENGTH: 21
<212> TYPE: RNA
<213> ORGANISM: Influenza B virus

<400> SEQUENCE: 470 aaagggcaa acuaaaaaga a                                               21

<210> SEQ ID NO 471
<211> LENGTH: 21
<212> TYPE: RNA
<213> ORGANISM: Influenza B virus

<400> SEQUENCE: 471
ggcagcaauu ucaacaacau u                                              21

<210> SEQ ID NO 472
<211> LENGTH: 21
<212> TYPE: RNA
<213> ORGANISM: Influenza B virus
```

-continued

<400> SEQUENCE: 472
aacuguagac aaauuaaccc a　　　　　　　　　　　　　　　　　　　　　　21

<210> SEQ ID NO 473
<211> LENGTH: 21
<212> TYPE: RNA
<213> ORGANISM: Influenza B virus

<400> SEQUENCE: 473
aagcauguuc uauagagaug g　　　　　　　　　　　　　　　　　　　　　　21

<210> SEQ ID NO 474
<211> LENGTH: 21
<212> TYPE: RNA
<213> ORGANISM: Influenza B virus

<400> SEQUENCE: 474
gugggcccaa cauuuacaau u　　　　　　　　　　　　　　　　　　　　　　21

<210> SEQ ID NO 475
<211> LENGTH: 21
<212> TYPE: RNA
<213> ORGANISM: Influenza B virus

<400> SEQUENCE: 475
cucgaacaaa ggaaaacagu a　　　　　　　　　　　　　　　　　　　　　　21

<210> SEQ ID NO 476
<211> LENGTH: 19
<212> TYPE: RNA
<213> ORGANISM: Influenza B virus

<400> SEQUENCE: 476
gacugaaggc ucaaauacc　　　　　　　　　　　　　　　　　　　　　　　19

<210> SEQ ID NO 477
<211> LENGTH: 21
<212> TYPE: RNA
<213> ORGANISM: Influenza B virus

<400> SEQUENCE: 477
aaaaaauugc cugcuaaaaa c　　　　　　　　　　　　　　　　　　　　　　21

<210> SEQ ID NO 478
<211> LENGTH: 19
<212> TYPE: RNA
<213> ORGANISM: Influenza B virus

<400> SEQUENCE: 478
cagaguggaa uacaucaaa　　　　　　　　　　　　　　　　　　　　　　　19

<210> SEQ ID NO 479
<211> LENGTH: 21
<212> TYPE: RNA
<213> ORGANISM: Influenza B virus

<400> SEQUENCE: 479
ccuccuuuag guugaaugau u　　　　　　　　　　　　　　　　　　　　　　21

<210> SEQ ID NO 480
<211> LENGTH: 19
<212> TYPE: RNA
<213> ORGANISM: Influenza B virus

```
<400> SEQUENCE: 480
caccggucuu guucuccaa                                              19

<210> SEQ ID NO 481
<211> LENGTH: 19
<212> TYPE: RNA
<213> ORGANISM: Influenza B virus

<400> SEQUENCE: 481 aucuguuag cauaccauu                                               19

<210> SEQ ID NO 482
<211> LENGTH: 19
<212> TYPE: RNA
<213> ORGANISM: Influenza B virus

<400> SEQUENCE: 482
gacuuuuacc gaacaugua                                              19

<210> SEQ ID NO 483
<211> LENGTH: 21
<212> TYPE: RNA
<213> ORGANISM: Influenza B virus

<400> SEQUENCE: 483
aauaugcuau cuaccuguu g                                            21

<210> SEQ ID NO 484
<211> LENGTH: 23
<212> TYPE: RNA
<213> ORGANISM: Influenza B virus

<400> SEQUENCE: 484
cugcaaucuu cugaugauuu ugc                                         23

<210> SEQ ID NO 485
<211> LENGTH: 21
<212> TYPE: RNA
<213> ORGANISM: Influenza B virus

<400> SEQUENCE: 485
ugcacaauua gauugcguuc u                                           21

<210> SEQ ID NO 486
<211> LENGTH: 23
<212> TYPE: RNA
<213> ORGANISM: Influenza B virus

<400> SEQUENCE: 486
ugggauggac ugcaaucuuc uga                                         23

<210> SEQ ID NO 487
<211> LENGTH: 21
<212> TYPE: RNA
<213> ORGANISM: Influenza B virus

<400> SEQUENCE: 487
aggaaugaca auaauaaaga a                                           21

<210> SEQ ID NO 488
<211> LENGTH: 21
<212> TYPE: RNA
<213> ORGANISM: Influenza B virus
```

```
<400> SEQUENCE: 488
uggaccauua cccgaagaca a                                              21

<210> SEQ ID NO 489
<211> LENGTH: 21
<212> TYPE: RNA
<213> ORGANISM: Influenza B virus

<400> SEQUENCE: 489
cacauggucc ugugaagaaa a                                              21

<210> SEQ ID NO 490
<211> LENGTH: 21
<212> TYPE: RNA
<213> ORGANISM: Influenza B virus

<400> SEQUENCE: 490
ccagagugga auacaucaaa a                                              21

<210> SEQ ID NO 491
<211> LENGTH: 21
<212> TYPE: RNA
<213> ORGANISM: Influenza B virus

<400> SEQUENCE: 491
aaacuugcau aucccagaaa u                                              21

<210> SEQ ID NO 492
<211> LENGTH: 19
<212> TYPE: RNA
<213> ORGANISM: Influenza B virus

<400> SEQUENCE: 492
gaggguuugu auuaguagu                                                 19

<210> SEQ ID NO 493
<211> LENGTH: 21
<212> TYPE: RNA
<213> ORGANISM: Influenza B virus

<400> SEQUENCE: 493
aggauuuaug auaacaagua a                                              21

<210> SEQ ID NO 494
<211> LENGTH: 21
<212> TYPE: RNA
<213> ORGANISM: Influenza B virus

<400> SEQUENCE: 494
aaguacaauc uaauggaccc u                                              21

<210> SEQ ID NO 495
<211> LENGTH: 21
<212> TYPE: RNA
<213> ORGANISM: Influenza B virus

<400> SEQUENCE: 495
aacaauaacc uccuuuaggu u                                              21

<210> SEQ ID NO 496
<211> LENGTH: 19
<212> TYPE: RNA
<213> ORGANISM: Influenza B virus
```

```
<400> SEQUENCE: 496
gcagauaugg caauaggaa                                              19

<210> SEQ ID NO 497
<211> LENGTH: 19
<212> TYPE: RNA
<213> ORGANISM: Influenza B virus

<400> SEQUENCE: 497 gccaucaau uguucauag                                               19

<210> SEQ ID NO 498
<211> LENGTH: 19
<212> TYPE: RNA
<213> ORGANISM: Influenza B virus

<400> SEQUENCE: 498
agcagcacua gguaucaaa                                              19

<210> SEQ ID NO 499
<211> LENGTH: 19
<212> TYPE: RNA
<213> ORGANISM: Influenza B virus

<400> SEQUENCE: 499
gggaauaaac augagcaaa                                              19

<210> SEQ ID NO 500
<211> LENGTH: 21
<212> TYPE: RNA
<213> ORGANISM: Influenza B virus

<400> SEQUENCE: 500
aaucuucuga ugauuuugcu c                                           21

<210> SEQ ID NO 501
<211> LENGTH: 19
<212> TYPE: RNA
<213> ORGANISM: Influenza B virus

<400> SEQUENCE: 501
cuggaaugau gaugggaau                                              19

<210> SEQ ID NO 502
<211> LENGTH: 19
<212> TYPE: RNA
<213> ORGANISM: Influenza B virus

<400> SEQUENCE: 502
gccaagauau cauugauuc                                              19

<210> SEQ ID NO 503
<211> LENGTH: 19
<212> TYPE: RNA
<213> ORGANISM: Influenza B virus

<400> SEQUENCE: 503
cccagaaaua guauugaag                                              19

<210> SEQ ID NO 504
<211> LENGTH: 19
<212> TYPE: RNA
<213> ORGANISM: Influenza B virus
```

```
<400> SEQUENCE: 504
cgacuuuuac cgaacaugu                                         19

<210> SEQ ID NO 505
<211> LENGTH: 19
<212> TYPE: RNA
<213> ORGANISM: Influenza B virus

<400> SEQUENCE: 505
cccaacauuu acaauuga                                          19

<210> SEQ ID NO 506
<211> LENGTH: 21
<212> TYPE: RNA
<213> ORGANISM: Influenza B virus

<400> SEQUENCE: 506
uacccauaca ggcagcaauu u                                      21

<210> SEQ ID NO 507
<211> LENGTH: 21
<212> TYPE: RNA
<213> ORGANISM: Influenza B virus

<400> SEQUENCE: 507
cagcacaaac agccauacaa u                                      21

<210> SEQ ID NO 508
<211> LENGTH: 19
<212> TYPE: RNA
<213> ORGANISM: Influenza B virus

<400> SEQUENCE: 508
gaaggcucaa auaccuugu                                         19

<210> SEQ ID NO 509
<211> LENGTH: 21
<212> TYPE: RNA
<213> ORGANISM: Influenza B virus

<400> SEQUENCE: 509
aggcaucaaa gaagcagaua u                                      21

<210> SEQ ID NO 510
<211> LENGTH: 19
<212> TYPE: RNA
<213> ORGANISM: Influenza B virus

<400> SEQUENCE: 510
agccauacaa uuguucaua                                         19

<210> SEQ ID NO 511
<211> LENGTH: 21
<212> TYPE: RNA
<213> ORGANISM: Influenza B virus

<400> SEQUENCE: 511
aauacaaauc agagguuug u                                       21

<210> SEQ ID NO 512
<211> LENGTH: 21
<212> TYPE: RNA
<213> ORGANISM: Influenza B virus
```

-continued

```
<400> SEQUENCE: 512
guucuggagg cuuuggauag a                                           21

<210> SEQ ID NO 513
<211> LENGTH: 19
<212> TYPE: RNA
<213> ORGANISM: Influenza B virus

<400> SEQUENCE: 513
gguuuguauu aguaguuga                                              19

<210> SEQ ID NO 514
<211> LENGTH: 21
<212> TYPE: RNA
<213> ORGANISM: Influenza B virus

<400> SEQUENCE: 514
gccagauugg gaaaaggauu u                                           21

<210> SEQ ID NO 515
<211> LENGTH: 19
<212> TYPE: RNA
<213> ORGANISM: Influenza B virus

<400> SEQUENCE: 515
ccacagagga gauuccaaa                                              19

<210> SEQ ID NO 516
<211> LENGTH: 21
<212> TYPE: RNA
<213> ORGANISM: Influenza B virus

<400> SEQUENCE: 516
aaaggaaaac aguauguuuc u                                           21

<210> SEQ ID NO 517
<211> LENGTH: 19
<212> TYPE: RNA
<213> ORGANISM: Influenza B virus

<400> SEQUENCE: 517
gcauaccauu agaaagaua                                              19

<210> SEQ ID NO 518
<211> LENGTH: 21
<212> TYPE: RNA
<213> ORGANISM: Influenza B virus

<400> SEQUENCE: 518
aaaaacagaa aggguuuccu c                                           21

<210> SEQ ID NO 519
<211> LENGTH: 21
<212> TYPE: RNA
<213> ORGANISM: Influenza B virus

<400> SEQUENCE: 519
gugccuaugc acaauuagau u                                           21

<210> SEQ ID NO 520
<211> LENGTH: 21
<212> TYPE: RNA
<213> ORGANISM: Influenza B virus
```

```
<400> SEQUENCE: 520
cagauggugg gcccaacauu u                                              21

<210> SEQ ID NO 521
<211> LENGTH: 21
<212> TYPE: RNA
<213> ORGANISM: Influenza B virus

<400> SEQUENCE: 521
ggagccuuua agaugaauau a                                              21

<210> SEQ ID NO 522
<211> LENGTH: 21
<212> TYPE: RNA
<213> ORGANISM: Influenza B virus

<400> SEQUENCE: 522
aaaaagaaaa guuacuguaa c                                              21

<210> SEQ ID NO 523
<211> LENGTH: 21
<212> TYPE: RNA
<213> ORGANISM: Influenza B virus

<400> SEQUENCE: 523
aauggucaca acuguagaca a                                              21

<210> SEQ ID NO 524
<211> LENGTH: 21
<212> TYPE: RNA
<213> ORGANISM: Influenza B virus

<400> SEQUENCE: 524
auggaugcac gacuagauua u                                              21

<210> SEQ ID NO 525
<211> LENGTH: 21
<212> TYPE: RNA
<213> ORGANISM: Influenza B virus

<400> SEQUENCE: 525
agcacaaaca gccauacaau u                                              21

<210> SEQ ID NO 526
<211> LENGTH: 21
<212> TYPE: RNA
<213> ORGANISM: Influenza B virus

<400> SEQUENCE: 526
ugcaaccgcu ggaauacaaa u                                              21

<210> SEQ ID NO 527
<211> LENGTH: 19
<212> TYPE: RNA
<213> ORGANISM: Influenza B virus

<400> SEQUENCE: 527
ggggagacag acuuucgau                                                 19

<210> SEQ ID NO 528
<211> LENGTH: 21
<212> TYPE: RNA
<213> ORGANISM: Influenza B virus
```

-continued

```
<400> SEQUENCE: 528
uaugggaugg acugcaaucu u                                              21

<210> SEQ ID NO 529
<211> LENGTH: 21
<212> TYPE: RNA
<213> ORGANISM: Influenza B virus

<400> SEQUENCE: 529
aagccugaaa ugacuuucuu c                                              21

<210> SEQ ID NO 530
<211> LENGTH: 19
<212> TYPE: RNA
<213> ORGANISM: Influenza B virus

<400> SEQUENCE: 530
cauacaggca gcaauuuca                                                 19

<210> SEQ ID NO 531
<211> LENGTH: 21
<212> TYPE: RNA
<213> ORGANISM: Influenza B virus

<400> SEQUENCE: 531
aacacuaaag gaagagaugg u                                              21

<210> SEQ ID NO 532
<211> LENGTH: 21
<212> TYPE: RNA
<213> ORGANISM: Influenza B virus

<400> SEQUENCE: 532
aaacuaaaaa gaagagcgau u                                              21

<210> SEQ ID NO 533
<211> LENGTH: 21
<212> TYPE: RNA
<213> ORGANISM: Influenza B virus

<400> SEQUENCE: 533
aaaucagagg guuuguauua g                                              21

<210> SEQ ID NO 534
<211> LENGTH: 21
<212> TYPE: RNA
<213> ORGANISM: Influenza B virus

<400> SEQUENCE: 534
aguggccaaa augcucagua a                                              21

<210> SEQ ID NO 535
<211> LENGTH: 19
<212> TYPE: RNA
<213> ORGANISM: Influenza B virus

<400> SEQUENCE: 535
caccuacaaa ugccacaga                                                 19

<210> SEQ ID NO 536
<211> LENGTH: 19
<212> TYPE: RNA
<213> ORGANISM: Influenza B virus
```

```
<400> SEQUENCE: 536
ggagcugaca aggguggau                                          19

<210> SEQ ID NO 537
<211> LENGTH: 23
<212> TYPE: RNA
<213> ORGANISM: Influenza B virus

<400> SEQUENCE: 537
uugcucuguu uguuaaugca aaa                                     23

<210> SEQ ID NO 538
<211> LENGTH: 19
<212> TYPE: RNA
<213> ORGANISM: Influenza B virus

<400> SEQUENCE: 538
ggucacaacu guagacaaa                                          19

<210> SEQ ID NO 539
<211> LENGTH: 21
<212> TYPE: RNA
<213> ORGANISM: Influenza B virus

<400> SEQUENCE: 539
auaaccagag acagcccaau u                                       21

<210> SEQ ID NO 540
<211> LENGTH: 21
<212> TYPE: RNA
<213> ORGANISM: Influenza B virus

<400> SEQUENCE: 540
aaauggacca uuacccgaag a                                       21

<210> SEQ ID NO 541
<211> LENGTH: 21
<212> TYPE: RNA
<213> ORGANISM: Influenza B virus

<400> SEQUENCE: 541
aauaaacgac uuuuaccgaa c                                       21

<210> SEQ ID NO 542
<211> LENGTH: 21
<212> TYPE: RNA
<213> ORGANISM: Influenza B virus

<400> SEQUENCE: 542
aauauaaaga aaaaauugcc u                                       21

<210> SEQ ID NO 543
<211> LENGTH: 23
<212> TYPE: RNA
<213> ORGANISM: Influenza B virus

<400> SEQUENCE: 543
aacgacuuuu accgaacaug uaa                                     23

<210> SEQ ID NO 544
<211> LENGTH: 21
<212> TYPE: RNA
<213> ORGANISM: Influenza B virus
```

-continued

```
<400> SEQUENCE: 544
caccggucuu guucuccaau a                                              21

<210> SEQ ID NO 545
<211> LENGTH: 21
<212> TYPE: RNA
<213> ORGANISM: Influenza B virus

<400> SEQUENCE: 545
aacagcacaa acagccauac a                                              21

<210> SEQ ID NO 546
<211> LENGTH: 19
<212> TYPE: RNA
<213> ORGANISM: Influenza B virus

<400> SEQUENCE: 546
cugaugauuu ugcucuguu                                                 19

<210> SEQ ID NO 547
<211> LENGTH: 21
<212> TYPE: RNA
<213> ORGANISM: Influenza B virus

<400> SEQUENCE: 547
ggagggauca gcaugacagu a                                              21

<210> SEQ ID NO 548
<211> LENGTH: 21
<212> TYPE: RNA
<213> ORGANISM: Influenza B virus

<400> SEQUENCE: 548
cagcacuagg uaucaaaaac a                                              21

<210> SEQ ID NO 549
<211> LENGTH: 23
<212> TYPE: RNA
<213> ORGANISM: Influenza B virus

<400> SEQUENCE: 549
gacauguaug gaaggaauaa acg                                            23

<210> SEQ ID NO 550
<211> LENGTH: 21
<212> TYPE: RNA
<213> ORGANISM: Influenza B virus

<400> SEQUENCE: 550
aaaagaaggc caaacuguca a                                              21

<210> SEQ ID NO 551
<211> LENGTH: 21
<212> TYPE: RNA
<213> ORGANISM: Influenza B virus

<400> SEQUENCE: 551 ugugggccc aacauuuaca a                                               21

<210> SEQ ID NO 552
<211> LENGTH: 21
<212> TYPE: RNA
<213> ORGANISM: Influenza B virus
```

-continued

```
<400> SEQUENCE: 552
cccgaagaca augagccaag u                                    21

<210> SEQ ID NO 553
<211> LENGTH: 21
<212> TYPE: RNA
<213> ORGANISM: Influenza B virus

<400> SEQUENCE: 553
aaaauggauu augaugcagu g                                    21

<210> SEQ ID NO 554
<211> LENGTH: 21
<212> TYPE: RNA
<213> ORGANISM: Influenza B virus

<400> SEQUENCE: 554
aacucauagu uggagaacca a                                    21

<210> SEQ ID NO 555
<211> LENGTH: 21
<212> TYPE: RNA
<213> ORGANISM: Influenza B virus

<400> SEQUENCE: 555
ugccacagag gagauuccaa a                                    21

<210> SEQ ID NO 556
<211> LENGTH: 21
<212> TYPE: RNA
<213> ORGANISM: Influenza B virus

<400> SEQUENCE: 556
aaugaugaug ggaauguuua a                                    21

<210> SEQ ID NO 557
<211> LENGTH: 21
<212> TYPE: RNA
<213> ORGANISM: Influenza B virus

<400> SEQUENCE: 557 aauguugaa uuuacaagca u                                     21

<210> SEQ ID NO 558
<211> LENGTH: 21
<212> TYPE: RNA
<213> ORGANISM: Influenza B virus

<400> SEQUENCE: 558
aaagaagcag auauaacucc a                                    21

<210> SEQ ID NO 559
<211> LENGTH: 23
<212> TYPE: RNA
<213> ORGANISM: Influenza B virus

<400> SEQUENCE: 559
ucccagaaau aguauugaag uac                                  23

<210> SEQ ID NO 560
<211> LENGTH: 21
<212> TYPE: RNA
<213> ORGANISM: Influenza B virus
```

```
<400> SEQUENCE: 560
aaucuagaac aaaguggacuuu g                                              21

<210> SEQ ID NO 561
<211> LENGTH: 21
<212> TYPE: RNA
<213> ORGANISM: Influenza B virus

<400> SEQUENCE: 561
ugacaguaac aggagacaau a                                                21

<210> SEQ ID NO 562
<211> LENGTH: 21
<212> TYPE: RNA
<213> ORGANISM: Influenza B virus

<400> SEQUENCE: 562
aaugcaaaag augaagagac a                                                21

<210> SEQ ID NO 563
<211> LENGTH: 19
<212> TYPE: RNA
<213> ORGANISM: Influenza B virus

<400> SEQUENCE: 563
guggccaaaa ugcucagua                                                   19

<210> SEQ ID NO 564
<211> LENGTH: 21
<212> TYPE: RNA
<213> ORGANISM: Influenza B virus

<400> SEQUENCE: 564
aaugauuuga auggagcuga c                                                21

<210> SEQ ID NO 565
<211> LENGTH: 19
<212> TYPE: RNA
<213> ORGANISM: Influenza B virus

<400> SEQUENCE: 565
gaguagcagc acuagguau                                                   19

<210> SEQ ID NO 566
<211> LENGTH: 21
<212> TYPE: RNA
<213> ORGANISM: Influenza B virus

<400> SEQUENCE: 566
ugguacccuu uugccaagau a                                                21

<210> SEQ ID NO 567
<211> LENGTH: 21
<212> TYPE: RNA
<213> ORGANISM: Influenza B virus

<400> SEQUENCE: 567
aacgacuuuu accgaacaug u                                                21

<210> SEQ ID NO 568
<211> LENGTH: 19
<212> TYPE: RNA
<213> ORGANISM: Influenza B virus
```

```
<400> SEQUENCE: 568
ccagauuggg aaaaggauu                                              19

<210> SEQ ID NO 569
<211> LENGTH: 21
<212> TYPE: RNA
<213> ORGANISM: Influenza B virus

<400> SEQUENCE: 569
uagaaagaua uaaugaagaa a                                           21

<210> SEQ ID NO 570
<211> LENGTH: 21
<212> TYPE: RNA
<213> ORGANISM: Influenza B virus

<400> SEQUENCE: 570
uggcaucaca ggauguacaa u                                           21

<210> SEQ ID NO 571
<211> LENGTH: 21
<212> TYPE: RNA
<213> ORGANISM: Influenza B virus

<400> SEQUENCE: 571
acaggaugua caaugguaga u                                           21

<210> SEQ ID NO 572
<211> LENGTH: 21
<212> TYPE: RNA
<213> ORGANISM: Influenza B virus

<400> SEQUENCE: 572
aaaagagcau ugucauuaaa c                                           21

<210> SEQ ID NO 573
<211> LENGTH: 21
<212> TYPE: RNA
<213> ORGANISM: Influenza B virus

<400> SEQUENCE: 573
uggaggcacu aauggucaca a                                           21

<210> SEQ ID NO 574
<211> LENGTH: 21
<212> TYPE: RNA
<213> ORGANISM: Influenza B virus

<400> SEQUENCE: 574
agcggagccu uuaagaugaa u                                           21

<210> SEQ ID NO 575
<211> LENGTH: 21
<212> TYPE: RNA
<213> ORGANISM: Influenza B virus

<400> SEQUENCE: 575
aaaguggaag gaaaaagaau g                                           21

<210> SEQ ID NO 576
<211> LENGTH: 19
<212> TYPE: RNA
<213> ORGANISM: Influenza B virus
```

```
<400> SEQUENCE: 576
aaggaagaga uggucuguu                                              19

<210> SEQ ID NO 577
<211> LENGTH: 21
<212> TYPE: RNA
<213> ORGANISM: Influenza B virus

<400> SEQUENCE: 577
ggcaucaaag aagcagauau a                                           21

<210> SEQ ID NO 578
<211> LENGTH: 21
<212> TYPE: RNA
<213> ORGANISM: Influenza B virus

<400> SEQUENCE: 578
aagauaucau ugauucauua g                                           21

<210> SEQ ID NO 579
<211> LENGTH: 21
<212> TYPE: RNA
<213> ORGANISM: Influenza B virus

<400> SEQUENCE: 579
caggcagcaa uuucaacaac a                                           21

<210> SEQ ID NO 580
<211> LENGTH: 19
<212> TYPE: RNA
<213> ORGANISM: Influenza B virus

<400> SEQUENCE: 580
cacaauuaga uugcguucu                                              19

<210> SEQ ID NO 581
<211> LENGTH: 19
<212> TYPE: RNA
<213> ORGANISM: Influenza B virus

<400> SEQUENCE: 581
gccuguuuua acagugcau                                              19

<210> SEQ ID NO 582
<211> LENGTH: 19
<212> TYPE: RNA
<213> ORGANISM: Influenza B virus

<400> SEQUENCE: 582
gaggaacaau gcuacgcua                                              19

<210> SEQ ID NO 583
<211> LENGTH: 23
<212> TYPE: RNA
<213> ORGANISM: Influenza B virus

<400> SEQUENCE: 583
gggaguagca gcacuaggua uca                                         23

<210> SEQ ID NO 584
<211> LENGTH: 21
<212> TYPE: RNA
<213> ORGANISM: Influenza B virus
```

-continued

```
<400> SEQUENCE: 584
agccagauug ggaaaaggau u                                              21

<210> SEQ ID NO 585
<211> LENGTH: 21
<212> TYPE: RNA
<213> ORGANISM: Influenza B virus

<400> SEQUENCE: 585
gaacacauga guacucgaac a                                              21

<210> SEQ ID NO 586
<211> LENGTH: 21
<212> TYPE: RNA
<213> ORGANISM: Influenza B virus

<400> SEQUENCE: 586
cucuucauag auguacccau a                                              21

<210> SEQ ID NO 587
<211> LENGTH: 21
<212> TYPE: RNA
<213> ORGANISM: Influenza B virus

<400> SEQUENCE: 587
aaagaauaua aagaaaaaau u                                              21

<210> SEQ ID NO 588
<211> LENGTH: 21
<212> TYPE: RNA
<213> ORGANISM: Influenza B virus

<400> SEQUENCE: 588
uggcagaugg ugggcccaac a                                              21

<210> SEQ ID NO 589
<211> LENGTH: 21
<212> TYPE: RNA
<213> ORGANISM: Influenza B virus

<400> SEQUENCE: 589
caguggccaa aaugcucagu a                                              21

<210> SEQ ID NO 590
<211> LENGTH: 21
<212> TYPE: RNA
<213> ORGANISM: Influenza B virus

<400> SEQUENCE: 590
gcaacggcac uaaacacaac a                                              21

<210> SEQ ID NO 591
<211> LENGTH: 19
<212> TYPE: RNA
<213> ORGANISM: Influenza B virus

<400> SEQUENCE: 591
guuggagaac caaaaggaa                                                 19

<210> SEQ ID NO 592
<211> LENGTH: 19
<212> TYPE: RNA
<213> ORGANISM: Influenza B virus
```

<400> SEQUENCE: 592
ggaauaaacg acuuuuacc　　　　　　　　　　　　　　　　　　　19

<210> SEQ ID NO 593
<211> LENGTH: 21
<212> TYPE: RNA
<213> ORGANISM: Influenza B virus

<400> SEQUENCE: 593
cagaagcgga gccuuuaaga u 21

<210> SEQ ID NO 594
<211> LENGTH: 23
<212> TYPE: RNA
<213> ORGANISM: Influenza B virus

<400> SEQUENCE: 594
acgacuuuua ccgaacaugu aaa 23

<210> SEQ ID NO 595
<211> LENGTH: 21
<212> TYPE: RNA
<213> ORGANISM: Influenza B virus

<400> SEQUENCE: 595
cggagccuuu aagaugaaua u 21

<210> SEQ ID NO 596
<211> LENGTH: 21
<212> TYPE: RNA
<213> ORGANISM: Influenza B virus

<400> SEQUENCE: 596
uauucccaug gaacgggaac a 21

<210> SEQ ID NO 597
<211> LENGTH: 19
<212> TYPE: RNA
<213> ORGANISM: Influenza B virus

<400> SEQUENCE: 597
gcaaccgcug gaauacaaa 19

<210> SEQ ID NO 598
<211> LENGTH: 19
<212> TYPE: RNA
<213> ORGANISM: Influenza B virus

<400> SEQUENCE: 598
ccaagauauc auugauuca 19

<210> SEQ ID NO 599
<211> LENGTH: 21
<212> TYPE: RNA
<213> ORGANISM: Influenza B virus

<400> SEQUENCE: 599
gagggaucag caugacagua a 21

<210> SEQ ID NO 600
<211> LENGTH: 19
<212> TYPE: RNA
<213> ORGANISM: Influenza B virus

```
<400> SEQUENCE: 600
ggcaucaaag aagcagaua                                                  19

<210> SEQ ID NO 601
<211> LENGTH: 19
<212> TYPE: RNA
<213> ORGANISM: Influenza B virus

<400> SEQUENCE: 601
ccugaaauga cuuucuucu                                                  19

<210> SEQ ID NO 602
<211> LENGTH: 19
<212> TYPE: RNA
<213> ORGANISM: Influenza B virus

<400> SEQUENCE: 602
augacaaaag augcugaaa                                                  19

<210> SEQ ID NO 603
<211> LENGTH: 21
<212> TYPE: RNA
<213> ORGANISM: Influenza B virus

<400> SEQUENCE: 603
uucuggaggc uuuggauaga a                                               21

<210> SEQ ID NO 604
<211> LENGTH: 19
<212> TYPE: RNA
<213> ORGANISM: Influenza B virus

<400> SEQUENCE: 604
gcaucuuugu cgccuggaa                                                  19

<210> SEQ ID NO 605
<211> LENGTH: 21
<212> TYPE: RNA
<213> ORGANISM: Influenza B virus

<400> SEQUENCE: 605
ugaggaacau ccaggucugu u                                               21

<210> SEQ ID NO 606
<211> LENGTH: 21
<212> TYPE: RNA
<213> ORGANISM: Influenza B virus

<400> SEQUENCE: 606
aacaauauga uuaacaaugg g                                               21

<210> SEQ ID NO 607
<211> LENGTH: 21
<212> TYPE: RNA
<213> ORGANISM: Influenza B virus

<400> SEQUENCE: 607
caccgugauc agaacacaug a                                               21

<210> SEQ ID NO 608
<211> LENGTH: 21
<212> TYPE: RNA
<213> ORGANISM: Influenza B virus
```

-continued

```
<400> SEQUENCE: 608
aaaaagaaga gcgauugcaa c                                              21

<210> SEQ ID NO 609
<211> LENGTH: 19
<212> TYPE: RNA
<213> ORGANISM: Influenza B virus

<400> SEQUENCE: 609
ggaacucaua guuggagaa                                                 19

<210> SEQ ID NO 610
<211> LENGTH: 19
<212> TYPE: RNA
<213> ORGANISM: Influenza B virus

<400> SEQUENCE: 610
cgaaacugga auguuugaa                                                 19

<210> SEQ ID NO 611
<211> LENGTH: 21
<212> TYPE: RNA
<213> ORGANISM: Influenza B virus

<400> SEQUENCE: 611
aaaaucccuu uguaggacau u                                              21

<210> SEQ ID NO 612
<211> LENGTH: 23
<212> TYPE: RNA
<213> ORGANISM: Influenza B virus

<400> SEQUENCE: 612
uggaaggaau aaacgacuuu uac                                            23

<210> SEQ ID NO 613
<211> LENGTH: 19
<212> TYPE: RNA
<213> ORGANISM: Influenza B virus

<400> SEQUENCE: 613
gagacagccc aauuugguu                                                 19

<210> SEQ ID NO 614
<211> LENGTH: 19
<212> TYPE: RNA
<213> ORGANISM: Influenza B virus

<400> SEQUENCE: 614 gguuccuca uaaagagaa                                                  19

<210> SEQ ID NO 615
<211> LENGTH: 21
<212> TYPE: RNA
<213> ORGANISM: Influenza B virus

<400> SEQUENCE: 615
aggguggauu gguacccuuu u                                              21

<210> SEQ ID NO 616
<211> LENGTH: 21
<212> TYPE: RNA
<213> ORGANISM: Influenza B virus
```

```
<400> SEQUENCE: 616
uuucuggcau cacaggaugu a                                              21

<210> SEQ ID NO 617
<211> LENGTH: 21
<212> TYPE: RNA
<213> ORGANISM: Influenza B virus

<400> SEQUENCE: 617
aaaacacuaa aggaagagau g                                              21

<210> SEQ ID NO 618
<211> LENGTH: 23
<212> TYPE: RNA
<213> ORGANISM: Influenza B virus

<400> SEQUENCE: 618
gacugcaauc uucugaugau uuu                                            23

<210> SEQ ID NO 619
<211> LENGTH: 21
<212> TYPE: RNA
<213> ORGANISM: Influenza B virus

<400> SEQUENCE: 619 gguggccca acauuuacaa u                                               21

<210> SEQ ID NO 620
<211> LENGTH: 21
<212> TYPE: RNA
<213> ORGANISM: Influenza B virus

<400> SEQUENCE: 620
aaacgacuuu uaccgaacau g                                              21

<210> SEQ ID NO 621
<211> LENGTH: 21
<212> TYPE: RNA
<213> ORGANISM: Influenza B virus

<400> SEQUENCE: 621
aaaaagaaug aaaauuauaa a                                              21

<210> SEQ ID NO 622
<211> LENGTH: 21
<212> TYPE: RNA
<213> ORGANISM: Influenza B virus

<400> SEQUENCE: 622
uguacccaua caggcagcaa u                                              21

<210> SEQ ID NO 623
<211> LENGTH: 19
<212> TYPE: RNA
<213> ORGANISM: Influenza B virus

<400> SEQUENCE: 623
gagaauacca augaaagua                                                 19

<210> SEQ ID NO 624
<211> LENGTH: 21
<212> TYPE: RNA
<213> ORGANISM: Influenza B virus
```

```
<400> SEQUENCE: 624
aaaagaugaa gagacaugua u                                              21

<210> SEQ ID NO 625
<211> LENGTH: 19
<212> TYPE: RNA
<213> ORGANISM: Influenza B virus

<400> SEQUENCE: 625
gcaacggcac uaaacacaa                                                 19

<210> SEQ ID NO 626
<211> LENGTH: 23
<212> TYPE: RNA
<213> ORGANISM: Influenza B virus

<400> SEQUENCE: 626
uuggaaacaa ggaauacuua ugg                                            23

<210> SEQ ID NO 627
<211> LENGTH: 21
<212> TYPE: RNA
<213> ORGANISM: Influenza B virus

<400> SEQUENCE: 627
aaacaaggaa uacuuauggg a                                              21

<210> SEQ ID NO 628
<211> LENGTH: 21
<212> TYPE: RNA
<213> ORGANISM: Influenza B virus

<400> SEQUENCE: 628
uuuggaguug cuggaguaaa u                                              21

<210> SEQ ID NO 629
<211> LENGTH: 23
<212> TYPE: RNA
<213> ORGANISM: Influenza B virus

<400> SEQUENCE: 629
uagcagcacu agguaucaaa aac                                            23

<210> SEQ ID NO 630
<211> LENGTH: 21
<212> TYPE: RNA
<213> ORGANISM: Influenza B virus

<400> SEQUENCE: 630
gccugcugca acggcacuaa a                                              21

<210> SEQ ID NO 631
<211> LENGTH: 21
<212> TYPE: RNA
<213> ORGANISM: Influenza B virus

<400> SEQUENCE: 631
ggaccauuac ccgaagacaa u                                              21

<210> SEQ ID NO 632
<211> LENGTH: 19
<212> TYPE: RNA
<213> ORGANISM: Influenza B virus
```

```
<400> SEQUENCE: 632
gcuacgcuaa auguugcaa                                              19

<210> SEQ ID NO 633
<211> LENGTH: 21
<212> TYPE: RNA
<213> ORGANISM: Influenza B virus

<400> SEQUENCE: 633
gaacgggaac aggccacaca a                                           21

<210> SEQ ID NO 634
<211> LENGTH: 23
<212> TYPE: RNA
<213> ORGANISM: Influenza B virus

<400> SEQUENCE: 634
augauuuugc ucuguuuguu aau                                         23

<210> SEQ ID NO 635
<211> LENGTH: 21
<212> TYPE: RNA
<213> ORGANISM: Influenza B virus

<400> SEQUENCE: 635
gagcagaagc ggagccuuua a                                           21

<210> SEQ ID NO 636
<211> LENGTH: 21
<212> TYPE: RNA
<213> ORGANISM: Influenza B virus

<400> SEQUENCE: 636
aaucagcaga uauggcaaua g                                           21

<210> SEQ ID NO 637
<211> LENGTH: 21
<212> TYPE: RNA
<213> ORGANISM: Influenza B virus

<400> SEQUENCE: 637
auuuggaguu gcuggaguaa a                                           21

<210> SEQ ID NO 638
<211> LENGTH: 21
<212> TYPE: RNA
<213> ORGANISM: Influenza B virus

<400> SEQUENCE: 638
aaacauugga aacaaggaau a                                           21

<210> SEQ ID NO 639
<211> LENGTH: 19
<212> TYPE: RNA
<213> ORGANISM: Influenza B virus

<400> SEQUENCE: 639
gacuuucgau uggacagua                                              19

<210> SEQ ID NO 640
<211> LENGTH: 19
<212> TYPE: RNA
<213> ORGANISM: Influenza B virus
```

-continued

<400> SEQUENCE: 640
gacaagccug aaaugacuu                                                  19

<210> SEQ ID NO 641
<211> LENGTH: 21
<212> TYPE: RNA
<213> ORGANISM: Influenza B virus

<400> SEQUENCE: 641
gagacaugua uggaaggaau a                                               21

<210> SEQ ID NO 642
<211> LENGTH: 21
<212> TYPE: RNA
<213> ORGANISM: Influenza B virus

<400> SEQUENCE: 642
aagcugaaac cauucuucaa u                                               21

<210> SEQ ID NO 643
<211> LENGTH: 21
<212> TYPE: RNA
<213> ORGANISM: Influenza B virus

<400> SEQUENCE: 643
gaagcggagc cuuuaagaug a                                               21

<210> SEQ ID NO 644
<211> LENGTH: 19
<212> TYPE: RNA
<213> ORGANISM: Influenza B virus

<400> SEQUENCE: 644
agcugaaacc auucuucaa                                                  19

<210> SEQ ID NO 645
<211> LENGTH: 21
<212> TYPE: RNA
<213> ORGANISM: Influenza B virus

<400> SEQUENCE: 645
acgggaacag gccacacaau a                                               21

<210> SEQ ID NO 646
<211> LENGTH: 21
<212> TYPE: RNA
<213> ORGANISM: Influenza B virus

<400> SEQUENCE: 646
aaagaaaagu uacuguaacg a                                               21

<210> SEQ ID NO 647
<211> LENGTH: 19
<212> TYPE: RNA
<213> ORGANISM: Influenza B virus

<400> SEQUENCE: 647
acuguaacga aacuggaau                                                  19

<210> SEQ ID NO 648
<211> LENGTH: 21
<212> TYPE: RNA
<213> ORGANISM: Influenza B virus

```
<400> SEQUENCE: 648
agauccaaca aauggaccau u                                        21

<210> SEQ ID NO 649
<211> LENGTH: 21
<212> TYPE: RNA
<213> ORGANISM: Influenza B virus

<400> SEQUENCE: 649
aaagaaugaa aauuauaaag g                                        21

<210> SEQ ID NO 650
<211> LENGTH: 19
<212> TYPE: RNA
<213> ORGANISM: Influenza B virus

<400> SEQUENCE: 650
ggaucagcau gacaguaac                                           19

<210> SEQ ID NO 651
<211> LENGTH: 21
<212> TYPE: RNA
<213> ORGANISM: Influenza B virus

<400> SEQUENCE: 651
cacaggaugu acaaugguag a                                        21

<210> SEQ ID NO 652
<211> LENGTH: 19
<212> TYPE: RNA
<213> ORGANISM: Influenza B virus

<400> SEQUENCE: 652
gcauauccca gaaauagua                                           19

<210> SEQ ID NO 653
<211> LENGTH: 21
<212> TYPE: RNA
<213> ORGANISM: Influenza B virus

<400> SEQUENCE: 653
aauuugagaa acuugcauau c                                        21

<210> SEQ ID NO 654
<211> LENGTH: 19
<212> TYPE: RNA
<213> ORGANISM: Influenza B virus

<400> SEQUENCE: 654
ggguggauug guacccuuu                                           19

<210> SEQ ID NO 655
<211> LENGTH: 21
<212> TYPE: RNA
<213> ORGANISM: Influenza B virus

<400> SEQUENCE: 655
auugguaccc uuuugccaag a                                        21

<210> SEQ ID NO 656
<211> LENGTH: 21
<212> TYPE: RNA
<213> ORGANISM: Influenza B virus
```

```
<400> SEQUENCE: 656
gcccguaggu ggaaaugaaa a                                              21

<210> SEQ ID NO 657
<211> LENGTH: 19
<212> TYPE: RNA
<213> ORGANISM: Influenza B virus

<400> SEQUENCE: 657
gccaaacugu caaaugcag                                                 19

<210> SEQ ID NO 658
<211> LENGTH: 21
<212> TYPE: RNA
<213> ORGANISM: Influenza B virus

<400> SEQUENCE: 658
guacucgaac aaaggaaaac a                                              21

<210> SEQ ID NO 659
<211> LENGTH: 21
<212> TYPE: RNA
<213> ORGANISM: Influenza B virus

<400> SEQUENCE: 659
aaggcaucaa agaagcagau a                                              21

<210> SEQ ID NO 660
<211> LENGTH: 19
<212> TYPE: RNA
<213> ORGANISM: Influenza B virus

<400> SEQUENCE: 660
guagcagcac uagguauca                                                 19

<210> SEQ ID NO 661
<211> LENGTH: 21
<212> TYPE: RNA
<213> ORGANISM: Influenza B virus

<400> SEQUENCE: 661
aaaaguuacu guaacgaaac u                                              21

<210> SEQ ID NO 662
<211> LENGTH: 21
<212> TYPE: RNA
<213> ORGANISM: Influenza B virus

<400> SEQUENCE: 662
aaacacaaug acaaaagaug c                                              21

<210> SEQ ID NO 663
<211> LENGTH: 23
<212> TYPE: RNA
<213> ORGANISM: Influenza B virus

<400> SEQUENCE: 663
agcacuaggu aucaaaaaca uug                                            23

<210> SEQ ID NO 664
<211> LENGTH: 21
<212> TYPE: RNA
<213> ORGANISM: Influenza B virus
```

```
<400> SEQUENCE: 664
aaucccuuug uaggacauuu g                                         21

<210> SEQ ID NO 665
<211> LENGTH: 21
<212> TYPE: RNA
<213> ORGANISM: Influenza B virus

<400> SEQUENCE: 665
acggcacuaa acacaacaau a                                         21

<210> SEQ ID NO 666
<211> LENGTH: 21
<212> TYPE: RNA
<213> ORGANISM: Influenza B virus

<400> SEQUENCE: 666
aauggaaauu ccuucauuug g                                         21

<210> SEQ ID NO 667
<211> LENGTH: 19
<212> TYPE: RNA
<213> ORGANISM: Influenza B virus

<400> SEQUENCE: 667
caggauaucc agaguggaa                                            19

<210> SEQ ID NO 668
<211> LENGTH: 19
<212> TYPE: RNA
<213> ORGANISM: Influenza B virus

<400> SEQUENCE: 668
agcacaaaca gccauacaa                                            19

<210> SEQ ID NO 669
<211> LENGTH: 19
<212> TYPE: RNA
<213> ORGANISM: Influenza B virus

<400> SEQUENCE: 669
cucuguuugu uaaugcaaa                                            19

<210> SEQ ID NO 670
<211> LENGTH: 21
<212> TYPE: RNA
<213> ORGANISM: Influenza B virus

<400> SEQUENCE: 670
aaagaacaau augauuaaca a                                         21

<210> SEQ ID NO 671
<211> LENGTH: 19
<212> TYPE: RNA
<213> ORGANISM: Influenza B virus

<400> SEQUENCE: 671
cgguuacuuc acccucaaa                                            19

<210> SEQ ID NO 672
<211> LENGTH: 21
<212> TYPE: RNA
<213> ORGANISM: Influenza B virus
```

-continued

```
<400> SEQUENCE: 672
aaagaaaaaa uugccugcua a                                              21

<210> SEQ ID NO 673
<211> LENGTH: 23
<212> TYPE: RNA
<213> ORGANISM: Influenza B virus

<400> SEQUENCE: 673
aggaaugaca auaauaaaga aca                                            23

<210> SEQ ID NO 674
<211> LENGTH: 21
<212> TYPE: RNA
<213> ORGANISM: Influenza B virus

<400> SEQUENCE: 674
gcguucugga ggcuuuggau a                                              21

<210> SEQ ID NO 675
<211> LENGTH: 19
<212> TYPE: RNA
<213> ORGANISM: Influenza B virus

<400> SEQUENCE: 675
gcgguuacuu cacccucaa                                                 19

<210> SEQ ID NO 676
<211> LENGTH: 19
<212> TYPE: RNA
<213> ORGANISM: Influenza B virus

<400> SEQUENCE: 676
accggucuug uucuccaau                                                 19

<210> SEQ ID NO 677
<211> LENGTH: 21
<212> TYPE: RNA
<213> ORGANISM: Influenza B virus

<400> SEQUENCE: 677
guacccauac aggcagcaau u                                              21

<210> SEQ ID NO 678
<211> LENGTH: 21
<212> TYPE: RNA
<213> ORGANISM: Influenza B virus

<400> SEQUENCE: 678
ugggcccaac auuuacaauu u                                              21

<210> SEQ ID NO 679
<211> LENGTH: 21
<212> TYPE: RNA
<213> ORGANISM: Influenza B virus

<400> SEQUENCE: 679
uggagcagaa gcggagccuu u                                              21

<210> SEQ ID NO 680
<211> LENGTH: 19
<212> TYPE: RNA
<213> ORGANISM: Influenza B virus
```

```
<400> SEQUENCE: 680
guaguauagc accggucuu                                                19

<210> SEQ ID NO 681
<211> LENGTH: 19
<212> TYPE: RNA
<213> ORGANISM: Influenza B virus

<400> SEQUENCE: 681
gggaaaagga uuuaugaua                                                19

<210> SEQ ID NO 682
<211> LENGTH: 19
<212> TYPE: RNA
<213> ORGANISM: Influenza B virus

<400> SEQUENCE: 682
gugaucagaa cacaugagu                                                19

<210> SEQ ID NO 683
<211> LENGTH: 21
<212> TYPE: RNA
<213> ORGANISM: Influenza B virus

<400> SEQUENCE: 683
aaguuacugu aacgaaacug g                                             21

<210> SEQ ID NO 684
<211> LENGTH: 23
<212> TYPE: RNA
<213> ORGANISM: Influenza B virus

<400> SEQUENCE: 684
ugcucuguuu guuaaugcaa aag                                           23

<210> SEQ ID NO 685
<211> LENGTH: 19
<212> TYPE: RNA
<213> ORGANISM: Influenza B virus

<400> SEQUENCE: 685
cagaaagggu uuccucaua                                                19

<210> SEQ ID NO 686
<211> LENGTH: 19
<212> TYPE: RNA
<213> ORGANISM: Influenza B virus

<400> SEQUENCE: 686
ccagaaauag uauugaagu                                                19

<210> SEQ ID NO 687
<211> LENGTH: 21
<212> TYPE: RNA
<213> ORGANISM: Influenza B virus

<400> SEQUENCE: 687
aaaugacuuu cuucucagua a                                             21

<210> SEQ ID NO 688
<211> LENGTH: 21
<212> TYPE: RNA
<213> ORGANISM: Influenza B virus
```

```
<400> SEQUENCE: 688
uaaccagaga cagcccaauu u                                              21

<210> SEQ ID NO 689
<211> LENGTH: 19
<212> TYPE: RNA
<213> ORGANISM: Influenza B virus

<400> SEQUENCE: 689
uggccaaaau gcucaguaa                                                 19

<210> SEQ ID NO 690
<211> LENGTH: 21
<212> TYPE: RNA
<213> ORGANISM: Influenza B virus

<400> SEQUENCE: 690
auggguccag caacagcaca a                                              21

<210> SEQ ID NO 691
<211> LENGTH: 21
<212> TYPE: RNA
<213> ORGANISM: Influenza B virus

<400> SEQUENCE: 691
aauuguucau agcugauuau a                                              21

<210> SEQ ID NO 692
<211> LENGTH: 19
<212> TYPE: RNA
<213> ORGANISM: Influenza B virus

<400> SEQUENCE: 692
gagauggauu uguaucuaa                                                 19

<210> SEQ ID NO 693
<211> LENGTH: 21
<212> TYPE: RNA
<213> ORGANISM: Influenza B virus

<400> SEQUENCE: 693
aagagcauug ucauuaaaca c                                              21

<210> SEQ ID NO 694
<211> LENGTH: 21
<212> TYPE: RNA
<213> ORGANISM: Influenza B virus

<400> SEQUENCE: 694
ccacacaaua gacaccguga u                                              21

<210> SEQ ID NO 695
<211> LENGTH: 23
<212> TYPE: RNA
<213> ORGANISM: Influenza B virus

<400> SEQUENCE: 695
agcagcacua gguaucaaaa aca                                            23

<210> SEQ ID NO 696
<211> LENGTH: 21
<212> TYPE: RNA
<213> ORGANISM: Influenza B virus
```

```
<400> SEQUENCE: 696
aaaccauucu ucaaugaaga a                                              21

<210> SEQ ID NO 697
<211> LENGTH: 19
<212> TYPE: RNA
<213> ORGANISM: Influenza B virus

<400> SEQUENCE: 697
gcagugucug gaacucaua                                                 19

<210> SEQ ID NO 698
<211> LENGTH: 19
<212> TYPE: RNA
<213> ORGANISM: Influenza B virus

<400> SEQUENCE: 698
gcauugucau uaaacacaa                                                 19

<210> SEQ ID NO 699
<211> LENGTH: 21
<212> TYPE: RNA
<213> ORGANISM: Influenza B virus

<400> SEQUENCE: 699
gggaacaggc cacacaauag a                                              21

<210> SEQ ID NO 700
<211> LENGTH: 21
<212> TYPE: RNA
<213> ORGANISM: Influenza B virus

<400> SEQUENCE: 700
agccaagugc cuaugcacaa u                                              21

<210> SEQ ID NO 701
<211> LENGTH: 21
<212> TYPE: RNA
<213> ORGANISM: Influenza B virus

<400> SEQUENCE: 701
cggcacuaaa cacaacaaua a                                              21

<210> SEQ ID NO 702
<211> LENGTH: 19
<212> TYPE: RNA
<213> ORGANISM: Influenza B virus

<400> SEQUENCE: 702
gucaaaugca guggccaaa                                                 19

<210> SEQ ID NO 703
<211> LENGTH: 21
<212> TYPE: RNA
<213> ORGANISM: Influenza B virus

<400> SEQUENCE: 703 aaacacaugag uacucgaaca a                                             21

<210> SEQ ID NO 704
<211> LENGTH: 21
<212> TYPE: RNA
<213> ORGANISM: Influenza B virus
```

```
<400> SEQUENCE: 704
aaaaaagcug aaaccauucu u                                      21

<210> SEQ ID NO 705
<211> LENGTH: 21
<212> TYPE: RNA
<213> ORGANISM: Influenza B virus

<400> SEQUENCE: 705
aauuauaaag gagcuauggg a                                      21

<210> SEQ ID NO 706
<211> LENGTH: 21
<212> TYPE: RNA
<213> ORGANISM: Influenza B virus

<400> SEQUENCE: 706
ucuggaggcu uuggauagaa u                                      21

<210> SEQ ID NO 707
<211> LENGTH: 19
<212> TYPE: RNA
<213> ORGANISM: Influenza B virus

<400> SEQUENCE: 707
gggagacaga cuuucgauu                                         19

<210> SEQ ID NO 708
<211> LENGTH: 21
<212> TYPE: RNA
<213> ORGANISM: Influenza B virus

<400> SEQUENCE: 708
aagugccuau gcacaauuag a                                      21

<210> SEQ ID NO 709
<211> LENGTH: 21
<212> TYPE: RNA
<213> ORGANISM: Influenza B virus

<400> SEQUENCE: 709
aagaaaaugg auuaugaugc a                                      21

<210> SEQ ID NO 710
<211> LENGTH: 21
<212> TYPE: RNA
<213> ORGANISM: Influenza B virus

<400> SEQUENCE: 710
aauaaacaug agcaaaaaga a                                      21

<210> SEQ ID NO 711
<211> LENGTH: 19
<212> TYPE: RNA
<213> ORGANISM: Influenza B virus

<400> SEQUENCE: 711
cugaaaccau ucuucaaug                                         19

<210> SEQ ID NO 712
<211> LENGTH: 19
<212> TYPE: RNA
<213> ORGANISM: Influenza B virus
```

```
<400> SEQUENCE: 712 agggugga uu gguacccuu                                           19

<210> SEQ ID NO 713
<211> LENGTH: 21
<212> TYPE: RNA
<213> ORGANISM: Influenza B virus

<400> SEQUENCE: 713
aauaccaaug aaaguaaaag a                                         21

<210> SEQ ID NO 714
<211> LENGTH: 21
<212> TYPE: RNA
<213> ORGANISM: Influenza B virus

<400> SEQUENCE: 714
gacaccguga ucagaacaca u                                         21

<210> SEQ ID NO 715
<211> LENGTH: 19
<212> TYPE: RNA
<213> ORGANISM: Influenza B virus

<400> SEQUENCE: 715
ccuggaauga ugaugggaa                                            19

<210> SEQ ID NO 716
<211> LENGTH: 21
<212> TYPE: RNA
<213> ORGANISM: Influenza B virus

<400> SEQUENCE: 716
uacaggcagc aauuucaaca a                                         21

<210> SEQ ID NO 717
<211> LENGTH: 19
<212> TYPE: RNA
<213> ORGANISM: Influenza B virus

<400> SEQUENCE: 717
gugggcccaa cauuuacaa                                            19

<210> SEQ ID NO 718
<211> LENGTH: 21
<212> TYPE: RNA
<213> ORGANISM: Influenza B virus

<400> SEQUENCE: 718
aaggaauacu uaugggaugg a                                         21

<210> SEQ ID NO 719
<211> LENGTH: 19
<212> TYPE: RNA
<213> ORGANISM: Influenza B virus

<400> SEQUENCE: 719
gagggaucag caugacagu                                            19

<210> SEQ ID NO 720
<211> LENGTH: 21
<212> TYPE: RNA
<213> ORGANISM: Influenza B virus
```

```
<400> SEQUENCE: 720
aaaugaauca gcagauaugg c                                    21

<210> SEQ ID NO 721
<211> LENGTH: 21
<212> TYPE: RNA
<213> ORGANISM: Influenza B virus

<400> SEQUENCE: 721
aaaacaguau guuucuggca u                                    21

<210> SEQ ID NO 722
<211> LENGTH: 21
<212> TYPE: RNA
<213> ORGANISM: Influenza B virus

<400> SEQUENCE: 722
aauaugauua acaaugggau g                                    21

<210> SEQ ID NO 723
<211> LENGTH: 21
<212> TYPE: RNA
<213> ORGANISM: Influenza B virus

<400> SEQUENCE: 723
aauggaugca cgacuagauu a                                    21

<210> SEQ ID NO 724
<211> LENGTH: 21
<212> TYPE: RNA
<213> ORGANISM: Influenza B virus

<400> SEQUENCE: 724
gagccaagug ccuaugcaca a                                    21

<210> SEQ ID NO 725
<211> LENGTH: 23
<212> TYPE: RNA
<213> ORGANISM: Influenza B virus

<400> SEQUENCE: 725
agguaucaaa aacauuggaa aca                                  23

<210> SEQ ID NO 726
<211> LENGTH: 21
<212> TYPE: RNA
<213> ORGANISM: Influenza B virus

<400> SEQUENCE: 726
aaacuggaau guuugaauuu a                                    21

<210> SEQ ID NO 727
<211> LENGTH: 19
<212> TYPE: RNA
<213> ORGANISM: Influenza B virus

<400> SEQUENCE: 727
ccaaaaggaa cagaucuau                                       19

<210> SEQ ID NO 728
<211> LENGTH: 23
<212> TYPE: RNA
<213> ORGANISM: Influenza B virus
```

```
<400> SEQUENCE: 728
uagguaucaa aaacauugga aac                                           23

<210> SEQ ID NO 729
<211> LENGTH: 19
<212> TYPE: RNA
<213> ORGANISM: Influenza B virus

<400> SEQUENCE: 729
gaguugcugg aguaaauga                                                19

<210> SEQ ID NO 730
<211> LENGTH: 19
<212> TYPE: RNA
<213> ORGANISM: Influenza B virus

<400> SEQUENCE: 730
aggacauuug ucuauugaa                                                19

<210> SEQ ID NO 731
<211> LENGTH: 21
<212> TYPE: RNA
<213> ORGANISM: Influenza B virus

<400> SEQUENCE: 731
aggcuauggc ccauagauua a                                             21

<210> SEQ ID NO 732
<211> LENGTH: 19
<212> TYPE: RNA
<213> ORGANISM: Influenza B virus

<400> SEQUENCE: 732
gccagauugg gaaaaggau                                                19

<210> SEQ ID NO 733
<211> LENGTH: 21
<212> TYPE: RNA
<213> ORGANISM: Influenza B virus

<400> SEQUENCE: 733
aaaaacauug gaaacaagga a                                             21

<210> SEQ ID NO 734
<211> LENGTH: 19
<212> TYPE: RNA
<213> ORGANISM: Influenza B virus

<400> SEQUENCE: 734
gagacaugua uggaaggaa                                                19

<210> SEQ ID NO 735
<211> LENGTH: 21
<212> TYPE: RNA
<213> ORGANISM: Influenza B virus

<400> SEQUENCE: 735
aacauuuaca auugagaaa c                                              21

<210> SEQ ID NO 736
<211> LENGTH: 19
<212> TYPE: RNA
<213> ORGANISM: Influenza B virus
```

-continued

```
<400> SEQUENCE: 736
guccugaucu guuuagcau                                              19

<210> SEQ ID NO 737
<211> LENGTH: 19
<212> TYPE: RNA
<213> ORGANISM: Influenza B virus

<400> SEQUENCE: 737
acgaaacugg aauguuuga                                              19

<210> SEQ ID NO 738
<211> LENGTH: 21
<212> TYPE: RNA
<213> ORGANISM: Influenza B virus

<400> SEQUENCE: 738
cagaggguuu guauuaguag u                                           21

<210> SEQ ID NO 739
<211> LENGTH: 21
<212> TYPE: RNA
<213> ORGANISM: Influenza B virus

<400> SEQUENCE: 739
gaggaacauc caggucuguu u                                           21

<210> SEQ ID NO 740
<211> LENGTH: 21
<212> TYPE: RNA
<213> ORGANISM: Influenza B virus

<400> SEQUENCE: 740
aaugaaaauu auaaaggagc u                                           21

<210> SEQ ID NO 741
<211> LENGTH: 21
<212> TYPE: RNA
<213> ORGANISM: Influenza B virus

<400> SEQUENCE: 741
cugcaacggc acuaaacaca a                                           21

<210> SEQ ID NO 742
<211> LENGTH: 21
<212> TYPE: RNA
<213> ORGANISM: Influenza B virus

<400> SEQUENCE: 742
aggagcuaug ggaaaacacu a                                           21

<210> SEQ ID NO 743
<211> LENGTH: 21
<212> TYPE: RNA
<213> ORGANISM: Influenza B virus

<400> SEQUENCE: 743
aaacagaaag gguuuccuca u                                           21

<210> SEQ ID NO 744
<211> LENGTH: 19
<212> TYPE: RNA
<213> ORGANISM: Influenza B virus
```

```
<400> SEQUENCE: 744
ccaauuuggu uccgggauu                                          19

<210> SEQ ID NO 745
<211> LENGTH: 23
<212> TYPE: RNA
<213> ORGANISM: Influenza B virus

<400> SEQUENCE: 745
ugggaauguu uaauaugcua ucu                                     23

<210> SEQ ID NO 746
<211> LENGTH: 21
<212> TYPE: RNA
<213> ORGANISM: Influenza B virus

<400> SEQUENCE: 746
aaagagaaua ccaaugaaag u                                       21

<210> SEQ ID NO 747
<211> LENGTH: 21
<212> TYPE: RNA
<213> ORGANISM: Influenza B virus

<400> SEQUENCE: 747
uugguacccu uuugccaaga u                                       21

<210> SEQ ID NO 748
<211> LENGTH: 19
<212> TYPE: RNA
<213> ORGANISM: Influenza B virus

<400> SEQUENCE: 748
guaacaggag acaauacua                                          19

<210> SEQ ID NO 749
<211> LENGTH: 21
<212> TYPE: RNA
<213> ORGANISM: Influenza B virus

<400> SEQUENCE: 749
gacugcaauc uucugaugau u                                       21

<210> SEQ ID NO 750
<211> LENGTH: 19
<212> TYPE: RNA
<213> ORGANISM: Influenza B virus

<400> SEQUENCE: 750
ggagcuaugg gaaaacacu                                          19

<210> SEQ ID NO 751
<211> LENGTH: 21
<212> TYPE: RNA
<213> ORGANISM: Influenza B virus

<400> SEQUENCE: 751
cuggcaucac aggauguaca a                                       21

<210> SEQ ID NO 752
<211> LENGTH: 19
<212> TYPE: RNA
<213> ORGANISM: Influenza B virus
```

```
<400> SEQUENCE: 752
gacugcaauc uucgauga                                              19

<210> SEQ ID NO 753
<211> LENGTH: 19
<212> TYPE: RNA
<213> ORGANISM: Influenza B virus

<400> SEQUENCE: 753
gucuauugaa ggcaucaaa                                             19

<210> SEQ ID NO 754
<211> LENGTH: 21
<212> TYPE: RNA
<213> ORGANISM: Influenza B virus

<400> SEQUENCE: 754
aaauaguauu gaaguacaau c                                          21

<210> SEQ ID NO 755
<211> LENGTH: 19
<212> TYPE: RNA
<213> ORGANISM: Influenza B virus

<400> SEQUENCE: 755
acacaauaga caccgugau                                             19

<210> SEQ ID NO 756
<211> LENGTH: 19
<212> TYPE: RNA
<213> ORGANISM: Influenza B virus

<400> SEQUENCE: 756
gcaguggcca aaaugcuca                                             19

<210> SEQ ID NO 757
<211> LENGTH: 19
<212> TYPE: RNA
<213> ORGANISM: Influenza B virus

<400> SEQUENCE: 757
gcaaaagaug aagagacau                                             19

<210> SEQ ID NO 758
<211> LENGTH: 21
<212> TYPE: RNA
<213> ORGANISM: Influenza B virus

<400> SEQUENCE: 758
uggguccagc aacagcacaa a                                          21

<210> SEQ ID NO 759
<211> LENGTH: 21
<212> TYPE: RNA
<213> ORGANISM: Influenza B virus

<400> SEQUENCE: 759
aauugccugc uaaaaacaga a                                          21

<210> SEQ ID NO 760
<211> LENGTH: 19
<212> TYPE: RNA
<213> ORGANISM: Influenza B virus
```

-continued

```
<400> SEQUENCE: 760
ggguuuguau uaguaguug                                                 19

<210> SEQ ID NO 761
<211> LENGTH: 21
<212> TYPE: RNA
<213> ORGANISM: Influenza B virus

<400> SEQUENCE: 761
aaaauuauaa aggagcuaug g                                              21

<210> SEQ ID NO 762
<211> LENGTH: 19
<212> TYPE: RNA
<213> ORGANISM: Influenza B virus

<400> SEQUENCE: 762
uggaaacaag gaauacuua                                                 19

<210> SEQ ID NO 763
<211> LENGTH: 21
<212> TYPE: RNA
<213> ORGANISM: Influenza B virus

<400> SEQUENCE: 763
guuccgggau uuuguagua u                                               21

<210> SEQ ID NO 764
<211> LENGTH: 21
<212> TYPE: RNA
<213> ORGANISM: Influenza B virus

<400> SEQUENCE: 764
gaggccuguu uuaacagugc a                                              21

<210> SEQ ID NO 765
<211> LENGTH: 21
<212> TYPE: RNA
<213> ORGANISM: Influenza B virus

<400> SEQUENCE: 765
aaaaggaaca gaucuauacu a                                              21

<210> SEQ ID NO 766
<211> LENGTH: 19
<212> TYPE: RNA
<213> ORGANISM: Influenza B virus

<400> SEQUENCE: 766
cgcuggaaua caaaucaga                                                 19

<210> SEQ ID NO 767
<211> LENGTH: 19
<212> TYPE: RNA
<213> ORGANISM: Influenza B virus

<400> SEQUENCE: 767
cuggaggcuu uggauagaa                                                 19

<210> SEQ ID NO 768
<211> LENGTH: 21
<212> TYPE: RNA
<213> ORGANISM: Influenza B virus
```

```
<400> SEQUENCE: 768
aaauuccuuc auuuggaguu g                                              21

<210> SEQ ID NO 769
<211> LENGTH: 19
<212> TYPE: RNA
<213> ORGANISM: Influenza B virus

<400> SEQUENCE: 769
ggaaaacacu aaaggaaga                                                 19

<210> SEQ ID NO 770
<211> LENGTH: 21
<212> TYPE: RNA
<213> ORGANISM: Influenza B virus

<400> SEQUENCE: 770
uagacaagcc ugaaaugacu u                                              21

<210> SEQ ID NO 771
<211> LENGTH: 21
<212> TYPE: RNA
<213> ORGANISM: Influenza B virus

<400> SEQUENCE: 771
aacgaaacug gaauguuuga a                                              21

<210> SEQ ID NO 772
<211> LENGTH: 21
<212> TYPE: RNA
<213> ORGANISM: Influenza B virus

<400> SEQUENCE: 772
aaugaaagua aaagacagga u                                              21

<210> SEQ ID NO 773
<211> LENGTH: 21
<212> TYPE: RNA
<213> ORGANISM: Influenza B virus

<400> SEQUENCE: 773
aaaggaagag auggucuguu a                                              21

<210> SEQ ID NO 774
<211> LENGTH: 19
<212> TYPE: RNA
<213> ORGANISM: Influenza B virus

<400> SEQUENCE: 774
cagcacaugg uccugugaa                                                 19

<210> SEQ ID NO 775
<211> LENGTH: 19
<212> TYPE: RNA
<213> ORGANISM: Influenza B virus

<400> SEQUENCE: 775
ccagagugga auacaucaa                                                 19

<210> SEQ ID NO 776
<211> LENGTH: 21
<212> TYPE: RNA
<213> ORGANISM: Influenza B virus
```

-continued

```
<400> SEQUENCE: 776
ucuggcauca caggauguac a                                        21

<210> SEQ ID NO 777
<211> LENGTH: 23
<212> TYPE: RNA
<213> ORGANISM: Influenza B virus

<400> SEQUENCE: 777
gagacaugua uggaaggaau aaa                                      23

<210> SEQ ID NO 778
<211> LENGTH: 19
<212> TYPE: RNA
<213> ORGANISM: Influenza B virus

<400> SEQUENCE: 778
cagauauggc aauaggaau                                           19

<210> SEQ ID NO 779
<211> LENGTH: 21
<212> TYPE: RNA
<213> ORGANISM: Influenza B virus

<400> SEQUENCE: 779
aaaaauaucu gugaaaaucu a                                        21

<210> SEQ ID NO 780
<211> LENGTH: 21
<212> TYPE: RNA
<213> ORGANISM: Influenza B virus

<400> SEQUENCE: 780
aacaguaugu uucuggcauc a                                        21

<210> SEQ ID NO 781
<211> LENGTH: 21
<212> TYPE: RNA
<213> ORGANISM: Influenza B virus

<400> SEQUENCE: 781
aaacaugagc aaaaagaaaa g                                        21

<210> SEQ ID NO 782
<211> LENGTH: 21
<212> TYPE: RNA
<213> ORGANISM: Influenza B virus

<400> SEQUENCE: 782
aauaaccucc uuuagguuga a                                        21

<210> SEQ ID NO 783
<211> LENGTH: 21
<212> TYPE: RNA
<213> ORGANISM: Influenza B virus

<400> SEQUENCE: 783
aacauguaaa uuauugggaa u                                        21

<210> SEQ ID NO 784
<211> LENGTH: 23
<212> TYPE: RNA
<213> ORGANISM: Influenza B virus
```

```
<400> SEQUENCE: 784
cagcacuagg uaucaaaaac auu                                              23

<210> SEQ ID NO 785
<211> LENGTH: 19
<212> TYPE: RNA
<213> ORGANISM: Influenza B virus

<400> SEQUENCE: 785
ccuccuuuag guugaauga                                                   19

<210> SEQ ID NO 786
<211> LENGTH: 19
<212> TYPE: RNA
<213> ORGANISM: Influenza B virus

<400> SEQUENCE: 786
ggguuuccuc auaaagaga                                                   19

<210> SEQ ID NO 787
<211> LENGTH: 19
<212> TYPE: RNA
<213> ORGANISM: Influenza B virus

<400> SEQUENCE: 787
ggccaaaaug cucaguaac                                                   19

<210> SEQ ID NO 788
<211> LENGTH: 23
<212> TYPE: RNA
<213> ORGANISM: Influenza B virus

<400> SEQUENCE: 788
agccuuuaag augaauauaa auc                                              23

<210> SEQ ID NO 789
<211> LENGTH: 19
<212> TYPE: RNA
<213> ORGANISM: Influenza B virus

<400> SEQUENCE: 789
cuccaauaaa auagccaga                                                   19

<210> SEQ ID NO 790
<211> LENGTH: 21
<212> TYPE: RNA
<213> ORGANISM: Influenza B virus

<400> SEQUENCE: 790
aaggaauaaa cgacuuuuac c                                                21

<210> SEQ ID NO 791
<211> LENGTH: 21
<212> TYPE: RNA
<213> ORGANISM: Influenza B virus

<400> SEQUENCE: 791
aaccuccuuu agguugaaug a                                                21

<210> SEQ ID NO 792
<211> LENGTH: 19
<212> TYPE: RNA
<213> ORGANISM: Influenza B virus
```

```
<400> SEQUENCE: 792
aggagauucc aaaguggaa                                               19

<210> SEQ ID NO 793
<211> LENGTH: 21
<212> TYPE: RNA
<213> ORGANISM: Influenza B virus

<400> SEQUENCE: 793
gcgguuacuu cacccucaaa a                                            21

<210> SEQ ID NO 794
<211> LENGTH: 21
<212> TYPE: RNA
<213> ORGANISM: Influenza B virus

<400> SEQUENCE: 794
gagcuauggg aaaacacuaa a                                            21

<210> SEQ ID NO 795
<211> LENGTH: 21
<212> TYPE: RNA
<213> ORGANISM: Influenza B virus

<400> SEQUENCE: 795
aaacagccau acaauuguuc a                                            21

<210> SEQ ID NO 796
<211> LENGTH: 21
<212> TYPE: RNA
<213> ORGANISM: Influenza B virus

<400> SEQUENCE: 796
aacuuggcua aaaauaucug u                                            21

<210> SEQ ID NO 797
<211> LENGTH: 21
<212> TYPE: RNA
<213> ORGANISM: Influenza B virus

<400> SEQUENCE: 797
aaccuuuuug aggccuguuu u                                            21

<210> SEQ ID NO 798
<211> LENGTH: 19
<212> TYPE: RNA
<213> ORGANISM: Influenza B virus

<400> SEQUENCE: 798
agacauguau ggaaggaau                                               19

<210> SEQ ID NO 799
<211> LENGTH: 19
<212> TYPE: RNA
<213> ORGANISM: Influenza B virus

<400> SEQUENCE: 799
cccucaaaau cccuuugua                                               19

<210> SEQ ID NO 800
<211> LENGTH: 19
<212> TYPE: RNA
<213> ORGANISM: Influenza B virus
```

```
<400> SEQUENCE: 800
aggaacaaug cuacgcuaa                                                    19

<210> SEQ ID NO 801
<211> LENGTH: 21
<212> TYPE: RNA
<213> ORGANISM: Influenza B virus

<400> SEQUENCE: 801
aaaagcugaa accauucuuc a                                                 21

<210> SEQ ID NO 802
<211> LENGTH: 21
<212> TYPE: RNA
<213> ORGANISM: Influenza B virus

<400> SEQUENCE: 802
auagacaccg ugaucagaac a                                                 21

<210> SEQ ID NO 803
<211> LENGTH: 19
<212> TYPE: RNA
<213> ORGANISM: Influenza B virus

<400> SEQUENCE: 803
ccugaucugu uuagcauac                                                    19

<210> SEQ ID NO 804
<211> LENGTH: 19
<212> TYPE: RNA
<213> ORGANISM: Influenza B virus

<400> SEQUENCE: 804
cagaggguuu guauuagua                                                    19

<210> SEQ ID NO 805
<211> LENGTH: 21
<212> TYPE: RNA
<213> ORGANISM: Influenza B virus

<400> SEQUENCE: 805
gaggcacuaa uggucacaac u                                                 21

<210> SEQ ID NO 806
<211> LENGTH: 21
<212> TYPE: RNA
<213> ORGANISM: Influenza B virus

<400> SEQUENCE: 806
aaucuaaugg acccugaaua c                                                 21

<210> SEQ ID NO 807
<211> LENGTH: 21
<212> TYPE: RNA
<213> ORGANISM: Influenza B virus

<400> SEQUENCE: 807
aauuuacaag cauguucuau a                                                 21

<210> SEQ ID NO 808
<211> LENGTH: 21
<212> TYPE: RNA
<213> ORGANISM: Influenza B virus
```

-continued

```
<400> SEQUENCE: 808
aaggaaaaag aaugaaaauu a                                        21

<210> SEQ ID NO 809
<211> LENGTH: 21
<212> TYPE: RNA
<213> ORGANISM: Influenza B virus

<400> SEQUENCE: 809
acugcccacc aggagggauc a                                        21

<210> SEQ ID NO 810
<211> LENGTH: 19
<212> TYPE: RNA
<213> ORGANISM: Influenza B virus

<400> SEQUENCE: 810
acagaaaggg uuuccucau                                           19

<210> SEQ ID NO 811
<211> LENGTH: 21
<212> TYPE: RNA
<213> ORGANISM: Influenza B virus

<400> SEQUENCE: 811
cggucuuguu cuccaauaaa a                                        21

<210> SEQ ID NO 812
<211> LENGTH: 21
<212> TYPE: RNA
<213> ORGANISM: Influenza B virus

<400> SEQUENCE: 812
aaaauuaaaa aagcugaaac c                                        21

<210> SEQ ID NO 813
<211> LENGTH: 21
<212> TYPE: RNA
<213> ORGANISM: Influenza B virus

<400> SEQUENCE: 813
aauuaaaaaa gcugaaacca u                                        21

<210> SEQ ID NO 814
<211> LENGTH: 21
<212> TYPE: RNA
<213> ORGANISM: Influenza B virus

<400> SEQUENCE: 814
aaaguaaaag acaggauauc c                                        21

<210> SEQ ID NO 815
<211> LENGTH: 21
<212> TYPE: RNA
<213> ORGANISM: Influenza B virus

<400> SEQUENCE: 815
auacaggcag caauuucaac a                                        21

<210> SEQ ID NO 816
<211> LENGTH: 21
<212> TYPE: RNA
<213> ORGANISM: Influenza B virus
```

```
<400> SEQUENCE: 816
aaacacaaca auaaccuccu u                                              21

<210> SEQ ID NO 817
<211> LENGTH: 21
<212> TYPE: RNA
<213> ORGANISM: Influenza B virus

<400> SEQUENCE: 817
agaugguggg cccaacauuu a                                              21

<210> SEQ ID NO 818
<211> LENGTH: 21
<212> TYPE: RNA
<213> ORGANISM: Influenza B virus

<400> SEQUENCE: 818
aacggcacua aacacaacaa u                                              21

<210> SEQ ID NO 819
<211> LENGTH: 21
<212> TYPE: RNA
<213> ORGANISM: Influenza B virus

<400> SEQUENCE: 819
gcggagccuu uaagaugaau a                                              21

<210> SEQ ID NO 820
<211> LENGTH: 21
<212> TYPE: RNA
<213> ORGANISM: Influenza B virus

<400> SEQUENCE: 820
aagaaggcca aacugucaaa u                                              21

<210> SEQ ID NO 821
<211> LENGTH: 21
<212> TYPE: RNA
<213> ORGANISM: Influenza B virus

<400> SEQUENCE: 821
aaauuauugg gaauaaacau g                                              21

<210> SEQ ID NO 822
<211> LENGTH: 19
<212> TYPE: RNA
<213> ORGANISM: Influenza B virus

<400> SEQUENCE: 822
caucuuuguc gccuggaau                                                 19

<210> SEQ ID NO 823
<211> LENGTH: 21
<212> TYPE: RNA
<213> ORGANISM: Influenza B virus

<400> SEQUENCE: 823
acccuuuugc caagauauca u                                              21

<210> SEQ ID NO 824
<211> LENGTH: 21
<212> TYPE: RNA
<213> ORGANISM: Influenza B virus
```

```
<400> SEQUENCE: 824
gcaccggucu uguucuccaa u                                      21

<210> SEQ ID NO 825
<211> LENGTH: 21
<212> TYPE: RNA
<213> ORGANISM: Influenza B virus

<400> SEQUENCE: 825
uuccgggauu uuuguaguau a                                      21

<210> SEQ ID NO 826
<211> LENGTH: 19
<212> TYPE: RNA
<213> ORGANISM: Influenza B virus

<400> SEQUENCE: 826
gguccagcaa cagcacaaa                                         19

<210> SEQ ID NO 827
<211> LENGTH: 21
<212> TYPE: RNA
<213> ORGANISM: Influenza B virus

<400> SEQUENCE: 827
gaggaacaau gcuacgcuaa a                                      21

<210> SEQ ID NO 828
<211> LENGTH: 21
<212> TYPE: RNA
<213> ORGANISM: Influenza B virus

<400> SEQUENCE: 828
aaaacuuggc uaaaaauauc u                                      21

<210> SEQ ID NO 829
<211> LENGTH: 19
<212> TYPE: RNA
<213> ORGANISM: Influenza B virus

<400> SEQUENCE: 829
cacauggucc ugugaagaa                                         19

<210> SEQ ID NO 830
<211> LENGTH: 21
<212> TYPE: RNA
<213> ORGANISM: Influenza B virus

<400> SEQUENCE: 830
aaccaaaagg aacagaucua u                                      21

<210> SEQ ID NO 831
<211> LENGTH: 21
<212> TYPE: RNA
<213> ORGANISM: Influenza B virus

<400> SEQUENCE: 831
aauacaucaa aagagcauug u                                      21

<210> SEQ ID NO 832
<211> LENGTH: 21
<212> TYPE: RNA
<213> ORGANISM: Influenza B virus
```

```
<400> SEQUENCE: 832
aagggcaaaa uuaaaaaagc u                                              21

<210> SEQ ID NO 833
<211> LENGTH: 21
<212> TYPE: RNA
<213> ORGANISM: Influenza B virus

<400> SEQUENCE: 833
aaugggaugg guccagcaac a                                              21

<210> SEQ ID NO 834
<211> LENGTH: 21
<212> TYPE: RNA
<213> ORGANISM: Influenza B virus

<400> SEQUENCE: 834
ggcccaacau uuacaauuug a                                              21

<210> SEQ ID NO 835
<211> LENGTH: 19
<212> TYPE: RNA
<213> ORGANISM: Influenza B virus

<400> SEQUENCE: 835
uccugaucug uuuagcaua                                                 19

<210> SEQ ID NO 836
<211> LENGTH: 21
<212> TYPE: RNA
<213> ORGANISM: Influenza B virus

<400> SEQUENCE: 836
aaggauuuau gauaacaagu a                                              21

<210> SEQ ID NO 837
<211> LENGTH: 19
<212> TYPE: RNA
<213> ORGANISM: Influenza B virus

<400> SEQUENCE: 837
ggcuuuggau agaauggau                                                 19

<210> SEQ ID NO 838
<211> LENGTH: 21
<212> TYPE: RNA
<213> ORGANISM: Influenza B virus

<400> SEQUENCE: 838
cagacuuucg auuggacagu a                                              21

<210> SEQ ID NO 839
<211> LENGTH: 19
<212> TYPE: RNA
<213> ORGANISM: Influenza B virus

<400> SEQUENCE: 839
aacccagggg agacagacu                                                 19

<210> SEQ ID NO 840
<211> LENGTH: 21
<212> TYPE: RNA
<213> ORGANISM: Influenza B virus
```

```
<400> SEQUENCE: 840
aaauaucugu gaaaaucuag a                                              21

<210> SEQ ID NO 841
<211> LENGTH: 21
<212> TYPE: RNA
<213> ORGANISM: Influenza B virus

<400> SEQUENCE: 841
aaaggguuuc cucauaaaga g                                              21

<210> SEQ ID NO 842
<211> LENGTH: 21
<212> TYPE: RNA
<213> ORGANISM: Influenza B virus

<400> SEQUENCE: 842
uuugcccgua gguggaaaug a                                              21

<210> SEQ ID NO 843
<211> LENGTH: 19
<212> TYPE: RNA
<213> ORGANISM: Influenza B virus

<400> SEQUENCE: 843
gggaucagca ugacaguaa                                                 19

<210> SEQ ID NO 844
<211> LENGTH: 19
<212> TYPE: RNA
<213> ORGANISM: Influenza B virus

<400> SEQUENCE: 844
cagcacaaac agccauaca                                                 19

<210> SEQ ID NO 845
<211> LENGTH: 21
<212> TYPE: RNA
<213> ORGANISM: Influenza B virus

<400> SEQUENCE: 845
aaaauugccu gcuaaaaaca g                                              21

<210> SEQ ID NO 846
<211> LENGTH: 19
<212> TYPE: RNA
<213> ORGANISM: Influenza B virus

<400> SEQUENCE: 846
gagcuauggg aaaacacua                                                 19

<210> SEQ ID NO 847
<211> LENGTH: 19
<212> TYPE: RNA
<213> ORGANISM: Influenza B virus

<400> SEQUENCE: 847
ggauggacug caaucuucu                                                 19

<210> SEQ ID NO 848
<211> LENGTH: 21
<212> TYPE: RNA
<213> ORGANISM: Influenza B virus
```

```
<400> SEQUENCE: 848
aauggauuau gaugcagugu c                                      21

<210> SEQ ID NO 849
<211> LENGTH: 21
<212> TYPE: RNA
<213> ORGANISM: Influenza B virus

<400> SEQUENCE: 849
aaaagacagg auauccagag u                                      21

<210> SEQ ID NO 850
<211> LENGTH: 21
<212> TYPE: RNA
<213> ORGANISM: Influenza B virus

<400> SEQUENCE: 850
uacuucaaua cuauuucugg g                                      21

<210> SEQ ID NO 851
<211> LENGTH: 23
<212> TYPE: RNA
<213> ORGANISM: Influenza B virus

<400> SEQUENCE: 851
cuguuuguua augcaaaaga uga                                    23

<210> SEQ ID NO 852
<211> LENGTH: 21
<212> TYPE: RNA
<213> ORGANISM: Influenza B virus

<400> SEQUENCE: 852
aaugguagau ccaacaaaug g                                      21

<210> SEQ ID NO 853
<211> LENGTH: 21
<212> TYPE: RNA
<213> ORGANISM: Influenza B virus

<400> SEQUENCE: 853
aaaugaaaag aaggccaaac u                                      21

<210> SEQ ID NO 854
<211> LENGTH: 21
<212> TYPE: RNA
<213> ORGANISM: Influenza B virus

<400> SEQUENCE: 854
gccuggaaug augaugggaa u                                      21

<210> SEQ ID NO 855
<211> LENGTH: 21
<212> TYPE: RNA
<213> ORGANISM: Influenza B virus

<400> SEQUENCE: 855
aacuuugcaa uggaaauucc u                                      21

<210> SEQ ID NO 856
<211> LENGTH: 21
<212> TYPE: RNA
<213> ORGANISM: Influenza B virus
```

-continued

```
<400> SEQUENCE: 856
aagaugaaga gacauguaug g                                             21

<210> SEQ ID NO 857
<211> LENGTH: 21
<212> TYPE: RNA
<213> ORGANISM: Influenza B virus

<400> SEQUENCE: 857
aauguuuaau augcuaucua c                                             21

<210> SEQ ID NO 858
<211> LENGTH: 21
<212> TYPE: RNA
<213> ORGANISM: Influenza B virus

<400> SEQUENCE: 858
uggccaaaau gcucaguaac u                                             21

<210> SEQ ID NO 859
<211> LENGTH: 21
<212> TYPE: RNA
<213> ORGANISM: Influenza B virus

<400> SEQUENCE: 859
aacaggagac aauacuaaau g                                             21

<210> SEQ ID NO 860
<211> LENGTH: 19
<212> TYPE: RNA
<213> ORGANISM: Influenza B virus

<400> SEQUENCE: 860
cuguaacgaa acuggaaug                                                19

<210> SEQ ID NO 861
<211> LENGTH: 21
<212> TYPE: RNA
<213> ORGANISM: Influenza B virus

<400> SEQUENCE: 861
uaccuugucc ugaucuguuu a                                             21

<210> SEQ ID NO 862
<211> LENGTH: 21
<212> TYPE: RNA
<213> ORGANISM: Influenza B virus

<400> SEQUENCE: 862 augggggcc caacauuuac a                                              21

<210> SEQ ID NO 863
<211> LENGTH: 21
<212> TYPE: RNA
<213> ORGANISM: Influenza B virus

<400> SEQUENCE: 863
uuggauacau gugauaaaca a                                             21

<210> SEQ ID NO 864
<211> LENGTH: 21
<212> TYPE: RNA
<213> ORGANISM: Influenza B virus
```

-continued

<400> SEQUENCE: 864
aggcagcaau uucaacaaca u                21

<210> SEQ ID NO 865
<211> LENGTH: 19
<212> TYPE: RNA
<213> ORGANISM: Influenza B virus

<400> SEQUENCE: 865
aggauaucca gaguggaau                   19

<210> SEQ ID NO 866
<211> LENGTH: 21
<212> TYPE: RNA
<213> ORGANISM: Influenza B virus

<400> SEQUENCE: 866
acaugguccu gugaagaaaa u                21

<210> SEQ ID NO 867
<211> LENGTH: 21
<212> TYPE: RNA
<213> ORGANISM: Influenza B virus

<400> SEQUENCE: 867
aaugacaaaa gaugcugaaa g                21

<210> SEQ ID NO 868
<211> LENGTH: 19
<212> TYPE: RNA
<213> ORGANISM: Influenza B virus

<400> SEQUENCE: 868
gagacaauac uaaauggaa                   19

<210> SEQ ID NO 869
<211> LENGTH: 19
<212> TYPE: RNA
<213> ORGANISM: Influenza B virus

<400> SEQUENCE: 869
ggauuaugau gcagugucu                   19

<210> SEQ ID NO 870
<211> LENGTH: 21
<212> TYPE: RNA
<213> ORGANISM: Influenza B virus

<400> SEQUENCE: 870
aggaacaaug cuacgcuaaa u                21

<210> SEQ ID NO 871
<211> LENGTH: 21
<212> TYPE: RNA
<213> ORGANISM: Influenza B virus

<400> SEQUENCE: 871
ucaguaaaga auauaaagaa a                21

<210> SEQ ID NO 872
<211> LENGTH: 19
<212> TYPE: RNA
<213> ORGANISM: Influenza B virus -continued

<400> SEQUENCE: 872
ucccaaguau cuggcugau                              19

<210> SEQ ID NO 873
<211> LENGTH: 21
<212> TYPE: RNA
<213> ORGANISM: Influenza B virus

<400> SEQUENCE: 873
augugccaag aagagccuaa a                           21

<210> SEQ ID NO 874
<211> LENGTH: 21
<212> TYPE: RNA
<213> ORGANISM: Influenza B virus

<400> SEQUENCE: 874
gcugggaaau agcauggaac u                           21

<210> SEQ ID NO 875
<211> LENGTH: 19
<212> TYPE: RNA
<213> ORGANISM: Influenza B virus

<400> SEQUENCE: 875 gauccuugg aaaagcacu                               19

<210> SEQ ID NO 876
<211> LENGTH: 21
<212> TYPE: RNA
<213> ORGANISM: Influenza B virus

<400> SEQUENCE: 876 aauuucuug acgaagaagg a                            21

<210> SEQ ID NO 877
<211> LENGTH: 19
<212> TYPE: RNA
<213> ORGANISM: Influenza B virus

<400> SEQUENCE: 877
cugcguccau cuagagguu                              19

<210> SEQ ID NO 878
<211> LENGTH: 21
<212> TYPE: RNA
<213> ORGANISM: Influenza B virus

<400> SEQUENCE: 878
aaccaugagc uaccagaagu u                           21

<210> SEQ ID NO 879
<211> LENGTH: 21
<212> TYPE: RNA
<213> ORGANISM: Influenza B virus

<400> SEQUENCE: 879
aaucaaugca acaaauggaa g                           21

<210> SEQ ID NO 880
<211> LENGTH: 19
<212> TYPE: RNA
<213> ORGANISM: Influenza B virus

```
<400> SEQUENCE: 880
uggguaauac agagugcau                                                     19

<210> SEQ ID NO 881
<211> LENGTH: 21
<212> TYPE: RNA
<213> ORGANISM: Influenza B virus

<400> SEQUENCE: 881
cuagcaagga ugucucccuu a                                                  21

<210> SEQ ID NO 882
<211> LENGTH: 19
<212> TYPE: RNA
<213> ORGANISM: Influenza B virus

<400> SEQUENCE: 882
guagcaauag augacgaaa                                                     19

<210> SEQ ID NO 883
<211> LENGTH: 21
<212> TYPE: RNA
<213> ORGANISM: Influenza B virus

<400> SEQUENCE: 883
gaagggaaag ggagagugcu a                                                  21

<210> SEQ ID NO 884
<211> LENGTH: 19
<212> TYPE: RNA
<213> ORGANISM: Influenza B virus

<400> SEQUENCE: 884
gggaaugcca agaaccaua                                                     19

<210> SEQ ID NO 885
<211> LENGTH: 21
<212> TYPE: RNA
<213> ORGANISM: Influenza B virus

<400> SEQUENCE: 885
gagggaaugc caagaaccau a                                                  21

<210> SEQ ID NO 886
<211> LENGTH: 21
<212> TYPE: RNA
<213> ORGANISM: Influenza B virus

<400> SEQUENCE: 886
aaaaccaaga gauuuauaga a                                                  21

<210> SEQ ID NO 887
<211> LENGTH: 23
<212> TYPE: RNA
<213> ORGANISM: Influenza B virus

<400> SEQUENCE: 887
gaagcaauug uugaacaaga auc                                                23

<210> SEQ ID NO 888
<211> LENGTH: 21
<212> TYPE: RNA
<213> ORGANISM: Influenza B virus
```

```
<400> SEQUENCE: 888
aaaugaaaug gggaauggaa g                                    21

<210> SEQ ID NO 889
<211> LENGTH: 19
<212> TYPE: RNA
<213> ORGANISM: Influenza B virus

<400> SEQUENCE: 889
cauguaggga gugaaagaa                                       19

<210> SEQ ID NO 890
<211> LENGTH: 19
<212> TYPE: RNA
<213> ORGANISM: Influenza B virus

<400> SEQUENCE: 890
gcuauguaau aagugacau                                       19

<210> SEQ ID NO 891
<211> LENGTH: 21
<212> TYPE: RNA
<213> ORGANISM: Influenza B virus

<400> SEQUENCE: 891
aauuuaguga agauccugaa u                                    21

<210> SEQ ID NO 892
<211> LENGTH: 19
<212> TYPE: RNA
<213> ORGANISM: Influenza B virus

<400> SEQUENCE: 892
cucaacacua cgggaucaa                                       19

<210> SEQ ID NO 893
<211> LENGTH: 21
<212> TYPE: RNA
<213> ORGANISM: Influenza B virus

<400> SEQUENCE: 893
acucccaagu aucuggcuga u                                    21

<210> SEQ ID NO 894
<211> LENGTH: 21
<212> TYPE: RNA
<213> ORGANISM: Influenza B virus

<400> SEQUENCE: 894
aaaauaauga aagaaguagc a                                    21

<210> SEQ ID NO 895
<211> LENGTH: 19
<212> TYPE: RNA
<213> ORGANISM: Influenza B virus

<400> SEQUENCE: 895
aggggaugga uuaacauac                                       19

<210> SEQ ID NO 896
<211> LENGTH: 19
<212> TYPE: RNA
<213> ORGANISM: Influenza B virus
```

```
<400> SEQUENCE: 896
ggaugucucc cuuaguauc                                                19

<210> SEQ ID NO 897
<211> LENGTH: 19
<212> TYPE: RNA
<213> ORGANISM: Influenza B virus

<400> SEQUENCE: 897 cagggaugg auuaacaua                                                 19

<210> SEQ ID NO 898
<211> LENGTH: 19
<212> TYPE: RNA
<213> ORGANISM: Influenza B virus

<400> SEQUENCE: 898
gcuacaauca agacuauuc                                                19

<210> SEQ ID NO 899
<211> LENGTH: 21
<212> TYPE: RNA
<213> ORGANISM: Influenza B virus

<400> SEQUENCE: 899 aaucaaaau aauaccaaua a                                              21

<210> SEQ ID NO 900
<211> LENGTH: 21
<212> TYPE: RNA
<213> ORGANISM: Influenza B virus

<400> SEQUENCE: 900
ugaaggaaug aggagcuaca u                                             21

<210> SEQ ID NO 901
<211> LENGTH: 21
<212> TYPE: RNA
<213> ORGANISM: Influenza B virus

<400> SEQUENCE: 901
aggaugucuc ccuuaguauc a                                             21

<210> SEQ ID NO 902
<211> LENGTH: 21
<212> TYPE: RNA
<213> ORGANISM: Influenza B virus

<400> SEQUENCE: 902
cccguggagc auguagggag u                                             21

<210> SEQ ID NO 903
<211> LENGTH: 21
<212> TYPE: RNA
<213> ORGANISM: Influenza B virus

<400> SEQUENCE: 903
aagauccuga auuacaacca g                                             21

<210> SEQ ID NO 904
<211> LENGTH: 19
<212> TYPE: RNA
<213> ORGANISM: Influenza B virus
```

```
<400> SEQUENCE: 904
ggguaauaca gagugcaua                                              19

<210> SEQ ID NO 905
<211> LENGTH: 21
<212> TYPE: RNA
<213> ORGANISM: Influenza B virus

<400> SEQUENCE: 905
ggagcaauag agagaaaucu a                                           21

<210> SEQ ID NO 906
<211> LENGTH: 21
<212> TYPE: RNA
<213> ORGANISM: Influenza B virus

<400> SEQUENCE: 906
aaagaaccaa gaaucaaaaa u                                           21

<210> SEQ ID NO 907
<211> LENGTH: 19
<212> TYPE: RNA
<213> ORGANISM: Influenza B virus

<400> SEQUENCE: 907
aggagaagaa gauguugaa                                              19

<210> SEQ ID NO 908
<211> LENGTH: 21
<212> TYPE: RNA
<213> ORGANISM: Influenza B virus

<400> SEQUENCE: 908
cggugcguuu gauuugucau a                                           21

<210> SEQ ID NO 909
<211> LENGTH: 19
<212> TYPE: RNA
<213> ORGANISM: Influenza B virus

<400> SEQUENCE: 909
cugauguugu aacaguugu                                              19

<210> SEQ ID NO 910
<211> LENGTH: 21
<212> TYPE: RNA
<213> ORGANISM: Influenza B virus

<400> SEQUENCE: 910
ggcugcuugg guucaaacag a                                           21

<210> SEQ ID NO 911
<211> LENGTH: 21
<212> TYPE: RNA
<213> ORGANISM: Influenza B virus

<400> SEQUENCE: 911
aauagggccu cacauuuaca a                                           21

<210> SEQ ID NO 912
<211> LENGTH: 19
<212> TYPE: RNA
<213> ORGANISM: Influenza B virus
```

```
<400> SEQUENCE: 912
caguauugga acucaagaa                                              19

<210> SEQ ID NO 913
<211> LENGTH: 21
<212> TYPE: RNA
<213> ORGANISM: Influenza B virus

<400> SEQUENCE: 913
aaucccuaaa aaauguagag u                                           21

<210> SEQ ID NO 914
<211> LENGTH: 23
<212> TYPE: RNA
<213> ORGANISM: Influenza B virus

<400> SEQUENCE: 914
gaaaauuucc uauggaagcu uug                                         23

<210> SEQ ID NO 915
<211> LENGTH: 19
<212> TYPE: RNA
<213> ORGANISM: Influenza B virus

<400> SEQUENCE: 915
cacagaacuu caggcugaa                                              19

<210> SEQ ID NO 916
<211> LENGTH: 19
<212> TYPE: RNA
<213> ORGANISM: Influenza B virus

<400> SEQUENCE: 916
gggaaaggga gagugcuaa                                              19

<210> SEQ ID NO 917
<211> LENGTH: 21
<212> TYPE: RNA
<213> ORGANISM: Influenza B virus

<400> SEQUENCE: 917
gaaaggagca auagagagaa a                                           21

<210> SEQ ID NO 918
<211> LENGTH: 19
<212> TYPE: RNA
<213> ORGANISM: Influenza B virus

<400> SEQUENCE: 918
gggaaagaac aaaauuuga                                              19

<210> SEQ ID NO 919
<211> LENGTH: 21
<212> TYPE: RNA
<213> ORGANISM: Influenza B virus

<400> SEQUENCE: 919
ucaagggaga cagaguaaau a                                           21

<210> SEQ ID NO 920
<211> LENGTH: 21
<212> TYPE: RNA
<213> ORGANISM: Influenza B virus
```

```
<400> SEQUENCE: 920
uugccgagug aauggcacaa a                                             21

<210> SEQ ID NO 921
<211> LENGTH: 21
<212> TYPE: RNA
<213> ORGANISM: Influenza B virus

<400> SEQUENCE: 921
aauggaagcu agaagauguc u                                             21

<210> SEQ ID NO 922
<211> LENGTH: 19
<212> TYPE: RNA
<213> ORGANISM: Influenza B virus

<400> SEQUENCE: 922
gagagacugu guaaauaca                                                19

<210> SEQ ID NO 923
<211> LENGTH: 21
<212> TYPE: RNA
<213> ORGANISM: Influenza B virus

<400> SEQUENCE: 923
aagggaaaga acaaaauuug a                                             21

<210> SEQ ID NO 924
<211> LENGTH: 19
<212> TYPE: RNA
<213> ORGANISM: Influenza B virus

<400> SEQUENCE: 924
ggccaaaaua uacuguguu                                                19

<210> SEQ ID NO 925
<211> LENGTH: 21
<212> TYPE: RNA
<213> ORGANISM: Influenza B virus

<400> SEQUENCE: 925
aaccagcaau gcuauucaac a                                             21

<210> SEQ ID NO 926
<211> LENGTH: 21
<212> TYPE: RNA
<213> ORGANISM: Influenza B virus

<400> SEQUENCE: 926
aauggcagaa uuuagugaag a                                             21

<210> SEQ ID NO 927
<211> LENGTH: 21
<212> TYPE: RNA
<213> ORGANISM: Influenza B virus

<400> SEQUENCE: 927
guuccagcug guuucuccaa u                                             21

<210> SEQ ID NO 928
<211> LENGTH: 21
<212> TYPE: RNA
<213> ORGANISM: Influenza B virus
```

```
<400> SEQUENCE: 928
agagggaaug uauucuggaa u                                          21

<210> SEQ ID NO 929
<211> LENGTH: 21
<212> TYPE: RNA
<213> ORGANISM: Influenza B virus

<400> SEQUENCE: 929
aauaauacca auaaccaaua g                                          21

<210> SEQ ID NO 930
<211> LENGTH: 19
<212> TYPE: RNA
<213> ORGANISM: Influenza B virus

<400> SEQUENCE: 930
ggacaaggga aagaacaaa                                             19

<210> SEQ ID NO 931
<211> LENGTH: 21
<212> TYPE: RNA
<213> ORGANISM: Influenza B virus

<400> SEQUENCE: 931
uucgacuuag agggaaugua u                                          21

<210> SEQ ID NO 932
<211> LENGTH: 21
<212> TYPE: RNA
<213> ORGANISM: Influenza B virus

<400> SEQUENCE: 932
acagaacuuc aggcugaauu a                                          21

<210> SEQ ID NO 933
<211> LENGTH: 19
<212> TYPE: RNA
<213> ORGANISM: Influenza B virus

<400> SEQUENCE: 933
agccaaagaa ugucuagaa                                             19

<210> SEQ ID NO 934
<211> LENGTH: 21
<212> TYPE: RNA
<213> ORGANISM: Influenza B virus

<400> SEQUENCE: 934
aauuugagac cacaauauga a                                          21

<210> SEQ ID NO 935
<211> LENGTH: 21
<212> TYPE: RNA
<213> ORGANISM: Influenza B virus

<400> SEQUENCE: 935
aaguaugugc uuuuucacac u                                          21

<210> SEQ ID NO 936
<211> LENGTH: 21
<212> TYPE: RNA
<213> ORGANISM: Influenza B virus
```

```
<400> SEQUENCE: 936
aagugacaug aauuucuug a                                              21

<210> SEQ ID NO 937
<211> LENGTH: 21
<212> TYPE: RNA
<213> ORGANISM: Influenza B virus

<400> SEQUENCE: 937
aaagaacaaa auuugagacc a                                             21

<210> SEQ ID NO 938
<211> LENGTH: 21
<212> TYPE: RNA
<213> ORGANISM: Influenza B virus

<400> SEQUENCE: 938
auugccgagu gaauggcaca a                                             21

<210> SEQ ID NO 939
<211> LENGTH: 21
<212> TYPE: RNA
<213> ORGANISM: Influenza B virus

<400> SEQUENCE: 939
aaagggagag ugcuaagcag a                                             21

<210> SEQ ID NO 940
<211> LENGTH: 19
<212> TYPE: RNA
<213> ORGANISM: Influenza B virus

<400> SEQUENCE: 940
caagcauuaa aggacagaa                                                19

<210> SEQ ID NO 941
<211> LENGTH: 21
<212> TYPE: RNA
<213> ORGANISM: Influenza B virus

<400> SEQUENCE: 941
aguccaaaaa accgaagaca u                                             21

<210> SEQ ID NO 942
<211> LENGTH: 19
<212> TYPE: RNA
<213> ORGANISM: Influenza B virus

<400> SEQUENCE: 942
agagcaugga auagagacu                                                19

<210> SEQ ID NO 943
<211> LENGTH: 19
<212> TYPE: RNA
<213> ORGANISM: Influenza B virus

<400> SEQUENCE: 943
caaccagcaa ugcuauuca                                                19

<210> SEQ ID NO 944
<211> LENGTH: 21
<212> TYPE: RNA
<213> ORGANISM: Influenza B virus
```

```
<400> SEQUENCE: 944
aagagccuaa aaucccuaaa a                                            21

<210> SEQ ID NO 945
<211> LENGTH: 21
<212> TYPE: RNA
<213> ORGANISM: Influenza B virus

<400> SEQUENCE: 945
ccagcauggg aaaauacaaa a                                            21

<210> SEQ ID NO 946
<211> LENGTH: 19
<212> TYPE: RNA
<213> ORGANISM: Influenza B virus

<400> SEQUENCE: 946
ggggagauac ugauguugu                                               19

<210> SEQ ID NO 947
<211> LENGTH: 21
<212> TYPE: RNA
<213> ORGANISM: Influenza B virus

<400> SEQUENCE: 947
ugccgagucu aggagacuuc u                                            21

<210> SEQ ID NO 948
<211> LENGTH: 21
<212> TYPE: RNA
<213> ORGANISM: Influenza B virus

<400> SEQUENCE: 948
aaaacuagua aaaggauccu u                                            21

<210> SEQ ID NO 949
<211> LENGTH: 19
<212> TYPE: RNA
<213> ORGANISM: Influenza B virus

<400> SEQUENCE: 949
ggagauacug auguuguaa                                               19

<210> SEQ ID NO 950
<211> LENGTH: 21
<212> TYPE: RNA
<213> ORGANISM: Influenza B virus

<400> SEQUENCE: 950
cuuggguaau acagagugca u                                            21

<210> SEQ ID NO 951
<211> LENGTH: 19
<212> TYPE: RNA
<213> ORGANISM: Influenza B virus

<400> SEQUENCE: 951
gaaugaggag cuacauaga                                               19

<210> SEQ ID NO 952
<211> LENGTH: 21
<212> TYPE: RNA
<213> ORGANISM: Influenza B virus
```

-continued

```
<400> SEQUENCE: 952
gccucacauu uacaaccaug a                                              21

<210> SEQ ID NO 953
<211> LENGTH: 21
<212> TYPE: RNA
<213> ORGANISM: Influenza B virus

<400> SEQUENCE: 953
ugugccaaga agagccuaaa a                                              21

<210> SEQ ID NO 954
<211> LENGTH: 19
<212> TYPE: RNA
<213> ORGANISM: Influenza B virus

<400> SEQUENCE: 954
gcuuuggaga gacugugua                                                 19

<210> SEQ ID NO 955
<211> LENGTH: 19
<212> TYPE: RNA
<213> ORGANISM: Influenza B virus

<400> SEQUENCE: 955
ccagagugga cucaggaaa                                                 19

<210> SEQ ID NO 956
<211> LENGTH: 19
<212> TYPE: RNA
<213> ORGANISM: Influenza B virus

<400> SEQUENCE: 956
ggauggucca aagauccuu                                                 19

<210> SEQ ID NO 957
<211> LENGTH: 19
<212> TYPE: RNA
<213> ORGANISM: Influenza B virus

<400> SEQUENCE: 957
gaagcuuugg agagacugu                                                 19

<210> SEQ ID NO 958
<211> LENGTH: 21
<212> TYPE: RNA
<213> ORGANISM: Influenza B virus

<400> SEQUENCE: 958
agggccucac auuuacaacc a                                              21

<210> SEQ ID NO 959
<211> LENGTH: 21
<212> TYPE: RNA
<213> ORGANISM: Influenza B virus

<400> SEQUENCE: 959
aggagcuaca uagacaauau a                                              21

<210> SEQ ID NO 960
<211> LENGTH: 23
<212> TYPE: RNA
<213> ORGANISM: Influenza B virus
```

```
<400> SEQUENCE: 960
uagggccaga cguagcaccc gug                                    23

<210> SEQ ID NO 961
<211> LENGTH: 21
<212> TYPE: RNA
<213> ORGANISM: Influenza B virus

<400> SEQUENCE: 961
uaggagacuu cuacuguuga u                                      21

<210> SEQ ID NO 962
<211> LENGTH: 19
<212> TYPE: RNA
<213> ORGANISM: Influenza B virus

<400> SEQUENCE: 962
agagaaaucu agcaaggau                                         19

<210> SEQ ID NO 963
<211> LENGTH: 21
<212> TYPE: RNA
<213> ORGANISM: Influenza B virus

<400> SEQUENCE: 963
agcaaugcca gcaugggaaa a                                      21

<210> SEQ ID NO 964
<211> LENGTH: 21
<212> TYPE: RNA
<213> ORGANISM: Influenza B virus

<400> SEQUENCE: 964
aagcagacuc acagaacuuc a                                      21

<210> SEQ ID NO 965
<211> LENGTH: 23
<212> TYPE: RNA
<213> ORGANISM: Influenza B virus

<400> SEQUENCE: 965
uagcaauaga ugacgaaaca aug                                    23

<210> SEQ ID NO 966
<211> LENGTH: 19
<212> TYPE: RNA
<213> ORGANISM: Influenza B virus

<400> SEQUENCE: 966
cuagaagaug ucugcuuca                                         19

<210> SEQ ID NO 967
<211> LENGTH: 19
<212> TYPE: RNA
<213> ORGANISM: Influenza B virus

<400> SEQUENCE: 967
ggugcguuug auuugucau                                         19

<210> SEQ ID NO 968
<211> LENGTH: 21
<212> TYPE: RNA
<213> ORGANISM: Influenza B virus
```

-continued

```
<400> SEQUENCE: 968
aauaaugaaa gaaguagcaa u                                              21

<210> SEQ ID NO 969
<211> LENGTH: 19
<212> TYPE: RNA
<213> ORGANISM: Influenza B virus

<400> SEQUENCE: 969
gaacaagaau caucgauac                                                 19

<210> SEQ ID NO 970
<211> LENGTH: 21
<212> TYPE: RNA
<213> ORGANISM: Influenza B virus

<400> SEQUENCE: 970
aaguaauuga gggaaugcca a                                              21

<210> SEQ ID NO 971
<211> LENGTH: 21
<212> TYPE: RNA
<213> ORGANISM: Influenza B virus

<400> SEQUENCE: 971
aaaacuuuca guauuggaac u                                              21

<210> SEQ ID NO 972
<211> LENGTH: 21
<212> TYPE: RNA
<213> ORGANISM: Influenza B virus

<400> SEQUENCE: 972
aauaaguaau gaggaaauga g                                              21

<210> SEQ ID NO 973
<211> LENGTH: 19
<212> TYPE: RNA
<213> ORGANISM: Influenza B virus

<400> SEQUENCE: 973
acaguuguaa cuuucgaau                                                 19

<210> SEQ ID NO 974
<211> LENGTH: 21
<212> TYPE: RNA
<213> ORGANISM: Influenza B virus

<400> SEQUENCE: 974
aaugaaagaa guagcaauag a                                              21

<210> SEQ ID NO 975
<211> LENGTH: 21
<212> TYPE: RNA
<213> ORGANISM: Influenza B virus

<400> SEQUENCE: 975
accaauaggg ccucacauuu a                                              21

<210> SEQ ID NO 976
<211> LENGTH: 21
<212> TYPE: RNA
<213> ORGANISM: Influenza B virus
```

-continued

```
<400> SEQUENCE: 976
ugagcuacca gaaguuccau a                                              21

<210> SEQ ID NO 977
<211> LENGTH: 21
<212> TYPE: RNA
<213> ORGANISM: Influenza B virus

<400> SEQUENCE: 977
gagcuaccag aaguuccaua u                                              21

<210> SEQ ID NO 978
<211> LENGTH: 21
<212> TYPE: RNA
<213> ORGANISM: Influenza B virus

<400> SEQUENCE: 978
aagggaaagg gagagugcua a                                              21

<210> SEQ ID NO 979
<211> LENGTH: 21
<212> TYPE: RNA
<213> ORGANISM: Influenza B virus

<400> SEQUENCE: 979
aaacagagau gaaucuauug a                                              21

<210> SEQ ID NO 980
<211> LENGTH: 23
<212> TYPE: RNA
<213> ORGANISM: Influenza B virus

<400> SEQUENCE: 980
uucuggaaua gaagaaugua uua                                            23

<210> SEQ ID NO 981
<211> LENGTH: 21
<212> TYPE: RNA
<213> ORGANISM: Influenza B virus

<400> SEQUENCE: 981
aacuaguaaa aggauccuuu g                                              21

<210> SEQ ID NO 982
<211> LENGTH: 19
<212> TYPE: RNA
<213> ORGANISM: Influenza B virus

<400> SEQUENCE: 982
gagauacuga uguuguaac                                                 19

<210> SEQ ID NO 983
<211> LENGTH: 23
<212> TYPE: RNA
<213> ORGANISM: Influenza B virus

<400> SEQUENCE: 983
gaacucaaga aggaaaacua gua                                            23

<210> SEQ ID NO 984
<211> LENGTH: 19
<212> TYPE: RNA
<213> ORGANISM: Influenza B virus
```

-continued

<400> SEQUENCE: 984
guaguacaga ccccagagu                                        19

<210> SEQ ID NO 985
<211> LENGTH: 21
<212> TYPE: RNA
<213> ORGANISM: Influenza B virus

<400> SEQUENCE: 985
gucuggcggu uaaaggacaa u                                     21

<210> SEQ ID NO 986
<211> LENGTH: 21
<212> TYPE: RNA
<213> ORGANISM: Influenza B virus

<400> SEQUENCE: 986
aaaauaauac caauaaccaa u                                     21

<210> SEQ ID NO 987
<211> LENGTH: 19
<212> TYPE: RNA
<213> ORGANISM: Influenza B virus

<400> SEQUENCE: 987
gaaagaagua gcaauagau                                        19

<210> SEQ ID NO 988
<211> LENGTH: 21
<212> TYPE: RNA
<213> ORGANISM: Influenza B virus

<400> SEQUENCE: 988
agggagugaa agaaggaaau a                                     21

<210> SEQ ID NO 989
<211> LENGTH: 19
<212> TYPE: RNA
<213> ORGANISM: Influenza B virus

<400> SEQUENCE: 989
cuuggacaaa caauaucua                                        19

<210> SEQ ID NO 990
<211> LENGTH: 21
<212> TYPE: RNA
<213> ORGANISM: Influenza B virus

<400> SEQUENCE: 990
gcaaggaugu cucccuuagu a                                     21

<210> SEQ ID NO 991
<211> LENGTH: 19
<212> TYPE: RNA
<213> ORGANISM: Influenza B virus

<400> SEQUENCE: 991
agaccacaau augaaguaa                                        19

<210> SEQ ID NO 992
<211> LENGTH: 23
<212> TYPE: RNA
<213> ORGANISM: Influenza B virus -continued

```
<400> SEQUENCE: 992
uagaugaaau aauggaugaa uaa                                            23

<210> SEQ ID NO 993
<211> LENGTH: 21
<212> TYPE: RNA
<213> ORGANISM: Influenza B virus

<400> SEQUENCE: 993
gaaggaauga ggagcuacau a                                              21

<210> SEQ ID NO 994
<211> LENGTH: 21
<212> TYPE: RNA
<213> ORGANISM: Influenza B virus

<400> SEQUENCE: 994
aacaaaagga uuggcugaug a                                              21

<210> SEQ ID NO 995
<211> LENGTH: 21
<212> TYPE: RNA
<213> ORGANISM: Influenza B virus

<400> SEQUENCE: 995
aaugaggaaa ugaguaacga g                                              21

<210> SEQ ID NO 996
<211> LENGTH: 21
<212> TYPE: RNA
<213> ORGANISM: Influenza B virus

<400> SEQUENCE: 996
aaccaagaga uuuauagaag u                                              21

<210> SEQ ID NO 997
<211> LENGTH: 21
<212> TYPE: RNA
<213> ORGANISM: Influenza B virus

<400> SEQUENCE: 997
gugccaagaa gagccuaaaa u                                              21

<210> SEQ ID NO 998
<211> LENGTH: 19
<212> TYPE: RNA
<213> ORGANISM: Influenza B virus

<400> SEQUENCE: 998
gugacaugaa uuuucuuga                                                 19

<210> SEQ ID NO 999
<211> LENGTH: 21
<212> TYPE: RNA
<213> ORGANISM: Influenza B virus

<400> SEQUENCE: 999
augccagcau gggaaaauac a                                              21

<210> SEQ ID NO 1000
<211> LENGTH: 21
<212> TYPE: RNA
<213> ORGANISM: Influenza B virus
```

```
<400> SEQUENCE: 1000
uugagcacuc ugacaaguaa a                                              21

<210> SEQ ID NO 1001
<211> LENGTH: 19
<212> TYPE: RNA
<213> ORGANISM: Influenza B virus

<400> SEQUENCE: 1001
gcuacauaga caauauaga                                                 19

<210> SEQ ID NO 1002
<211> LENGTH: 21
<212> TYPE: RNA
<213> ORGANISM: Influenza B virus

<400> SEQUENCE: 1002
aacaaaugga agcaauuguu g                                              21

<210> SEQ ID NO 1003
<211> LENGTH: 19
<212> TYPE: RNA
<213> ORGANISM: Influenza B virus

<400> SEQUENCE: 1003
cacucugaca aguaaaaga                                                 19

<210> SEQ ID NO 1004
<211> LENGTH: 21
<212> TYPE: RNA
<213> ORGANISM: Influenza B virus

<400> SEQUENCE: 1004
aacuuucagu auuggaacuc a                                              21

<210> SEQ ID NO 1005
<211> LENGTH: 19
<212> TYPE: RNA
<213> ORGANISM: Influenza B virus

<400> SEQUENCE: 1005
uccaaaugaa augggaau                                                  19

<210> SEQ ID NO 1006
<211> LENGTH: 19
<212> TYPE: RNA
<213> ORGANISM: Influenza B virus

<400> SEQUENCE: 1006
gcaauagaga gaaaucuag                                                 19

<210> SEQ ID NO 1007
<211> LENGTH: 21
<212> TYPE: RNA
<213> ORGANISM: Influenza B virus

<400> SEQUENCE: 1007
aaggacauag uacucaauuu a                                              21

<210> SEQ ID NO 1008
<211> LENGTH: 21
<212> TYPE: RNA
<213> ORGANISM: Influenza B virus
```

-continued

```
<400> SEQUENCE: 1008
cuggcgguua aaggacaauc u                                        21

<210> SEQ ID NO 1009
<211> LENGTH: 19
<212> TYPE: RNA
<213> ORGANISM: Influenza B virus

<400> SEQUENCE: 1009
gcuuggguuc aaacagaga                                           19

<210> SEQ ID NO 1010
<211> LENGTH: 21
<212> TYPE: RNA
<213> ORGANISM: Influenza B virus

<400> SEQUENCE: 1010
gagcagaagc ggugcguuug a                                        21

<210> SEQ ID NO 1011
<211> LENGTH: 21
<212> TYPE: RNA
<213> ORGANISM: Influenza B virus

<400> SEQUENCE: 1011
ggaucaaacu gacccaauau u                                        21

<210> SEQ ID NO 1012
<211> LENGTH: 19
<212> TYPE: RNA
<213> ORGANISM: Influenza B virus

<400> SEQUENCE: 1012
augccaagaa ccauagcau                                           19

<210> SEQ ID NO 1013
<211> LENGTH: 19
<212> TYPE: RNA
<213> ORGANISM: Influenza B virus

<400> SEQUENCE: 1013
acccgaaagg agcaauaga                                           19

<210> SEQ ID NO 1014
<211> LENGTH: 19
<212> TYPE: RNA
<213> ORGANISM: Influenza B virus

<400> SEQUENCE: 1014
cucaagagca uggaauaga                                           19

<210> SEQ ID NO 1015
<211> LENGTH: 21
<212> TYPE: RNA
<213> ORGANISM: Influenza B virus

<400> SEQUENCE: 1015
aagaagagcc uaaaauccu a                                         21

<210> SEQ ID NO 1016
<211> LENGTH: 21
<212> TYPE: RNA
<213> ORGANISM: Influenza B virus
```

-continued

```
<400> SEQUENCE: 1016
aaaagcacua agaguaauau u                                              21

<210> SEQ ID NO 1017
<211> LENGTH: 21
<212> TYPE: RNA
<213> ORGANISM: Influenza B virus

<400> SEQUENCE: 1017
aaaaggauug gcugaugauu a                                              21

<210> SEQ ID NO 1018
<211> LENGTH: 21
<212> TYPE: RNA
<213> ORGANISM: Influenza B virus

<400> SEQUENCE: 1018
augaggaaau gaguaacgag u                                              21

<210> SEQ ID NO 1019
<211> LENGTH: 21
<212> TYPE: RNA
<213> ORGANISM: Influenza B virus

<400> SEQUENCE: 1019
cagucacacc uaaaaaguug a                                              21

<210> SEQ ID NO 1020
<211> LENGTH: 21
<212> TYPE: RNA
<213> ORGANISM: Influenza B virus

<400> SEQUENCE: 1020
uacgggauca aacugaccca a                                              21

<210> SEQ ID NO 1021
<211> LENGTH: 21
<212> TYPE: RNA
<213> ORGANISM: Influenza B virus

<400> SEQUENCE: 1021
aaaaaugcac uguuucuac u                                               21

<210> SEQ ID NO 1022
<211> LENGTH: 21
<212> TYPE: RNA
<213> ORGANISM: Influenza B virus

<400> SEQUENCE: 1022
ugccagcaug ggaaaauaca a                                              21

<210> SEQ ID NO 1023
<211> LENGTH: 23
<212> TYPE: RNA
<213> ORGANISM: Influenza B virus

<400> SEQUENCE: 1023
gagccuaaaa ucccuaaaaa aug                                            23

<210> SEQ ID NO 1024
<211> LENGTH: 21
<212> TYPE: RNA
<213> ORGANISM: Influenza B virus
```

```
<400> SEQUENCE: 1024
aaaucaacua cuguaaggcc u                                              21

<210> SEQ ID NO 1025
<211> LENGTH: 21
<212> TYPE: RNA
<213> ORGANISM: Influenza B virus

<400> SEQUENCE: 1025
ggcccuuggg uguucgacuu a                                              21

<210> SEQ ID NO 1026
<211> LENGTH: 21
<212> TYPE: RNA
<213> ORGANISM: Influenza B virus

<400> SEQUENCE: 1026
gcugguuucu ccaauuuuga a                                              21

<210> SEQ ID NO 1027
<211> LENGTH: 21
<212> TYPE: RNA
<213> ORGANISM: Influenza B virus

<400> SEQUENCE: 1027
aagagcucug gaccuaccag a                                              21

<210> SEQ ID NO 1028
<211> LENGTH: 23
<212> TYPE: RNA
<213> ORGANISM: Influenza B virus

<400> SEQUENCE: 1028
augaaauaau ggaugaauaa aag                                            23

<210> SEQ ID NO 1029
<211> LENGTH: 21
<212> TYPE: RNA
<213> ORGANISM: Influenza B virus

<400> SEQUENCE: 1029
aaucaaaaau gcacguguuu c                                              21

<210> SEQ ID NO 1030
<211> LENGTH: 21
<212> TYPE: RNA
<213> ORGANISM: Influenza B virus

<400> SEQUENCE: 1030
aggccucuac aguuaugaug a                                              21

<210> SEQ ID NO 1031
<211> LENGTH: 21
<212> TYPE: RNA
<213> ORGANISM: Influenza B virus

<400> SEQUENCE: 1031
aaauagcccc aaaacuuuca g                                              21

<210> SEQ ID NO 1032
<211> LENGTH: 19
<212> TYPE: RNA
<213> ORGANISM: Influenza B virus
```

```
<400> SEQUENCE: 1032
ggaaaagcac uaagaguaa                                                    19

<210> SEQ ID NO 1033
<211> LENGTH: 21
<212> TYPE: RNA
<213> ORGANISM: Influenza B virus

<400> SEQUENCE: 1033
gaagcggugc guuugauuug u                                                 21

<210> SEQ ID NO 1034
<211> LENGTH: 19
<212> TYPE: RNA
<213> ORGANISM: Influenza B virus

<400> SEQUENCE: 1034
agacaauaua gacccgaaa                                                    19

<210> SEQ ID NO 1035
<211> LENGTH: 19
<212> TYPE: RNA
<213> ORGANISM: Influenza B virus

<400> SEQUENCE: 1035
cccuugggua auacagagu                                                    19

<210> SEQ ID NO 1036
<211> LENGTH: 21
<212> TYPE: RNA
<213> ORGANISM: Influenza B virus

<400> SEQUENCE: 1036
caaggauguc ucccuuagua u                                                 21

<210> SEQ ID NO 1037
<211> LENGTH: 21
<212> TYPE: RNA
<213> ORGANISM: Influenza B virus

<400> SEQUENCE: 1037
ucugcgucca ucuagagguu u                                                 21

<210> SEQ ID NO 1038
<211> LENGTH: 19
<212> TYPE: RNA
<213> ORGANISM: Influenza B virus

<400> SEQUENCE: 1038
ggagcaugua gggagugaa                                                    19

<210> SEQ ID NO 1039
<211> LENGTH: 21
<212> TYPE: RNA
<213> ORGANISM: Influenza B virus

<400> SEQUENCE: 1039
aaggaaaagc auauacagca u                                                 21

<210> SEQ ID NO 1040
<211> LENGTH: 19
<212> TYPE: RNA
<213> ORGANISM: Influenza B virus
```

-continued

```
<400> SEQUENCE: 1040
gggaggaccu aagaccaau                                              19

<210> SEQ ID NO 1041
<211> LENGTH: 19
<212> TYPE: RNA
<213> ORGANISM: Influenza B virus

<400> SEQUENCE: 1041
cgauacaagg auaugacau                                              19

<210> SEQ ID NO 1042
<211> LENGTH: 21
<212> TYPE: RNA
<213> ORGANISM: Influenza B virus

<400> SEQUENCE: 1042
aagaaggaaa agcauauaca g                                           21

<210> SEQ ID NO 1043
<211> LENGTH: 19
<212> TYPE: RNA
<213> ORGANISM: Influenza B virus

<400> SEQUENCE: 1043
ugcaacaaau ggaagcaau                                              19

<210> SEQ ID NO 1044
<211> LENGTH: 21
<212> TYPE: RNA
<213> ORGANISM: Influenza B virus

<400> SEQUENCE: 1044
aaauacaaua aguaaugagg a                                           21

<210> SEQ ID NO 1045
<211> LENGTH: 21
<212> TYPE: RNA
<213> ORGANISM: Influenza B virus

<400> SEQUENCE: 1045
uucaagggag acagaguaaa u                                           21

<210> SEQ ID NO 1046
<211> LENGTH: 19
<212> TYPE: RNA
<213> ORGANISM: Influenza B virus

<400> SEQUENCE: 1046
gugcguuuga uuugucaua                                              19

<210> SEQ ID NO 1047
<211> LENGTH: 23
<212> TYPE: RNA
<213> ORGANISM: Influenza B virus

<400> SEQUENCE: 1047
gagugaaaga aggaaauacu uug                                         23

<210> SEQ ID NO 1048
<211> LENGTH: 21
<212> TYPE: RNA
<213> ORGANISM: Influenza B virus
```

```
<400> SEQUENCE: 1048
aagaaucauc gauacaagga u                                              21

<210> SEQ ID NO 1049
<211> LENGTH: 19
<212> TYPE: RNA
<213> ORGANISM: Influenza B virus

<400> SEQUENCE: 1049
ccagacuaca auaauacaa                                                 19

<210> SEQ ID NO 1050
<211> LENGTH: 19
<212> TYPE: RNA
<213> ORGANISM: Influenza B virus

<400> SEQUENCE: 1050
gcauguaggg agugaaaga                                                 19

<210> SEQ ID NO 1051
<211> LENGTH: 21
<212> TYPE: RNA
<213> ORGANISM: Influenza B virus

<400> SEQUENCE: 1051
aaauggaagc aauuguugaa c                                              21

<210> SEQ ID NO 1052
<211> LENGTH: 21
<212> TYPE: RNA
<213> ORGANISM: Influenza B virus

<400> SEQUENCE: 1052
cuguaaggcc ucuacaguua u                                              21

<210> SEQ ID NO 1053
<211> LENGTH: 19
<212> TYPE: RNA
<213> ORGANISM: Influenza B virus

<400> SEQUENCE: 1053
gagaccacaa uaugaagua                                                 19

<210> SEQ ID NO 1054
<211> LENGTH: 19
<212> TYPE: RNA
<213> ORGANISM: Influenza B virus

<400> SEQUENCE: 1054
gccucuacag uuaugauga                                                 19

<210> SEQ ID NO 1055
<211> LENGTH: 19
<212> TYPE: RNA
<213> ORGANISM: Influenza B virus

<400> SEQUENCE: 1055
agggagugaa agaaggaaa                                                 19

<210> SEQ ID NO 1056
<211> LENGTH: 21
<212> TYPE: RNA
<213> ORGANISM: Influenza B virus
```

```
<400> SEQUENCE: 1056
aaguuggaau aacaaaagga u                                       21

<210> SEQ ID NO 1057
<211> LENGTH: 21
<212> TYPE: RNA
<213> ORGANISM: Influenza B virus

<400> SEQUENCE: 1057 gcuuggaga gacuguguaa a                                        21

<210> SEQ ID NO 1058
<211> LENGTH: 21
<212> TYPE: RNA
<213> ORGANISM: Influenza B virus

<400> SEQUENCE: 1058 uugguaaua cagagugcau a                                        21

<210> SEQ ID NO 1059
<211> LENGTH: 19
<212> TYPE: RNA
<213> ORGANISM: Influenza B virus

<400> SEQUENCE: 1059
cgaaacaaug ugccaagaa                                          19

<210> SEQ ID NO 1060
<211> LENGTH: 19
<212> TYPE: RNA
<213> ORGANISM: Influenza B virus

<400> SEQUENCE: 1060
gaguggcugc uugggouca                                          19

<210> SEQ ID NO 1061
<211> LENGTH: 21
<212> TYPE: RNA
<213> ORGANISM: Influenza B virus

<400> SEQUENCE: 1061
aagaaggaaa acuaguaaaa g                                       21

<210> SEQ ID NO 1062
<211> LENGTH: 19
<212> TYPE: RNA
<213> ORGANISM: Influenza B virus

<400> SEQUENCE: 1062
gguuaaagga caaucucau                                          19

<210> SEQ ID NO 1063
<211> LENGTH: 21
<212> TYPE: RNA
<213> ORGANISM: Influenza B virus

<400> SEQUENCE: 1063
uuagcucaag agcauggaau a                                       21

<210> SEQ ID NO 1064
<211> LENGTH: 19
<212> TYPE: RNA
<213> ORGANISM: Influenza B virus
```

```
<400> SEQUENCE: 1064
aggauaugac augaccaaa                                            19

<210> SEQ ID NO 1065
<211> LENGTH: 21
<212> TYPE: RNA
<213> ORGANISM: Influenza B virus

<400> SEQUENCE: 1065
gccgagucua ggagacuucu a                                         21

<210> SEQ ID NO 1066
<211> LENGTH: 21
<212> TYPE: RNA
<213> ORGANISM: Influenza B virus

<400> SEQUENCE: 1066
aaaaggaucc uuuggaaaag c                                         21

<210> SEQ ID NO 1067
<211> LENGTH: 21
<212> TYPE: RNA
<213> ORGANISM: Influenza B virus

<400> SEQUENCE: 1067
guggccaaaa uauacugugu u                                         21

<210> SEQ ID NO 1068
<211> LENGTH: 21
<212> TYPE: RNA
<213> ORGANISM: Influenza B virus

<400> SEQUENCE: 1068
aaggauauga caugaccaaa g                                         21

<210> SEQ ID NO 1069
<211> LENGTH: 19
<212> TYPE: RNA
<213> ORGANISM: Influenza B virus

<400> SEQUENCE: 1069
uggccaaaau auacugugu                                            19

<210> SEQ ID NO 1070
<211> LENGTH: 19
<212> TYPE: RNA
<213> ORGANISM: Influenza B virus

<400> SEQUENCE: 1070
gaaggacaag ggaaagaac                                            19

<210> SEQ ID NO 1071
<211> LENGTH: 21
<212> TYPE: RNA
<213> ORGANISM: Influenza B virus

<400> SEQUENCE: 1071
gacucaggaa aguggccaaa a                                         21

<210> SEQ ID NO 1072
<211> LENGTH: 21
<212> TYPE: RNA
<213> ORGANISM: Influenza B virus
```

```
<400> SEQUENCE: 1072
aagaaucaaa aaugcacgug u                                              21

<210> SEQ ID NO 1073
<211> LENGTH: 21
<212> TYPE: RNA
<213> ORGANISM: Influenza B virus

<400> SEQUENCE: 1073
uacaaccaug agcuaccaga a                                              21

<210> SEQ ID NO 1074
<211> LENGTH: 21
<212> TYPE: RNA
<213> ORGANISM: Influenza B virus

<400> SEQUENCE: 1074
gcuaccagaa guuccauaua a                                              21

<210> SEQ ID NO 1075
<211> LENGTH: 19
<212> TYPE: RNA
<213> ORGANISM: Influenza B virus

<400> SEQUENCE: 1075
gaaggaauga ggagcuaca                                                 19

<210> SEQ ID NO 1076
<211> LENGTH: 23
<212> TYPE: RNA
<213> ORGANISM: Influenza B virus

<400> SEQUENCE: 1076
aucaguagau gaaauaaugg aug                                            23

<210> SEQ ID NO 1077
<211> LENGTH: 21
<212> TYPE: RNA
<213> ORGANISM: Influenza B virus

<400> SEQUENCE: 1077
ucaggaaagu ggccaaaaua u                                              21

<210> SEQ ID NO 1078
<211> LENGTH: 21
<212> TYPE: RNA
<213> ORGANISM: Influenza B virus

<400> SEQUENCE: 1078
ggccaauaug acugagggaa a                                              21

<210> SEQ ID NO 1079
<211> LENGTH: 21
<212> TYPE: RNA
<213> ORGANISM: Influenza B virus

<400> SEQUENCE: 1079
auagacccga aaggagcaau a                                              21

<210> SEQ ID NO 1080
<211> LENGTH: 21
<212> TYPE: RNA
<213> ORGANISM: Influenza B virus
```

```
<400> SEQUENCE: 1080
aaaaaaugua gaguggcugc u                                              21

<210> SEQ ID NO 1081
<211> LENGTH: 19
<212> TYPE: RNA
<213> ORGANISM: Influenza B virus

<400> SEQUENCE: 1081
agcaaggaug ucucccuua                                                 19

<210> SEQ ID NO 1082
<211> LENGTH: 21
<212> TYPE: RNA
<213> ORGANISM: Influenza B virus

<400> SEQUENCE: 1082
aaaauuugag accacaauau g                                              21

<210> SEQ ID NO 1083
<211> LENGTH: 21
<212> TYPE: RNA
<213> ORGANISM: Influenza B virus

<400> SEQUENCE: 1083
aagcauauac agcauuagaa g                                              21

<210> SEQ ID NO 1084
<211> LENGTH: 21
<212> TYPE: RNA
<213> ORGANISM: Influenza B virus

<400> SEQUENCE: 1084
uagggaguga aagaaggaaa u                                              21

<210> SEQ ID NO 1085
<211> LENGTH: 21
<212> TYPE: RNA
<213> ORGANISM: Influenza B virus

<400> SEQUENCE: 1085
aacccuuggg uaauacagag u                                              21

<210> SEQ ID NO 1086
<211> LENGTH: 19
<212> TYPE: RNA
<213> ORGANISM: Influenza B virus

<400> SEQUENCE: 1086
cagcuacaau caagacuau                                                 19

<210> SEQ ID NO 1087
<211> LENGTH: 19
<212> TYPE: RNA
<213> ORGANISM: Influenza B virus

<400> SEQUENCE: 1087
gaguaacgag uuacagaaa                                                 19

<210> SEQ ID NO 1088
<211> LENGTH: 21
<212> TYPE: RNA
<213> ORGANISM: Influenza B virus
```

-continued

```
<400> SEQUENCE: 1088
aaggauuggc ugaugauuac u                                              21

<210> SEQ ID NO 1089
<211> LENGTH: 21
<212> TYPE: RNA
<213> ORGANISM: Influenza B virus

<400> SEQUENCE: 1089
uagaaucagu agaugaaaua a                                              21

<210> SEQ ID NO 1090
<211> LENGTH: 21
<212> TYPE: RNA
<213> ORGANISM: Influenza B virus

<400> SEQUENCE: 1090
gcucuggacc uaccagaaau a                                              21

<210> SEQ ID NO 1091
<211> LENGTH: 19
<212> TYPE: RNA
<213> ORGANISM: Influenza B virus

<400> SEQUENCE: 1091
agcuagaaga ugucugcuu                                                 19

<210> SEQ ID NO 1092
<211> LENGTH: 21
<212> TYPE: RNA
<213> ORGANISM: Influenza B virus

<400> SEQUENCE: 1092
aauuacaacc agcaaugcua u                                              21

<210> SEQ ID NO 1093
<211> LENGTH: 21
<212> TYPE: RNA
<213> ORGANISM: Influenza B virus

<400> SEQUENCE: 1093
augacugagg gaaaguccaa a                                              21

<210> SEQ ID NO 1094
<211> LENGTH: 19
<212> TYPE: RNA
<213> ORGANISM: Influenza B virus

<400> SEQUENCE: 1094
gggaucaaac ugacccaau                                                 19

<210> SEQ ID NO 1095
<211> LENGTH: 21
<212> TYPE: RNA
<213> ORGANISM: Influenza B virus

<400> SEQUENCE: 1095
aaaaagaaag aaaagcuggg a                                              21

<210> SEQ ID NO 1096
<211> LENGTH: 21
<212> TYPE: RNA
<213> ORGANISM: Influenza B virus
```

<210> SEQ ID NO 1097
<211> LENGTH: 21
<212> TYPE: RNA
<213> ORGANISM: Influenza B virus

<400> SEQUENCE: 1096
gaccaauagg gccucacauu u          21

<210> SEQ ID NO 1097
<211> LENGTH: 21
<212> TYPE: RNA
<213> ORGANISM: Influenza B virus

<400> SEQUENCE: 1097
ugggagggaa aaaucugugu a          21

<210> SEQ ID NO 1098
<211> LENGTH: 21
<212> TYPE: RNA
<213> ORGANISM: Influenza B virus

<400> SEQUENCE: 1098
gcaaugccag caugggaaaa u          21

<210> SEQ ID NO 1099
<211> LENGTH: 23
<212> TYPE: RNA
<213> ORGANISM: Influenza B virus

<400> SEQUENCE: 1099
caagaaacuu ccagacuaca aua          23

<210> SEQ ID NO 1100
<211> LENGTH: 19
<212> TYPE: RNA
<213> ORGANISM: Influenza B virus

<400> SEQUENCE: 1100
agggaaugcc aagaaccau          19

<210> SEQ ID NO 1101
<211> LENGTH: 21
<212> TYPE: RNA
<213> ORGANISM: Influenza B virus

<400> SEQUENCE: 1101
uuugugagug ggagggaaaa a          21

<210> SEQ ID NO 1102
<211> LENGTH: 21
<212> TYPE: RNA
<213> ORGANISM: Influenza B virus

<400> SEQUENCE: 1102
ggacaaggga aagaacaaaa u          21

<210> SEQ ID NO 1103
<211> LENGTH: 19
<212> TYPE: RNA
<213> ORGANISM: Influenza B virus

<400> SEQUENCE: 1103
ccuauggcaa guucucaua          19

<210> SEQ ID NO 1104
<211> LENGTH: 19
<212> TYPE: RNA
<213> ORGANISM: Influenza B virus -continued

```
<400> SEQUENCE: 1104
ggaaaugagu aacgaguua                                              19

<210> SEQ ID NO 1105
<211> LENGTH: 21
<212> TYPE: RNA
<213> ORGANISM: Influenza B virus

<400> SEQUENCE: 1105
aaagaaguag caauagauga c                                           21

<210> SEQ ID NO 1106
<211> LENGTH: 21
<212> TYPE: RNA
<213> ORGANISM: Influenza B virus

<400> SEQUENCE: 1106
caaccaugag cuaccagaag u                                           21

<210> SEQ ID NO 1107
<211> LENGTH: 21
<212> TYPE: RNA
<213> ORGANISM: Influenza B virus

<400> SEQUENCE: 1107
aaguagcaau agaugacgaa a                                           21

<210> SEQ ID NO 1108
<211> LENGTH: 21
<212> TYPE: RNA
<213> ORGANISM: Influenza B virus

<400> SEQUENCE: 1108 aaaaucaaa auaauaccaa u                                            21

<210> SEQ ID NO 1109
<211> LENGTH: 19
<212> TYPE: RNA
<213> ORGANISM: Influenza B virus

<400> SEQUENCE: 1109
aguuccauau aaugccuuu                                              19

<210> SEQ ID NO 1110
<211> LENGTH: 19
<212> TYPE: RNA
<213> ORGANISM: Influenza B virus

<400> SEQUENCE: 1110
cacuucauug uugaaugaa                                              19

<210> SEQ ID NO 1111
<211> LENGTH: 19
<212> TYPE: RNA
<213> ORGANISM: Influenza B virus

<400> SEQUENCE: 1111
aggaaugagg agcuacaua                                              19

<210> SEQ ID NO 1112
<211> LENGTH: 21
<212> TYPE: RNA
<213> ORGANISM: Influenza B virus
```

-continued

```
<400> SEQUENCE: 1112
uaucuguucc agcugguuuc u                                              21

<210> SEQ ID NO 1113
<211> LENGTH: 21
<212> TYPE: RNA
<213> ORGANISM: Influenza B virus

<400> SEQUENCE: 1113
aaaagcauau acagcauuag a                                              21

<210> SEQ ID NO 1114
<211> LENGTH: 21
<212> TYPE: RNA
<213> ORGANISM: Influenza B virus

<400> SEQUENCE: 1114
accgaagaca uuagccaaag a                                              21

<210> SEQ ID NO 1115
<211> LENGTH: 21
<212> TYPE: RNA
<213> ORGANISM: Influenza B virus

<400> SEQUENCE: 1115
ugaggagcua cauagacaau a                                              21

<210> SEQ ID NO 1116
<211> LENGTH: 21
<212> TYPE: RNA
<213> ORGANISM: Influenza B virus

<400> SEQUENCE: 1116
aacauaccag aaaauaauga a                                              21

<210> SEQ ID NO 1117
<211> LENGTH: 21
<212> TYPE: RNA
<213> ORGANISM: Influenza B virus

<400> SEQUENCE: 1117
acucaggaaa guggccaaaa u                                              21

<210> SEQ ID NO 1118
<211> LENGTH: 21
<212> TYPE: RNA
<213> ORGANISM: Influenza B virus

<400> SEQUENCE: 1118
auggcaaguu cucauaggag a                                              21

<210> SEQ ID NO 1119
<211> LENGTH: 21
<212> TYPE: RNA
<213> ORGANISM: Influenza B virus

<400> SEQUENCE: 1119
cacagaacuu caggcugaau u                                              21

<210> SEQ ID NO 1120
<211> LENGTH: 19
<212> TYPE: RNA
<213> ORGANISM: Influenza B virus
```

-continued

```
<400> SEQUENCE: 1120
gguccaaaga uccuuagcu                                              19

<210> SEQ ID NO 1121
<211> LENGTH: 19
<212> TYPE: RNA
<213> ORGANISM: Influenza B virus

<400> SEQUENCE: 1121
cgaguuacag aaaaccaau                                              19

<210> SEQ ID NO 1122
<211> LENGTH: 19
<212> TYPE: RNA
<213> ORGANISM: Influenza B virus

<400> SEQUENCE: 1122
gacgaagaag gaaaagcau                                              19

<210> SEQ ID NO 1123
<211> LENGTH: 21
<212> TYPE: RNA
<213> ORGANISM: Influenza B virus

<400> SEQUENCE: 1123
ucaggcugaa uuaagucuga a                                           21

<210> SEQ ID NO 1124
<211> LENGTH: 19
<212> TYPE: RNA
<213> ORGANISM: Influenza B virus

<400> SEQUENCE: 1124
agcuaccaga aguuccaua                                              19

<210> SEQ ID NO 1125
<211> LENGTH: 19
<212> TYPE: RNA
<213> ORGANISM: Influenza B virus

<400> SEQUENCE: 1125
ucuccaauuu ugaaggaau                                              19

<210> SEQ ID NO 1126
<211> LENGTH: 21
<212> TYPE: RNA
<213> ORGANISM: Influenza B virus

<400> SEQUENCE: 1126
ugggaggacc uaagaccaau a                                           21

<210> SEQ ID NO 1127
<211> LENGTH: 21
<212> TYPE: RNA
<213> ORGANISM: Influenza B virus

<400> SEQUENCE: 1127
caaugccagc augggaaaau a                                           21

<210> SEQ ID NO 1128
<211> LENGTH: 19
<212> TYPE: RNA
<213> ORGANISM: Influenza B virus
```

-continued

```
<400> SEQUENCE: 1128
gcggugcguu ugauuuguc                                            19

<210> SEQ ID NO 1129
<211> LENGTH: 21
<212> TYPE: RNA
<213> ORGANISM: Influenza B virus

<400> SEQUENCE: 1129
aagagauuua uagaaguugg a                                         21

<210> SEQ ID NO 1130
<211> LENGTH: 21
<212> TYPE: RNA
<213> ORGANISM: Influenza B virus

<400> SEQUENCE: 1130
gcuuuauggu cuggcgguua a                                         21

<210> SEQ ID NO 1131
<211> LENGTH: 19
<212> TYPE: RNA
<213> ORGANISM: Influenza B virus

<400> SEQUENCE: 1131
cugguuucuc caauuuuga                                            19

<210> SEQ ID NO 1132
<211> LENGTH: 21
<212> TYPE: RNA
<213> ORGANISM: Influenza B virus

<400> SEQUENCE: 1132
aauagaugac gaaacaaugu g                                         21

<210> SEQ ID NO 1133
<211> LENGTH: 21
<212> TYPE: RNA
<213> ORGANISM: Influenza B virus

<400> SEQUENCE: 1133
aauaacaaaa ggauuggcug a                                         21

<210> SEQ ID NO 1134
<211> LENGTH: 19
<212> TYPE: RNA
<213> ORGANISM: Influenza B virus

<400> SEQUENCE: 1134
cugcuucaau caaugcaac                                            19

<210> SEQ ID NO 1135
<211> LENGTH: 19
<212> TYPE: RNA
<213> ORGANISM: Influenza B virus

<400> SEQUENCE: 1135
ugcguccauc uagagguuu                                            19

<210> SEQ ID NO 1136
<211> LENGTH: 19
<212> TYPE: RNA
<213> ORGANISM: Influenza B virus
```

```
<400> SEQUENCE: 1136
cacaggggau ggauuaaca                                              19

<210> SEQ ID NO 1137
<211> LENGTH: 21
<212> TYPE: RNA
<213> ORGANISM: Influenza B virus

<400> SEQUENCE: 1137 ggcccucuaca guuaugauga a                                          21

<210> SEQ ID NO 1138
<211> LENGTH: 21
<212> TYPE: RNA
<213> ORGANISM: Influenza B virus

<400> SEQUENCE: 1138
guccaaaaaa ccgaagacau u                                           21

<210> SEQ ID NO 1139
<211> LENGTH: 21
<212> TYPE: RNA
<213> ORGANISM: Influenza B virus

<400> SEQUENCE: 1139
cagaacuuca ggcugaauua a                                           21

<210> SEQ ID NO 1140
<211> LENGTH: 19
<212> TYPE: RNA
<213> ORGANISM: Influenza B virus

<400> SEQUENCE: 1140
aggaugucuc ccuuaguau                                              19

<210> SEQ ID NO 1141
<211> LENGTH: 21
<212> TYPE: RNA
<213> ORGANISM: Influenza B virus

<400> SEQUENCE: 1141
aagcacuaag aguaauauuu a                                           21

<210> SEQ ID NO 1142
<211> LENGTH: 23
<212> TYPE: RNA
<213> ORGANISM: Influenza B virus

<400> SEQUENCE: 1142
gaugcacuau guauuuggaa aug                                         23

<210> SEQ ID NO 1143
<211> LENGTH: 21
<212> TYPE: RNA
<213> ORGANISM: Influenza B virus

<400> SEQUENCE: 1143
agugccgagu cuaggagacu u                                           21

<210> SEQ ID NO 1144
<211> LENGTH: 21
<212> TYPE: RNA
<213> ORGANISM: Influenza B virus
```

-continued

```
<400> SEQUENCE: 1144
aacaaaauuu gagaccacaa u                                        21

<210> SEQ ID NO 1145
<211> LENGTH: 19
<212> TYPE: RNA
<213> ORGANISM: Influenza B virus

<400> SEQUENCE: 1145
gaaccauagc auggauggu                                           19

<210> SEQ ID NO 1146
<211> LENGTH: 19
<212> TYPE: RNA
<213> ORGANISM: Influenza B virus

<400> SEQUENCE: 1146
aggaaaugag uaacgaguu                                           19

<210> SEQ ID NO 1147
<211> LENGTH: 23
<212> TYPE: RNA
<213> ORGANISM: Influenza B virus

<400> SEQUENCE: 1147
gaauguauua guaacaaccc uug                                      23

<210> SEQ ID NO 1148
<211> LENGTH: 19
<212> TYPE: RNA
<213> ORGANISM: Influenza B virus

<400> SEQUENCE: 1148
gacuaaggga uauaucugu                                           19

<210> SEQ ID NO 1149
<211> LENGTH: 21
<212> TYPE: RNA
<213> ORGANISM: Influenza B virus

<400> SEQUENCE: 1149
aauaagugac augaauuuuc u                                        21

<210> SEQ ID NO 1150
<211> LENGTH: 23
<212> TYPE: RNA
<213> ORGANISM: Influenza B virus

<400> SEQUENCE: 1150
gagaccacaa uaugaaguaa uug                                      23

<210> SEQ ID NO 1151
<211> LENGTH: 21
<212> TYPE: RNA
<213> ORGANISM: Influenza B virus

<400> SEQUENCE: 1151
ugccgaguga auggcacaaa u                                        21

<210> SEQ ID NO 1152
<211> LENGTH: 21
<212> TYPE: RNA
<213> ORGANISM: Influenza B virus
```

<400> SEQUENCE: 1152
aaucuauuga gcacucugac a                                             21

<210> SEQ ID NO 1153
<211> LENGTH: 21
<212> TYPE: RNA
<213> ORGANISM: Influenza B virus

<400> SEQUENCE: 1153
agcucuggac cuaccagaaa u                                             21

<210> SEQ ID NO 1154
<211> LENGTH: 21
<212> TYPE: RNA
<213> ORGANISM: Influenza B virus

<400> SEQUENCE: 1154
aaccaagaau caaaaaugca c                                             21

<210> SEQ ID NO 1155
<211> LENGTH: 19
<212> TYPE: RNA
<213> ORGANISM: Influenza B virus

<400> SEQUENCE: 1155
ggguucaaac agagaugaa                                                19

<210> SEQ ID NO 1156
<211> LENGTH: 21
<212> TYPE: RNA
<213> ORGANISM: Influenza B virus

<400> SEQUENCE: 1156
gggcccuugg guguucgacu u                                             21

<210> SEQ ID NO 1157
<211> LENGTH: 21
<212> TYPE: RNA
<213> ORGANISM: Influenza B virus

<400> SEQUENCE: 1157
agcuaccaga aguuccauau a                                             21

<210> SEQ ID NO 1158
<211> LENGTH: 19
<212> TYPE: RNA
<213> ORGANISM: Influenza B virus

<400> SEQUENCE: 1158
caagaaggaa aacuaguaa                                                19

<210> SEQ ID NO 1159
<211> LENGTH: 21
<212> TYPE: RNA
<213> ORGANISM: Influenza B virus

<400> SEQUENCE: 1159
gacgaagaag gaaaagcaua u                                             21

<210> SEQ ID NO 1160
<211> LENGTH: 19
<212> TYPE: RNA
<213> ORGANISM: Influenza B virus

<400> SEQUENCE: 1160
ccaucuagag guuugcuau                                                19

<210> SEQ ID NO 1161
<211> LENGTH: 21
<212> TYPE: RNA
<213> ORGANISM: Influenza B virus

<400> SEQUENCE: 1161
aauuguugaa caagaaucau c                                             21

<210> SEQ ID NO 1162
<211> LENGTH: 23
<212> TYPE: RNA
<213> ORGANISM: Influenza B virus

<400> SEQUENCE: 1162
gacaagggaa agaacaaaau uug                                           23

<210> SEQ ID NO 1163
<211> LENGTH: 21
<212> TYPE: RNA
<213> ORGANISM: Influenza B virus

<400> SEQUENCE: 1163
guuuaggauu ggcucccuau u                                             21

<210> SEQ ID NO 1164
<211> LENGTH: 21
<212> TYPE: RNA
<213> ORGANISM: Influenza B virus

<400> SEQUENCE: 1164
aaugcuauuc aacaucugcg u                                             21

<210> SEQ ID NO 1165
<211> LENGTH: 21
<212> TYPE: RNA
<213> ORGANISM: Influenza B virus

<400> SEQUENCE: 1165
aaucaucgau acaaggauau g                                             21

<210> SEQ ID NO 1166
<211> LENGTH: 21
<212> TYPE: RNA
<213> ORGANISM: Influenza B virus

<400> SEQUENCE: 1166
gcggugcguu ugauuuguca u                                             21

<210> SEQ ID NO 1167
<211> LENGTH: 21
<212> TYPE: RNA
<213> ORGANISM: Influenza B virus

<400> SEQUENCE: 1167
gagggaaugu auucuggaau a                                             21

<210> SEQ ID NO 1168
<211> LENGTH: 21
<212> TYPE: RNA
<213> ORGANISM: Influenza B virus

```
<400> SEQUENCE: 1168
aaagaaggaa auacuuuguu a                                      21

<210> SEQ ID NO 1169
<211> LENGTH: 21
<212> TYPE: RNA
<213> ORGANISM: Influenza B virus

<400> SEQUENCE: 1169
uugaaggaau gaggagcuac a                                      21

<210> SEQ ID NO 1170
<211> LENGTH: 21
<212> TYPE: RNA
<213> ORGANISM: Influenza B virus

<400> SEQUENCE: 1170
gccagcaugg gaaaauacaa a                                      21

<210> SEQ ID NO 1171
<211> LENGTH: 19
<212> TYPE: RNA
<213> ORGANISM: Influenza B virus

<400> SEQUENCE: 1171
gaaugguugg gcuuugaaa                                         19

<210> SEQ ID NO 1172
<211> LENGTH: 19
<212> TYPE: RNA
<213> ORGANISM: Influenza B virus

<400> SEQUENCE: 1172
ggccucuaca guuaugaug                                         19

<210> SEQ ID NO 1173
<211> LENGTH: 19
<212> TYPE: RNA
<213> ORGANISM: Influenza B virus

<400> SEQUENCE: 1173
gcaaugccag caugggaaa                                         19

<210> SEQ ID NO 1174
<211> LENGTH: 19
<212> TYPE: RNA
<213> ORGANISM: Influenza B virus

<400> SEQUENCE: 1174
gcuagaagau gucugcuuc                                         19

<210> SEQ ID NO 1175
<211> LENGTH: 19
<212> TYPE: RNA
<213> ORGANISM: Influenza B virus

<400> SEQUENCE: 1175
cuucaaucaa ugcaacaaa                                         19

<210> SEQ ID NO 1176
<211> LENGTH: 21
<212> TYPE: RNA
<213> ORGANISM: Influenza B virus
```

```
<400> SEQUENCE: 1176
aggacaaggg aaagaacaaa a                                              21

<210> SEQ ID NO 1177
<211> LENGTH: 21
<212> TYPE: RNA
<213> ORGANISM: Influenza B virus

<400> SEQUENCE: 1177
aaggaaauac uuuguuaaug a                                              21

<210> SEQ ID NO 1178
<211> LENGTH: 21
<212> TYPE: RNA
<213> ORGANISM: Influenza B virus

<400> SEQUENCE: 1178
aaaauucccu auggaagcuu u                                              21

<210> SEQ ID NO 1179
<211> LENGTH: 19
<212> TYPE: RNA
<213> ORGANISM: Influenza B virus

<400> SEQUENCE: 1179
gauguuguaa caguuguaa                                                 19

<210> SEQ ID NO 1180
<211> LENGTH: 21
<212> TYPE: RNA
<213> ORGANISM: Influenza B virus

<400> SEQUENCE: 1180
cucaggaaag uggccaaaau a                                              21

<210> SEQ ID NO 1181
<211> LENGTH: 23
<212> TYPE: RNA
<213> ORGANISM: Influenza B virus

<400> SEQUENCE: 1181
gaaauagcau ggaacugaug aua                                            23

<210> SEQ ID NO 1182
<211> LENGTH: 21
<212> TYPE: RNA
<213> ORGANISM: Influenza B virus

<400> SEQUENCE: 1182
aacgaguuac agaaaaccaa u                                              21

<210> SEQ ID NO 1183
<211> LENGTH: 21
<212> TYPE: RNA
<213> ORGANISM: Influenza B virus

<400> SEQUENCE: 1183
ucgacuuaga gggaauguau u                                              21

<210> SEQ ID NO 1184
<211> LENGTH: 21
<212> TYPE: RNA
<213> ORGANISM: Influenza B virus
```

-continued

```
<400> SEQUENCE: 1184
aaugcaacaa auggaagcaa u                                              21

<210> SEQ ID NO 1185
<211> LENGTH: 21
<212> TYPE: RNA
<213> ORGANISM: Influenza B virus

<400> SEQUENCE: 1185
gccgagugaa uggcacaaau a                                              21

<210> SEQ ID NO 1186
<211> LENGTH: 19
<212> TYPE: RNA
<213> ORGANISM: Influenza B virus

<400> SEQUENCE: 1186
gcaaugcuau ucaacaucu                                                 19

<210> SEQ ID NO 1187
<211> LENGTH: 21
<212> TYPE: RNA
<213> ORGANISM: Influenza B virus

<400> SEQUENCE: 1187
cuuuaugguc uggcgguuaa a                                              21

<210> SEQ ID NO 1188
<211> LENGTH: 21
<212> TYPE: RNA
<213> ORGANISM: Influenza B virus

<400> SEQUENCE: 1188
gagugcauac ugguucaaug a                                              21

<210> SEQ ID NO 1189
<211> LENGTH: 21
<212> TYPE: RNA
<213> ORGANISM: Influenza B virus

<400> SEQUENCE: 1189
gaagagccua aaaucccuaa a                                              21

<210> SEQ ID NO 1190
<211> LENGTH: 19
<212> TYPE: RNA
<213> ORGANISM: Influenza B virus

<400> SEQUENCE: 1190
gccaaagaau gucuagaaa                                                 19

<210> SEQ ID NO 1191
<211> LENGTH: 21
<212> TYPE: RNA
<213> ORGANISM: Influenza B virus

<400> SEQUENCE: 1191
ccagcugguu ucuccaauuu u                                              21

<210> SEQ ID NO 1192
<211> LENGTH: 21
<212> TYPE: RNA
<213> ORGANISM: Influenza B virus
```

```
<400> SEQUENCE: 1192
accagcaaug cuauucaaca u                                      21

<210> SEQ ID NO 1193
<211> LENGTH: 19
<212> TYPE: RNA
<213> ORGANISM: Influenza B virus

<400> SEQUENCE: 1193
gaugguccaa agauccuua                                         19

<210> SEQ ID NO 1194
<211> LENGTH: 19
<212> TYPE: RNA
<213> ORGANISM: Influenza B virus

<400> SEQUENCE: 1194
ggcugaauua agucugaaa                                         19

<210> SEQ ID NO 1195
<211> LENGTH: 21
<212> TYPE: RNA
<213> ORGANISM: Influenza B virus

<400> SEQUENCE: 1195
cagaagcggu gcguuugauu u                                      21

<210> SEQ ID NO 1196
<211> LENGTH: 21
<212> TYPE: RNA
<213> ORGANISM: Influenza B virus

<400> SEQUENCE: 1196
aaaaccaauu augccaagug g                                      21

<210> SEQ ID NO 1197
<211> LENGTH: 21
<212> TYPE: RNA
<213> ORGANISM: Influenza B virus

<400> SEQUENCE: 1197
aaaugaguaa cgaguuacag a                                      21

<210> SEQ ID NO 1198
<211> LENGTH: 21
<212> TYPE: RNA
<213> ORGANISM: Influenza B virus

<400> SEQUENCE: 1198
aagcaauugu ugaacaagaa u                                      21

<210> SEQ ID NO 1199
<211> LENGTH: 21
<212> TYPE: RNA
<213> ORGANISM: Influenza B virus

<400> SEQUENCE: 1199
aaguaaugag gaaaugagua a                                      21

<210> SEQ ID NO 1200
<211> LENGTH: 19
<212> TYPE: RNA
<213> ORGANISM: Influenza B virus
```

-continued

```
<400> SEQUENCE: 1200
cggugcguuu gauuuguca                                                   19

<210> SEQ ID NO 1201
<211> LENGTH: 21
<212> TYPE: RNA
<213> ORGANISM: Influenza B virus

<400> SEQUENCE: 1201
cucccaagua ucuggcugau u                                                21

<210> SEQ ID NO 1202
<211> LENGTH: 21
<212> TYPE: RNA
<213> ORGANISM: Influenza B virus

<400> SEQUENCE: 1202
agcaaggaug ucucccuuag u                                                21

<210> SEQ ID NO 1203
<211> LENGTH: 21
<212> TYPE: RNA
<213> ORGANISM: Influenza B virus

<400> SEQUENCE: 1203
caggaaagug gccaaaauau a                                                21

<210> SEQ ID NO 1204
<211> LENGTH: 21
<212> TYPE: RNA
<213> ORGANISM: Influenza B virus

<400> SEQUENCE: 1204
aacaagaauc aucgauacaa g                                                21

<210> SEQ ID NO 1205
<211> LENGTH: 21
<212> TYPE: RNA
<213> ORGANISM: Influenza B virus

<400> SEQUENCE: 1205
agaccaauag ggccucacau u                                                21

<210> SEQ ID NO 1206
<211> LENGTH: 21
<212> TYPE: RNA
<213> ORGANISM: Influenza B virus

<400> SEQUENCE: 1206 aauuccuau ggaagcuuug g                                                 21

<210> SEQ ID NO 1207
<211> LENGTH: 21
<212> TYPE: RNA
<213> ORGANISM: Influenza B virus

<400> SEQUENCE: 1207
aagaugucug cuucaaucaa u                                                21

<210> SEQ ID NO 1208
<211> LENGTH: 19
<212> TYPE: RNA
<213> ORGANISM: Influenza B virus
```

-continued

<400> SEQUENCE: 1208
ggagagugcu aagcagacu                                                    19

<210> SEQ ID NO 1209
<211> LENGTH: 21
<212> TYPE: RNA
<213> ORGANISM: Influenza B virus

<400> SEQUENCE: 1209
aaggacaagg gaaagaacaa a                                                 21

<210> SEQ ID NO 1210
<211> LENGTH: 19
<212> TYPE: RNA
<213> ORGANISM: Influenza B virus

<400> SEQUENCE: 1210
gacuucuacu guugauuca                                                    19

<210> SEQ ID NO 1211
<211> LENGTH: 21
<212> TYPE: RNA
<213> ORGANISM: Influenza B virus

<400> SEQUENCE: 1211
uucaggcuga auuaagucug a                                                 21

<210> SEQ ID NO 1212
<211> LENGTH: 21
<212> TYPE: RNA
<213> ORGANISM: Influenza B virus

<400> SEQUENCE: 1212
agggagagug cuaagcagac u                                                 21

<210> SEQ ID NO 1213
<211> LENGTH: 21
<212> TYPE: RNA
<213> ORGANISM: Influenza B virus

<400> SEQUENCE: 1213
ugacugaggg aaaguccaaa a                                                 21

<210> SEQ ID NO 1214
<211> LENGTH: 23
<212> TYPE: RNA
<213> ORGANISM: Influenza B virus

<400> SEQUENCE: 1214
gaaggaaaac uaguaaaagg auc                                               23

<210> SEQ ID NO 1215
<211> LENGTH: 19
<212> TYPE: RNA
<213> ORGANISM: Influenza B virus

<400> SEQUENCE: 1215
gaggaaauga guaacgagu                                                    19

<210> SEQ ID NO 1216
<211> LENGTH: 21
<212> TYPE: RNA
<213> ORGANISM: Influenza B virus -continued

```
<400> SEQUENCE: 1216
ugagcacucu gacaaguaaa a                                              21

<210> SEQ ID NO 1217
<211> LENGTH: 19
<212> TYPE: RNA
<213> ORGANISM: Influenza B virus

<400> SEQUENCE: 1217
cuguaaggcc ucuacaguu                                                 19

<210> SEQ ID NO 1218
<211> LENGTH: 21
<212> TYPE: RNA
<213> ORGANISM: Influenza B virus

<400> SEQUENCE: 1218
aaugaggagc uacauagaca a                                              21

<210> SEQ ID NO 1219
<211> LENGTH: 19
<212> TYPE: RNA
<213> ORGANISM: Influenza B virus

<400> SEQUENCE: 1219
cguggagcau guagggagu                                                 19

<210> SEQ ID NO 1220
<211> LENGTH: 21
<212> TYPE: RNA
<213> ORGANISM: Influenza B virus

<400> SEQUENCE: 1220
aaggaaaacu aguaaaagga u                                              21

<210> SEQ ID NO 1221
<211> LENGTH: 19
<212> TYPE: RNA
<213> ORGANISM: Influenza B virus

<400> SEQUENCE: 1221
guuggaauaa caaaaggau                                                 19

<210> SEQ ID NO 1222
<211> LENGTH: 21
<212> TYPE: RNA
<213> ORGANISM: Influenza B virus

<400> SEQUENCE: 1222
aauaugaagu aauugaggga a                                              21

<210> SEQ ID NO 1223
<211> LENGTH: 21
<212> TYPE: RNA
<213> ORGANISM: Influenza B virus

<400> SEQUENCE: 1223 aaaucccua aaaauguag a                                                21

<210> SEQ ID NO 1224
<211> LENGTH: 21
<212> TYPE: RNA
<213> ORGANISM: Influenza B virus
```

```
<400> SEQUENCE: 1224
aauagagacu cccaaguauc u                                              21

<210> SEQ ID NO 1225
<211> LENGTH: 21
<212> TYPE: RNA
<213> ORGANISM: Influenza B virus

<400> SEQUENCE: 1225
aaguaucugg cugauuuguu u                                              21

<210> SEQ ID NO 1226
<211> LENGTH: 21
<212> TYPE: RNA
<213> ORGANISM: Influenza B virus

<400> SEQUENCE: 1226
aacucaagaa ggaaaacuag u                                              21

<210> SEQ ID NO 1227
<211> LENGTH: 21
<212> TYPE: RNA
<213> ORGANISM: Influenza B virus

<400> SEQUENCE: 1227
ucccaaguau cuggcugauu u                                              21

<210> SEQ ID NO 1228
<211> LENGTH: 19
<212> TYPE: RNA
<213> ORGANISM: Influenza B virus

<400> SEQUENCE: 1228
gcuaagcaga cucacagaa                                                 19

<210> SEQ ID NO 1229
<211> LENGTH: 21
<212> TYPE: RNA
<213> ORGANISM: Influenza B virus

<400> SEQUENCE: 1229
uuuaggauug gcucccuauu u                                              21

<210> SEQ ID NO 1230
<211> LENGTH: 19
<212> TYPE: RNA
<213> ORGANISM: Influenza B virus

<400> SEQUENCE: 1230
gagcuaccag aaguuccau                                                 19

<210> SEQ ID NO 1231
<211> LENGTH: 19
<212> TYPE: RNA
<213> ORGANISM: Influenza B virus

<400> SEQUENCE: 1231
ggcacaaaua agauccaaa                                                 19

<210> SEQ ID NO 1232
<211> LENGTH: 21
<212> TYPE: RNA
<213> ORGANISM: Influenza B virus
```

-continued

```
<400> SEQUENCE: 1232
aaugccagag augucaaaga a                                              21

<210> SEQ ID NO 1233
<211> LENGTH: 21
<212> TYPE: RNA
<213> ORGANISM: Influenza B virus

<400> SEQUENCE: 1233
gagggcuauu gagagacauc a                                              21

<210> SEQ ID NO 1234
<211> LENGTH: 19
<212> TYPE: RNA
<213> ORGANISM: Influenza B virus

<400> SEQUENCE: 1234
gagauaaaga agagcgucu                                                 19

<210> SEQ ID NO 1235
<211> LENGTH: 19
<212> TYPE: RNA
<213> ORGANISM: Influenza B virus

<400> SEQUENCE: 1235
cucuaugguu ggguacgaa                                                 19

<210> SEQ ID NO 1236
<211> LENGTH: 21
<212> TYPE: RNA
<213> ORGANISM: Influenza B virus

<400> SEQUENCE: 1236
gugauggcuu caguggacua a                                              21

<210> SEQ ID NO 1237
<211> LENGTH: 21
<212> TYPE: RNA
<213> ORGANISM: Influenza B virus

<400> SEQUENCE: 1237
guacgaagcc auggcucuuu a                                              21

<210> SEQ ID NO 1238
<211> LENGTH: 23
<212> TYPE: RNA
<213> ORGANISM: Influenza B virus

<400> SEQUENCE: 1238
caaucaaagg agguggaacu uua                                            23

<210> SEQ ID NO 1239
<211> LENGTH: 21
<212> TYPE: RNA
<213> ORGANISM: Influenza B virus

<400> SEQUENCE: 1239
gguaucaaca cugggacaau u                                              21

<210> SEQ ID NO 1240
<211> LENGTH: 21
<212> TYPE: RNA
<213> ORGANISM: Influenza B virus
```

```
<400> SEQUENCE: 1240 aagaaaaga augccagaga u                                      21

<210> SEQ ID NO 1241
<211> LENGTH: 21
<212> TYPE: RNA
<213> ORGANISM: Influenza B virus

<400> SEQUENCE: 1241
aagaaaacca guggaaaugc u                                     21

<210> SEQ ID NO 1242
<211> LENGTH: 19
<212> TYPE: RNA
<213> ORGANISM: Influenza B virus

<400> SEQUENCE: 1242
gcagacauug aagaucuaa                                        19

<210> SEQ ID NO 1243
<211> LENGTH: 21
<212> TYPE: RNA
<213> ORGANISM: Influenza B virus

<400> SEQUENCE: 1243
aaaagaacug aaaaucaaaa u                                     21

<210> SEQ ID NO 1244
<211> LENGTH: 21
<212> TYPE: RNA
<213> ORGANISM: Influenza B virus

<400> SEQUENCE: 1244
aaaaggcucu aguugaucaa g                                     21

<210> SEQ ID NO 1245
<211> LENGTH: 21
<212> TYPE: RNA
<213> ORGANISM: Influenza B virus

<400> SEQUENCE: 1245
uacgccaaaa uaccucaacu a                                     21

<210> SEQ ID NO 1246
<211> LENGTH: 21
<212> TYPE: RNA
<213> ORGANISM: Influenza B virus

<400> SEQUENCE: 1246
aagauucuuc ugaaucuaaa a                                     21

<210> SEQ ID NO 1247
<211> LENGTH: 19
<212> TYPE: RNA
<213> ORGANISM: Influenza B virus

<400> SEQUENCE: 1247
gcuguaagaa gaaugcugu                                        19

<210> SEQ ID NO 1248
<211> LENGTH: 21
<212> TYPE: RNA
<213> ORGANISM: Influenza B virus
```

```
<400> SEQUENCE: 1248
ggagggacac agcagaggau u                                              21

<210> SEQ ID NO 1249
<211> LENGTH: 21
<212> TYPE: RNA
<213> ORGANISM: Influenza B virus

<400> SEQUENCE: 1249
acugggacaa uugacaaaac a                                              21

<210> SEQ ID NO 1250
<211> LENGTH: 21
<212> TYPE: RNA
<213> ORGANISM: Influenza B virus

<400> SEQUENCE: 1250
gcaccuuuua caagauggua a                                              21

<210> SEQ ID NO 1251
<211> LENGTH: 19
<212> TYPE: RNA
<213> ORGANISM: Influenza B virus

<400> SEQUENCE: 1251
ggaagagcaa uggcugaca                                                 19

<210> SEQ ID NO 1252
<211> LENGTH: 21
<212> TYPE: RNA
<213> ORGANISM: Influenza B virus

<400> SEQUENCE: 1252
uggcugccac ugaugacaag a                                              21

<210> SEQ ID NO 1253
<211> LENGTH: 21
<212> TYPE: RNA
<213> ORGANISM: Influenza B virus

<400> SEQUENCE: 1253
ugggacaacc agaccaauca u                                              21

<210> SEQ ID NO 1254
<211> LENGTH: 21
<212> TYPE: RNA
<213> ORGANISM: Influenza B virus

<400> SEQUENCE: 1254
aaaauguuuc aaauaucaga c                                              21

<210> SEQ ID NO 1255
<211> LENGTH: 21
<212> TYPE: RNA
<213> ORGANISM: Influenza B virus

<400> SEQUENCE: 1255
gaugucaaag aagggaaaga a                                              21

<210> SEQ ID NO 1256
<211> LENGTH: 21
<212> TYPE: RNA
<213> ORGANISM: Influenza B virus
```

```
<400> SEQUENCE: 1256
ugcgcaugcu guggaaagaa u                                              21

<210> SEQ ID NO 1257
<211> LENGTH: 21
<212> TYPE: RNA
<213> ORGANISM: Influenza B virus

<400> SEQUENCE: 1257
guuggacuug acccuucauu a                                              21

<210> SEQ ID NO 1258
<211> LENGTH: 23
<212> TYPE: RNA
<213> ORGANISM: Influenza B virus

<400> SEQUENCE: 1258
aacaggcaca gaauucaagc cua                                            23

<210> SEQ ID NO 1259
<211> LENGTH: 19
<212> TYPE: RNA
<213> ORGANISM: Influenza B virus

<400> SEQUENCE: 1259
cagacauuga agaucuaac                                                 19

<210> SEQ ID NO 1260
<211> LENGTH: 21
<212> TYPE: RNA
<213> ORGANISM: Influenza B virus

<400> SEQUENCE: 1260
aaaaucaaaa uguccaacau g                                              21

<210> SEQ ID NO 1261
<211> LENGTH: 21
<212> TYPE: RNA
<213> ORGANISM: Influenza B virus

<400> SEQUENCE: 1261
aaucuaaaaa acaaaugcuc u                                              21

<210> SEQ ID NO 1262
<211> LENGTH: 21
<212> TYPE: RNA
<213> ORGANISM: Influenza B virus

<400> SEQUENCE: 1262
aacacuggga caauugacaa a                                              21

<210> SEQ ID NO 1263
<211> LENGTH: 21
<212> TYPE: RNA
<213> ORGANISM: Influenza B virus

<400> SEQUENCE: 1263
ugauggcuuc aguggacuaa a                                              21

<210> SEQ ID NO 1264
<211> LENGTH: 21
<212> TYPE: RNA
<213> ORGANISM: Influenza B virus
```

```
<400> SEQUENCE: 1264
aagaaaaugu uucaaauauc a                                         21

<210> SEQ ID NO 1265
<211> LENGTH: 21
<212> TYPE: RNA
<213> ORGANISM: Influenza B virus

<400> SEQUENCE: 1265
gaguuggacu ugacccuuca u                                         21

<210> SEQ ID NO 1266
<211> LENGTH: 21
<212> TYPE: RNA
<213> ORGANISM: Influenza B virus

<400> SEQUENCE: 1266
accaucuacu ucagcccuau a                                         21

<210> SEQ ID NO 1267
<211> LENGTH: 21
<212> TYPE: RNA
<213> ORGANISM: Influenza B virus

<400> SEQUENCE: 1267
ggugcuuccc auaagcauuu a                                         21

<210> SEQ ID NO 1268
<211> LENGTH: 19
<212> TYPE: RNA
<213> ORGANISM: Influenza B virus

<400> SEQUENCE: 1268
gcuucggagc ugccuauga                                            19

<210> SEQ ID NO 1269
<211> LENGTH: 19
<212> TYPE: RNA
<213> ORGANISM: Influenza B virus

<400> SEQUENCE: 1269
ggaagcacaa uccccagaa                                            19

<210> SEQ ID NO 1270
<211> LENGTH: 21
<212> TYPE: RNA
<213> ORGANISM: Influenza B virus

<400> SEQUENCE: 1270
uggacuugac ccuucauuaa u                                         21

<210> SEQ ID NO 1271
<211> LENGTH: 19
<212> TYPE: RNA
<213> ORGANISM: Influenza B virus

<400> SEQUENCE: 1271
gcuauugaga gacaucaaa                                            19

<210> SEQ ID NO 1272
<211> LENGTH: 21
<212> TYPE: RNA
<213> ORGANISM: Influenza B virus
```

-continued

<400> SEQUENCE: 1272
aucuacuuca gcccuauaag a                                             21

<210> SEQ ID NO 1273
<211> LENGTH: 21
<212> TYPE: RNA
<213> ORGANISM: Influenza B virus

<400> SEQUENCE: 1273
ugaaacuggg cgaauucuau a                                             21

<210> SEQ ID NO 1274
<211> LENGTH: 19
<212> TYPE: RNA
<213> ORGANISM: Influenza B virus

<400> SEQUENCE: 1274
ucgcaauuau ucuucaugu                                                19

<210> SEQ ID NO 1275
<211> LENGTH: 21
<212> TYPE: RNA
<213> ORGANISM: Influenza B virus

<400> SEQUENCE: 1275
acacugggac aauugacaaa a                                             21

<210> SEQ ID NO 1276
<211> LENGTH: 21
<212> TYPE: RNA
<213> ORGANISM: Influenza B virus

<400> SEQUENCE: 1276
gccacugaug acaagaaaac u                                             21

<210> SEQ ID NO 1277
<211> LENGTH: 21
<212> TYPE: RNA
<213> ORGANISM: Influenza B virus

<400> SEQUENCE: 1277
aaaugcuuuc auugggaaga a                                             21

<210> SEQ ID NO 1278
<211> LENGTH: 21
<212> TYPE: RNA
<213> ORGANISM: Influenza B virus

<400> SEQUENCE: 1278
gaugucuguu uccaaagauc a                                             21

<210> SEQ ID NO 1279
<211> LENGTH: 21
<212> TYPE: RNA
<213> ORGANISM: Influenza B virus

<400> SEQUENCE: 1279
aaagaucaaa ggcacuaaaa a                                             21

<210> SEQ ID NO 1280
<211> LENGTH: 19
<212> TYPE: RNA
<213> ORGANISM: Influenza B virus -continued

<400> SEQUENCE: 1280
gcucuaguug aucaaguga                                              19

<210> SEQ ID NO 1281
<211> LENGTH: 21
<212> TYPE: RNA
<213> ORGANISM: Influenza B virus

<400> SEQUENCE: 1281
aauugacaaa acaccggaag a                                           21

<210> SEQ ID NO 1282
<211> LENGTH: 19
<212> TYPE: RNA
<213> ORGANISM: Influenza B virus

<400> SEQUENCE: 1282
cacaagcagu gaagcugau                                              19

<210> SEQ ID NO 1283
<211> LENGTH: 19
<212> TYPE: RNA
<213> ORGANISM: Influenza B virus

<400> SEQUENCE: 1283
cccaacaaaa ggcucuagu                                              19

<210> SEQ ID NO 1284
<211> LENGTH: 21
<212> TYPE: RNA
<213> ORGANISM: Influenza B virus

<400> SEQUENCE: 1284
aagaauggga gaugaugcaa a                                           21

<210> SEQ ID NO 1285
<211> LENGTH: 19
<212> TYPE: RNA
<213> ORGANISM: Influenza B virus

<400> SEQUENCE: 1285
cagggauugc agacauuga                                              19

<210> SEQ ID NO 1286
<211> LENGTH: 19
<212> TYPE: RNA
<213> ORGANISM: Influenza B virus

<400> SEQUENCE: 1286
gaaacugggc gaauucuau                                              19

<210> SEQ ID NO 1287
<211> LENGTH: 21
<212> TYPE: RNA
<213> ORGANISM: Influenza B virus

<400> SEQUENCE: 1287
gaaugccaga gaugucaaag a                                           21

<210> SEQ ID NO 1288
<211> LENGTH: 19
<212> TYPE: RNA
<213> ORGANISM: Influenza B virus

```
<400> SEQUENCE: 1288
gguucaaugu ugaagagua                                          19

<210> SEQ ID NO 1289
<211> LENGTH: 21
<212> TYPE: RNA
<213> ORGANISM: Influenza B virus

<400> SEQUENCE: 1289
aaguaccagu aaaagaacug a                                       21

<210> SEQ ID NO 1290
<211> LENGTH: 21
<212> TYPE: RNA
<213> ORGANISM: Influenza B virus

<400> SEQUENCE: 1290
aaugccagag augucaaaga a                                       21

<210> SEQ ID NO 1291
<211> LENGTH: 19
<212> TYPE: RNA
<213> ORGANISM: Influenza B virus

<400> SEQUENCE: 1291
cguaguaugg ucguuguua                                          19

<210> SEQ ID NO 1292
<211> LENGTH: 21
<212> TYPE: RNA
<213> ORGANISM: Influenza B virus

<400> SEQUENCE: 1292
aaccagugga aaugcuuuca u                                       21

<210> SEQ ID NO 1293
<211> LENGTH: 23
<212> TYPE: RNA
<213> ORGANISM: Influenza B virus

<400> SEQUENCE: 1293
aucaaaggag guggaacuuu agu                                     23

<210> SEQ ID NO 1294
<211> LENGTH: 19
<212> TYPE: RNA
<213> ORGANISM: Influenza B virus

<400> SEQUENCE: 1294
ccaucuacuu cagcccuau                                          19

<210> SEQ ID NO 1295
<211> LENGTH: 21
<212> TYPE: RNA
<213> ORGANISM: Influenza B virus

<400> SEQUENCE: 1295
gauugggcau ucacagauga a                                       21

<210> SEQ ID NO 1296
<211> LENGTH: 19
<212> TYPE: RNA
<213> ORGANISM: Influenza B virus
```

```
<400> SEQUENCE: 1296
gccccaacaa aaggcucua                                              19

<210> SEQ ID NO 1297
<211> LENGTH: 21
<212> TYPE: RNA
<213> ORGANISM: Influenza B virus

<400> SEQUENCE: 1297
aaaacaccgg aagaaauaac u                                           21

<210> SEQ ID NO 1298
<211> LENGTH: 21
<212> TYPE: RNA
<213> ORGANISM: Influenza B virus

<400> SEQUENCE: 1298
augucggaag gaaaacccaa a                                           21

<210> SEQ ID NO 1299
<211> LENGTH: 21
<212> TYPE: RNA
<213> ORGANISM: Influenza B virus

<400> SEQUENCE: 1299
ggcugaagcc auucgauuua u                                           21

<210> SEQ ID NO 1300
<211> LENGTH: 21
<212> TYPE: RNA
<213> ORGANISM: Influenza B virus

<400> SEQUENCE: 1300
aggcccucug uggcgagcaa a                                           21

<210> SEQ ID NO 1301
<211> LENGTH: 21
<212> TYPE: RNA
<213> ORGANISM: Influenza B virus

<400> SEQUENCE: 1301
aauuccagaa gaaaaagaau g                                           21

<210> SEQ ID NO 1302
<211> LENGTH: 19
<212> TYPE: RNA
<213> ORGANISM: Influenza B virus

<400> SEQUENCE: 1302
cugcauuaac aggcacaga                                              19

<210> SEQ ID NO 1303
<211> LENGTH: 21
<212> TYPE: RNA
<213> ORGANISM: Influenza B virus

<400> SEQUENCE: 1303
gggcgaauuc uauaaccaga u                                           21

<210> SEQ ID NO 1304
<211> LENGTH: 21
<212> TYPE: RNA
<213> ORGANISM: Influenza B virus
```

```
<400> SEQUENCE: 1304
aagaaaacug aauuccagaa g                                          21

<210> SEQ ID NO 1305
<211> LENGTH: 21
<212> TYPE: RNA
<213> ORGANISM: Influenza B virus

<400> SEQUENCE: 1305
aacaaaauag acacuaugac u                                          21

<210> SEQ ID NO 1306
<211> LENGTH: 21
<212> TYPE: RNA
<213> ORGANISM: Influenza B virus

<400> SEQUENCE: 1306
aaaauaaaua uaaaaaaugc u                                          21

<210> SEQ ID NO 1307
<211> LENGTH: 19
<212> TYPE: RNA
<213> ORGANISM: Influenza B virus

<400> SEQUENCE: 1307
gccaaaauac cucaacuag                                             19

<210> SEQ ID NO 1308
<211> LENGTH: 19
<212> TYPE: RNA
<213> ORGANISM: Influenza B virus

<400> SEQUENCE: 1308
gucuguuucc aaagaucaa                                             19

<210> SEQ ID NO 1309
<211> LENGTH: 21
<212> TYPE: RNA
<213> ORGANISM: Influenza B virus

<400> SEQUENCE: 1309
aagcacagca uuuucuugug a                                          21

<210> SEQ ID NO 1310
<211> LENGTH: 21
<212> TYPE: RNA
<213> ORGANISM: Influenza B virus

<400> SEQUENCE: 1310
gcugccacug augacaagaa a                                          21

<210> SEQ ID NO 1311
<211> LENGTH: 19
<212> TYPE: RNA
<213> ORGANISM: Influenza B virus

<400> SEQUENCE: 1311
gucaaagaag ggaaagaag                                             19

<210> SEQ ID NO 1312
<211> LENGTH: 19
<212> TYPE: RNA
<213> ORGANISM: Influenza B virus
```

```
<400> SEQUENCE: 1312
gggauugcag acauugaag                                         19

<210> SEQ ID NO 1313
<211> LENGTH: 21
<212> TYPE: RNA
<213> ORGANISM: Influenza B virus

<400> SEQUENCE: 1313
aauguuucaa auaucagaca a                                      21

<210> SEQ ID NO 1314
<211> LENGTH: 21
<212> TYPE: RNA
<213> ORGANISM: Influenza B virus

<400> SEQUENCE: 1314
aaagaaugcc agagauguca a                                      21

<210> SEQ ID NO 1315
<211> LENGTH: 21
<212> TYPE: RNA
<213> ORGANISM: Influenza B virus

<400> SEQUENCE: 1315
aacauggaua uugacgguau c                                      21

<210> SEQ ID NO 1316
<211> LENGTH: 19
<212> TYPE: RNA
<213> ORGANISM: Influenza B virus

<400> SEQUENCE: 1316
ccucaacuag gguucaaug                                         19

<210> SEQ ID NO 1317
<211> LENGTH: 21
<212> TYPE: RNA
<213> ORGANISM: Influenza B virus

<400> SEQUENCE: 1317
caguggacua aaucacauaa u                                      21

<210> SEQ ID NO 1318
<211> LENGTH: 21
<212> TYPE: RNA
<213> ORGANISM: Influenza B virus

<400> SEQUENCE: 1318
gacaaaacac cggaagaaau a                                      21

<210> SEQ ID NO 1319
<211> LENGTH: 19
<212> TYPE: RNA
<213> ORGANISM: Influenza B virus

<400> SEQUENCE: 1319
ggcaacaccu guuuccaua                                         19

<210> SEQ ID NO 1320
<211> LENGTH: 19
<212> TYPE: RNA
<213> ORGANISM: Influenza B virus
```

-continued

```
<400> SEQUENCE: 1320
uggcaacacc uguuuccau                                              19

<210> SEQ ID NO 1321
<211> LENGTH: 19
<212> TYPE: RNA
<213> ORGANISM: Influenza B virus

<400> SEQUENCE: 1321
ggcucuuuac aauauggca                                              19

<210> SEQ ID NO 1322
<211> LENGTH: 21
<212> TYPE: RNA
<213> ORGANISM: Influenza B virus

<400> SEQUENCE: 1322
aauaccucaa cuagguuca a                                            21

<210> SEQ ID NO 1323
<211> LENGTH: 21
<212> TYPE: RNA
<213> ORGANISM: Influenza B virus

<400> SEQUENCE: 1323
gcgcaugcug uggaaagaau u                                           21

<210> SEQ ID NO 1324
<211> LENGTH: 21
<212> TYPE: RNA
<213> ORGANISM: Influenza B virus

<400> SEQUENCE: 1324
guuuggaaug ugggucuuua u                                           21

<210> SEQ ID NO 1325
<211> LENGTH: 21
<212> TYPE: RNA
<213> ORGANISM: Influenza B virus

<400> SEQUENCE: 1325
aaucaaagga gguggaacuu u                                           21

<210> SEQ ID NO 1326
<211> LENGTH: 21
<212> TYPE: RNA
<213> ORGANISM: Influenza B virus

<400> SEQUENCE: 1326
aauaaauaua aaaaaugcug u                                           21

<210> SEQ ID NO 1327
<211> LENGTH: 19
<212> TYPE: RNA
<213> ORGANISM: Influenza B virus

<400> SEQUENCE: 1327
ggauauugac gguaucaac                                              19

<210> SEQ ID NO 1328
<211> LENGTH: 19
<212> TYPE: RNA
<213> ORGANISM: Influenza B virus
```

-continued

```
<400> SEQUENCE: 1328
ggguucaaug uugaagagu                                                    19

<210> SEQ ID NO 1329
<211> LENGTH: 21
<212> TYPE: RNA
<213> ORGANISM: Influenza B virus

<400> SEQUENCE: 1329
aaaaccagug gaaaugcuuu c                                                 21

<210> SEQ ID NO 1330
<211> LENGTH: 19
<212> TYPE: RNA
<213> ORGANISM: Influenza B virus

<400> SEQUENCE: 1330
gcaaaagaua aaucgcaau                                                    19

<210> SEQ ID NO 1331
<211> LENGTH: 21
<212> TYPE: RNA
<213> ORGANISM: Influenza B virus

<400> SEQUENCE: 1331
aaccaucuac uucagcccua u                                                 21

<210> SEQ ID NO 1332
<211> LENGTH: 21
<212> TYPE: RNA
<213> ORGANISM: Influenza B virus

<400> SEQUENCE: 1332
aaucaaaaug uccaacaugg a                                                 21

<210> SEQ ID NO 1333
<211> LENGTH: 23
<212> TYPE: RNA
<213> ORGANISM: Influenza B virus

<400> SEQUENCE: 1333
augugggugu uuauucuuau uaa                                               23

<210> SEQ ID NO 1334
<211> LENGTH: 19
<212> TYPE: RNA
<213> ORGANISM: Influenza B virus

<400> SEQUENCE: 1334
ggcgugaugc agaugucaa                                                    19

<210> SEQ ID NO 1335
<211> LENGTH: 19
<212> TYPE: RNA
<213> ORGANISM: Influenza B virus

<400> SEQUENCE: 1335
gagagaaacc uaauccaaa                                                    19

<210> SEQ ID NO 1336
<211> LENGTH: 21
<212> TYPE: RNA
<213> ORGANISM: Influenza B virus
```

-continued

```
<400> SEQUENCE: 1336
aaauuccaau uaagcagacc a                                              21

<210> SEQ ID NO 1337
<211> LENGTH: 19
<212> TYPE: RNA
<213> ORGANISM: Influenza B virus

<400> SEQUENCE: 1337 ccaugaaaa gauucuucu                                                  19

<210> SEQ ID NO 1338
<211> LENGTH: 21
<212> TYPE: RNA
<213> ORGANISM: Influenza B virus

<400> SEQUENCE: 1338
ggcugccacu gaugacaaga a                                              21

<210> SEQ ID NO 1339
<211> LENGTH: 21
<212> TYPE: RNA
<213> ORGANISM: Influenza B virus

<400> SEQUENCE: 1339
aaaaccaauc ccguugaaau u                                              21

<210> SEQ ID NO 1340
<211> LENGTH: 21
<212> TYPE: RNA
<213> ORGANISM: Influenza B virus

<400> SEQUENCE: 1340
aacugaauuc cagaagaaaa a                                              21

<210> SEQ ID NO 1341
<211> LENGTH: 21
<212> TYPE: RNA
<213> ORGANISM: Influenza B virus

<400> SEQUENCE: 1341
gacuugaccc uucauuaauc a                                              21

<210> SEQ ID NO 1342
<211> LENGTH: 21
<212> TYPE: RNA
<213> ORGANISM: Influenza B virus

<400> SEQUENCE: 1342
aagugaucgg aaguagaaau c                                              21

<210> SEQ ID NO 1343
<211> LENGTH: 21
<212> TYPE: RNA
<213> ORGANISM: Influenza B virus

<400> SEQUENCE: 1343
aaaaacaaaa ccaaucccgu u                                              21

<210> SEQ ID NO 1344
<211> LENGTH: 21
<212> TYPE: RNA
<213> ORGANISM: Influenza B virus
```

```
<400> SEQUENCE: 1344
agcuggacuc aacgaugaca u                                          21

<210> SEQ ID NO 1345
<211> LENGTH: 19
<212> TYPE: RNA
<213> ORGANISM: Influenza B virus

<400> SEQUENCE: 1345
cucguaguau ggucguugu                                             19

<210> SEQ ID NO 1346
<211> LENGTH: 21
<212> TYPE: RNA
<213> ORGANISM: Influenza B virus

<400> SEQUENCE: 1346
aaugugggug uuuauucuua u                                          21

<210> SEQ ID NO 1347
<211> LENGTH: 21
<212> TYPE: RNA
<213> ORGANISM: Influenza B virus

<400> SEQUENCE: 1347
aagcauuuac gccaaaauac c                                          21

<210> SEQ ID NO 1348
<211> LENGTH: 21
<212> TYPE: RNA
<213> ORGANISM: Influenza B virus

<400> SEQUENCE: 1348
gaaacugggc gaauucuaua a                                          21

<210> SEQ ID NO 1349
<211> LENGTH: 19
<212> TYPE: RNA
<213> ORGANISM: Influenza B virus

<400> SEQUENCE: 1349
gacucaacga ugacaugga                                             19

<210> SEQ ID NO 1350
<211> LENGTH: 21
<212> TYPE: RNA
<213> ORGANISM: Influenza B virus

<400> SEQUENCE: 1350
aguuggacuu gacccuucau u                                          21

<210> SEQ ID NO 1351
<211> LENGTH: 21
<212> TYPE: RNA
<213> ORGANISM: Influenza B virus

<400> SEQUENCE: 1351
gguagugaaa cugggcgaau u                                          21

<210> SEQ ID NO 1352
<211> LENGTH: 19
<212> TYPE: RNA
<213> ORGANISM: Influenza B virus
```

-continued

<400> SEQUENCE: 1352
uccaguuuug ggcuccaau                                                  19

<210> SEQ ID NO 1353
<211> LENGTH: 21
<212> TYPE: RNA
<213> ORGANISM: Influenza B virus

<400> SEQUENCE: 1353
aaacugggcg aauucuauaa c                                               21

<210> SEQ ID NO 1354
<211> LENGTH: 19
<212> TYPE: RNA
<213> ORGANISM: Influenza B virus

<400> SEQUENCE: 1354
guacgaagcc auggcucuu                                                  19

<210> SEQ ID NO 1355
<211> LENGTH: 21
<212> TYPE: RNA
<213> ORGANISM: Influenza B virus

<400> SEQUENCE: 1355
aaagaauucu auggcugcc a                                                21

<210> SEQ ID NO 1356
<211> LENGTH: 21
<212> TYPE: RNA
<213> ORGANISM: Influenza B virus

<400> SEQUENCE: 1356
aaaacugaau uccagaagaa a                                               21

<210> SEQ ID NO 1357
<211> LENGTH: 21
<212> TYPE: RNA
<213> ORGANISM: Influenza B virus

<400> SEQUENCE: 1357
aaaaagaaug ccagagaugu c                                               21

<210> SEQ ID NO 1358
<211> LENGTH: 21
<212> TYPE: RNA
<213> ORGANISM: Influenza B virus

<400> SEQUENCE: 1358
ggagagaaac cuaauccaaa a                                               21

<210> SEQ ID NO 1359
<211> LENGTH: 19
<212> TYPE: RNA
<213> ORGANISM: Influenza B virus

<400> SEQUENCE: 1359
cgccaaaaua ccucaacua                                                  19

<210> SEQ ID NO 1360
<211> LENGTH: 21
<212> TYPE: RNA
<213> ORGANISM: Influenza B virus

```
<400> SEQUENCE: 1360
augcgcaugc uguggaaaga a                                        21

<210> SEQ ID NO 1361
<211> LENGTH: 19
<212> TYPE: RNA
<213> ORGANISM: Influenza B virus

<400> SEQUENCE: 1361
cagcauuuuc uugugaacu                                           19

<210> SEQ ID NO 1362
<211> LENGTH: 21
<212> TYPE: RNA
<213> ORGANISM: Influenza B virus

<400> SEQUENCE: 1362
aaaccuaauc caaaaugcgc a                                        21

<210> SEQ ID NO 1363
<211> LENGTH: 19
<212> TYPE: RNA
<213> ORGANISM: Influenza B virus

<400> SEQUENCE: 1363
gaacuucaag uaccaguaa                                           19

<210> SEQ ID NO 1364
<211> LENGTH: 19
<212> TYPE: RNA
<213> ORGANISM: Influenza B virus

<400> SEQUENCE: 1364
ggcuccaaug accagaucu                                           19

<210> SEQ ID NO 1365
<211> LENGTH: 19
<212> TYPE: RNA
<213> ORGANISM: Influenza B virus

<400> SEQUENCE: 1365
gcucuuuaca auauggcaa                                           19

<210> SEQ ID NO 1366
<211> LENGTH: 19
<212> TYPE: RNA
<213> ORGANISM: Influenza B virus

<400> SEQUENCE: 1366
ccgacagaga uaaagaaga                                           19

<210> SEQ ID NO 1367
<211> LENGTH: 19
<212> TYPE: RNA
<213> ORGANISM: Influenza B virus

<400> SEQUENCE: 1367
gcaacuggug uugcaauca                                           19

<210> SEQ ID NO 1368
<211> LENGTH: 21
<212> TYPE: RNA
<213> ORGANISM: Influenza B virus
```

```
<400> SEQUENCE: 1368
agggacacag cagaggauua u                                              21

<210> SEQ ID NO 1369
<211> LENGTH: 19
<212> TYPE: RNA
<213> ORGANISM: Influenza B virus

<400> SEQUENCE: 1369
gaucaaguga ucggaagua                                                 19

<210> SEQ ID NO 1370
<211> LENGTH: 21
<212> TYPE: RNA
<213> ORGANISM: Influenza B virus

<400> SEQUENCE: 1370
aaagaagagc gucuacaaca u                                              21

<210> SEQ ID NO 1371
<211> LENGTH: 21
<212> TYPE: RNA
<213> ORGANISM: Influenza B virus

<400> SEQUENCE: 1371
gagcgucuac aacaugguag u                                              21

<210> SEQ ID NO 1372
<211> LENGTH: 21
<212> TYPE: RNA
<213> ORGANISM: Influenza B virus

<400> SEQUENCE: 1372
aaauaucaga caaaaacaaa a                                              21

<210> SEQ ID NO 1373
<211> LENGTH: 21
<212> TYPE: RNA
<213> ORGANISM: Influenza B virus

<400> SEQUENCE: 1373
aaaauagaca cuaugacugu g                                              21

<210> SEQ ID NO 1374
<211> LENGTH: 19
<212> TYPE: RNA
<213> ORGANISM: Influenza B virus

<400> SEQUENCE: 1374
gaugaaugau gucuguuuc                                                 19

<210> SEQ ID NO 1375
<211> LENGTH: 21
<212> TYPE: RNA
<213> ORGANISM: Influenza B virus

<400> SEQUENCE: 1375
aauguugaag aguacucuau g                                              21

<210> SEQ ID NO 1376
<211> LENGTH: 21
<212> TYPE: RNA
<213> ORGANISM: Influenza B virus
```

-continued

<400> SEQUENCE: 1376
aagggaaaga agaaauagau c  21

<210> SEQ ID NO 1377
<211> LENGTH: 19
<212> TYPE: RNA
<213> ORGANISM: Influenza B virus

<400> SEQUENCE: 1377
gagggcuauu gagagacau  19

<210> SEQ ID NO 1378
<211> LENGTH: 19
<212> TYPE: RNA
<213> ORGANISM: Influenza B virus

<400> SEQUENCE: 1378
cuggacucaa cgaugacau  19

<210> SEQ ID NO 1379
<211> LENGTH: 21
<212> TYPE: RNA
<213> ORGANISM: Influenza B virus

<400> SEQUENCE: 1379
cacagcauuu ucuugugaac u  21

<210> SEQ ID NO 1380
<211> LENGTH: 21
<212> TYPE: RNA
<213> ORGANISM: Influenza B virus

<400> SEQUENCE: 1380
aacuaggguu caauguugaa g  21

<210> SEQ ID NO 1381
<211> LENGTH: 21
<212> TYPE: RNA
<213> ORGANISM: Influenza B virus

<400> SEQUENCE: 1381
aacugaaaau caaaaugucc a  21

<210> SEQ ID NO 1382
<211> LENGTH: 19
<212> TYPE: RNA
<213> ORGANISM: Influenza B virus

<400> SEQUENCE: 1382
cagaugaaug augucuguu  19

<210> SEQ ID NO 1383
<211> LENGTH: 21
<212> TYPE: RNA
<213> ORGANISM: Influenza B virus

<400> SEQUENCE: 1383
cccaccaagc aacaaacgaa u  21

<210> SEQ ID NO 1384
<211> LENGTH: 21
<212> TYPE: RNA
<213> ORGANISM: Influenza B virus -continued

<400> SEQUENCE: 1384
aauagacacu augacuguga u                                              21

<210> SEQ ID NO 1385
<211> LENGTH: 21
<212> TYPE: RNA
<213> ORGANISM: Influenza B virus

<400> SEQUENCE: 1385
aagccauucg auuuauagga a                                              21

<210> SEQ ID NO 1386
<211> LENGTH: 21
<212> TYPE: RNA
<213> ORGANISM: Influenza B virus

<400> SEQUENCE: 1386
auuggcugcc acugaugaca a                                              21

<210> SEQ ID NO 1387
<211> LENGTH: 21
<212> TYPE: RNA
<213> ORGANISM: Influenza B virus

<400> SEQUENCE: 1387
cuucagugga cuaaaucaca u                                              21

<210> SEQ ID NO 1388
<211> LENGTH: 19
<212> TYPE: RNA
<213> ORGANISM: Influenza B virus

<400> SEQUENCE: 1388
caccaagcaa caaacgaau                                                 19

<210> SEQ ID NO 1389
<211> LENGTH: 21
<212> TYPE: RNA
<213> ORGANISM: Influenza B virus

<400> SEQUENCE: 1389
acaccggaag aaauaacuuc u                                              21

<210> SEQ ID NO 1390
<211> LENGTH: 21
<212> TYPE: RNA
<213> ORGANISM: Influenza B virus

<400> SEQUENCE: 1390
aaugggagau gaugcaaaag a                                              21

<210> SEQ ID NO 1391
<211> LENGTH: 21
<212> TYPE: RNA
<213> ORGANISM: Influenza B virus

<400> SEQUENCE: 1391
uuccaaagau caaaggcacu a                                              21

<210> SEQ ID NO 1392
<211> LENGTH: 19
<212> TYPE: RNA
<213> ORGANISM: Influenza B virus -continued

```
<400> SEQUENCE: 1392
gcagcucuga uguccauca                                              19

<210> SEQ ID NO 1393
<211> LENGTH: 21
<212> TYPE: RNA
<213> ORGANISM: Influenza B virus

<400> SEQUENCE: 1393
gggcauucac agaugaauga u                                           21

<210> SEQ ID NO 1394
<211> LENGTH: 21
<212> TYPE: RNA
<213> ORGANISM: Influenza B virus

<400> SEQUENCE: 1394
caagugaucg gaaguagaaa u                                           21

<210> SEQ ID NO 1395
<211> LENGTH: 21
<212> TYPE: RNA
<213> ORGANISM: Influenza B virus

<400> SEQUENCE: 1395
aaacaggagg caccuuuuac a                                           21

<210> SEQ ID NO 1396
<211> LENGTH: 21
<212> TYPE: RNA
<213> ORGANISM: Influenza B virus

<400> SEQUENCE: 1396
agccauggcu cuuuacaaua u                                           21

<210> SEQ ID NO 1397
<211> LENGTH: 19
<212> TYPE: RNA
<213> ORGANISM: Influenza B virus

<400> SEQUENCE: 1397
cuccaguuuu gggcuccaa                                              19

<210> SEQ ID NO 1398
<211> LENGTH: 23
<212> TYPE: RNA
<213> ORGANISM: Influenza B virus

<400> SEQUENCE: 1398
auggagagaa accuaaucca aaa                                         23

<210> SEQ ID NO 1399
<211> LENGTH: 21
<212> TYPE: RNA
<213> ORGANISM: Influenza B virus

<400> SEQUENCE: 1399
cagugggaca accagaccaa u                                           21

<210> SEQ ID NO 1400
<211> LENGTH: 21
<212> TYPE: RNA
<213> ORGANISM: Influenza B virus
```

```
<400> SEQUENCE: 1400
aagaugauga augacucaau g                                         21

<210> SEQ ID NO 1401
<211> LENGTH: 19
<212> TYPE: RNA
<213> ORGANISM: Influenza B virus

<400> SEQUENCE: 1401
ggagaugaug caaaagaua                                            19

<210> SEQ ID NO 1402
<211> LENGTH: 21
<212> TYPE: RNA
<213> ORGANISM: Influenza B virus

<400> SEQUENCE: 1402
aauucuauaa ccagaugaug g                                         21

<210> SEQ ID NO 1403
<211> LENGTH: 19
<212> TYPE: RNA
<213> ORGANISM: Influenza B virus

<400> SEQUENCE: 1403
guagugaaac ugggcgaau                                            19

<210> SEQ ID NO 1404
<211> LENGTH: 21
<212> TYPE: RNA
<213> ORGANISM: Influenza B virus

<400> SEQUENCE: 1404
aaucccguug aaauuccaau u                                         21

<210> SEQ ID NO 1405
<211> LENGTH: 21
<212> TYPE: RNA
<213> ORGANISM: Influenza B virus

<400> SEQUENCE: 1405
aaaaugucca acauggauau u                                         21

<210> SEQ ID NO 1406
<211> LENGTH: 19
<212> TYPE: RNA
<213> ORGANISM: Influenza B virus

<400> SEQUENCE: 1406
gacccuucau uaaucagua                                            19

<210> SEQ ID NO 1407
<211> LENGTH: 21
<212> TYPE: RNA
<213> ORGANISM: Influenza B virus

<400> SEQUENCE: 1407
aaaauaccuc aacuaggguu c                                         21

<210> SEQ ID NO 1408
<211> LENGTH: 21
<212> TYPE: RNA
<213> ORGANISM: Influenza B virus
```

```
<400> SEQUENCE: 1408
gcaugcugug gaaagaauuc u                                              21

<210> SEQ ID NO 1409
<211> LENGTH: 21
<212> TYPE: RNA
<213> ORGANISM: Influenza B virus

<400> SEQUENCE: 1409
aacaccuguu uccauauuaa g                                              21

<210> SEQ ID NO 1410
<211> LENGTH: 21
<212> TYPE: RNA
<213> ORGANISM: Influenza B virus

<400> SEQUENCE: 1410
caugcugugg aaagaauucu a                                              21

<210> SEQ ID NO 1411
<211> LENGTH: 19
<212> TYPE: RNA
<213> ORGANISM: Influenza B virus

<400> SEQUENCE: 1411
cacagcauuu ucuugugaa                                                 19

<210> SEQ ID NO 1412
<211> LENGTH: 21
<212> TYPE: RNA
<213> ORGANISM: Influenza B virus

<400> SEQUENCE: 1412
aaugcgcaug cuguggaaag a                                              21

<210> SEQ ID NO 1413
<211> LENGTH: 21
<212> TYPE: RNA
<213> ORGANISM: Influenza B virus

<400> SEQUENCE: 1413
aaugaugucu guuccaaag a                                               21

<210> SEQ ID NO 1414
<211> LENGTH: 19
<212> TYPE: RNA
<213> ORGANISM: Influenza B virus

<400> SEQUENCE: 1414
ggguuuccau guuccagca                                                 19

<210> SEQ ID NO 1415
<211> LENGTH: 19
<212> TYPE: RNA
<213> ORGANISM: Influenza B virus

<400> SEQUENCE: 1415
ggaaagaaga aauagauca                                                 19

<210> SEQ ID NO 1416
<211> LENGTH: 19
<212> TYPE: RNA
<213> ORGANISM: Influenza B virus
```

```
<400> SEQUENCE: 1416
ggaacaggug gaaggaaug                                                        19

<210> SEQ ID NO 1417
<211> LENGTH: 21
<212> TYPE: RNA
<213> ORGANISM: Influenza B virus

<400> SEQUENCE: 1417
aagccauggc ucuuuacaau a                                                     21

<210> SEQ ID NO 1418
<211> LENGTH: 21
<212> TYPE: RNA
<213> ORGANISM: Influenza B virus

<400> SEQUENCE: 1418
aaaucuacuc aagaugauga a                                                     21

<210> SEQ ID NO 1419
<211> LENGTH: 21
<212> TYPE: RNA
<213> ORGANISM: Influenza B virus

<400> SEQUENCE: 1419
agccaagacu gccuaugaaa a                                                     21

<210> SEQ ID NO 1420
<211> LENGTH: 21
<212> TYPE: RNA
<213> ORGANISM: Influenza B virus

<400> SEQUENCE: 1420
cacagaugaa ugaugucugu u                                                     21

<210> SEQ ID NO 1421
<211> LENGTH: 19
<212> TYPE: RNA
<213> ORGANISM: Influenza B virus

<400> SEQUENCE: 1421
caguggacua aaucacaua                                                        19

<210> SEQ ID NO 1422
<211> LENGTH: 19
<212> TYPE: RNA
<213> ORGANISM: Influenza B virus

<400> SEQUENCE: 1422
guggaacuuu aguggcuga                                                        19

<210> SEQ ID NO 1423
<211> LENGTH: 21
<212> TYPE: RNA
<213> ORGANISM: Influenza B virus

<400> SEQUENCE: 1423
augacaugga gagaaaccua a                                                     21

<210> SEQ ID NO 1424
<211> LENGTH: 21
<212> TYPE: RNA
<213> ORGANISM: Influenza B virus
```

-continued

```
<400> SEQUENCE: 1424
gugggacaac cagaccaauc a                                             21

<210> SEQ ID NO 1425
<211> LENGTH: 21
<212> TYPE: RNA
<213> ORGANISM: Influenza B virus

<400> SEQUENCE: 1425
aauguccaac auggauauug a                                             21

<210> SEQ ID NO 1426
<211> LENGTH: 19
<212> TYPE: RNA
<213> ORGANISM: Influenza B virus

<400> SEQUENCE: 1426
ccuguuucca uauuaagaa                                                19

<210> SEQ ID NO 1427
<211> LENGTH: 21
<212> TYPE: RNA
<213> ORGANISM: Influenza B virus

<400> SEQUENCE: 1427
aaacaaaacc aaucccguug a                                             21

<210> SEQ ID NO 1428
<211> LENGTH: 21
<212> TYPE: RNA
<213> ORGANISM: Influenza B virus

<400> SEQUENCE: 1428
gggcgugaug cagaugucaa a                                             21

<210> SEQ ID NO 1429
<211> LENGTH: 21
<212> TYPE: RNA
<213> ORGANISM: Influenza B virus

<400> SEQUENCE: 1429
aacaaaaggc ucuaguugau c                                             21

<210> SEQ ID NO 1430
<211> LENGTH: 21
<212> TYPE: RNA
<213> ORGANISM: Influenza B virus

<400> SEQUENCE: 1430
aaaagauucu ucugaaucua a                                             21

<210> SEQ ID NO 1431
<211> LENGTH: 19
<212> TYPE: RNA
<213> ORGANISM: Influenza B virus

<400> SEQUENCE: 1431
cacagaauuc aagccuaga                                                19

<210> SEQ ID NO 1432
<211> LENGTH: 21
<212> TYPE: RNA
<213> ORGANISM: Influenza B virus
```

-continued

<400> SEQUENCE: 1432
ugacaaaaca ccggaagaaa u          21

<210> SEQ ID NO 1433
<211> LENGTH: 21
<212> TYPE: RNA
<213> ORGANISM: Influenza B virus

<400> SEQUENCE: 1433
ggagcagaag cacagcauuu u 21

<210> SEQ ID NO 1434
<211> LENGTH: 21
<212> TYPE: RNA
<213> ORGANISM: Influenza B virus

<400> SEQUENCE: 1434
cacagcagag gauuaugaug a 21

<210> SEQ ID NO 1435
<211> LENGTH: 19
<212> TYPE: RNA
<213> ORGANISM: Influenza B virus

<400> SEQUENCE: 1435
cacugggaca auugacaaa 19

<210> SEQ ID NO 1436
<211> LENGTH: 19
<212> TYPE: RNA
<213> ORGANISM: Influenza B virus

<400> SEQUENCE: 1436
gguaucaaca cugggacaa 19

<210> SEQ ID NO 1437
<211> LENGTH: 21
<212> TYPE: RNA
<213> ORGANISM: Influenza B virus

<400> SEQUENCE: 1437
aagacugccu augaaaagau u 21

<210> SEQ ID NO 1438
<211> LENGTH: 21
<212> TYPE: RNA
<213> ORGANISM: Influenza B virus

<400> SEQUENCE: 1438
aucccguuga aauuccaauu a 21

<210> SEQ ID NO 1439
<211> LENGTH: 21
<212> TYPE: RNA
<213> ORGANISM: Influenza B virus

<400> SEQUENCE: 1439
uggagcagaa gcacagcauu u 21

<210> SEQ ID NO 1440
<211> LENGTH: 19
<212> TYPE: RNA
<213> ORGANISM: Influenza B virus

```
<400> SEQUENCE: 1440
acgaugacau ggagagaaa                                              19

<210> SEQ ID NO 1441
<211> LENGTH: 21
<212> TYPE: RNA
<213> ORGANISM: Influenza B virus

<400> SEQUENCE: 1441
aaugacucaa uggcuaagaa a                                           21

<210> SEQ ID NO 1442
<211> LENGTH: 21
<212> TYPE: RNA
<213> ORGANISM: Influenza B virus

<400> SEQUENCE: 1442
uggcuucagu ggacuaaauc a                                           21

<210> SEQ ID NO 1443
<211> LENGTH: 21
<212> TYPE: RNA
<213> ORGANISM: Influenza B virus

<400> SEQUENCE: 1443
aaaggcacua aaaagaguug g                                           21

<210> SEQ ID NO 1444
<211> LENGTH: 19
<212> TYPE: RNA
<213> ORGANISM: Influenza B virus

<400> SEQUENCE: 1444
acgccaaaau accucaacu                                              19

<210> SEQ ID NO 1445
<211> LENGTH: 21
<212> TYPE: RNA
<213> ORGANISM: Influenza B virus

<400> SEQUENCE: 1445
aacuucaagu accaguaaaa g                                           21

<210> SEQ ID NO 1446
<211> LENGTH: 19
<212> TYPE: RNA
<213> ORGANISM: Influenza B virus

<400> SEQUENCE: 1446
caacaaacga auccguaac                                              19

<210> SEQ ID NO 1447
<211> LENGTH: 19
<212> TYPE: RNA
<213> ORGANISM: Influenza B virus

<400> SEQUENCE: 1447
cugagaguuu ugucugcau                                              19

<210> SEQ ID NO 1448
<211> LENGTH: 21
<212> TYPE: RNA
<213> ORGANISM: Influenza B virus
```

```
<400> SEQUENCE: 1448
uggagagaaa ccuaauccaa a                                              21

<210> SEQ ID NO 1449
<211> LENGTH: 21
<212> TYPE: RNA
<213> ORGANISM: Influenza B virus

<400> SEQUENCE: 1449
aaccagugga aaugcuuuca u                                              21

<210> SEQ ID NO 1450
<211> LENGTH: 19
<212> TYPE: RNA
<213> ORGANISM: Influenza B virus

<400> SEQUENCE: 1450
gagacaucaa agccaagac                                                 19

<210> SEQ ID NO 1451
<211> LENGTH: 23
<212> TYPE: RNA
<213> ORGANISM: Influenza B virus

<400> SEQUENCE: 1451
agggcuauug agagacauca aag                                            23

<210> SEQ ID NO 1452
<211> LENGTH: 19
<212> TYPE: RNA
<213> ORGANISM: Influenza B virus

<400> SEQUENCE: 1452
cagcucugau guccaucaa                                                 19

<210> SEQ ID NO 1453
<211> LENGTH: 19
<212> TYPE: RNA
<213> ORGANISM: Influenza B virus

<400> SEQUENCE: 1453
gggcuauuga gagacauca                                                 19

<210> SEQ ID NO 1454
<211> LENGTH: 21
<212> TYPE: RNA
<213> ORGANISM: Influenza B virus

<400> SEQUENCE: 1454
aaagaaggga aagaagaaau a                                              21

<210> SEQ ID NO 1455
<211> LENGTH: 21
<212> TYPE: RNA
<213> ORGANISM: Influenza B virus

<400> SEQUENCE: 1455
aagaacugaa aaucaaaaug u                                              21

<210> SEQ ID NO 1456
<211> LENGTH: 21
<212> TYPE: RNA
<213> ORGANISM: Influenza B virus
```

-continued

```
<400> SEQUENCE: 1456
gaugcagaug ucaaaggaaa u                                              21

<210> SEQ ID NO 1457
<211> LENGTH: 21
<212> TYPE: RNA
<213> ORGANISM: Influenza B virus

<400> SEQUENCE: 1457
aacaccggaa gaaauaacuu c                                              21

<210> SEQ ID NO 1458
<211> LENGTH: 21
<212> TYPE: RNA
<213> ORGANISM: Influenza B virus

<400> SEQUENCE: 1458
aaagcaacaa aauagacacu a                                              21

<210> SEQ ID NO 1459
<211> LENGTH: 19
<212> TYPE: RNA
<213> ORGANISM: Influenza B virus

<400> SEQUENCE: 1459
aggcucuagu ugaucaagu                                                 19

<210> SEQ ID NO 1460
<211> LENGTH: 19
<212> TYPE: RNA
<213> ORGANISM: Influenza B virus

<400> SEQUENCE: 1460
aggaacaggu ggaaggaau                                                 19

<210> SEQ ID NO 1461
<211> LENGTH: 23
<212> TYPE: RNA
<213> ORGANISM: Influenza B virus

<400> SEQUENCE: 1461
gaccaggaaa gaaaaagaag auu                                            23

<210> SEQ ID NO 1462
<211> LENGTH: 23
<212> TYPE: RNA
<213> ORGANISM: Influenza B virus

<400> SEQUENCE: 1462
gagagaaaaa ugagaagaug ugu                                            23

<210> SEQ ID NO 1463
<211> LENGTH: 23
<212> TYPE: RNA
<213> ORGANISM: Influenza B virus

<400> SEQUENCE: 1463
uaacugauau acaaaaagca cua                                            23

<210> SEQ ID NO 1464
<211> LENGTH: 23
<212> TYPE: RNA
<213> ORGANISM: Influenza B virus
```

-continued

```
<400> SEQUENCE: 1464
aaggagaaga cguccaaaaa cug                                            23

<210> SEQ ID NO 1465
<211> LENGTH: 23
<212> TYPE: RNA
<213> ORGANISM: Influenza B virus

<400> SEQUENCE: 1465
caauugccua ccugcuuuca uug                                            23

<210> SEQ ID NO 1466
<211> LENGTH: 21
<212> TYPE: RNA
<213> ORGANISM: Influenza B virus

<400> SEQUENCE: 1466
gaagagcugc aaagcaacau u                                              21

<210> SEQ ID NO 1467
<211> LENGTH: 21
<212> TYPE: RNA
<213> ORGANISM: Influenza B virus

<400> SEQUENCE: 1467
uugguucggu gggaaagaau u                                              21

<210> SEQ ID NO 1468
<211> LENGTH: 19
<212> TYPE: RNA
<213> ORGANISM: Influenza B virus

<400> SEQUENCE: 1468
cccuuaccau ggacaucua                                                 19

<210> SEQ ID NO 1469
<211> LENGTH: 21
<212> TYPE: RNA
<213> ORGANISM: Influenza B virus

<400> SEQUENCE: 1469
aauuuugaga cacaguuacc a                                              21

<210> SEQ ID NO 1470
<211> LENGTH: 23
<212> TYPE: RNA
<213> ORGANISM: Influenza B virus

<400> SEQUENCE: 1470
cugugcuuug ugcgagaaac aag                                            23

<210> SEQ ID NO 1471
<211> LENGTH: 19
<212> TYPE: RNA
<213> ORGANISM: Influenza B virus

<400> SEQUENCE: 1471
gcugcuguuc augccgaaa                                                 19

<210> SEQ ID NO 1472
<211> LENGTH: 23
<212> TYPE: RNA
<213> ORGANISM: Influenza B virus
```

-continued

<400> SEQUENCE: 1472
cauuaaauuc aauuuuuacu gua                                    23

<210> SEQ ID NO 1473
<211> LENGTH: 21
<212> TYPE: RNA
<213> ORGANISM: Influenza B virus

<400> SEQUENCE: 1473
caaagcagaa cuagcagaaa a                                      21

<210> SEQ ID NO 1474
<211> LENGTH: 23
<212> TYPE: RNA
<213> ORGANISM: Influenza B virus

<400> SEQUENCE: 1474
cugcuuucau ugacagaaga ugg                                    23

<210> SEQ ID NO 1475
<211> LENGTH: 21
<212> TYPE: RNA
<213> ORGANISM: Influenza B virus

<400> SEQUENCE: 1475
cagagcucua ugggaaauuc a                                      21

<210> SEQ ID NO 1476
<211> LENGTH: 21
<212> TYPE: RNA
<213> ORGANISM: Influenza B virus

<400> SEQUENCE: 1476
aggaaguacu cucugacaac a                                      21

<210> SEQ ID NO 1477
<211> LENGTH: 23
<212> TYPE: RNA
<213> ORGANISM: Influenza B virus

<400> SEQUENCE: 1477
uuggugccuc uaucugcuuu uua                                    23

<210> SEQ ID NO 1478
<211> LENGTH: 21
<212> TYPE: RNA
<213> ORGANISM: Influenza B virus

<400> SEQUENCE: 1478
uucagcucuu gugaagaaau a                                      21

<210> SEQ ID NO 1479
<211> LENGTH: 23
<212> TYPE: RNA
<213> ORGANISM: Influenza B virus

<400> SEQUENCE: 1479
gucgcuguuu ggagacacaa uug                                    23

<210> SEQ ID NO 1480
<211> LENGTH: 19
<212> TYPE: RNA
<213> ORGANISM: Influenza B virus

<400> SEQUENCE: 1480
ccauccugac cuguuccau 19

<210> SEQ ID NO 1481
<211> LENGTH: 23
<212> TYPE: RNA
<213> ORGANISM: Influenza B virus

<400> SEQUENCE: 1481
uucuagcuga gagaaaaaug aga 23

<210> SEQ ID NO 1482
<211> LENGTH: 21
<212> TYPE: RNA
<213> ORGANISM: Influenza B virus

<400> SEQUENCE: 1482
agugagacga gaaaugcaga u 21

<210> SEQ ID NO 1483
<211> LENGTH: 21
<212> TYPE: RNA
<213> ORGANISM: Influenza B virus

<400> SEQUENCE: 1483
uugccuaccu gcuuucauug a 21

<210> SEQ ID NO 1484
<211> LENGTH: 23
<212> TYPE: RNA
<213> ORGANISM: Influenza B virus

<400> SEQUENCE: 1484
uggagauaga agaauugcau uaa 23

<210> SEQ ID NO 1485
<211> LENGTH: 23
<212> TYPE: RNA
<213> ORGANISM: Influenza B virus

<400> SEQUENCE: 1485
cagcaaaaac aaugaaugga aug 23

<210> SEQ ID NO 1486
<211> LENGTH: 19
<212> TYPE: RNA
<213> ORGANISM: Influenza B virus

<400> SEQUENCE: 1486
gacauuggag gcaaugaaa 19

<210> SEQ ID NO 1487
<211> LENGTH: 21
<212> TYPE: RNA
<213> ORGANISM: Influenza B virus

<400> SEQUENCE: 1487
gguccaaaca aagagacaau a 21

<210> SEQ ID NO 1488
<211> LENGTH: 21
<212> TYPE: RNA
<213> ORGANISM: Influenza B virus

```
<400> SEQUENCE: 1488
cugcaaagca acauuggagu a                                                  21

<210> SEQ ID NO 1489
<211> LENGTH: 19
<212> TYPE: RNA
<213> ORGANISM: Influenza B virus

<400> SEQUENCE: 1489
ccucuauaag cacccagaa                                                     19

<210> SEQ ID NO 1490
<211> LENGTH: 23
<212> TYPE: RNA
<213> ORGANISM: Influenza B virus

<400> SEQUENCE: 1490
cauaguaauu gaggggcuuu cug                                                23

<210> SEQ ID NO 1491
<211> LENGTH: 23
<212> TYPE: RNA
<213> ORGANISM: Influenza B virus

<400> SEQUENCE: 1491
uaauuggugc cucuaucugc uuu                                                23

<210> SEQ ID NO 1492
<211> LENGTH: 21
<212> TYPE: RNA
<213> ORGANISM: Influenza B virus

<400> SEQUENCE: 1492
aaaugagaag augugugagc u                                                  21

<210> SEQ ID NO 1493
<211> LENGTH: 23
<212> TYPE: RNA
<213> ORGANISM: Influenza B virus

<400> SEQUENCE: 1493
caguuuugga gauagaagaa uug                                                23

<210> SEQ ID NO 1494
<211> LENGTH: 21
<212> TYPE: RNA
<213> ORGANISM: Influenza B virus

<400> SEQUENCE: 1494
aauugcaaag gauguaaugg a                                                  21

<210> SEQ ID NO 1495
<211> LENGTH: 23
<212> TYPE: RNA
<213> ORGANISM: Influenza B virus

<400> SEQUENCE: 1495
gacacaguua ccaaaaagaa auc                                                23

<210> SEQ ID NO 1496
<211> LENGTH: 21
<212> TYPE: RNA
<213> ORGANISM: Influenza B virus
```

<400> SEQUENCE: 1496
aagaugugug agcuuucaug a				21

<210> SEQ ID NO 1497
<211> LENGTH: 21
<212> TYPE: RNA
<213> ORGANISM: Influenza B virus

<400> SEQUENCE: 1497
aacaaaagau gcuuaacuga u				21

<210> SEQ ID NO 1498
<211> LENGTH: 21
<212> TYPE: RNA
<213> ORGANISM: Influenza B virus

<400> SEQUENCE: 1498
ugccucuauc ugcuuuuuaa a				21

<210> SEQ ID NO 1499
<211> LENGTH: 21
<212> TYPE: RNA
<213> ORGANISM: Influenza B virus

<400> SEQUENCE: 1499
aacagcaaca aaaaagaaag g				21

<210> SEQ ID NO 1500
<211> LENGTH: 21
<212> TYPE: RNA
<213> ORGANISM: Influenza B virus

<400> SEQUENCE: 1500
aaaaggucca aacaaagaga c				21

<210> SEQ ID NO 1501
<211> LENGTH: 21
<212> TYPE: RNA
<213> ORGANISM: Influenza B virus

<400> SEQUENCE: 1501
ggaaggaauu gcaaaggaug u				21

<210> SEQ ID NO 1502
<211> LENGTH: 23
<212> TYPE: RNA
<213> ORGANISM: Influenza B virus

<400> SEQUENCE: 1502
acccaaagac caggaaagaa aaa			23

<210> SEQ ID NO 1503
<211> LENGTH: 23
<212> TYPE: RNA
<213> ORGANISM: Influenza B virus

<400> SEQUENCE: 1503
gacucugccu uggaauggau aaa			23

<210> SEQ ID NO 1504
<211> LENGTH: 21
<212> TYPE: RNA
<213> ORGANISM: Influenza B virus -continued

```
<400> SEQUENCE: 1504
aagaaauauc uauaaugcua g                                          21

<210> SEQ ID NO 1505
<211> LENGTH: 19
<212> TYPE: RNA
<213> ORGANISM: Influenza B virus

<400> SEQUENCE: 1505
gaccuaugaa uccucugau                                             19

<210> SEQ ID NO 1506
<211> LENGTH: 23
<212> TYPE: RNA
<213> ORGANISM: Influenza B virus

<400> SEQUENCE: 1506
gagacacagu uaccaaaaag aaa                                        23

<210> SEQ ID NO 1507
<211> LENGTH: 21
<212> TYPE: RNA
<213> ORGANISM: Influenza B virus

<400> SEQUENCE: 1507
uccaggccaa agaaacaaug a                                          21

<210> SEQ ID NO 1508
<211> LENGTH: 21
<212> TYPE: RNA
<213> ORGANISM: Influenza B virus

<400> SEQUENCE: 1508
cuuggacaau agggcauuug a                                          21

<210> SEQ ID NO 1509
<211> LENGTH: 21
<212> TYPE: RNA
<213> ORGANISM: Influenza B virus

<400> SEQUENCE: 1509
gauggagaag gcaaagcaga a                                          21

<210> SEQ ID NO 1510
<211> LENGTH: 21
<212> TYPE: RNA
<213> ORGANISM: Influenza B virus

<400> SEQUENCE: 1510
aauaaaaaug ggugaaacag u                                          21

<210> SEQ ID NO 1511
<211> LENGTH: 19
<212> TYPE: RNA
<213> ORGANISM: Influenza B virus

<400> SEQUENCE: 1511
cagcguggag auccugcuu                                             19

<210> SEQ ID NO 1512
<211> LENGTH: 23
<212> TYPE: RNA
<213> ORGANISM: Influenza B virus
```

-continued

```
<400> SEQUENCE: 1512
aagcagaacu agcagaaaaa uua                                          23

<210> SEQ ID NO 1513
<211> LENGTH: 21
<212> TYPE: RNA
<213> ORGANISM: Influenza B virus

<400> SEQUENCE: 1513
aagagauaau aaaaaugggu g                                            21

<210> SEQ ID NO 1514
<211> LENGTH: 23
<212> TYPE: RNA
<213> ORGANISM: Influenza B virus

<400> SEQUENCE: 1514
aaccauuuca gauucuuuca auu                                          23

<210> SEQ ID NO 1515
<211> LENGTH: 23
<212> TYPE: RNA
<213> ORGANISM: Influenza B virus

<400> SEQUENCE: 1515
uaaugcuaga accauuucag auu                                          23

<210> SEQ ID NO 1516
<211> LENGTH: 19
<212> TYPE: RNA
<213> ORGANISM: Influenza B virus

<400> SEQUENCE: 1516
gaguauguuc uuaaugagu                                               19

<210> SEQ ID NO 1517
<211> LENGTH: 19
<212> TYPE: RNA
<213> ORGANISM: Influenza B virus

<400> SEQUENCE: 1517
ccucuaccuc ucagcacu                                                19

<210> SEQ ID NO 1518
<211> LENGTH: 23
<212> TYPE: RNA
<213> ORGANISM: Influenza B virus

<400> SEQUENCE: 1518
cccaaagacc aggaaagaaa aag                                          23

<210> SEQ ID NO 1519
<211> LENGTH: 21
<212> TYPE: RNA
<213> ORGANISM: Influenza B virus

<400> SEQUENCE: 1519
gggaacaaca gcaacaaaaa a                                            21

<210> SEQ ID NO 1520
<211> LENGTH: 23
<212> TYPE: RNA
<213> ORGANISM: Influenza B virus
```

-continued

```
<400> SEQUENCE: 1520
gagacaauaa acagagaggu auc                                           23

<210> SEQ ID NO 1521
<211> LENGTH: 23
<212> TYPE: RNA
<213> ORGANISM: Influenza B virus

<400> SEQUENCE: 1521
ggcuuucugc cgaagagaua aua                                           23

<210> SEQ ID NO 1522
<211> LENGTH: 21
<212> TYPE: RNA
<213> ORGANISM: Influenza B virus

<400> SEQUENCE: 1522
gcgagaaaca agcaucacau u                                             21

<210> SEQ ID NO 1523
<211> LENGTH: 23
<212> TYPE: RNA
<213> ORGANISM: Influenza B virus

<400> SEQUENCE: 1523
gucucauggu cauguaccua aau                                           23

<210> SEQ ID NO 1524
<211> LENGTH: 21
<212> TYPE: RNA
<213> ORGANISM: Influenza B virus

<400> SEQUENCE: 1524
aacauuggag uacugagauc u                                             21

<210> SEQ ID NO 1525
<211> LENGTH: 23
<212> TYPE: RNA
<213> ORGANISM: Influenza B virus

<400> SEQUENCE: 1525
uucaauuugu ucuuuuaucu uau                                           23

<210> SEQ ID NO 1526
<211> LENGTH: 21
<212> TYPE: RNA
<213> ORGANISM: Influenza B virus

<400> SEQUENCE: 1526
agauggucuc agcuaugaac a                                             21

<210> SEQ ID NO 1527
<211> LENGTH: 21
<212> TYPE: RNA
<213> ORGANISM: Influenza B virus

<400> SEQUENCE: 1527
cuuucugccg aagagauaau a                                             21

<210> SEQ ID NO 1528
<211> LENGTH: 23
<212> TYPE: RNA
<213> ORGANISM: Influenza B virus
```

```
<400> SEQUENCE: 1528
accauuucag auucuuucaa uuu                                           23

<210> SEQ ID NO 1529
<211> LENGTH: 21
<212> TYPE: RNA
<213> ORGANISM: Influenza B virus

<400> SEQUENCE: 1529
aaaaaugaga agauguguga g                                             21

<210> SEQ ID NO 1530
<211> LENGTH: 21
<212> TYPE: RNA
<213> ORGANISM: Influenza B virus

<400> SEQUENCE: 1530
aaacccaaag accaggaaag a                                             21

<210> SEQ ID NO 1531
<211> LENGTH: 21
<212> TYPE: RNA
<213> ORGANISM: Influenza B virus

<400> SEQUENCE: 1531
aaccauuuca gauucuuuca a                                             21

<210> SEQ ID NO 1532
<211> LENGTH: 21
<212> TYPE: RNA
<213> ORGANISM: Influenza B virus

<400> SEQUENCE: 1532
aaggccugau ucuagcugag a                                             21

<210> SEQ ID NO 1533
<211> LENGTH: 23
<212> TYPE: RNA
<213> ORGANISM: Influenza B virus

<400> SEQUENCE: 1533
augcuagaac cauuucagau ucu                                           23

<210> SEQ ID NO 1534
<211> LENGTH: 21
<212> TYPE: RNA
<213> ORGANISM: Influenza B virus

<400> SEQUENCE: 1534
gacucugccu uggaauggau a                                             21

<210> SEQ ID NO 1535
<211> LENGTH: 21
<212> TYPE: RNA
<213> ORGANISM: Influenza B virus

<400> SEQUENCE: 1535
aacugauaua caaaaagcac u                                             21

<210> SEQ ID NO 1536
<211> LENGTH: 19
<212> TYPE: RNA
<213> ORGANISM: Influenza B virus
```

```
<400> SEQUENCE: 1536
gcccaagauc cucaacguu                                            19

<210> SEQ ID NO 1537
<211> LENGTH: 21
<212> TYPE: RNA
<213> ORGANISM: Influenza B virus

<400> SEQUENCE: 1537
aaauaaaaag aggaguaaac a                                         21

<210> SEQ ID NO 1538
<211> LENGTH: 21
<212> TYPE: RNA
<213> ORGANISM: Influenza B virus

<400> SEQUENCE: 1538
aacacagcaa aaacaaugaa u                                         21

<210> SEQ ID NO 1539
<211> LENGTH: 21
<212> TYPE: RNA
<213> ORGANISM: Influenza B virus

<400> SEQUENCE: 1539
aaauagcaga aggccaugaa a                                         21

<210> SEQ ID NO 1540
<211> LENGTH: 19
<212> TYPE: RNA
<213> ORGANISM: Influenza B virus

<400> SEQUENCE: 1540
gacuagcagu ggcaucuuc                                            19

<210> SEQ ID NO 1541
<211> LENGTH: 23
<212> TYPE: RNA
<213> ORGANISM: Influenza B virus

<400> SEQUENCE: 1541
ugccucuauc ugcuuuuuaa aac                                       23

<210> SEQ ID NO 1542
<211> LENGTH: 23
<212> TYPE: RNA
<213> ORGANISM: Influenza B virus

<400> SEQUENCE: 1542
uggaauggau aaaaaacaaa aga                                       23

<210> SEQ ID NO 1543
<211> LENGTH: 23
<212> TYPE: RNA
<213> ORGANISM: Influenza B virus

<400> SEQUENCE: 1543
aggaauugca aaggauguaa ugg                                       23

<210> SEQ ID NO 1544
<211> LENGTH: 23
<212> TYPE: RNA
<213> ORGANISM: Influenza B virus
```

```
<400> SEQUENCE: 1544
uauugaguga ccacauagua auu                                          23

<210> SEQ ID NO 1545
<211> LENGTH: 19
<212> TYPE: RNA
<213> ORGANISM: Influenza B virus

<400> SEQUENCE: 1545
aggagaccaa gaaggaagu                                               19

<210> SEQ ID NO 1546
<211> LENGTH: 23
<212> TYPE: RNA
<213> ORGANISM: Influenza B virus

<400> SEQUENCE: 1546
aaauccaggc caaagaaaca aug                                          23

<210> SEQ ID NO 1547
<211> LENGTH: 21
<212> TYPE: RNA
<213> ORGANISM: Influenza B virus

<400> SEQUENCE: 1547
aagcagagcu cuaugggaaa u                                            21

<210> SEQ ID NO 1548
<211> LENGTH: 23
<212> TYPE: RNA
<213> ORGANISM: Influenza B virus

<400> SEQUENCE: 1548
uauacaaaaa gcacuaauug gug                                          23

<210> SEQ ID NO 1549
<211> LENGTH: 23
<212> TYPE: RNA
<213> ORGANISM: Influenza B virus

<400> SEQUENCE: 1549
aaacuaggaa cgcucugugc uuu                                          23

<210> SEQ ID NO 1550
<211> LENGTH: 23
<212> TYPE: RNA
<213> ORGANISM: Influenza B virus

<400> SEQUENCE: 1550
gaccaggaaa gaaaagaag auu                                           23

<210> SEQ ID NO 1551
<211> LENGTH: 21
<212> TYPE: RNA
<213> ORGANISM: Influenza B virus

<400> SEQUENCE: 1551
aagaugcuua acugauauac a                                            21

<210> SEQ ID NO 1552
<211> LENGTH: 19
<212> TYPE: RNA
<213> ORGANISM: Influenza B virus
```

```
<400> SEQUENCE: 1552
ggaaagccca ggguggucaa                                              19

<210> SEQ ID NO 1553
<211> LENGTH: 23
<212> TYPE: RNA
<213> ORGANISM: Influenza B virus

<400> SEQUENCE: 1553
gagacacaau ugccuaccug cuu                                          23

<210> SEQ ID NO 1554
<211> LENGTH: 23
<212> TYPE: RNA
<213> ORGANISM: Influenza B virus

<400> SEQUENCE: 1554
cauggcuugg acaauagggc auu                                          23

<210> SEQ ID NO 1555
<211> LENGTH: 23
<212> TYPE: RNA
<213> ORGANISM: Influenza B virus

<400> SEQUENCE: 1555
uaucuauaau gcuagaacca uuu                                          23

<210> SEQ ID NO 1556
<211> LENGTH: 19
<212> TYPE: RNA
<213> ORGANISM: Influenza B virus

<400> SEQUENCE: 1556
cugucaccaa cuucaacuc                                               19

<210> SEQ ID NO 1557
<211> LENGTH: 21
<212> TYPE: RNA
<213> ORGANISM: Influenza B virus

<400> SEQUENCE: 1557
aacaaaaaag aaaggccuga u                                            21

<210> SEQ ID NO 1558
<211> LENGTH: 21
<212> TYPE: RNA
<213> ORGANISM: Influenza B virus

<400> SEQUENCE: 1558
ugguucggug ggaaagaauu u                                            21

<210> SEQ ID NO 1559
<211> LENGTH: 19
<212> TYPE: RNA
<213> ORGANISM: Influenza B virus

<400> SEQUENCE: 1559
aggacauugc cccaagaua                                               19

<210> SEQ ID NO 1560
<211> LENGTH: 23
<212> TYPE: RNA
<213> ORGANISM: Influenza B virus
```

-continued

```
<400> SEQUENCE: 1560
augaaaauac gaauaaaagg ucc                                           23

<210> SEQ ID NO 1561
<211> LENGTH: 19
<212> TYPE: RNA
<213> ORGANISM: Influenza B virus

<400> SEQUENCE: 1561
ccagugggca gaaucugaa                                                19

<210> SEQ ID NO 1562
<211> LENGTH: 21
<212> TYPE: RNA
<213> ORGANISM: Influenza B virus

<400> SEQUENCE: 1562
gagguauuga gugaccacau a                                             21

<210> SEQ ID NO 1563
<211> LENGTH: 23
<212> TYPE: RNA
<213> ORGANISM: Influenza B virus

<400> SEQUENCE: 1563
cggagugaga cgagaaaugc aga                                           23

<210> SEQ ID NO 1564
<211> LENGTH: 19
<212> TYPE: RNA
<213> ORGANISM: Influenza B virus

<400> SEQUENCE: 1564
gcaucucgag guggagcuu                                                19

<210> SEQ ID NO 1565
<211> LENGTH: 21
<212> TYPE: RNA
<213> ORGANISM: Influenza B virus

<400> SEQUENCE: 1565
gagcuuucau gaagcauuug a                                             21

<210> SEQ ID NO 1566
<211> LENGTH: 21
<212> TYPE: RNA
<213> ORGANISM: Influenza B virus

<400> SEQUENCE: 1566
aaacagagag guaucaauuu u                                             21

<210> SEQ ID NO 1567
<211> LENGTH: 23
<212> TYPE: RNA
<213> ORGANISM: Influenza B virus

<400> SEQUENCE: 1567
gaagaauugc auuaaauuca auu                                           23

<210> SEQ ID NO 1568
<211> LENGTH: 19
<212> TYPE: RNA
<213> ORGANISM: Influenza B virus
```

-continued

```
<400> SEQUENCE: 1568
gaccaucccu auggcaucu                                            19

<210> SEQ ID NO 1569
<211> LENGTH: 19
<212> TYPE: RNA
<213> ORGANISM: Influenza B virus

<400> SEQUENCE: 1569
ccaugccagu ggccuacaa                                            19

<210> SEQ ID NO 1570
<211> LENGTH: 23
<212> TYPE: RNA
<213> ORGANISM: Influenza B virus

<400> SEQUENCE: 1570
gggcuuucug ccgaagagau aau                                       23

<210> SEQ ID NO 1571
<211> LENGTH: 21
<212> TYPE: RNA
<213> ORGANISM: Influenza B virus

<400> SEQUENCE: 1571
gucgcuguuu ggagacacaa u                                         21

<210> SEQ ID NO 1572
<211> LENGTH: 21
<212> TYPE: RNA
<213> ORGANISM: Influenza B virus

<400> SEQUENCE: 1572
aaugggugaa acaguuuggg a                                         21

<210> SEQ ID NO 1573
<211> LENGTH: 21
<212> TYPE: RNA
<213> ORGANISM: Influenza B virus

<400> SEQUENCE: 1573
cucaugguca uguaccuaaa u                                         21

<210> SEQ ID NO 1574
<211> LENGTH: 21
<212> TYPE: RNA
<213> ORGANISM: Influenza B virus

<400> SEQUENCE: 1574
cugugcuuug ugcgagaaac a                                         21

<210> SEQ ID NO 1575
<211> LENGTH: 21
<212> TYPE: RNA
<213> ORGANISM: Influenza B virus

<400> SEQUENCE: 1575
aauuuguucu uuaucuuau c                                          21

<210> SEQ ID NO 1576
<211> LENGTH: 23
<212> TYPE: RNA
<213> ORGANISM: Influenza B virus
```

-continued

```
<400> SEQUENCE: 1576
aagaccagga agaaaaaga aga                                          23

<210> SEQ ID NO 1577
<211> LENGTH: 23
<212> TYPE: RNA
<213> ORGANISM: Influenza B virus

<400> SEQUENCE: 1577
gggaaauuca gcucuuguga aga                                         23

<210> SEQ ID NO 1578
<211> LENGTH: 21
<212> TYPE: RNA
<213> ORGANISM: Influenza B virus

<400> SEQUENCE: 1578
cccaaagacc aggaaagaaa a                                           21

<210> SEQ ID NO 1579
<211> LENGTH: 21
<212> TYPE: RNA
<213> ORGANISM: Influenza B virus

<400> SEQUENCE: 1579
aaaaagaaga uucaucacag a                                           21

<210> SEQ ID NO 1580
<211> LENGTH: 23
<212> TYPE: RNA
<213> ORGANISM: Influenza B virus

<400> SEQUENCE: 1580
aacaaaaaag aaaggccuga uuc                                         23

<210> SEQ ID NO 1581
<211> LENGTH: 23
<212> TYPE: RNA
<213> ORGANISM: Influenza B virus

<400> SEQUENCE: 1581
uugcauuaaa uucaauuuuu acu                                         23

<210> SEQ ID NO 1582
<211> LENGTH: 23
<212> TYPE: RNA
<213> ORGANISM: Influenza B virus

<400> SEQUENCE: 1582
aaacaaaaga ugcuuaacug aua                                         23

<210> SEQ ID NO 1583
<211> LENGTH: 23
<212> TYPE: RNA
<213> ORGANISM: Influenza B virus

<400> SEQUENCE: 1583
ugggaacaac agcaacaaaa aag                                         23

<210> SEQ ID NO 1584
<211> LENGTH: 23
<212> TYPE: RNA
<213> ORGANISM: Influenza B virus
```

```
<400> SEQUENCE: 1584
cacuaauugg ugccucuauc ugc                                        23

<210> SEQ ID NO 1585
<211> LENGTH: 21
<212> TYPE: RNA
<213> ORGANISM: Influenza B virus

<400> SEQUENCE: 1585
augucgcugu uuggagacac a                                          21

<210> SEQ ID NO 1586
<211> LENGTH: 23
<212> TYPE: RNA
<213> ORGANISM: Influenza B virus

<400> SEQUENCE: 1586
uaauaaaaau ggugaaaca guu                                         23

<210> SEQ ID NO 1587
<211> LENGTH: 23
<212> TYPE: RNA
<213> ORGANISM: Influenza B virus

<400> SEQUENCE: 1587
ugccgaagag auaauaaaaa ugg                                        23

<210> SEQ ID NO 1588
<211> LENGTH: 21
<212> TYPE: RNA
<213> ORGANISM: Influenza B virus

<400> SEQUENCE: 1588
aacaacagca acaaaaaaga a                                          21

<210> SEQ ID NO 1589
<211> LENGTH: 23
<212> TYPE: RNA
<213> ORGANISM: Influenza B virus

<400> SEQUENCE: 1589
gagugaccac auaguaauug agg                                        23

<210> SEQ ID NO 1590
<211> LENGTH: 21
<212> TYPE: RNA
<213> ORGANISM: Influenza B virus

<400> SEQUENCE: 1590
cguccaaaaa cuggcagaag a                                          21

<210> SEQ ID NO 1591
<211> LENGTH: 23
<212> TYPE: RNA
<213> ORGANISM: Influenza B virus

<400> SEQUENCE: 1591
caaaaaagaa aggccugauu cua                                        23

<210> SEQ ID NO 1592
<211> LENGTH: 23
<212> TYPE: RNA
<213> ORGANISM: Influenza B virus
```

-continued

```
<400> SEQUENCE: 1592
caugaaagcu cagcgcuacu aua                                        23

<210> SEQ ID NO 1593
<211> LENGTH: 19
<212> TYPE: RNA
<213> ORGANISM: Influenza B virus

<400> SEQUENCE: 1593
gucucuguga ugcugauca                                             19

<210> SEQ ID NO 1594
<211> LENGTH: 23
<212> TYPE: RNA
<213> ORGANISM: Influenza B virus

<400> SEQUENCE: 1594
cugacaacau ggagguauug agu                                        23

<210> SEQ ID NO 1595
<211> LENGTH: 19
<212> TYPE: RNA
<213> ORGANISM: Influenza B virus

<400> SEQUENCE: 1595
acccguacug ucaccaacu                                             19

<210> SEQ ID NO 1596
<211> LENGTH: 21
<212> TYPE: RNA
<213> ORGANISM: Influenza B virus

<400> SEQUENCE: 1596
aaauccugga aauuauucaa u                                          21

<210> SEQ ID NO 1597
<211> LENGTH: 23
<212> TYPE: RNA
<213> ORGANISM: Influenza B virus

<400> SEQUENCE: 1597
caguuuugga gauagaagaa uug                                        23

<210> SEQ ID NO 1598
<211> LENGTH: 23
<212> TYPE: RNA
<213> ORGANISM: Influenza B virus

<400> SEQUENCE: 1598
auggucaugu accuaaaucc ugg                                        23

<210> SEQ ID NO 1599
<211> LENGTH: 21
<212> TYPE: RNA
<213> ORGANISM: Influenza B virus

<400> SEQUENCE: 1599
ggauguaaug gaagugcuaa a                                          21

<210> SEQ ID NO 1600
<211> LENGTH: 21
<212> TYPE: RNA
<213> ORGANISM: Influenza B virus
```

-continued

```
<400> SEQUENCE: 1600
cagaagagcu gcaaagcaac a                                             21

<210> SEQ ID NO 1601
<211> LENGTH: 21
<212> TYPE: RNA
<213> ORGANISM: Influenza B virus

<400> SEQUENCE: 1601
cucuccauuu cauggcuugg a                                             21

<210> SEQ ID NO 1602
<211> LENGTH: 21
<212> TYPE: RNA
<213> ORGANISM: Influenza B virus

<400> SEQUENCE: 1602
aauaaacaga gagguaucaa u                                             21

<210> SEQ ID NO 1603
<211> LENGTH: 23
<212> TYPE: RNA
<213> ORGANISM: Influenza B virus

<400> SEQUENCE: 1603
gacacaauug ccuaccugcu uuc                                           23

<210> SEQ ID NO 1604
<211> LENGTH: 21
<212> TYPE: RNA
<213> ORGANISM: Influenza B virus

<400> SEQUENCE: 1604
aaaaggagaa gacguccaaa a                                             21

<210> SEQ ID NO 1605
<211> LENGTH: 21
<212> TYPE: RNA
<213> ORGANISM: Influenza B virus

<400> SEQUENCE: 1605
aaagaaacaa ugaaggaagu a                                             21

<210> SEQ ID NO 1606
<211> LENGTH: 21
<212> TYPE: RNA
<213> ORGANISM: Influenza B virus

<400> SEQUENCE: 1606
aaagcaacau uggaguacug a                                             21

<210> SEQ ID NO 1607
<211> LENGTH: 19
<212> TYPE: RNA
<213> ORGANISM: Influenza B virus

<400> SEQUENCE: 1607
caggagugug aaguacaga                                                19

<210> SEQ ID NO 1608
<211> LENGTH: 21
<212> TYPE: RNA
<213> ORGANISM: Influenza B virus
```

```
<400> SEQUENCE: 1608
aaaaaagaaa ggccugauuc u                                              21

<210> SEQ ID NO 1609
<211> LENGTH: 21
<212> TYPE: RNA
<213> ORGANISM: Influenza B virus

<400> SEQUENCE: 1609
augagaagau gugugagcuu u                                              21

<210> SEQ ID NO 1610
<211> LENGTH: 21
<212> TYPE: RNA
<213> ORGANISM: Influenza B virus

<400> SEQUENCE: 1610
gggcuuucug ccgaagagau a                                              21

<210> SEQ ID NO 1611
<211> LENGTH: 23
<212> TYPE: RNA
<213> ORGANISM: Influenza B virus

<400> SEQUENCE: 1611
gagaagaugu gugagcuuuc aug                                            23

<210> SEQ ID NO 1612
<211> LENGTH: 19
<212> TYPE: RNA
<213> ORGANISM: Influenza B virus

<400> SEQUENCE: 1612
gaucgcauca cccuugagu                                                 19

<210> SEQ ID NO 1613
<211> LENGTH: 21
<212> TYPE: RNA
<213> ORGANISM: Influenza B virus

<400> SEQUENCE: 1613
gaaggcaaag cagaacuagc a                                              21

<210> SEQ ID NO 1614
<211> LENGTH: 21
<212> TYPE: RNA
<213> ORGANISM: Influenza B virus

<400> SEQUENCE: 1614
aagguccaaa caaagagaca a                                              21

<210> SEQ ID NO 1615
<211> LENGTH: 21
<212> TYPE: RNA
<213> ORGANISM: Influenza B virus

<400> SEQUENCE: 1615
ucgcuguuug gagacacaau u                                              21

<210> SEQ ID NO 1616
<211> LENGTH: 23
<212> TYPE: RNA
<213> ORGANISM: Influenza B virus
```

```
<400> SEQUENCE: 1616
aaaauuacac uguugguucg gug                                              23

<210> SEQ ID NO 1617
<211> LENGTH: 21
<212> TYPE: RNA
<213> ORGANISM: Influenza B virus

<400> SEQUENCE: 1617
ucagcuauga acacagcaaa a                                                21

<210> SEQ ID NO 1618
<211> LENGTH: 23
<212> TYPE: RNA
<213> ORGANISM: Influenza B virus

<400> SEQUENCE: 1618
aggagaagac guccaaaaac ugg                                              23

<210> SEQ ID NO 1619
<211> LENGTH: 21
<212> TYPE: RNA
<213> ORGANISM: Influenza B virus

<400> SEQUENCE: 1619
aaaaggagaa gacguccaaa a                                                21

<210> SEQ ID NO 1620
<211> LENGTH: 19
<212> TYPE: RNA
<213> ORGANISM: Influenza B virus

<400> SEQUENCE: 1620
accugaacca ugauucugu                                                   19

<210> SEQ ID NO 1621
<211> LENGTH: 21
<212> TYPE: RNA
<213> ORGANISM: Influenza B virus

<400> SEQUENCE: 1621
aaaagaaugg ggaaggaauu g                                                21

<210> SEQ ID NO 1622
<211> LENGTH: 19
<212> TYPE: RNA
<213> ORGANISM: Influenza B virus

<400> SEQUENCE: 1622
ccaucuucaa ggagaccaa                                                   19

<210> SEQ ID NO 1623
<211> LENGTH: 19
<212> TYPE: RNA
<213> ORGANISM: Influenza B virus

<400> SEQUENCE: 1623
ccucaccaau gucgucuuc                                                   19

<210> SEQ ID NO 1624
<211> LENGTH: 21
<212> TYPE: RNA
<213> ORGANISM: Influenza B virus
```

```
<400> SEQUENCE: 1624
aaaaauuaca cguugguuc g                                          21

<210> SEQ ID NO 1625
<211> LENGTH: 23
<212> TYPE: RNA
<213> ORGANISM: Influenza B virus

<400> SEQUENCE: 1625
aagcagagcu cuaugggaaa uuc                                       23

<210> SEQ ID NO 1626
<211> LENGTH: 23
<212> TYPE: RNA
<213> ORGANISM: Influenza B virus

<400> SEQUENCE: 1626
gaaacaauga aggaaguacu cuc                                       23

<210> SEQ ID NO 1627
<211> LENGTH: 21
<212> TYPE: RNA
<213> ORGANISM: Influenza B virus

<400> SEQUENCE: 1627
acccaaagac caggaaagaa a                                         21

<210> SEQ ID NO 1628
<211> LENGTH: 21
<212> TYPE: RNA
<213> ORGANISM: Influenza B virus

<400> SEQUENCE: 1628
ucucugacaa cauggaggua u                                         21

<210> SEQ ID NO 1629
<211> LENGTH: 23
<212> TYPE: RNA
<213> ORGANISM: Influenza B virus

<400> SEQUENCE: 1629
gaacacagca aaacaauga aug                                        23

<210> SEQ ID NO 1630
<211> LENGTH: 23
<212> TYPE: RNA
<213> ORGANISM: Influenza B virus

<400> SEQUENCE: 1630
uaaauccugg aaauuauuca aug                                       23

<210> SEQ ID NO 1631
<211> LENGTH: 19
<212> TYPE: RNA
<213> ORGANISM: Influenza B virus

<400> SEQUENCE: 1631
ccaguggccu acaaggaau                                            19

<210> SEQ ID NO 1632
<211> LENGTH: 23
<212> TYPE: RNA
<213> ORGANISM: Influenza B virus
```

```
<400> SEQUENCE: 1632
cugccuugga auggauaaaa aac                                          23

<210> SEQ ID NO 1633
<211> LENGTH: 23
<212> TYPE: RNA
<213> ORGANISM: Influenza B virus

<400> SEQUENCE: 1633
gaccuagacu cugccuugga aug                                          23

<210> SEQ ID NO 1634
<211> LENGTH: 19
<212> TYPE: RNA
<213> ORGANISM: Influenza B virus

<400> SEQUENCE: 1634
gucagaugag caaggacau                                               19

<210> SEQ ID NO 1635
<211> LENGTH: 19
<212> TYPE: RNA
<213> ORGANISM: Influenza B virus

<400> SEQUENCE: 1635
cugugaugcu gaucaauca                                               19

<210> SEQ ID NO 1636
<211> LENGTH: 23
<212> TYPE: RNA
<213> ORGANISM: Influenza B virus

<400> SEQUENCE: 1636
gccuaccugc uuucauugac aga                                          23

<210> SEQ ID NO 1637
<211> LENGTH: 21
<212> TYPE: RNA
<213> ORGANISM: Influenza B virus

<400> SEQUENCE: 1637
ugcagauggu cucagcuaug a                                            21

<210> SEQ ID NO 1638
<211> LENGTH: 19
<212> TYPE: RNA
<213> ORGANISM: Influenza B virus

<400> SEQUENCE: 1638
augacaaugg aguccugau                                               19

<210> SEQ ID NO 1639
<211> LENGTH: 23
<212> TYPE: RNA
<213> ORGANISM: Influenza B virus

<400> SEQUENCE: 1639
cugccgaaga gauaauaaaa aug                                          23

<210> SEQ ID NO 1640
<211> LENGTH: 19
<212> TYPE: RNA
<213> ORGANISM: Influenza B virus
```

```
<400> SEQUENCE: 1640
ccugaccugu uccaucuca                                              19

<210> SEQ ID NO 1641
<211> LENGTH: 23
<212> TYPE: RNA
<213> ORGANISM: Influenza B virus

<400> SEQUENCE: 1641
accaggaaag aaaaagaaga uuc                                         23

<210> SEQ ID NO 1642
<211> LENGTH: 23
<212> TYPE: RNA
<213> ORGANISM: Influenza B virus

<400> SEQUENCE: 1642
accuagacuc ugccuuggaa ugg                                         23

<210> SEQ ID NO 1643
<211> LENGTH: 19
<212> TYPE: RNA
<213> ORGANISM: Influenza B virus

<400> SEQUENCE: 1643
agcauauacu gacacauac                                              19

<210> SEQ ID NO 1644
<211> LENGTH: 19
<212> TYPE: RNA
<213> ORGANISM: Influenza B virus

<400> SEQUENCE: 1644
gggauacuac aauggaaca                                              19

<210> SEQ ID NO 1645
<211> LENGTH: 19
<212> TYPE: RNA
<213> ORGANISM: Influenza B virus

<400> SEQUENCE: 1645
cuugcucuua guggaguaa                                              19

<210> SEQ ID NO 1646
<211> LENGTH: 21
<212> TYPE: RNA
<213> ORGANISM: Influenza B virus

<400> SEQUENCE: 1646
auggagaccc auggacugac a                                           21

<210> SEQ ID NO 1647
<211> LENGTH: 21
<212> TYPE: RNA
<213> ORGANISM: Influenza B virus

<400> SEQUENCE: 1647
uggaggaaug guugagucug u                                           21

<210> SEQ ID NO 1648
<211> LENGTH: 19
<212> TYPE: RNA
<213> ORGANISM: Influenza B virus
```

-continued

```
<400> SEQUENCE: 1648
ggcucaggac aacugcuau                                                    19

<210> SEQ ID NO 1649
<211> LENGTH: 23
<212> TYPE: RNA
<213> ORGANISM: Influenza B virus

<400> SEQUENCE: 1649
gagaagacag aaacaagcua agg                                               23

<210> SEQ ID NO 1650
<211> LENGTH: 23
<212> TYPE: RNA
<213> ORGANISM: Influenza B virus

<400> SEQUENCE: 1650
agggccgaau aauaaaagaa aua                                               23

<210> SEQ ID NO 1651
<211> LENGTH: 23
<212> TYPE: RNA
<213> ORGANISM: Influenza B virus

<400> SEQUENCE: 1651
gacacuguca cagguguuga uau                                               23

<210> SEQ ID NO 1652
<211> LENGTH: 21
<212> TYPE: RNA
<213> ORGANISM: Influenza B virus

<400> SEQUENCE: 1652
aaugcaaaca cuuugcucua a                                                 21

<210> SEQ ID NO 1653
<211> LENGTH: 21
<212> TYPE: RNA
<213> ORGANISM: Influenza B virus

<400> SEQUENCE: 1653
ugugcaaacg caucaaaugu u                                                 21

<210> SEQ ID NO 1654
<211> LENGTH: 21
<212> TYPE: RNA
<213> ORGANISM: Influenza B virus

<400> SEQUENCE: 1654
aaacguuaac ccuauuccuc a                                                 21

<210> SEQ ID NO 1655
<211> LENGTH: 23
<212> TYPE: RNA
<213> ORGANISM: Influenza B virus

<400> SEQUENCE: 1655
uuguccuuac ugaacuuaau ugu                                               23

<210> SEQ ID NO 1656
<211> LENGTH: 19
<212> TYPE: RNA
<213> ORGANISM: Influenza B virus
```

```
<400> SEQUENCE: 1656
gacacuucuu cucccagaa                                                19

<210> SEQ ID NO 1657
<211> LENGTH: 21
<212> TYPE: RNA
<213> ORGANISM: Influenza B virus

<400> SEQUENCE: 1657
auggcucugu aauggaggaa u                                             21

<210> SEQ ID NO 1658
<211> LENGTH: 23
<212> TYPE: RNA
<213> ORGANISM: Influenza B virus

<400> SEQUENCE: 1658
auggcucagc uucagguauu agu                                           23

<210> SEQ ID NO 1659
<211> LENGTH: 19
<212> TYPE: RNA
<213> ORGANISM: Influenza B virus

<400> SEQUENCE: 1659
ggagaagcau auacugaca                                                19

<210> SEQ ID NO 1660
<211> LENGTH: 21
<212> TYPE: RNA
<213> ORGANISM: Influenza B virus

<400> SEQUENCE: 1660
aaagacccuu ugucaaauua a                                             21

<210> SEQ ID NO 1661
<211> LENGTH: 21
<212> TYPE: RNA
<213> ORGANISM: Influenza B virus

<400> SEQUENCE: 1661
caccagcaau gcccuuggau u                                             21

<210> SEQ ID NO 1662
<211> LENGTH: 23
<212> TYPE: RNA
<213> ORGANISM: Influenza B virus

<400> SEQUENCE: 1662
uccccuguau ugggauagag aug                                           23

<210> SEQ ID NO 1663
<211> LENGTH: 23
<212> TYPE: RNA
<213> ORGANISM: Influenza B virus

<400> SEQUENCE: 1663
uccuauuuug uuugaacaau ugu                                           23

<210> SEQ ID NO 1664
<211> LENGTH: 21
<212> TYPE: RNA
<213> ORGANISM: Influenza B virus
```

```
<400> SEQUENCE: 1664
agucuguucu aaacccuuug u                                              21

<210> SEQ ID NO 1665
<211> LENGTH: 21
<212> TYPE: RNA
<213> ORGANISM: Influenza B virus

<400> SEQUENCE: 1665
augcggauuu gccagcaaua a                                              21

<210> SEQ ID NO 1666
<211> LENGTH: 23
<212> TYPE: RNA
<213> ORGANISM: Influenza B virus

<400> SEQUENCE: 1666
gggauagaga ugguacauga ugg                                            23

<210> SEQ ID NO 1667
<211> LENGTH: 23
<212> TYPE: RNA
<213> ORGANISM: Influenza B virus

<400> SEQUENCE: 1667
auccuaagaa cacaagaaag ugc                                            23

<210> SEQ ID NO 1668
<211> LENGTH: 21
<212> TYPE: RNA
<213> ORGANISM: Influenza B virus

<400> SEQUENCE: 1668
ggaugggacu guaugucaag u                                              21

<210> SEQ ID NO 1669
<211> LENGTH: 19
<212> TYPE: RNA
<213> ORGANISM: Influenza B virus

<400> SEQUENCE: 1669
aggaaugguu gagucuguu                                                 19

<210> SEQ ID NO 1670
<211> LENGTH: 21
<212> TYPE: RNA
<213> ORGANISM: Influenza B virus

<400> SEQUENCE: 1670
gauucgagag ggccgaauaa u                                              21

<210> SEQ ID NO 1671
<211> LENGTH: 23
<212> TYPE: RNA
<213> ORGANISM: Influenza B virus

<400> SEQUENCE: 1671
uugaacaauu guccuuacug aac                                            23

<210> SEQ ID NO 1672
<211> LENGTH: 19
<212> TYPE: RNA
<213> ORGANISM: Influenza B virus
```

-continued

```
<400> SEQUENCE: 1672
auccuaagaa cacaagaaa                                                  19

<210> SEQ ID NO 1673
<211> LENGTH: 23
<212> TYPE: RNA
<213> ORGANISM: Influenza B virus

<400> SEQUENCE: 1673
ugcuacccuc aacuauacaa acg                                             23

<210> SEQ ID NO 1674
<211> LENGTH: 23
<212> TYPE: RNA
<213> ORGANISM: Influenza B virus

<400> SEQUENCE: 1674
cucuuagugg aguaaugguu uca                                             23

<210> SEQ ID NO 1675
<211> LENGTH: 19
<212> TYPE: RNA
<213> ORGANISM: Influenza B virus

<400> SEQUENCE: 1675
guggaccaaa ggaaugcaa                                                  19

<210> SEQ ID NO 1676
<211> LENGTH: 21
<212> TYPE: RNA
<213> ORGANISM: Influenza B virus

<400> SEQUENCE: 1676
cuccuuuggc uucgaaauaa a                                               21

<210> SEQ ID NO 1677
<211> LENGTH: 21
<212> TYPE: RNA
<213> ORGANISM: Influenza B virus

<400> SEQUENCE: 1677
ugugucagcu ucacugucau a                                               21

<210> SEQ ID NO 1678
<211> LENGTH: 21
<212> TYPE: RNA
<213> ORGANISM: Influenza B virus

<400> SEQUENCE: 1678
ugagucuguu cuaaacccuu u                                               21

<210> SEQ ID NO 1679
<211> LENGTH: 19
<212> TYPE: RNA
<213> ORGANISM: Influenza B virus

<400> SEQUENCE: 1679
cgggcucaac cuuucagaa                                                  19

<210> SEQ ID NO 1680
<211> LENGTH: 21
<212> TYPE: RNA
<213> ORGANISM: Influenza B virus
```

```
<400> SEQUENCE: 1680
aacauacuga agaaugcaca u                                     21

<210> SEQ ID NO 1681
<211> LENGTH: 19
<212> TYPE: RNA
<213> ORGANISM: Influenza B virus

<400> SEQUENCE: 1681
agcuucacug ucauacuua                                        19

<210> SEQ ID NO 1682
<211> LENGTH: 21
<212> TYPE: RNA
<213> ORGANISM: Influenza B virus

<400> SEQUENCE: 1682
aaaagaaaua uuuccaacag g                                     21

<210> SEQ ID NO 1683
<211> LENGTH: 21
<212> TYPE: RNA
<213> ORGANISM: Influenza B virus

<400> SEQUENCE: 1683
gaguugaugg cccugacagu a                                     21

<210> SEQ ID NO 1684
<211> LENGTH: 21
<212> TYPE: RNA
<213> ORGANISM: Influenza B virus

<400> SEQUENCE: 1684
caagggagga uuuguucauc a                                     21

<210> SEQ ID NO 1685
<211> LENGTH: 21
<212> TYPE: RNA
<213> ORGANISM: Influenza B virus

<400> SEQUENCE: 1685
cgcaugccau gauggugaaag a                                    21

<210> SEQ ID NO 1686
<211> LENGTH: 21
<212> TYPE: RNA
<213> ORGANISM: Influenza B virus

<400> SEQUENCE: 1686
aaugucuaaa acuaaaagga u                                     21

<210> SEQ ID NO 1687
<211> LENGTH: 23
<212> TYPE: RNA
<213> ORGANISM: Influenza B virus

<400> SEQUENCE: 1687
agcaacagcc auuuacuguu uaa                                   23

<210> SEQ ID NO 1688
<211> LENGTH: 21
<212> TYPE: RNA
<213> ORGANISM: Influenza B virus
```

```
<400> SEQUENCE: 1688
ugaugugcac agagacuuau u                                         21

<210> SEQ ID NO 1689
<211> LENGTH: 23
<212> TYPE: RNA
<213> ORGANISM: Influenza B virus

<400> SEQUENCE: 1689
gggaaauugu uaucuuauga uaa                                       23

<210> SEQ ID NO 1690
<211> LENGTH: 21
<212> TYPE: RNA
<213> ORGANISM: Influenza B virus

<400> SEQUENCE: 1690
uggaccaaag gaaugcaaac a                                         21

<210> SEQ ID NO 1691
<211> LENGTH: 21
<212> TYPE: RNA
<213> ORGANISM: Influenza B virus

<400> SEQUENCE: 1691
augggacacu gucacaggug u                                         21

<210> SEQ ID NO 1692
<211> LENGTH: 21
<212> TYPE: RNA
<213> ORGANISM: Influenza B virus

<400> SEQUENCE: 1692
cagguauuag ugagugcaga u                                         21

<210> SEQ ID NO 1693
<211> LENGTH: 21
<212> TYPE: RNA
<213> ORGANISM: Influenza B virus

<400> SEQUENCE: 1693
acacugucac agguguugau a                                         21

<210> SEQ ID NO 1694
<211> LENGTH: 21
<212> TYPE: RNA
<213> ORGANISM: Influenza B virus

<400> SEQUENCE: 1694
guccgcaugc caugauggua a                                         21

<210> SEQ ID NO 1695
<211> LENGTH: 19
<212> TYPE: RNA
<213> ORGANISM: Influenza B virus

<400> SEQUENCE: 1695
cgaacaaugu cuaaaacua                                            19

<210> SEQ ID NO 1696
<211> LENGTH: 21
<212> TYPE: RNA
<213> ORGANISM: Influenza B virus
```

```
<400> SEQUENCE: 1696
gaguggacau acccgcguuu a                                    21

<210> SEQ ID NO 1697
<211> LENGTH: 21
<212> TYPE: RNA
<213> ORGANISM: Influenza B virus

<400> SEQUENCE: 1697
guacuccuuu ggcuucgaaa u                                    21

<210> SEQ ID NO 1698
<211> LENGTH: 21
<212> TYPE: RNA
<213> ORGANISM: Influenza B virus

<400> SEQUENCE: 1698
ugcaccagca augcccuugg a                                    21

<210> SEQ ID NO 1699
<211> LENGTH: 21
<212> TYPE: RNA
<213> ORGANISM: Influenza B virus

<400> SEQUENCE: 1699
aaggagacuu ggcacucagc a                                    21

<210> SEQ ID NO 1700
<211> LENGTH: 21
<212> TYPE: RNA
<213> ORGANISM: Influenza B virus

<400> SEQUENCE: 1700
uccgcaugcc augaugguaa a                                    21

<210> SEQ ID NO 1701
<211> LENGTH: 21
<212> TYPE: RNA
<213> ORGANISM: Influenza B virus

<400> SEQUENCE: 1701
gccagcaaua aaaccauaga a                                    21

<210> SEQ ID NO 1702
<211> LENGTH: 23
<212> TYPE: RNA
<213> ORGANISM: Influenza B virus

<400> SEQUENCE: 1702
uucgaaauaa aagauaagaa aug                                  23

<210> SEQ ID NO 1703
<211> LENGTH: 23
<212> TYPE: RNA
<213> ORGANISM: Influenza B virus

<400> SEQUENCE: 1703
aucaagggag gauuuguuca uca                                  23

<210> SEQ ID NO 1704
<211> LENGTH: 23
<212> TYPE: RNA
<213> ORGANISM: Influenza B virus
```

-continued

<400> SEQUENCE: 1704
guccuuacug aacuuaauug uuu                                    23

<210> SEQ ID NO 1705
<211> LENGTH: 21
<212> TYPE: RNA
<213> ORGANISM: Influenza B virus

<400> SEQUENCE: 1705
aaaaagaccc uuugucaaau u                                      21

<210> SEQ ID NO 1706
<211> LENGTH: 23
<212> TYPE: RNA
<213> ORGANISM: Influenza B virus

<400> SEQUENCE: 1706
acccuuuguc aaauuaaaug ugg                                    23

<210> SEQ ID NO 1707
<211> LENGTH: 21
<212> TYPE: RNA
<213> ORGANISM: Influenza B virus

<400> SEQUENCE: 1707
cagcaacagc cauuuacugu u                                      21

<210> SEQ ID NO 1708
<211> LENGTH: 19
<212> TYPE: RNA
<213> ORGANISM: Influenza B virus

<400> SEQUENCE: 1708
ccuguagaga uaacaguua                                         19

<210> SEQ ID NO 1709
<211> LENGTH: 21
<212> TYPE: RNA
<213> ORGANISM: Influenza B virus

<400> SEQUENCE: 1709
ucagcuucac ugucauacuu a                                      21

<210> SEQ ID NO 1710
<211> LENGTH: 19
<212> TYPE: RNA
<213> ORGANISM: Influenza B virus

<400> SEQUENCE: 1710
gaguggacau acccgcguu                                         19

<210> SEQ ID NO 1711
<211> LENGTH: 21
<212> TYPE: RNA
<213> ORGANISM: Influenza B virus

<400> SEQUENCE: 1711
aaugcuaccc ucaacuauac a                                      21

<210> SEQ ID NO 1712
<211> LENGTH: 21
<212> TYPE: RNA
<213> ORGANISM: Influenza B virus -continued

```
<400> SEQUENCE: 1712
caggacaacu gcuaugggac a                                              21

<210> SEQ ID NO 1713
<211> LENGTH: 23
<212> TYPE: RNA
<213> ORGANISM: Influenza B virus

<400> SEQUENCE: 1713
gugccuguag agauaacagu uac                                            23

<210> SEQ ID NO 1714
<211> LENGTH: 23
<212> TYPE: RNA
<213> ORGANISM: Influenza B virus

<400> SEQUENCE: 1714
ugcucuuagu ggaguaaugg uuu                                            23

<210> SEQ ID NO 1715
<211> LENGTH: 23
<212> TYPE: RNA
<213> ORGANISM: Influenza B virus

<400> SEQUENCE: 1715
cucagcuuca gguauuagug agu                                            23

<210> SEQ ID NO 1716
<211> LENGTH: 21
<212> TYPE: RNA
<213> ORGANISM: Influenza B virus

<400> SEQUENCE: 1716
ggcucagcuu cagguauuag u                                              21

<210> SEQ ID NO 1717
<211> LENGTH: 21
<212> TYPE: RNA
<213> ORGANISM: Influenza B virus

<400> SEQUENCE: 1717
ugcuacccuc aacuauacaa a                                              21

<210> SEQ ID NO 1718
<211> LENGTH: 21
<212> TYPE: RNA
<213> ORGANISM: Influenza B virus

<400> SEQUENCE: 1718
aaugcccuug gauugugcaa a                                              21

<210> SEQ ID NO 1719
<211> LENGTH: 23
<212> TYPE: RNA
<213> ORGANISM: Influenza B virus

<400> SEQUENCE: 1719
gagggccgaa uaauaaaaga aau                                            23

<210> SEQ ID NO 1720
<211> LENGTH: 21
<212> TYPE: RNA
<213> ORGANISM: Influenza B virus
```

-continued

```
<400> SEQUENCE: 1720
cagaccagau gauggaagca u                                              21

<210> SEQ ID NO 1721
<211> LENGTH: 23
<212> TYPE: RNA
<213> ORGANISM: Influenza B virus

<400> SEQUENCE: 1721
ucggauauau ugcuaaaauu uuc                                            23

<210> SEQ ID NO 1722
<211> LENGTH: 21
<212> TYPE: RNA
<213> ORGANISM: Influenza B virus

<400> SEQUENCE: 1722
augggcucag gacaacugcu a                                              21

<210> SEQ ID NO 1723
<211> LENGTH: 19
<212> TYPE: RNA
<213> ORGANISM: Influenza B virus

<400> SEQUENCE: 1723
cccucaacua uacaaacgu                                                 19

<210> SEQ ID NO 1724
<211> LENGTH: 19
<212> TYPE: RNA
<213> ORGANISM: Influenza B virus

<400> SEQUENCE: 1724
agucuguucu aaacccuuu                                                 19

<210> SEQ ID NO 1725
<211> LENGTH: 19
<212> TYPE: RNA
<213> ORGANISM: Influenza B virus

<400> SEQUENCE: 1725
gcaaacaaca uccuaagaa                                                 19

<210> SEQ ID NO 1726
<211> LENGTH: 21
<212> TYPE: RNA
<213> ORGANISM: Influenza B virus

<400> SEQUENCE: 1726
aaaaccauag aaugugccug u                                              21

<210> SEQ ID NO 1727
<211> LENGTH: 19
<212> TYPE: RNA
<213> ORGANISM: Influenza B virus

<400> SEQUENCE: 1727
ggaugggacu guaugucaa                                                 19

<210> SEQ ID NO 1728
<211> LENGTH: 19
<212> TYPE: RNA
<213> ORGANISM: Influenza B virus
```

```
<400> SEQUENCE: 1728
gacacauacc auuccuaug                                                    19

<210> SEQ ID NO 1729
<211> LENGTH: 21
<212> TYPE: RNA
<213> ORGANISM: Influenza B virus

<400> SEQUENCE: 1729
aauauggaga agcauauacu g                                                 21

<210> SEQ ID NO 1730
<211> LENGTH: 19
<212> TYPE: RNA
<213> ORGANISM: Influenza B virus

<400> SEQUENCE: 1730
accauagaau gugccugua                                                    19

<210> SEQ ID NO 1731
<211> LENGTH: 23
<212> TYPE: RNA
<213> ORGANISM: Influenza B virus

<400> SEQUENCE: 1731 aggggagug uuauuaucac uau                                                23

<210> SEQ ID NO 1732
<211> LENGTH: 21
<212> TYPE: RNA
<213> ORGANISM: Influenza B virus

<400> SEQUENCE: 1732
aaaaucccaa caguagaaaa c                                                 21

<210> SEQ ID NO 1733
<211> LENGTH: 21
<212> TYPE: RNA
<213> ORGANISM: Influenza B virus

<400> SEQUENCE: 1733
ucggagaaac caaaggaaac u                                                 21

<210> SEQ ID NO 1734
<211> LENGTH: 23
<212> TYPE: RNA
<213> ORGANISM: Influenza B virus

<400> SEQUENCE: 1734
cucgaacaau gucuaaaacu aaa                                               23

<210> SEQ ID NO 1735
<211> LENGTH: 19
<212> TYPE: RNA
<213> ORGANISM: Influenza B virus

<400> SEQUENCE: 1735
ggggaguguu auuaucacu                                                    19

<210> SEQ ID NO 1736
<211> LENGTH: 21
<212> TYPE: RNA
<213> ORGANISM: Influenza B virus
```

```
<400> SEQUENCE: 1736
augggacugu augucaagua u                                             21

<210> SEQ ID NO 1737
<211> LENGTH: 21
<212> TYPE: RNA
<213> ORGANISM: Influenza B virus

<400> SEQUENCE: 1737
caugcggauu ugccagcaau a                                             21

<210> SEQ ID NO 1738
<211> LENGTH: 23
<212> TYPE: RNA
<213> ORGANISM: Influenza B virus

<400> SEQUENCE: 1738
ugcaucgggg gaaauuguua ucu                                           23

<210> SEQ ID NO 1739
<211> LENGTH: 23
<212> TYPE: RNA
<213> ORGANISM: Influenza B virus

<400> SEQUENCE: 1739
uuguuaucuu augauaacug aug                                           23

<210> SEQ ID NO 1740
<211> LENGTH: 21
<212> TYPE: RNA
<213> ORGANISM: Influenza B virus

<400> SEQUENCE: 1740
cucccagaac cggaguggac a                                             21

<210> SEQ ID NO 1741
<211> LENGTH: 21
<212> TYPE: RNA
<213> ORGANISM: Influenza B virus

<400> SEQUENCE: 1741
uguggaccaa aggaaugcaa a                                             21

<210> SEQ ID NO 1742
<211> LENGTH: 19
<212> TYPE: RNA
<213> ORGANISM: Influenza B virus

<400> SEQUENCE: 1742
gugguacucu cgaacaaug                                                19

<210> SEQ ID NO 1743
<211> LENGTH: 21
<212> TYPE: RNA
<213> ORGANISM: Influenza B virus

<400> SEQUENCE: 1743
aaacacuuug cucuaaccca u                                             21

<210> SEQ ID NO 1744
<211> LENGTH: 21
<212> TYPE: RNA
<213> ORGANISM: Influenza B virus
```

-continued

```
<400> SEQUENCE: 1744
aaaauuuuca ccaacagaaa u                                        21

<210> SEQ ID NO 1745
<211> LENGTH: 19
<212> TYPE: RNA
<213> ORGANISM: Influenza B virus

<400> SEQUENCE: 1745
gugucagcuu cacugucau                                           19

<210> SEQ ID NO 1746
<211> LENGTH: 23
<212> TYPE: RNA
<213> ORGANISM: Influenza B virus

<400> SEQUENCE: 1746
aacaguuaca cagcaaaaag acc                                      23

<210> SEQ ID NO 1747
<211> LENGTH: 23
<212> TYPE: RNA
<213> ORGANISM: Influenza B virus

<400> SEQUENCE: 1747
uccuuuggcu ucgaaauaaa aga                                      23

<210> SEQ ID NO 1748
<211> LENGTH: 19
<212> TYPE: RNA
<213> ORGANISM: Influenza B virus

<400> SEQUENCE: 1748
gagaagacag aaacaagcu                                           19

<210> SEQ ID NO 1749
<211> LENGTH: 21
<212> TYPE: RNA
<213> ORGANISM: Influenza B virus

<400> SEQUENCE: 1749
cacugucaca gguguugaua u                                        21

<210> SEQ ID NO 1750
<211> LENGTH: 21
<212> TYPE: RNA
<213> ORGANISM: Influenza B virus

<400> SEQUENCE: 1750
aaaauaaaau auggagaagc a                                        21

<210> SEQ ID NO 1751
<211> LENGTH: 23
<212> TYPE: RNA
<213> ORGANISM: Influenza B virus

<400> SEQUENCE: 1751
guccgcaugc caugauggua aag                                      23

<210> SEQ ID NO 1752
<211> LENGTH: 21
<212> TYPE: RNA
<213> ORGANISM: Influenza B virus
```

```
<400> SEQUENCE: 1752
aauuucaguc aaauugggua a                                          21

<210> SEQ ID NO 1753
<211> LENGTH: 23
<212> TYPE: RNA
<213> ORGANISM: Influenza B virus

<400> SEQUENCE: 1753
aacccuuugu uccuauuuug uuu                                        23

<210> SEQ ID NO 1754
<211> LENGTH: 19
<212> TYPE: RNA
<213> ORGANISM: Influenza B virus

<400> SEQUENCE: 1754
gcuucacugu cauacuuac                                             19

<210> SEQ ID NO 1755
<211> LENGTH: 21
<212> TYPE: RNA
<213> ORGANISM: Influenza B virus

<400> SEQUENCE: 1755
ugucagcuuc acugucauac u                                          21

<210> SEQ ID NO 1756
<211> LENGTH: 23
<212> TYPE: RNA
<213> ORGANISM: Influenza B virus

<400> SEQUENCE: 1756
agcccaacca ggggauacu aca                                         23

<210> SEQ ID NO 1757
<211> LENGTH: 19
<212> TYPE: RNA
<213> ORGANISM: Influenza B virus

<400> SEQUENCE: 1757
guguugauau ggcucugua                                             19

<210> SEQ ID NO 1758
<211> LENGTH: 23
<212> TYPE: RNA
<213> ORGANISM: Influenza B virus

<400> SEQUENCE: 1758
uucgagaggg ccgaauaaua aaa                                        23

<210> SEQ ID NO 1759
<211> LENGTH: 23
<212> TYPE: RNA
<213> ORGANISM: Influenza B virus

<400> SEQUENCE: 1759
uacuccuuug gcuucgaaau aaa                                        23

<210> SEQ ID NO 1760
<211> LENGTH: 19
<212> TYPE: RNA
<213> ORGANISM: Influenza B virus
```

```
<400> SEQUENCE: 1760
ccuugcucuu aguggagua                                           19

<210> SEQ ID NO 1761
<211> LENGTH: 21
<212> TYPE: RNA
<213> ORGANISM: Influenza B virus

<400> SEQUENCE: 1761
aaccuuuuau ugcuugugga c                                        21

<210> SEQ ID NO 1762
<211> LENGTH: 21
<212> TYPE: RNA
<213> ORGANISM: Influenza B virus

<400> SEQUENCE: 1762
uaacagggcc uugugaaucu a                                        21

<210> SEQ ID NO 1763
<211> LENGTH: 23
<212> TYPE: RNA
<213> ORGANISM: Influenza B virus

<400> SEQUENCE: 1763
cuccuaauua gcccucauag auu                                      23

<210> SEQ ID NO 1764
<211> LENGTH: 21
<212> TYPE: RNA
<213> ORGANISM: Influenza B virus

<400> SEQUENCE: 1764
aauuuucacc aacagaaaua a                                        21

<210> SEQ ID NO 1765
<211> LENGTH: 21
<212> TYPE: RNA
<213> ORGANISM: Influenza B virus

<400> SEQUENCE: 1765
aaacccuuug uuccuauuuu g                                        21

<210> SEQ ID NO 1766
<211> LENGTH: 21
<212> TYPE: RNA
<213> ORGANISM: Influenza B virus

<400> SEQUENCE: 1766
ugccuguaga gauaacaguu a                                        21

<210> SEQ ID NO 1767
<211> LENGTH: 19
<212> TYPE: RNA
<213> ORGANISM: Influenza B virus

<400> SEQUENCE: 1767
ggccgaauaa uaaaagaaa                                           19

<210> SEQ ID NO 1768
<211> LENGTH: 19
<212> TYPE: RNA
<213> ORGANISM: Influenza B virus
```

```
<400> SEQUENCE: 1768
gaacaaugcu acccucaac                                        19

<210> SEQ ID NO 1769
<211> LENGTH: 19
<212> TYPE: RNA
<213> ORGANISM: Influenza B virus

<400> SEQUENCE: 1769
gggccgaaua auaaaagaa                                        19

<210> SEQ ID NO 1770
<211> LENGTH: 21
<212> TYPE: RNA
<213> ORGANISM: Influenza B virus

<400> SEQUENCE: 1770
caggcuguga accguucugc a                                     21

<210> SEQ ID NO 1771
<211> LENGTH: 21
<212> TYPE: RNA
<213> ORGANISM: Influenza B virus

<400> SEQUENCE: 1771
guugauggcc cugacaguaa u                                     21

<210> SEQ ID NO 1772
<211> LENGTH: 21
<212> TYPE: RNA
<213> ORGANISM: Influenza B virus

<400> SEQUENCE: 1772
ugggauagag augguacaug a                                     21

<210> SEQ ID NO 1773
<211> LENGTH: 21
<212> TYPE: RNA
<213> ORGANISM: Influenza B virus

<400> SEQUENCE: 1773
gguccgcaug ccaugauggu a                                     21

<210> SEQ ID NO 1774
<211> LENGTH: 19
<212> TYPE: RNA
<213> ORGANISM: Influenza B virus

<400> SEQUENCE: 1774
ggauagagau gguacauga                                        19

<210> SEQ ID NO 1775
<211> LENGTH: 21
<212> TYPE: RNA
<213> ORGANISM: Influenza B virus

<400> SEQUENCE: 1775
guucaggcug ugaaccguuc u                                     21

<210> SEQ ID NO 1776
<211> LENGTH: 23
<212> TYPE: RNA
<213> ORGANISM: Influenza B virus
```

-continued

```
<400> SEQUENCE: 1776
uccuuacuga acuuaauugu uuc                                              23

<210> SEQ ID NO 1777
<211> LENGTH: 21
<212> TYPE: RNA
<213> ORGANISM: Influenza B virus

<400> SEQUENCE: 1777
acagggccuu gugaaucuaa u                                                21

<210> SEQ ID NO 1778
<211> LENGTH: 19
<212> TYPE: RNA
<213> ORGANISM: Influenza B virus

<400> SEQUENCE: 1778
augguaaaga auggacaua                                                   19

<210> SEQ ID NO 1779
<211> LENGTH: 23
<212> TYPE: RNA
<213> ORGANISM: Influenza B virus

<400> SEQUENCE: 1779
aagcuaaggc aucuaauuuc agu                                              23

<210> SEQ ID NO 1780
<211> LENGTH: 23
<212> TYPE: RNA
<213> ORGANISM: Influenza B virus

<400> SEQUENCE: 1780
cggauauauu gcuaaaauuu uca                                              23

<210> SEQ ID NO 1781
<211> LENGTH: 19
<212> TYPE: RNA
<213> ORGANISM: Influenza B virus

<400> SEQUENCE: 1781
gaaugugccu guagagaua                                                   19

<210> SEQ ID NO 1782
<211> LENGTH: 21
<212> TYPE: RNA
<213> ORGANISM: Influenza B virus

<400> SEQUENCE: 1782
acaaugcuac ccucaacuau a                                                21

<210> SEQ ID NO 1783
<211> LENGTH: 19
<212> TYPE: RNA
<213> ORGANISM: Influenza B virus

<400> SEQUENCE: 1783
gggaguguua uuaucacua                                                   19

<210> SEQ ID NO 1784
<211> LENGTH: 21
<212> TYPE: RNA
<213> ORGANISM: Influenza B virus
```

-continued

```
<400> SEQUENCE: 1784
uuaacccuau uccucacauc a                                              21

<210> SEQ ID NO 1785
<211> LENGTH: 19
<212> TYPE: RNA
<213> ORGANISM: Influenza B virus

<400> SEQUENCE: 1785
gaccagauga uggaagcau                                                 19

<210> SEQ ID NO 1786
<211> LENGTH: 21
<212> TYPE: RNA
<213> ORGANISM: Influenza B virus

<400> SEQUENCE: 1786
gucuguucua aacccuuugu u                                              21

<210> SEQ ID NO 1787
<211> LENGTH: 19
<212> TYPE: RNA
<213> ORGANISM: Influenza B virus

<400> SEQUENCE: 1787
gacuguaugu caaguauga                                                 19

<210> SEQ ID NO 1788
<211> LENGTH: 21
<212> TYPE: RNA
<213> ORGANISM: Influenza B virus

<400> SEQUENCE: 1788
gggacuguau gucaaguaug a                                              21

<210> SEQ ID NO 1789
<211> LENGTH: 23
<212> TYPE: RNA
<213> ORGANISM: Influenza B virus

<400> SEQUENCE: 1789
caguaaugca uugcucaaaa uaa                                            23

<210> SEQ ID NO 1790
<211> LENGTH: 21
<212> TYPE: RNA
<213> ORGANISM: Influenza B virus

<400> SEQUENCE: 1790
aacagggccu ugugaaucua a                                              21

<210> SEQ ID NO 1791
<211> LENGTH: 23
<212> TYPE: RNA
<213> ORGANISM: Influenza B virus

<400> SEQUENCE: 1791
uugugcaaac gcaucaaaug uuc                                            23

<210> SEQ ID NO 1792
<211> LENGTH: 23
<212> TYPE: RNA
<213> ORGANISM: Influenza B virus
```

```
<400> SEQUENCE: 1792
augcauugcu caaaauaaaa uau                                              23

<210> SEQ ID NO 1793
<211> LENGTH: 21
<212> TYPE: RNA
<213> ORGANISM: Influenza B virus

<400> SEQUENCE: 1793
aaaugaacaa ugcuacccuc a                                                21

<210> SEQ ID NO 1794
<211> LENGTH: 21
<212> TYPE: RNA
<213> ORGANISM: Influenza B virus

<400> SEQUENCE: 1794
gcaugccaug augguaaaga a                                                21

<210> SEQ ID NO 1795
<211> LENGTH: 23
<212> TYPE: RNA
<213> ORGANISM: Influenza B virus

<400> SEQUENCE: 1795
cgggggaaau uguuaucuua uga                                              23

<210> SEQ ID NO 1796
<211> LENGTH: 23
<212> TYPE: RNA
<213> ORGANISM: Influenza B virus

<400> SEQUENCE: 1796
aacauccuaa gaacacaaga aag                                              23

<210> SEQ ID NO 1797
<211> LENGTH: 19
<212> TYPE: RNA
<213> ORGANISM: Influenza B virus

<400> SEQUENCE: 1797
ccucaacuau acaaacguu                                                   19

<210> SEQ ID NO 1798
<211> LENGTH: 19
<212> TYPE: RNA
<213> ORGANISM: Influenza B virus

<400> SEQUENCE: 1798
gacugacagu gaugcccuu                                                   19

<210> SEQ ID NO 1799
<211> LENGTH: 21
<212> TYPE: RNA
<213> ORGANISM: Influenza B virus

<400> SEQUENCE: 1799
acugacacau accauuccua u                                                21

<210> SEQ ID NO 1800
<211> LENGTH: 21
<212> TYPE: RNA
<213> ORGANISM: Influenza B virus
```

```
<400> SEQUENCE: 1800
uacccucaac uauacaaacg u                                              21

<210> SEQ ID NO 1801
<211> LENGTH: 21
<212> TYPE: RNA
<213> ORGANISM: Influenza B virus

<400> SEQUENCE: 1801
acucagcucc cuugauaaua a                                              21

<210> SEQ ID NO 1802
<211> LENGTH: 23
<212> TYPE: RNA
<213> ORGANISM: Influenza B virus

<400> SEQUENCE: 1802
accauuccua ugcaaacaac auc                                            23

<210> SEQ ID NO 1803
<211> LENGTH: 21
<212> TYPE: RNA
<213> ORGANISM: Influenza B virus

<400> SEQUENCE: 1803
aaauuguuau cuuaugauaa c                                              21

<210> SEQ ID NO 1804
<211> LENGTH: 23
<212> TYPE: RNA
<213> ORGANISM: Influenza B virus

<400> SEQUENCE: 1804
aacaagagaa gacagaaaca agc                                            23

<210> SEQ ID NO 1805
<211> LENGTH: 23
<212> TYPE: RNA
<213> ORGANISM: Influenza B virus

<400> SEQUENCE: 1805
gaccaaagga augcaaacac uuu                                            23

<210> SEQ ID NO 1806
<211> LENGTH: 21
<212> TYPE: RNA
<213> ORGANISM: Influenza B virus

<400> SEQUENCE: 1806
uggacauacc cgcguuuauc u                                              21

<210> SEQ ID NO 1807
<211> LENGTH: 21
<212> TYPE: RNA
<213> ORGANISM: Influenza B virus

<400> SEQUENCE: 1807
aacaaugucu aaaacuaaaa g                                              21

<210> SEQ ID NO 1808
<211> LENGTH: 23
<212> TYPE: RNA
<213> ORGANISM: Influenza B virus
```

-continued

```
<400> SEQUENCE: 1808
aggaugggga ugggacugua ugu                                           23

<210> SEQ ID NO 1809
<211> LENGTH: 23
<212> TYPE: RNA
<213> ORGANISM: Influenza B virus

<400> SEQUENCE: 1809
cucuguaaug gaggaauggu uga                                           23

<210> SEQ ID NO 1810
<211> LENGTH: 21
<212> TYPE: RNA
<213> ORGANISM: Influenza B virus

<400> SEQUENCE: 1810
auggagaagc auauacugac a                                             21

<210> SEQ ID NO 1811
<211> LENGTH: 23
<212> TYPE: RNA
<213> ORGANISM: Influenza B virus

<400> SEQUENCE: 1811
ggccgaauaa uaaaagaaau auu                                           23

<210> SEQ ID NO 1812
<211> LENGTH: 21
<212> TYPE: RNA
<213> ORGANISM: Influenza B virus

<400> SEQUENCE: 1812
ccuugcucuu aguggaguaa u                                             21

<210> SEQ ID NO 1813
<211> LENGTH: 19
<212> TYPE: RNA
<213> ORGANISM: Influenza B virus

<400> SEQUENCE: 1813
cccucauaga uucggagaa                                                19

<210> SEQ ID NO 1814
<211> LENGTH: 21
<212> TYPE: RNA
<213> ORGANISM: Influenza B virus

<400> SEQUENCE: 1814
cugugaaccg uucugcaaca a                                             21

<210> SEQ ID NO 1815
<211> LENGTH: 19
<212> TYPE: RNA
<213> ORGANISM: Influenza B virus

<400> SEQUENCE: 1815
ggacauauau cggaguuga                                                19

<210> SEQ ID NO 1816
<211> LENGTH: 21
<212> TYPE: RNA
<213> ORGANISM: Influenza B virus
```

-continued

```
<400> SEQUENCE: 1816
aaaagauaag aaaugugaug u                                              21

<210> SEQ ID NO 1817
<211> LENGTH: 23
<212> TYPE: RNA
<213> ORGANISM: Influenza B virus

<400> SEQUENCE: 1817
uacuuacuau auucggauau auu                                            23

<210> SEQ ID NO 1818
<211> LENGTH: 23
<212> TYPE: RNA
<213> ORGANISM: Influenza B virus

<400> SEQUENCE: 1818
cacugucaca gguguugaua ugg                                            23

<210> SEQ ID NO 1819
<211> LENGTH: 23
<212> TYPE: RNA
<213> ORGANISM: Influenza B virus

<400> SEQUENCE: 1819
ggcucagcuu cagguauuag uga                                            23

<210> SEQ ID NO 1820
<211> LENGTH: 19
<212> TYPE: RNA
<213> ORGANISM: Influenza B virus

<400> SEQUENCE: 1820
ggacacuguc acagguguu                                                 19

<210> SEQ ID NO 1821
<211> LENGTH: 21
<212> TYPE: RNA
<213> ORGANISM: Influenza B virus

<400> SEQUENCE: 1821
aacucagcuc ccuugauaau a                                              21

<210> SEQ ID NO 1822
<211> LENGTH: 19
<212> TYPE: RNA
<213> ORGANISM: Influenza B virus

<400> SEQUENCE: 1822
gcaauaaaac cauagaaug                                                 19

<210> SEQ ID NO 1823
<211> LENGTH: 21
<212> TYPE: RNA
<213> ORGANISM: Influenza B virus

<400> SEQUENCE: 1823
agaccagaug auggaagcau a                                              21

<210> SEQ ID NO 1824
<211> LENGTH: 21
<212> TYPE: RNA
<213> ORGANISM: Influenza B virus
```

```
<400> SEQUENCE: 1824
gucagcuuca cugucauacu u                                        21

<210> SEQ ID NO 1825
<211> LENGTH: 19
<212> TYPE: RNA
<213> ORGANISM: Influenza B virus

<400> SEQUENCE: 1825
cucauagauu cggagaaac                                           19

<210> SEQ ID NO 1826
<211> LENGTH: 23
<212> TYPE: RNA
<213> ORGANISM: Influenza B virus

<400> SEQUENCE: 1826
cacauaccau uccuaugcaa aca                                      23

<210> SEQ ID NO 1827
<211> LENGTH: 23
<212> TYPE: RNA
<213> ORGANISM: Influenza B virus

<400> SEQUENCE: 1827
aggcaucuaa uuucagucaa auu                                      23

<210> SEQ ID NO 1828
<211> LENGTH: 21
<212> TYPE: RNA
<213> ORGANISM: Influenza B virus

<400> SEQUENCE: 1828
ggugguacuc ucgaacaaug u                                        21

<210> SEQ ID NO 1829
<211> LENGTH: 19
<212> TYPE: RNA
<213> ORGANISM: Influenza B virus

<400> SEQUENCE: 1829
gaagacagaa acaagcuaa                                           19

<210> SEQ ID NO 1830
<211> LENGTH: 23
<212> TYPE: RNA
<213> ORGANISM: Influenza B virus

<400> SEQUENCE: 1830
uccgcaugcc augaugguaa aga                                      23

<210> SEQ ID NO 1831
<211> LENGTH: 21
<212> TYPE: RNA
<213> ORGANISM: Influenza B virus

<400> SEQUENCE: 1831
gagacugaua cagcagaaau a                                        21

<210> SEQ ID NO 1832
<211> LENGTH: 23
<212> TYPE: RNA
<213> ORGANISM: Influenza B virus
```

-continued

```
<400> SEQUENCE: 1832
uccaacagga agaguaaaac aua                                          23

<210> SEQ ID NO 1833
<211> LENGTH: 21
<212> TYPE: RNA
<213> ORGANISM: Influenza B virus

<400> SEQUENCE: 1833
cccucaacua uacaaacguu a                                            21

<210> SEQ ID NO 1834
<211> LENGTH: 19
<212> TYPE: RNA
<213> ORGANISM: Influenza B virus

<400> SEQUENCE: 1834
ggaaccuuuu auugcuugu                                               19

<210> SEQ ID NO 1835
<211> LENGTH: 21
<212> TYPE: RNA
<213> ORGANISM: Influenza B virus

<400> SEQUENCE: 1835
acacuuugcu cuaacccauu a                                            21

<210> SEQ ID NO 1836
<211> LENGTH: 21
<212> TYPE: RNA
<213> ORGANISM: Influenza B virus

<400> SEQUENCE: 1836
agaaugugcc uguagagaua a                                            21

<210> SEQ ID NO 1837
<211> LENGTH: 21
<212> TYPE: RNA
<213> ORGANISM: Influenza B virus

<400> SEQUENCE: 1837
gauggcccug acaguaaugc a                                            21

<210> SEQ ID NO 1838
<211> LENGTH: 21
<212> TYPE: RNA
<213> ORGANISM: Influenza B virus

<400> SEQUENCE: 1838
agcaacagcc auuuacuguu u                                            21

<210> SEQ ID NO 1839
<211> LENGTH: 19
<212> TYPE: RNA
<213> ORGANISM: Influenza B virus

<400> SEQUENCE: 1839
gguacaugau gguggaaag                                               19

<210> SEQ ID NO 1840
<211> LENGTH: 21
<212> TYPE: RNA
<213> ORGANISM: Influenza B virus
```

```
<400> SEQUENCE: 1840
gcugugaacc guucugcaac a                                              21

<210> SEQ ID NO 1841
<211> LENGTH: 21
<212> TYPE: RNA
<213> ORGANISM: Influenza B virus

<400> SEQUENCE: 1841
aagauucgag agggccgaau a                                              21

<210> SEQ ID NO 1842
<211> LENGTH: 21
<212> TYPE: RNA
<213> ORGANISM: Influenza B virus

<400> SEQUENCE: 1842
gaugcccuug cucuuagugg a                                              21

<210> SEQ ID NO 1843
<211> LENGTH: 21
<212> TYPE: RNA
<213> ORGANISM: Influenza B virus

<400> SEQUENCE: 1843
uauugggaua gagaugguac a                                              21

<210> SEQ ID NO 1844
<211> LENGTH: 21
<212> TYPE: RNA
<213> ORGANISM: Influenza B virus

<400> SEQUENCE: 1844
gaagaaugca caugcggauu u                                              21

<210> SEQ ID NO 1845
<211> LENGTH: 21
<212> TYPE: RNA
<213> ORGANISM: Influenza B virus

<400> SEQUENCE: 1845
cgagagggcc gaauaauaaa a                                              21

<210> SEQ ID NO 1846
<211> LENGTH: 19
<212> TYPE: RNA
<213> ORGANISM: Influenza B virus

<400> SEQUENCE: 1846
gauggggaug ggacuguau                                                 19

<210> SEQ ID NO 1847
<211> LENGTH: 21
<212> TYPE: RNA
<213> ORGANISM: Influenza B virus

<400> SEQUENCE: 1847
ggaggcauca agggaggauu u                                              21

<210> SEQ ID NO 1848
<211> LENGTH: 21
<212> TYPE: RNA
<213> ORGANISM: Influenza B virus
```

-continued

```
<400> SEQUENCE: 1848
cacucagcag caacagccau u                                         21

<210> SEQ ID NO 1849
<211> LENGTH: 19
<212> TYPE: RNA
<213> ORGANISM: Influenza B virus

<400> SEQUENCE: 1849
ggaccaaagg aaugcaaac                                            19

<210> SEQ ID NO 1850
<211> LENGTH: 21
<212> TYPE: RNA
<213> ORGANISM: Influenza B virus

<400> SEQUENCE: 1850 gcggauugc cagcaauaaa a                                          21

<210> SEQ ID NO 1851
<211> LENGTH: 21
<212> TYPE: RNA
<213> ORGANISM: Influenza B virus

<400> SEQUENCE: 1851
aaggaaacuc agcucccuug a                                         21

<210> SEQ ID NO 1852
<211> LENGTH: 21
<212> TYPE: RNA
<213> ORGANISM: Influenza B virus

<400> SEQUENCE: 1852
ccgggcucaa ccuuucagaa a                                         21

<210> SEQ ID NO 1853
<211> LENGTH: 19
<212> TYPE: RNA
<213> ORGANISM: Influenza B virus

<400> SEQUENCE: 1853
ccuaauuagc ccucauaga                                            19

<210> SEQ ID NO 1854
<211> LENGTH: 23
<212> TYPE: RNA
<213> ORGANISM: Influenza B virus

<400> SEQUENCE: 1854
acccuuuguu ccuauuuugu uug                                       23

<210> SEQ ID NO 1855
<211> LENGTH: 21
<212> TYPE: RNA
<213> ORGANISM: Influenza B virus

<400> SEQUENCE: 1855
uccaacagga agaguaaaac a                                         21

<210> SEQ ID NO 1856
<211> LENGTH: 19
<212> TYPE: RNA
<213> ORGANISM: Influenza B virus
```

-continued

```
<400> SEQUENCE: 1856
gcauccaaga uuggaaggu                                              19

<210> SEQ ID NO 1857
<211> LENGTH: 19
<212> TYPE: RNA
<213> ORGANISM: Influenza B virus

<400> SEQUENCE: 1857
gccuguagag auaacaguu                                              19

<210> SEQ ID NO 1858
<211> LENGTH: 19
<212> TYPE: RNA
<213> ORGANISM: Influenza B virus

<400> SEQUENCE: 1858
augggacugu augucaagu                                              19

<210> SEQ ID NO 1859
<211> LENGTH: 23
<212> TYPE: RNA
<213> ORGANISM: Influenza B virus

<400> SEQUENCE: 1859
ugcaaacgca ucaaauguuc agg                                         23

<210> SEQ ID NO 1860
<211> LENGTH: 21
<212> TYPE: RNA
<213> ORGANISM: Influenza B virus

<400> SEQUENCE: 1860
aaaccauaga augugccugu a                                           21

<210> SEQ ID NO 1861
<211> LENGTH: 21
<212> TYPE: RNA
<213> ORGANISM: Influenza B virus

<400> SEQUENCE: 1861
aacaguuaca cagcaaaaag a                                           21

<210> SEQ ID NO 1862
<211> LENGTH: 21
<212> TYPE: RNA
<213> ORGANISM: Influenza B virus

<400> SEQUENCE: 1862
gacaguaaug cauugcucaa a                                           21

<210> SEQ ID NO 1863
<211> LENGTH: 23
<212> TYPE: RNA
<213> ORGANISM: Influenza B virus

<400> SEQUENCE: 1863
augggacugu augucaagua uga                                         23

<210> SEQ ID NO 1864
<211> LENGTH: 23
<212> TYPE: RNA
<213> ORGANISM: Influenza B virus
```

```
<400> SEQUENCE: 1864 aucggggaa auuguuaucu uau                                          23

<210> SEQ ID NO 1865
<211> LENGTH: 19
<212> TYPE: RNA
<213> ORGANISM: Influenza B virus

<400> SEQUENCE: 1865
auggcucagc uucagguau                                              19

<210> SEQ ID NO 1866
<211> LENGTH: 21
<212> TYPE: RNA
<213> ORGANISM: Influenza B virus

<400> SEQUENCE: 1866
ggcaucaagg gaggauuugu u                                           21

<210> SEQ ID NO 1867
<211> LENGTH: 23
<212> TYPE: RNA
<213> ORGANISM: Influenza B virus

<400> SEQUENCE: 1867
aacagggccu ugugaaucua aug                                         23

<210> SEQ ID NO 1868
<211> LENGTH: 21
<212> TYPE: RNA
<213> ORGANISM: Influenza B virus

<400> SEQUENCE: 1868
cucagcuuca gguauuagug a                                           21

<210> SEQ ID NO 1869
<211> LENGTH: 19
<212> TYPE: RNA
<213> ORGANISM: Influenza B virus

<400> SEQUENCE: 1869 gguucaaug gaagaaccu                                               19

<210> SEQ ID NO 1870
<211> LENGTH: 23
<212> TYPE: RNA
<213> ORGANISM: Influenza B virus

<400> SEQUENCE: 1870
gugcacagag acuuauuugg aca                                         23

<210> SEQ ID NO 1871
<211> LENGTH: 23
<212> TYPE: RNA
<213> ORGANISM: Influenza B virus

<400> SEQUENCE: 1871
agcaauaaaa ccauagaaug ugc                                         23

<210> SEQ ID NO 1872
<211> LENGTH: 23
<212> TYPE: RNA
<213> ORGANISM: Influenza B virus
```

```
<400> SEQUENCE: 1872
uggacauacc cgcguuuauc uug                                              23

<210> SEQ ID NO 1873
<211> LENGTH: 23
<212> TYPE: RNA
<213> ORGANISM: Influenza B virus

<400> SEQUENCE: 1873
gugaaccguu cugcaacaaa agg                                              23

<210> SEQ ID NO 1874
<211> LENGTH: 23
<212> TYPE: RNA
<213> ORGANISM: Influenza B virus

<400> SEQUENCE: 1874
aacaaugcua cccucaacua uac                                              23

<210> SEQ ID NO 1875
<211> LENGTH: 23
<212> TYPE: RNA
<213> ORGANISM: Influenza B virus

<400> SEQUENCE: 1875
gucagcuuca cugucauacu uac                                              23

<210> SEQ ID NO 1876
<211> LENGTH: 19
<212> TYPE: RNA
<213> ORGANISM: Influenza B virus

<400> SEQUENCE: 1876
gaacaagaga agacagaaa                                                   19

<210> SEQ ID NO 1877
<211> LENGTH: 21
<212> TYPE: RNA
<213> ORGANISM: Influenza B virus

<400> SEQUENCE: 1877
aauaaaauau ggagaagcau a                                                21

<210> SEQ ID NO 1878
<211> LENGTH: 19
<212> TYPE: RNA
<213> ORGANISM: Influenza B virus

<400> SEQUENCE: 1878
gcuuguggac caaaggaau                                                   19

<210> SEQ ID NO 1879
<211> LENGTH: 19
<212> TYPE: RNA
<213> ORGANISM: Influenza B virus

<400> SEQUENCE: 1879
gaguaaaaca uacugaaga                                                   19

<210> SEQ ID NO 1880
<211> LENGTH: 23
<212> TYPE: RNA
<213> ORGANISM: Influenza B virus
```

-continued

```
<400> SEQUENCE: 1880
uacugacaca uaccauuccu aug                                        23

<210> SEQ ID NO 1881
<211> LENGTH: 19
<212> TYPE: RNA
<213> ORGANISM: Influenza B virus

<400> SEQUENCE: 1881
cugcuauggg acacuguca                                             19

<210> SEQ ID NO 1882
<211> LENGTH: 23
<212> TYPE: RNA
<213> ORGANISM: Influenza B virus

<400> SEQUENCE: 1882
gagugcagau uucuuaagau ucg                                        23

<210> SEQ ID NO 1883
<211> LENGTH: 21
<212> TYPE: RNA
<213> ORGANISM: Influenza B virus

<400> SEQUENCE: 1883
ggaagguggu acucucgaac a                                          21

<210> SEQ ID NO 1884
<211> LENGTH: 23
<212> TYPE: RNA
<213> ORGANISM: Influenza B virus

<400> SEQUENCE: 1884
ucgaaauaaa agauaagaaa ugu                                        23

<210> SEQ ID NO 1885
<211> LENGTH: 19
<212> TYPE: RNA
<213> ORGANISM: Influenza B virus

<400> SEQUENCE: 1885
cuguagagau aacaguuac                                             19

<210> SEQ ID NO 1886
<211> LENGTH: 23
<212> TYPE: RNA
<213> ORGANISM: Influenza B virus

<400> SEQUENCE: 1886
gagacugaua cagcagaaau aag                                        23

<210> SEQ ID NO 1887
<211> LENGTH: 23
<212> TYPE: RNA
<213> ORGANISM: Influenza B virus

<400> SEQUENCE: 1887
aacaagcuaa ggcaucuaau uuc                                        23

<210> SEQ ID NO 1888
<211> LENGTH: 21
<212> TYPE: RNA
<213> ORGANISM: Influenza B virus
```

-continued

```
<400> SEQUENCE: 1888
agggaggauu uguucaucaa a                                            21

<210> SEQ ID NO 1889
<211> LENGTH: 21
<212> TYPE: RNA
<213> ORGANISM: Influenza B virus

<400> SEQUENCE: 1889
aaagaauggc auccaagauu g                                            21

<210> SEQ ID NO 1890
<211> LENGTH: 23
<212> TYPE: RNA
<213> ORGANISM: Influenza B virus

<400> SEQUENCE: 1890
ugguacucuc gaacaauguc uaa                                          23

<210> SEQ ID NO 1891
<211> LENGTH: 19
<212> TYPE: RNA
<213> ORGANISM: Influenza B virus

<400> SEQUENCE: 1891
gguaaaaucc caacaguag                                               19

<210> SEQ ID NO 1892
<211> LENGTH: 23
<212> TYPE: RNA
<213> ORGANISM: Influenza B virus

<400> SEQUENCE: 1892
uuguugcuac ugaugaucuu aca                                          23

<210> SEQ ID NO 1893
<211> LENGTH: 21
<212> TYPE: RNA
<213> ORGANISM: Influenza B virus

<400> SEQUENCE: 1893
accagggagg ugccuugaug a                                            21

<210> SEQ ID NO 1894
<211> LENGTH: 19
<212> TYPE: RNA
<213> ORGANISM: Influenza B virus

<400> SEQUENCE: 1894
cugcauagau ugaaugcau                                               19

<210> SEQ ID NO 1895
<211> LENGTH: 23
<212> TYPE: RNA
<213> ORGANISM: Influenza B virus

<400> SEQUENCE: 1895
augucucuug aagagagaaa agc                                          23

<210> SEQ ID NO 1896
<211> LENGTH: 21
<212> TYPE: RNA
<213> ORGANISM: Influenza B virus
```

```
<400> SEQUENCE: 1896
agccugaaag uaaaaggaug u                                              21

<210> SEQ ID NO 1897
<211> LENGTH: 21
<212> TYPE: RNA
<213> ORGANISM: Influenza B virus

<400> SEQUENCE: 1897
aaagggauau acguaaugua u                                              21

<210> SEQ ID NO 1898
<211> LENGTH: 21
<212> TYPE: RNA
<213> ORGANISM: Influenza B virus

<400> SEQUENCE: 1898
cuggagugcu augaaaggcu u                                              21

<210> SEQ ID NO 1899
<211> LENGTH: 21
<212> TYPE: RNA
<213> ORGANISM: Influenza B virus

<400> SEQUENCE: 1899
agaguguugg uaaacggaac a                                              21

<210> SEQ ID NO 1900
<211> LENGTH: 23
<212> TYPE: RNA
<213> ORGANISM: Influenza B virus

<400> SEQUENCE: 1900
aucauuauua gaaacauugu aug                                            23

<210> SEQ ID NO 1901
<211> LENGTH: 21
<212> TYPE: RNA
<213> ORGANISM: Influenza B virus

<400> SEQUENCE: 1901
ugagccugaa aguaaaagga u                                              21

<210> SEQ ID NO 1902
<211> LENGTH: 21
<212> TYPE: RNA
<213> ORGANISM: Influenza B virus

<400> SEQUENCE: 1902
caaauagcaa cuguccgaaa u                                              21

<210> SEQ ID NO 1903
<211> LENGTH: 21
<212> TYPE: RNA
<213> ORGANISM: Influenza B virus

<400> SEQUENCE: 1903
gaaggacauu caaagccaau u                                              21

<210> SEQ ID NO 1904
<211> LENGTH: 21
<212> TYPE: RNA
<213> ORGANISM: Influenza B virus
```

```
<400> SEQUENCE: 1904
uacaguggag gaugaagaag a                                              21

<210> SEQ ID NO 1905
<211> LENGTH: 21
<212> TYPE: RNA
<213> ORGANISM: Influenza B virus

<400> SEQUENCE: 1905
agcaacuguc cgaaauacaa u                                              21

<210> SEQ ID NO 1906
<211> LENGTH: 23
<212> TYPE: RNA
<213> ORGANISM: Influenza B virus

<400> SEQUENCE: 1906
caucggaucc ucaacucacu cuu                                            23

<210> SEQ ID NO 1907
<211> LENGTH: 19
<212> TYPE: RNA
<213> ORGANISM: Influenza B virus

<400> SEQUENCE: 1907
aggguuugag ccauacugu                                                 19

<210> SEQ ID NO 1908
<211> LENGTH: 19
<212> TYPE: RNA
<213> ORGANISM: Influenza B virus

<400> SEQUENCE: 1908
ggguuugagc cauacugua                                                 19

<210> SEQ ID NO 1909
<211> LENGTH: 23
<212> TYPE: RNA
<213> ORGANISM: Influenza B virus

<400> SEQUENCE: 1909
aagaugcaag gcaaaagaua aaa                                            23

<210> SEQ ID NO 1910
<211> LENGTH: 21
<212> TYPE: RNA
<213> ORGANISM: Influenza B virus

<400> SEQUENCE: 1910
uugagguggg uccgggagca a                                              21

<210> SEQ ID NO 1911
<211> LENGTH: 21
<212> TYPE: RNA
<213> ORGANISM: Influenza B virus

<400> SEQUENCE: 1911
cgagcgucuu aaugaaggac a                                              21

<210> SEQ ID NO 1912
<211> LENGTH: 23
<212> TYPE: RNA
<213> ORGANISM: Influenza B virus
```

```
<400> SEQUENCE: 1912
uaaacagacu aaagagaaaa uua                                    23

<210> SEQ ID NO 1913
<211> LENGTH: 23
<212> TYPE: RNA
<213> ORGANISM: Influenza B virus

<400> SEQUENCE: 1913
aggcuuguug cuaaacuugu ugc                                    23

<210> SEQ ID NO 1914
<211> LENGTH: 23
<212> TYPE: RNA
<213> ORGANISM: Influenza B virus

<400> SEQUENCE: 1914
aacaaaagug agccugaaag uaa                                    23

<210> SEQ ID NO 1915
<211> LENGTH: 19
<212> TYPE: RNA
<213> ORGANISM: Influenza B virus

<400> SEQUENCE: 1915
gggacaugaa caacaaaga                                         19

<210> SEQ ID NO 1916
<211> LENGTH: 21
<212> TYPE: RNA
<213> ORGANISM: Influenza B virus

<400> SEQUENCE: 1916
uggagugcua ugaaaggcuu u                                      21

<210> SEQ ID NO 1917
<211> LENGTH: 21
<212> TYPE: RNA
<213> ORGANISM: Influenza B virus

<400> SEQUENCE: 1917
uguccuugag aguguuggua a                                      21

<210> SEQ ID NO 1918
<211> LENGTH: 21
<212> TYPE: RNA
<213> ORGANISM: Influenza B virus

<400> SEQUENCE: 1918
guugauggcc caacugaaau a                                      21

<210> SEQ ID NO 1919
<211> LENGTH: 21
<212> TYPE: RNA
<213> ORGANISM: Influenza B virus

<400> SEQUENCE: 1919
aacucugcau agauugaaug c                                      21

<210> SEQ ID NO 1920
<211> LENGTH: 19
<212> TYPE: RNA
<213> ORGANISM: Influenza B virus
```

-continued

```
<400> SEQUENCE: 1920
gagaaaagca auuggagua                                              19

<210> SEQ ID NO 1921
<211> LENGTH: 21
<212> TYPE: RNA
<213> ORGANISM: Influenza B virus

<400> SEQUENCE: 1921
aagcaauugg aguaaaaaug a                                           21

<210> SEQ ID NO 1922
<211> LENGTH: 23
<212> TYPE: RNA
<213> ORGANISM: Influenza B virus

<400> SEQUENCE: 1922
caaguccuua ucaacucugc aua                                         23

<210> SEQ ID NO 1923
<211> LENGTH: 23
<212> TYPE: RNA
<213> ORGANISM: Influenza B virus

<400> SEQUENCE: 1923
aagggaaguu ccguuugaca aua                                         23

<210> SEQ ID NO 1924
<211> LENGTH: 21
<212> TYPE: RNA
<213> ORGANISM: Influenza B virus

<400> SEQUENCE: 1924
uuggucaaga gcaccgauua u                                           21

<210> SEQ ID NO 1925
<211> LENGTH: 21
<212> TYPE: RNA
<213> ORGANISM: Influenza B virus

<400> SEQUENCE: 1925
ugaaggacau ucaaagccaa u                                           21

<210> SEQ ID NO 1926
<211> LENGTH: 23
<212> TYPE: RNA
<213> ORGANISM: Influenza B virus

<400> SEQUENCE: 1926
aaccaaugcc accauaaacu uug                                         23

<210> SEQ ID NO 1927
<211> LENGTH: 23
<212> TYPE: RNA
<213> ORGANISM: Influenza B virus

<400> SEQUENCE: 1927
gucuuaauga aggacauuca aag                                         23

<210> SEQ ID NO 1928
<211> LENGTH: 23
<212> TYPE: RNA
<213> ORGANISM: Influenza B virus
```

```
<400> SEQUENCE: 1928
uuguuccaca aaacaguaau agc                                          23

<210> SEQ ID NO 1929
<211> LENGTH: 23
<212> TYPE: RNA
<213> ORGANISM: Influenza B virus

<400> SEQUENCE: 1929
aaguuccguu ugacaauaaa aag                                          23

<210> SEQ ID NO 1930
<211> LENGTH: 19
<212> TYPE: RNA
<213> ORGANISM: Influenza B virus

<400> SEQUENCE: 1930
gcaccgauua ucaccagaa                                               19

<210> SEQ ID NO 1931
<211> LENGTH: 19
<212> TYPE: RNA
<213> ORGANISM: Influenza B virus

<400> SEQUENCE: 1931
ccacaaaaca guaauagcu                                               19

<210> SEQ ID NO 1932
<211> LENGTH: 21
<212> TYPE: RNA
<213> ORGANISM: Influenza B virus

<400> SEQUENCE: 1932
aaaagauaaa agaggaagua a                                            21

<210> SEQ ID NO 1933
<211> LENGTH: 23
<212> TYPE: RNA
<213> ORGANISM: Influenza B virus

<400> SEQUENCE: 1933
uagacugguc acagaagaac uuu                                          23

<210> SEQ ID NO 1934
<211> LENGTH: 21
<212> TYPE: RNA
<213> ORGANISM: Influenza B virus

<400> SEQUENCE: 1934
aauugaaggg uuugagccau a                                            21

<210> SEQ ID NO 1935
<211> LENGTH: 19
<212> TYPE: RNA
<213> ORGANISM: Influenza B virus

<400> SEQUENCE: 1935
ggauacaagu ccuuaucaa                                               19

<210> SEQ ID NO 1936
<211> LENGTH: 23
<212> TYPE: RNA
<213> ORGANISM: Influenza B virus
```

-continued

```
<400> SEQUENCE: 1936
gggauauacg uaauguauug ucc                                              23

<210> SEQ ID NO 1937
<211> LENGTH: 23
<212> TYPE: RNA
<213> ORGANISM: Influenza B virus

<400> SEQUENCE: 1937
gagcaaccaa ugccaccaua aac                                              23

<210> SEQ ID NO 1938
<211> LENGTH: 21
<212> TYPE: RNA
<213> ORGANISM: Influenza B virus

<400> SEQUENCE: 1938
aagggacaug aacaacaaag a                                                21

<210> SEQ ID NO 1939
<211> LENGTH: 23
<212> TYPE: RNA
<213> ORGANISM: Influenza B virus

<400> SEQUENCE: 1939
augaauccau cugcuggaau uga                                              23

<210> SEQ ID NO 1940
<211> LENGTH: 19
<212> TYPE: RNA
<213> ORGANISM: Influenza B virus

<400> SEQUENCE: 1940
caccagaaga gggagacaa                                                   19

<210> SEQ ID NO 1941
<211> LENGTH: 21
<212> TYPE: RNA
<213> ORGANISM: Influenza B virus

<400> SEQUENCE: 1941
agggacauga acaacaaaga u                                                21

<210> SEQ ID NO 1942
<211> LENGTH: 21
<212> TYPE: RNA
<213> ORGANISM: Influenza B virus

<400> SEQUENCE: 1942
aaacacucag aaagaaggga a                                                21

<210> SEQ ID NO 1943
<211> LENGTH: 23
<212> TYPE: RNA
<213> ORGANISM: Influenza B virus

<400> SEQUENCE: 1943
gagccugaaa guaaaaggau guc                                              23

<210> SEQ ID NO 1944
<211> LENGTH: 21
<212> TYPE: RNA
<213> ORGANISM: Influenza B virus
```

-continued

```
<400> SEQUENCE: 1944
aaaaguuccu caaauagcaa c                                              21

<210> SEQ ID NO 1945
<211> LENGTH: 19
<212> TYPE: RNA
<213> ORGANISM: Influenza B virus

<400> SEQUENCE: 1945
gaggugccuu gaugacaua                                                 19

<210> SEQ ID NO 1946
<211> LENGTH: 23
<212> TYPE: RNA
<213> ORGANISM: Influenza B virus

<400> SEQUENCE: 1946
aaagggauau acguaaugua uug                                            23

<210> SEQ ID NO 1947
<211> LENGTH: 21
<212> TYPE: RNA
<213> ORGANISM: Influenza B virus

<400> SEQUENCE: 1947
aucccaauuu ggucaagagc a                                              21

<210> SEQ ID NO 1948
<211> LENGTH: 23
<212> TYPE: RNA
<213> ORGANISM: Influenza B virus

<400> SEQUENCE: 1948
uaaacuuuga agcaggaauu cug                                            23

<210> SEQ ID NO 1949
<211> LENGTH: 21
<212> TYPE: RNA
<213> ORGANISM: Influenza B virus

<400> SEQUENCE: 1949
agcaaccaau gccaccauaa a                                              21

<210> SEQ ID NO 1950
<211> LENGTH: 21
<212> TYPE: RNA
<213> ORGANISM: Influenza B virus

<400> SEQUENCE: 1950
gguggagguc uuaucccaau u                                              21

<210> SEQ ID NO 1951
<211> LENGTH: 23
<212> TYPE: RNA
<213> ORGANISM: Influenza B virus

<400> SEQUENCE: 1951
guccuugaga guguuggu aa acg                                           23

<210> SEQ ID NO 1952
<211> LENGTH: 21
<212> TYPE: RNA
<213> ORGANISM: Influenza B virus
```

-continued

```
<400> SEQUENCE: 1952
caugaccaca acacaaauug a                                              21

<210> SEQ ID NO 1953
<211> LENGTH: 23
<212> TYPE: RNA
<213> ORGANISM: Influenza B virus

<400> SEQUENCE: 1953
gaaacugcgg ugggagucuu auc                                            23

<210> SEQ ID NO 1954
<211> LENGTH: 21
<212> TYPE: RNA
<213> ORGANISM: Influenza B virus

<400> SEQUENCE: 1954
gcaacugucc gaaauacaau u                                              21

<210> SEQ ID NO 1955
<211> LENGTH: 23
<212> TYPE: RNA
<213> ORGANISM: Influenza B virus

<400> SEQUENCE: 1955
aacaccaggg aggugccuug aug                                            23

<210> SEQ ID NO 1956
<211> LENGTH: 21
<212> TYPE: RNA
<213> ORGANISM: Influenza B virus

<400> SEQUENCE: 1956
aagagagaaa agcaauugga g                                              21

<210> SEQ ID NO 1957
<211> LENGTH: 23
<212> TYPE: RNA
<213> ORGANISM: Influenza B virus

<400> SEQUENCE: 1957
uccucaaaca ccccaaugga uac                                            23

<210> SEQ ID NO 1958
<211> LENGTH: 21
<212> TYPE: RNA
<213> ORGANISM: Influenza B virus

<400> SEQUENCE: 1958
gggaggugcc uugaugacau a                                              21

<210> SEQ ID NO 1959
<211> LENGTH: 21
<212> TYPE: RNA
<213> ORGANISM: Influenza B virus

<400> SEQUENCE: 1959
aagaagggaa guuccguuug a                                              21

<210> SEQ ID NO 1960
<211> LENGTH: 21
<212> TYPE: RNA
<213> ORGANISM: Influenza B virus
```

-continued

```
<400> SEQUENCE: 1960
aaaagcaauu ggaguaaaaa u                                          21

<210> SEQ ID NO 1961
<211> LENGTH: 23
<212> TYPE: RNA
<213> ORGANISM: Influenza B virus

<400> SEQUENCE: 1961
aucaacucug cauagauuga aug                                        23

<210> SEQ ID NO 1962
<211> LENGTH: 23
<212> TYPE: RNA
<213> ORGANISM: Influenza B virus

<400> SEQUENCE: 1962
caccagaaga gggagacaau uag                                        23

<210> SEQ ID NO 1963
<211> LENGTH: 21
<212> TYPE: RNA
<213> ORGANISM: Influenza B virus

<400> SEQUENCE: 1963
agagcccuug acuacccugg u                                          21

<210> SEQ ID NO 1964
<211> LENGTH: 21
<212> TYPE: RNA
<213> ORGANISM: Influenza B virus

<400> SEQUENCE: 1964
ggcccaacug aaauaguauu a                                          21

<210> SEQ ID NO 1965
<211> LENGTH: 21
<212> TYPE: RNA
<213> ORGANISM: Influenza B virus

<400> SEQUENCE: 1965
gagccauacu guaugaaaag u                                          21

<210> SEQ ID NO 1966
<211> LENGTH: 21
<212> TYPE: RNA
<213> ORGANISM: Influenza B virus

<400> SEQUENCE: 1966
gaccagagug gaaggcuugu u                                          21

<210> SEQ ID NO 1967
<211> LENGTH: 21
<212> TYPE: RNA
<213> ORGANISM: Influenza B virus

<400> SEQUENCE: 1967
ugcuggaauu gaagggguug a                                          21

<210> SEQ ID NO 1968
<211> LENGTH: 21
<212> TYPE: RNA
<213> ORGANISM: Influenza B virus
```

-continued

```
<400> SEQUENCE: 1968
aagugagccu gaaaguaaaa g                                              21

<210> SEQ ID NO 1969
<211> LENGTH: 19
<212> TYPE: RNA
<213> ORGANISM: Influenza B virus

<400> SEQUENCE: 1969
ggaggugccu ugaugacau                                                 19

<210> SEQ ID NO 1970
<211> LENGTH: 21
<212> TYPE: RNA
<213> ORGANISM: Influenza B virus

<400> SEQUENCE: 1970
aacugaaaua guauuaaggg a                                              21

<210> SEQ ID NO 1971
<211> LENGTH: 19
<212> TYPE: RNA
<213> ORGANISM: Influenza B virus

<400> SEQUENCE: 1971
cggauccuca acucacucu                                                 19

<210> SEQ ID NO 1972
<211> LENGTH: 23
<212> TYPE: RNA
<213> ORGANISM: Influenza B virus

<400> SEQUENCE: 1972
caguaauagc uaacagcucc aua                                            23

<210> SEQ ID NO 1973
<211> LENGTH: 23
<212> TYPE: RNA
<213> ORGANISM: Influenza B virus

<400> SEQUENCE: 1973
gggaaguucc guuugacaau aaa                                            23

<210> SEQ ID NO 1974
<211> LENGTH: 21
<212> TYPE: RNA
<213> ORGANISM: Influenza B virus

<400> SEQUENCE: 1974
cauggcaaag agcccuugac u                                              21

<210> SEQ ID NO 1975
<211> LENGTH: 21
<212> TYPE: RNA
<213> ORGANISM: Influenza B virus

<400> SEQUENCE: 1975
aacaaagaug caaggcaaaa g                                              21

<210> SEQ ID NO 1976
<211> LENGTH: 21
<212> TYPE: RNA
<213> ORGANISM: Influenza B virus
```

-continued

<400> SEQUENCE: 1976
cagggaggug ccuugaugac a    21

<210> SEQ ID NO 1977
<211> LENGTH: 21
<212> TYPE: RNA
<213> ORGANISM: Influenza B virus

<400> SEQUENCE: 1977
gaccacaaca caaauugagg u    21

<210> SEQ ID NO 1978
<211> LENGTH: 19
<212> TYPE: RNA
<213> ORGANISM: Influenza B virus

<400> SEQUENCE: 1978
ggaugugguu gaaguguac    19

<210> SEQ ID NO 1979
<211> LENGTH: 19
<212> TYPE: RNA
<213> ORGANISM: Influenza B virus

<400> SEQUENCE: 1979
ccucaaacac cccaaugga    19

<210> SEQ ID NO 1980
<211> LENGTH: 23
<212> TYPE: RNA
<213> ORGANISM: Influenza B virus

<400> SEQUENCE: 1980
aacauauugu uccacaaaac agu    23

<210> SEQ ID NO 1981
<211> LENGTH: 21
<212> TYPE: RNA
<213> ORGANISM: Influenza B virus

<400> SEQUENCE: 1981
aaaguacucc uauuuaugaa u    21

<210> SEQ ID NO 1982
<211> LENGTH: 23
<212> TYPE: RNA
<213> ORGANISM: Influenza B virus

<400> SEQUENCE: 1982
aacuuuaucu uuuaaguaaa aga    23

<210> SEQ ID NO 1983
<211> LENGTH: 21
<212> TYPE: RNA
<213> ORGANISM: Influenza B virus

<400> SEQUENCE: 1983 gcgguggag ucuuauccca a    21

<210> SEQ ID NO 1984
<211> LENGTH: 21
<212> TYPE: RNA
<213> ORGANISM: Influenza B virus -continued

```
<400> SEQUENCE: 1984
aaaaggaugu cucuugaaga g                                              21

<210> SEQ ID NO 1985
<211> LENGTH: 21
<212> TYPE: RNA
<213> ORGANISM: Influenza B virus

<400> SEQUENCE: 1985
gugagccuga aaguaaaagg a                                              21

<210> SEQ ID NO 1986
<211> LENGTH: 21
<212> TYPE: RNA
<213> ORGANISM: Influenza B virus

<400> SEQUENCE: 1986
agggaggugc cuugaugaca u                                              21

<210> SEQ ID NO 1987
<211> LENGTH: 21
<212> TYPE: RNA
<213> ORGANISM: Influenza B virus

<400> SEQUENCE: 1987
aacucacucu ucgagcgucu u                                              21

<210> SEQ ID NO 1988
<211> LENGTH: 23
<212> TYPE: RNA
<213> ORGANISM: Influenza B virus

<400> SEQUENCE: 1988
gugagccuga aaguaaaagg aug                                            23

<210> SEQ ID NO 1989
<211> LENGTH: 19
<212> TYPE: RNA
<213> ORGANISM: Influenza B virus

<400> SEQUENCE: 1989
gugggagucu uaucccaau                                                 19

<210> SEQ ID NO 1990
<211> LENGTH: 23
<212> TYPE: RNA
<213> ORGANISM: Influenza B virus

<400> SEQUENCE: 1990
caacucacuc uucgagcguc uua                                            23

<210> SEQ ID NO 1991
<211> LENGTH: 23
<212> TYPE: RNA
<213> ORGANISM: Influenza B virus

<400> SEQUENCE: 1991
cucuucgagc gucuuaauga agg                                            23

<210> SEQ ID NO 1992
<211> LENGTH: 21
<212> TYPE: RNA
<213> ORGANISM: Influenza B virus
```

-continued

<400> SEQUENCE: 1992
aauagcuaac agcuccauaa u                                          21

<210> SEQ ID NO 1993
<211> LENGTH: 21
<212> TYPE: RNA
<213> ORGANISM: Influenza B virus

<400> SEQUENCE: 1993
acccugguca agaccgccua a                                          21

<210> SEQ ID NO 1994
<211> LENGTH: 21
<212> TYPE: RNA
<213> ORGANISM: Influenza B virus

<400> SEQUENCE: 1994
cucugcauag auugaaugca u                                          21

<210> SEQ ID NO 1995
<211> LENGTH: 23
<212> TYPE: RNA
<213> ORGANISM: Influenza B virus

<400> SEQUENCE: 1995
gagccauacu guaugaaaag uuc                                        23

<210> SEQ ID NO 1996
<211> LENGTH: 23
<212> TYPE: RNA
<213> ORGANISM: Influenza B virus

<400> SEQUENCE: 1996
cucacucuuc gagcgucuua aug                                        23

<210> SEQ ID NO 1997
<211> LENGTH: 21
<212> TYPE: RNA
<213> ORGANISM: Influenza B virus

<400> SEQUENCE: 1997
aaugaaggac auucaaagcc a                                          21

<210> SEQ ID NO 1998
<211> LENGTH: 19
<212> TYPE: RNA
<213> ORGANISM: Influenza B virus

<400> SEQUENCE: 1998
cuccuauuua ugaauccau                                             19

<210> SEQ ID NO 1999
<211> LENGTH: 23
<212> TYPE: RNA
<213> ORGANISM: Influenza B virus

<400> SEQUENCE: 1999
uagcaacugu ccgaaauaca auu                                        23

<210> SEQ ID NO 2000
<211> LENGTH: 21
<212> TYPE: RNA
<213> ORGANISM: Influenza B virus

```
<400> SEQUENCE: 2000
cccuggucaa gaccgccuaa a                                               21

<210> SEQ ID NO 2001
<211> LENGTH: 19
<212> TYPE: RNA
<213> ORGANISM: Influenza B virus

<400> SEQUENCE: 2001
ggugccuuga ugacauaga                                                  19

<210> SEQ ID NO 2002
<211> LENGTH: 23
<212> TYPE: RNA
<213> ORGANISM: Influenza B virus

<400> SEQUENCE: 2002
ugcuacugau gaucuuacag ugg                                             23

<210> SEQ ID NO 2003
<211> LENGTH: 23
<212> TYPE: RNA
<213> ORGANISM: Influenza B virus

<400> SEQUENCE: 2003
gaagcaggaa uucuggagug cua                                             23

<210> SEQ ID NO 2004
<211> LENGTH: 19
<212> TYPE: RNA
<213> ORGANISM: Influenza B virus

<400> SEQUENCE: 2004
gccuugauga cauagaaga                                                  19

<210> SEQ ID NO 2005
<211> LENGTH: 21
<212> TYPE: RNA
<213> ORGANISM: Influenza B virus

<400> SEQUENCE: 2005
caaccaaugc caccauaaac u                                               21

<210> SEQ ID NO 2006
<211> LENGTH: 21
<212> TYPE: RNA
<213> ORGANISM: Influenza B virus

<400> SEQUENCE: 2006
aaaaagggau auacguaaug u                                               21

<210> SEQ ID NO 2007
<211> LENGTH: 23
<212> TYPE: RNA
<213> ORGANISM: Influenza B virus

<400> SEQUENCE: 2007
uaaaagggga uauacguaau gua                                             23

<210> SEQ ID NO 2008
<211> LENGTH: 23
<212> TYPE: RNA
<213> ORGANISM: Influenza B virus
```

```
<400> SEQUENCE: 2008
aagcaauugg aguaaaaaug aug                                    23

<210> SEQ ID NO 2009
<211> LENGTH: 23
<212> TYPE: RNA
<213> ORGANISM: Influenza B virus

<400> SEQUENCE: 2009
auggauacaa guccuuauca acu                                    23

<210> SEQ ID NO 2010
<211> LENGTH: 23
<212> TYPE: RNA
<213> ORGANISM: Influenza B virus

<400> SEQUENCE: 2010
aagggacaug aacaacaaag aug                                    23

<210> SEQ ID NO 2011
<211> LENGTH: 21
<212> TYPE: RNA
<213> ORGANISM: Influenza B virus

<400> SEQUENCE: 2011
aagcaggaau ucuggagugc u                                      21

<210> SEQ ID NO 2012
<211> LENGTH: 21
<212> TYPE: RNA
<213> ORGANISM: Influenza B virus

<400> SEQUENCE: 2012
augugguuga aguguacagc a                                      21

<210> SEQ ID NO 2013
<211> LENGTH: 21
<212> TYPE: RNA
<213> ORGANISM: Influenza B virus

<400> SEQUENCE: 2013
gauggcccaa cugaaauagu a                                      21

<210> SEQ ID NO 2014
<211> LENGTH: 19
<212> TYPE: RNA
<213> ORGANISM: Influenza B virus

<400> SEQUENCE: 2014
gagcaaccaa ugccaccau                                         19

<210> SEQ ID NO 2015
<211> LENGTH: 21
<212> TYPE: RNA
<213> ORGANISM: Influenza B virus

<400> SEQUENCE: 2015
aacaugacca caacacaaau u                                      21

<210> SEQ ID NO 2016
<211> LENGTH: 21
<212> TYPE: RNA
<213> ORGANISM: Influenza B virus
```

-continued

<210> SEQ ID NO 2016
<211> LENGTH: 21
<212> TYPE: RNA
<213> ORGANISM: Influenza B virus

<400> SEQUENCE: 2016
agaggaagua aacacucaga a                                              21

<210> SEQ ID NO 2017
<211> LENGTH: 23
<212> TYPE: RNA
<213> ORGANISM: Influenza B virus

<400> SEQUENCE: 2017
cauaugacca gaguggaagg cuu                                            23

<210> SEQ ID NO 2018
<211> LENGTH: 21
<212> TYPE: RNA
<213> ORGANISM: Influenza B virus

<400> SEQUENCE: 2018
aaaagugagc cugaaaguaa a                                              21

<210> SEQ ID NO 2019
<211> LENGTH: 19
<212> TYPE: RNA
<213> ORGANISM: Influenza B virus

<400> SEQUENCE: 2019
ugcuaaacuu guugcuacu                                                 19

<210> SEQ ID NO 2020
<211> LENGTH: 21
<212> TYPE: RNA
<213> ORGANISM: Influenza B virus

<400> SEQUENCE: 2020
aauugaugau aacauauugu u                                              21

<210> SEQ ID NO 2021
<211> LENGTH: 23
<212> TYPE: RNA
<213> ORGANISM: Influenza B virus

<400> SEQUENCE: 2021
gauacaaguc cuuaucaacu cug                                            23

<210> SEQ ID NO 2022
<211> LENGTH: 21
<212> TYPE: RNA
<213> ORGANISM: Influenza B virus

<400> SEQUENCE: 2022
aaccaaugcc accauaaacu u                                              21

<210> SEQ ID NO 2023
<211> LENGTH: 21
<212> TYPE: RNA
<213> ORGANISM: Influenza B virus

<400> SEQUENCE: 2023
gcccuugacu acccugguca a                                              21

<210> SEQ ID NO 2024
<211> LENGTH: 21
<212> TYPE: RNA
<213> ORGANISM: Influenza B virus -continued

<400> SEQUENCE: 2024
aaacauugua ugaaaugaag g                                            21

<210> SEQ ID NO 2025
<211> LENGTH: 21
<212> TYPE: RNA
<213> ORGANISM: Influenza B virus

<400> SEQUENCE: 2025
acacucagaa agaagggaag u                                            21

<210> SEQ ID NO 2026
<211> LENGTH: 23
<212> TYPE: RNA
<213> ORGANISM: Influenza B virus

<400> SEQUENCE: 2026
uaaaaaugau gaaaguacuc cua                                          23

<210> SEQ ID NO 2027
<211> LENGTH: 21
<212> TYPE: RNA
<213> ORGANISM: Influenza B virus

<400> SEQUENCE: 2027
agcugacaug guuguaucau u                                            21

<210> SEQ ID NO 2028
<211> LENGTH: 19
<212> TYPE: RNA
<213> ORGANISM: Influenza B virus

<400> SEQUENCE: 2028
gcuccauaau agcugacau                                               19

<210> SEQ ID NO 2029
<211> LENGTH: 21
<212> TYPE: RNA
<213> ORGANISM: Influenza B virus

<400> SEQUENCE: 2029
aagggaaguu ccguuugaca a                                            21

<210> SEQ ID NO 2030
<211> LENGTH: 23
<212> TYPE: RNA
<213> ORGANISM: Influenza B virus

<400> SEQUENCE: 2030
caacaugacc acaacacaaa uug                                          23

<210> SEQ ID NO 2031
<211> LENGTH: 21
<212> TYPE: RNA
<213> ORGANISM: Influenza B virus

<400> SEQUENCE: 2031
aaggguuuga gccauacugu a                                            21

<210> SEQ ID NO 2032
<211> LENGTH: 19
<212> TYPE: RNA
<213> ORGANISM: Influenza B virus -continued

<400> SEQUENCE: 2032
ccaucggauc cucaacuca                                         19

<210> SEQ ID NO 2033
<211> LENGTH: 21
<212> TYPE: RNA
<213> ORGANISM: Influenza B virus

<400> SEQUENCE: 2033
acuggucaca gaagaacuuu a                                      21

<210> SEQ ID NO 2034
<211> LENGTH: 23
<212> TYPE: RNA
<213> ORGANISM: Influenza B virus

<400> SEQUENCE: 2034
agggacauga acaacaaaga ugc                                    23

<210> SEQ ID NO 2035
<211> LENGTH: 23
<212> TYPE: RNA
<213> ORGANISM: Influenza B virus

<400> SEQUENCE: 2035
aaggguuuga gccauacugu aug                                    23

<210> SEQ ID NO 2036
<211> LENGTH: 21
<212> TYPE: RNA
<213> ORGANISM: Influenza B virus

<400> SEQUENCE: 2036
augaauccau cugcuggaau u                                      21

<210> SEQ ID NO 2037
<211> LENGTH: 19
<212> TYPE: RNA
<213> ORGANISM: Influenza B virus

<400> SEQUENCE: 2037
caguggagga ugaagaaga                                         19

<210> SEQ ID NO 2038
<211> LENGTH: 19
<212> TYPE: RNA
<213> ORGANISM: Influenza B virus

<400> SEQUENCE: 2038
ggcuuguugc uaaacuugu                                         19

<210> SEQ ID NO 2039
<211> LENGTH: 21
<212> TYPE: RNA
<213> ORGANISM: Influenza B virus

<400> SEQUENCE: 2039
aaaugaagga ugugguugaa g                                      21

<210> SEQ ID NO 2040
<211> LENGTH: 23
<212> TYPE: RNA
<213> ORGANISM: Influenza B virus

```
<400> SEQUENCE: 2040
uacaguggag gaugaagaag aug                                           23

<210> SEQ ID NO 2041
<211> LENGTH: 23
<212> TYPE: RNA
<213> ORGANISM: Influenza B virus

<400> SEQUENCE: 2041
gauggccauc ggauccucaa cuc                                           23

<210> SEQ ID NO 2042
<211> LENGTH: 23
<212> TYPE: RNA
<213> ORGANISM: Influenza B virus

<400> SEQUENCE: 2042
uugagccaua cuguaugaaa agu                                           23

<210> SEQ ID NO 2043
<211> LENGTH: 21
<212> TYPE: RNA
<213> ORGANISM: Influenza B virus

<400> SEQUENCE: 2043
gaggauguug auggcccaac u                                             21

<210> SEQ ID NO 2044
<211> LENGTH: 19
<212> TYPE: RNA
<213> ORGANISM: Influenza B virus

<400> SEQUENCE: 2044
gcgucuuaau gaaggacau                                                19

<210> SEQ ID NO 2045
<211> LENGTH: 21
<212> TYPE: RNA
<213> ORGANISM: Influenza B virus

<400> SEQUENCE: 2045
ucaccagaag agggagacaa u                                             21

<210> SEQ ID NO 2046
<211> LENGTH: 21
<212> TYPE: RNA
<213> ORGANISM: Influenza B virus

<400> SEQUENCE: 2046
agcgucuuaa ugaaggacau u                                             21

<210> SEQ ID NO 2047
<211> LENGTH: 21
<212> TYPE: RNA
<213> ORGANISM: Influenza B virus

<400> SEQUENCE: 2047
cgggagcaac caaugccacc a                                             21

<210> SEQ ID NO 2048
<211> LENGTH: 19
<212> TYPE: RNA
<213> ORGANISM: Influenza B virus
```

<400> SEQUENCE: 2048
gccaccauaa acuuugaag                                          19

<210> SEQ ID NO 2049
<211> LENGTH: 19
<212> TYPE: RNA
<213> ORGANISM: Influenza B virus

<400> SEQUENCE: 2049
gaccgccuaa acagacuaa                                          19

<210> SEQ ID NO 2050
<211> LENGTH: 23
<212> TYPE: RNA
<213> ORGANISM: Influenza B virus

<400> SEQUENCE: 2050
agcaauugga guaaaaauga uga                                     23

<210> SEQ ID NO 2051
<211> LENGTH: 21
<212> TYPE: RNA
<213> ORGANISM: Influenza B virus

<400> SEQUENCE: 2051
aaagagaaaa uuagagucaa g                                       21

<210> SEQ ID NO 2052
<211> LENGTH: 19
<212> TYPE: RNA
<213> ORGANISM: Influenza B virus

<400> SEQUENCE: 2052
gcaacugucc gaaauacaa                                          19

<210> SEQ ID NO 2053
<211> LENGTH: 21
<212> TYPE: RNA
<213> ORGANISM: Influenza B virus

<400> SEQUENCE: 2053
ccaauggaua caaguccuua u                                       21

<210> SEQ ID NO 2054
<211> LENGTH: 21
<212> TYPE: RNA
<213> ORGANISM: Influenza B virus

<400> SEQUENCE: 2054
gaaggguuug agccauacug u                                       21

<210> SEQ ID NO 2055
<211> LENGTH: 21
<212> TYPE: RNA
<213> ORGANISM: Influenza B virus

<400> SEQUENCE: 2055
guugcuaaac uuguugcuac u                                       21

<210> SEQ ID NO 2056
<211> LENGTH: 21
<212> TYPE: RNA
<213> ORGANISM: Influenza B virus

```
<400> SEQUENCE: 2056
gaguggaagg cuuguugcua a                                        21

<210> SEQ ID NO 2057
<211> LENGTH: 21
<212> TYPE: RNA
<213> ORGANISM: Influenza B virus

<400> SEQUENCE: 2057
aggugggucc gggagcaacc a                                        21

<210> SEQ ID NO 2058
<211> LENGTH: 23
<212> TYPE: RNA
<213> ORGANISM: Influenza B virus

<400> SEQUENCE: 2058
aaaagaauug augauaacau auu                                      23

<210> SEQ ID NO 2059
<211> LENGTH: 23
<212> TYPE: RNA
<213> ORGANISM: Influenza B virus

<400> SEQUENCE: 2059
uagacugguc acagaagaac uuu                                      23

<210> SEQ ID NO 2060
<211> LENGTH: 21
<212> TYPE: RNA
<213> ORGANISM: Influenza B virus

<400> SEQUENCE: 2060
cggugggagu cuuaucccaa u                                        21

<210> SEQ ID NO 2061
<211> LENGTH: 21
<212> TYPE: RNA
<213> ORGANISM: Influenza B virus

<400> SEQUENCE: 2061
uagcaacugu ccgaaauaca a                                        21

<210> SEQ ID NO 2062
<211> LENGTH: 21
<212> TYPE: RNA
<213> ORGANISM: Influenza B virus

<400> SEQUENCE: 2062
aacagugaag augagcaucu a                                        21

<210> SEQ ID NO 2063
<211> LENGTH: 23
<212> TYPE: RNA
<213> ORGANISM: Influenza B virus

<400> SEQUENCE: 2063
uaauaaaagg guccuugccu uua                                      23

<210> SEQ ID NO 2064
<211> LENGTH: 19
<212> TYPE: RNA
<213> ORGANISM: Influenza B virus
```

```
<400> SEQUENCE: 2064
gcacuugaga gaaaacuaa                                                  19

<210> SEQ ID NO 2065
<211> LENGTH: 21
<212> TYPE: RNA
<213> ORGANISM: Influenza B virus

<400> SEQUENCE: 2065
ggaggauggg aaggaaugau u                                               21

<210> SEQ ID NO 2066
<211> LENGTH: 21
<212> TYPE: RNA
<213> ORGANISM: Influenza B virus

<400> SEQUENCE: 2066
gacuuggaac uucaggaucu u                                               21

<210> SEQ ID NO 2067
<211> LENGTH: 21
<212> TYPE: RNA
<213> ORGANISM: Influenza B virus

<400> SEQUENCE: 2067
aaauacggug gauuaaacaa a                                               21

<210> SEQ ID NO 2068
<211> LENGTH: 21
<212> TYPE: RNA
<213> ORGANISM: Influenza B virus

<400> SEQUENCE: 2068
ucccacuuuu gauucacuga a                                               21

<210> SEQ ID NO 2069
<211> LENGTH: 21
<212> TYPE: RNA
<213> ORGANISM: Influenza B virus

<400> SEQUENCE: 2069
ggguuccauu cugaugacaa a                                               21

<210> SEQ ID NO 2070
<211> LENGTH: 21
<212> TYPE: RNA
<213> ORGANISM: Influenza B virus

<400> SEQUENCE: 2070
aaaacccaaa ugaaaaaccu c                                               21

<210> SEQ ID NO 2071
<211> LENGTH: 21
<212> TYPE: RNA
<213> ORGANISM: Influenza B virus

<400> SEQUENCE: 2071
aaacaagaua acaaaaaauc u                                               21

<210> SEQ ID NO 2072
<211> LENGTH: 23
<212> TYPE: RNA
<213> ORGANISM: Influenza B virus
```

```
<400> SEQUENCE: 2072
accuccugca aaacuauuaa agg                                              23

<210> SEQ ID NO 2073
<211> LENGTH: 19
<212> TYPE: RNA
<213> ORGANISM: Influenza B virus

<400> SEQUENCE: 2073
cccaaucuuc ucagaggau                                                   19

<210> SEQ ID NO 2074
<211> LENGTH: 23
<212> TYPE: RNA
<213> ORGANISM: Influenza B virus

<400> SEQUENCE: 2074
gcgauaccau ugacaacaac acc                                              23

<210> SEQ ID NO 2075
<211> LENGTH: 19
<212> TYPE: RNA
<213> ORGANISM: Influenza B virus

<400> SEQUENCE: 2075
accauacuau acugcucua                                                   19

<210> SEQ ID NO 2076
<211> LENGTH: 19
<212> TYPE: RNA
<213> ORGANISM: Influenza B virus

<400> SEQUENCE: 2076
gcggcagaau uguuguuga                                                   19

<210> SEQ ID NO 2077
<211> LENGTH: 19
<212> TYPE: RNA
<213> ORGANISM: Influenza B virus

<400> SEQUENCE: 2077
cacacaucug uacaaaaga                                                   19

<210> SEQ ID NO 2078
<211> LENGTH: 23
<212> TYPE: RNA
<213> ORGANISM: Influenza B virus

<400> SEQUENCE: 2078
gaaaacagga acaauugucu auc                                              23

<210> SEQ ID NO 2079
<211> LENGTH: 23
<212> TYPE: RNA
<213> ORGANISM: Influenza B virus

<400> SEQUENCE: 2079
uauagaccuc cugcaaaacu auu                                              23

<210> SEQ ID NO 2080
<211> LENGTH: 21
<212> TYPE: RNA
<213> ORGANISM: Influenza B virus
```

-continued

```
<400> SEQUENCE: 2080
aauggaugcu ucgaaaccaa a                                              21

<210> SEQ ID NO 2081
<211> LENGTH: 19
<212> TYPE: RNA
<213> ORGANISM: Influenza B virus

<400> SEQUENCE: 2081
cagcuaccca aucuucuca                                                 19

<210> SEQ ID NO 2082
<211> LENGTH: 23
<212> TYPE: RNA
<213> ORGANISM: Influenza B virus

<400> SEQUENCE: 2082
cacaaaauga aggcaauaau ugu                                            23

<210> SEQ ID NO 2083
<211> LENGTH: 23
<212> TYPE: RNA
<213> ORGANISM: Influenza B virus

<400> SEQUENCE: 2083
caccucaucu gcuaauggaa uaa                                            23

<210> SEQ ID NO 2084
<211> LENGTH: 23
<212> TYPE: RNA
<213> ORGANISM: Influenza B virus

<400> SEQUENCE: 2084
aacaucguca aacucaccuc aug                                            23

<210> SEQ ID NO 2085
<211> LENGTH: 23
<212> TYPE: RNA
<213> ORGANISM: Influenza B virus

<400> SEQUENCE: 2085
gaccuccugc aaaacuauua aag                                            23

<210> SEQ ID NO 2086
<211> LENGTH: 23
<212> TYPE: RNA
<213> ORGANISM: Influenza B virus

<400> SEQUENCE: 2086
uugaugauag cuauuuuuau ugu                                            23

<210> SEQ ID NO 2087
<211> LENGTH: 21
<212> TYPE: RNA
<213> ORGANISM: Influenza B virus

<400> SEQUENCE: 2087
aauaugggug aaaacaccuu u                                              21

<210> SEQ ID NO 2088
<211> LENGTH: 21
<212> TYPE: RNA
<213> ORGANISM: Influenza B virus
```

```
<400> SEQUENCE: 2088
gugcgauacc auugacaaca a                                              21

<210> SEQ ID NO 2089
<211> LENGTH: 19
<212> TYPE: RNA
<213> ORGANISM: Influenza B virus

<400> SEQUENCE: 2089
gaguggcagg agcaaagua                                                 19

<210> SEQ ID NO 2090
<211> LENGTH: 23
<212> TYPE: RNA
<213> ORGANISM: Influenza B virus

<400> SEQUENCE: 2090
cugucccaag ggacaacaac aaa                                            23

<210> SEQ ID NO 2091
<211> LENGTH: 21
<212> TYPE: RNA
<213> ORGANISM: Influenza B virus

<400> SEQUENCE: 2091
uugccuuuaa uuggugaagc a                                              21

<210> SEQ ID NO 2092
<211> LENGTH: 19
<212> TYPE: RNA
<213> ORGANISM: Influenza B virus

<400> SEQUENCE: 2092
cuucucagag gauaugaaa                                                 19

<210> SEQ ID NO 2093
<211> LENGTH: 23
<212> TYPE: RNA
<213> ORGANISM: Influenza B virus

<400> SEQUENCE: 2093
aaugugacug gugcgauacc auu                                            23

<210> SEQ ID NO 2094
<211> LENGTH: 19
<212> TYPE: RNA
<213> ORGANISM: Influenza B virus

<400> SEQUENCE: 2094
cgcagaaaag gcaccagga                                                 19

<210> SEQ ID NO 2095
<211> LENGTH: 23
<212> TYPE: RNA
<213> ORGANISM: Influenza B virus

<400> SEQUENCE: 2095
gauagcugcu ggcaccuuua aug                                            23

<210> SEQ ID NO 2096
<211> LENGTH: 23
<212> TYPE: RNA
<213> ORGANISM: Influenza B virus
```

```
<400> SEQUENCE: 2096
cucaacugcu gcuucuaguu ugg                                          23

<210> SEQ ID NO 2097
<211> LENGTH: 21
<212> TYPE: RNA
<213> ORGANISM: Influenza B virus

<400> SEQUENCE: 2097
aaguucaccu caucugcuaa u                                            21

<210> SEQ ID NO 2098
<211> LENGTH: 23
<212> TYPE: RNA
<213> ORGANISM: Influenza B virus

<400> SEQUENCE: 2098
aagcuugcca auggaaccaa aua                                          23

<210> SEQ ID NO 2099
<211> LENGTH: 21
<212> TYPE: RNA
<213> ORGANISM: Influenza B virus

<400> SEQUENCE: 2099
aacuccauaa cgaaauacuc g                                            21

<210> SEQ ID NO 2100
<211> LENGTH: 23
<212> TYPE: RNA
<213> ORGANISM: Influenza B virus

<400> SEQUENCE: 2100
accacacauc uguacaaaag aag                                          23

<210> SEQ ID NO 2101
<211> LENGTH: 23
<212> TYPE: RNA
<213> ORGANISM: Influenza B virus

<400> SEQUENCE: 2101
uagggaaugg augcuucgaa acc                                          23

<210> SEQ ID NO 2102
<211> LENGTH: 19
<212> TYPE: RNA
<213> ORGANISM: Influenza B virus

<400> SEQUENCE: 2102
gccauggaug aacuccaua                                               19

<210> SEQ ID NO 2103
<211> LENGTH: 23
<212> TYPE: RNA
<213> ORGANISM: Influenza B virus

<400> SEQUENCE: 2103
ugcccaauau gggugaaaac acc                                          23

<210> SEQ ID NO 2104
<211> LENGTH: 23
<212> TYPE: RNA
<213> ORGANISM: Influenza B virus
```

-continued

```
<400> SEQUENCE: 2104
auggauugga uaccauacu aua                                      23

<210> SEQ ID NO 2105
<211> LENGTH: 19
<212> TYPE: RNA
<213> ORGANISM: Influenza B virus

<400> SEQUENCE: 2105
gccuuacuac acaggagaa                                          19

<210> SEQ ID NO 2106
<211> LENGTH: 21
<212> TYPE: RNA
<213> ORGANISM: Influenza B virus

<400> SEQUENCE: 2106
aauaauugua cuacucaugg u                                       21

<210> SEQ ID NO 2107
<211> LENGTH: 21
<212> TYPE: RNA
<213> ORGANISM: Influenza B virus

<400> SEQUENCE: 2107
acaccuucgg caaaagcuuc a                                       21

<210> SEQ ID NO 2108
<211> LENGTH: 21
<212> TYPE: RNA
<213> ORGANISM: Influenza B virus

<400> SEQUENCE: 2108
auagaccucc ugcaaaacua u                                       21

<210> SEQ ID NO 2109
<211> LENGTH: 21
<212> TYPE: RNA
<213> ORGANISM: Influenza B virus

<400> SEQUENCE: 2109
cuacacagga gaacaugcaa a                                       21

<210> SEQ ID NO 2110
<211> LENGTH: 23
<212> TYPE: RNA
<213> ORGANISM: Influenza B virus

<400> SEQUENCE: 2110
aauuacuguu uggggguucc auu                                     23

<210> SEQ ID NO 2111
<211> LENGTH: 23
<212> TYPE: RNA
<213> ORGANISM: Influenza B virus

<400> SEQUENCE: 2111
aucuucucag aggauaugaa aaa                                     23

<210> SEQ ID NO 2112
<211> LENGTH: 19
<212> TYPE: RNA
<213> ORGANISM: Influenza B virus
```

```
<400> SEQUENCE: 2112
cucacaaaua gaacuugca                                             19

<210> SEQ ID NO 2113
<211> LENGTH: 23
<212> TYPE: RNA
<213> ORGANISM: Influenza B virus

<400> SEQUENCE: 2113
cugacacaau aagcucacaa aua                                        23

<210> SEQ ID NO 2114
<211> LENGTH: 21
<212> TYPE: RNA
<213> ORGANISM: Influenza B virus

<400> SEQUENCE: 2114
gccauaggaa auugcccaau a                                          21

<210> SEQ ID NO 2115
<211> LENGTH: 23
<212> TYPE: RNA
<213> ORGANISM: Influenza B virus

<400> SEQUENCE: 2115
aaccacacau uauguuucuc aga                                        23

<210> SEQ ID NO 2116
<211> LENGTH: 21
<212> TYPE: RNA
<213> ORGANISM: Influenza B virus

<400> SEQUENCE: 2116
ucuugcucca ucugucuaua a                                          21

<210> SEQ ID NO 2117
<211> LENGTH: 23
<212> TYPE: RNA
<213> ORGANISM: Influenza B virus

<400> SEQUENCE: 2117
uagaaguacc acacaucugu aca                                        23

<210> SEQ ID NO 2118
<211> LENGTH: 23
<212> TYPE: RNA
<213> ORGANISM: Influenza B virus

<400> SEQUENCE: 2118
aucucagagc ugacacaaua agc                                        23

<210> SEQ ID NO 2119
<211> LENGTH: 21
<212> TYPE: RNA
<213> ORGANISM: Influenza B virus

<400> SEQUENCE: 2119
cuauuggcac uugagagaaa a                                          21

<210> SEQ ID NO 2120
<211> LENGTH: 23
<212> TYPE: RNA
<213> ORGANISM: Influenza B virus
```

```
<400> SEQUENCE: 2120
caggaacaau ugucuaucaa aga                                    23

<210> SEQ ID NO 2121
<211> LENGTH: 21
<212> TYPE: RNA
<213> ORGANISM: Influenza B virus

<400> SEQUENCE: 2121
guuuggcugu aacauugaug a                                      21

<210> SEQ ID NO 2122
<211> LENGTH: 21
<212> TYPE: RNA
<213> ORGANISM: Influenza B virus

<400> SEQUENCE: 2122
uccacgaagu cagaccuguu a                                      21

<210> SEQ ID NO 2123
<211> LENGTH: 21
<212> TYPE: RNA
<213> ORGANISM: Influenza B virus

<400> SEQUENCE: 2123
uucccacuuu ugauucacug a                                      21

<210> SEQ ID NO 2124
<211> LENGTH: 23
<212> TYPE: RNA
<213> ORGANISM: Influenza B virus

<400> SEQUENCE: 2124
aacauccaau gcagaucgaa ucu                                    23

<210> SEQ ID NO 2125
<211> LENGTH: 21
<212> TYPE: RNA
<213> ORGANISM: Influenza B virus

<400> SEQUENCE: 2125
aaccacacau uauguuucuc a                                      21

<210> SEQ ID NO 2126
<211> LENGTH: 21
<212> TYPE: RNA
<213> ORGANISM: Influenza B virus

<400> SEQUENCE: 2126
aaauccucaa aaguucaccu c                                      21

<210> SEQ ID NO 2127
<211> LENGTH: 21
<212> TYPE: RNA
<213> ORGANISM: Influenza B virus

<400> SEQUENCE: 2127
uagaacuugc agucuugcuu u                                      21

<210> SEQ ID NO 2128
<211> LENGTH: 21
<212> TYPE: RNA
<213> ORGANISM: Influenza B virus
```

-continued

```
<400> SEQUENCE: 2128
caccucaucu gcuaauggaa u                                               21

<210> SEQ ID NO 2129
<211> LENGTH: 21
<212> TYPE: RNA
<213> ORGANISM: Influenza B virus

<400> SEQUENCE: 2129
auggagacuc aaauccucaa a                                               21

<210> SEQ ID NO 2130
<211> LENGTH: 23
<212> TYPE: RNA
<213> ORGANISM: Influenza B virus

<400> SEQUENCE: 2130
gauagcuauu uuauuguuu aua                                              23

<210> SEQ ID NO 2131
<211> LENGTH: 23
<212> TYPE: RNA
<213> ORGANISM: Influenza B virus

<400> SEQUENCE: 2131
caccaggagg acccuacaga cuu                                             23

<210> SEQ ID NO 2132
<211> LENGTH: 21
<212> TYPE: RNA
<213> ORGANISM: Influenza B virus

<400> SEQUENCE: 2132
cucaugguag uaacauccaa u                                               21

<210> SEQ ID NO 2133
<211> LENGTH: 19
<212> TYPE: RNA
<213> ORGANISM: Influenza B virus

<400> SEQUENCE: 2133
caacaaaaca gcaacgaau                                                  19

<210> SEQ ID NO 2134
<211> LENGTH: 23
<212> TYPE: RNA
<213> ORGANISM: Influenza B virus

<400> SEQUENCE: 2134 ggggguuccau ucugaugaca aaa                                            23

<210> SEQ ID NO 2135
<211> LENGTH: 23
<212> TYPE: RNA
<213> ORGANISM: Influenza B virus

<400> SEQUENCE: 2135
uucuuugagu gaguuagaag uaa                                             23

<210> SEQ ID NO 2136
<211> LENGTH: 23
<212> TYPE: RNA
<213> ORGANISM: Influenza B virus
```

-continued

<400> SEQUENCE: 2136
gaucuccaga gacaauguuu cuu                                        23

<210> SEQ ID NO 2137
<211> LENGTH: 21
<212> TYPE: RNA
<213> ORGANISM: Influenza B virus

<400> SEQUENCE: 2137
acccaaucuu cucagaggau a                                          21

<210> SEQ ID NO 2138
<211> LENGTH: 21
<212> TYPE: RNA
<213> ORGANISM: Influenza B virus

<400> SEQUENCE: 2138
aucuccagag acaauguuuc u                                          21

<210> SEQ ID NO 2139
<211> LENGTH: 23
<212> TYPE: RNA
<213> ORGANISM: Influenza B virus

<400> SEQUENCE: 2139
aaggaaaauu aagcccugua uuu                                        23

<210> SEQ ID NO 2140
<211> LENGTH: 23
<212> TYPE: RNA
<213> ORGANISM: Influenza B virus

<400> SEQUENCE: 2140
gaguggcagu ggcagcagac cuu                                        23

<210> SEQ ID NO 2141
<211> LENGTH: 23
<212> TYPE: RNA
<213> ORGANISM: Influenza B virus

<400> SEQUENCE: 2141
aggaaaauua agcccuguau uuu                                        23

<210> SEQ ID NO 2142
<211> LENGTH: 21
<212> TYPE: RNA
<213> ORGANISM: Influenza B virus

<400> SEQUENCE: 2142
guggucaaaa cagcuacuca a                                          21

<210> SEQ ID NO 2143
<211> LENGTH: 21
<212> TYPE: RNA
<213> ORGANISM: Influenza B virus

<400> SEQUENCE: 2143
ggaugaacuc cauaacgaaa u                                          21

<210> SEQ ID NO 2144
<211> LENGTH: 19
<212> TYPE: RNA
<213> ORGANISM: Influenza B virus -continued

```
<400> SEQUENCE: 2144
gcuucgaaac caaacacaa                                              19

<210> SEQ ID NO 2145
<211> LENGTH: 23
<212> TYPE: RNA
<213> ORGANISM: Influenza B virus

<400> SEQUENCE: 2145
aauuggugaa gcagauugcc uuc                                         23

<210> SEQ ID NO 2146
<211> LENGTH: 19
<212> TYPE: RNA
<213> ORGANISM: Influenza B virus

<400> SEQUENCE: 2146
guggugccau ggaugaacu                                              19

<210> SEQ ID NO 2147
<211> LENGTH: 21
<212> TYPE: RNA
<213> ORGANISM: Influenza B virus

<400> SEQUENCE: 2147
aguaccacac aucuguacaa a                                           21

<210> SEQ ID NO 2148
<211> LENGTH: 21
<212> TYPE: RNA
<213> ORGANISM: Influenza B virus

<400> SEQUENCE: 2148
aagcggauuu uucgcaacaa u                                           21

<210> SEQ ID NO 2149
<211> LENGTH: 23
<212> TYPE: RNA
<213> ORGANISM: Influenza B virus

<400> SEQUENCE: 2149
gauaacaucg ucaaacucac cuc                                         23

<210> SEQ ID NO 2150
<211> LENGTH: 23
<212> TYPE: RNA
<213> ORGANISM: Influenza B virus

<400> SEQUENCE: 2150
aaucucaauu cuuugaguga guu                                         23

<210> SEQ ID NO 2151
<211> LENGTH: 21
<212> TYPE: RNA
<213> ORGANISM: Influenza B virus

<400> SEQUENCE: 2151
aauuguacua cucaugguag u                                           21

<210> SEQ ID NO 2152
<211> LENGTH: 23
<212> TYPE: RNA
<213> ORGANISM: Influenza B virus
```

```
<400> SEQUENCE: 2152
uggcaggagc aaaguaauaa aag                                          23

<210> SEQ ID NO 2153
<211> LENGTH: 21
<212> TYPE: RNA
<213> ORGANISM: Influenza B virus

<400> SEQUENCE: 2153
aauaauaaac agugaagaug a                                            21

<210> SEQ ID NO 2154
<211> LENGTH: 21
<212> TYPE: RNA
<213> ORGANISM: Influenza B virus

<400> SEQUENCE: 2154
aacauccaau gcagaucgaa u                                            21

<210> SEQ ID NO 2155
<211> LENGTH: 21
<212> TYPE: RNA
<213> ORGANISM: Influenza B virus

<400> SEQUENCE: 2155
accuccugca aaacuauuaa a                                            21

<210> SEQ ID NO 2156
<211> LENGTH: 23
<212> TYPE: RNA
<213> ORGANISM: Influenza B virus

<400> SEQUENCE: 2156
cacacauuau guuucucaga uug                                          23

<210> SEQ ID NO 2157
<211> LENGTH: 19
<212> TYPE: RNA
<213> ORGANISM: Influenza B virus

<400> SEQUENCE: 2157
cauccaaugc agaucgaau                                               19

<210> SEQ ID NO 2158
<211> LENGTH: 21
<212> TYPE: RNA
<213> ORGANISM: Influenza B virus

<400> SEQUENCE: 2158
aaaagggucc uugccuuuaa u                                            21

<210> SEQ ID NO 2159
<211> LENGTH: 21
<212> TYPE: RNA
<213> ORGANISM: Influenza B virus

<400> SEQUENCE: 2159
cgcuaccagu aaaagcggau u                                            21

<210> SEQ ID NO 2160
<211> LENGTH: 19
<212> TYPE: RNA
<213> ORGANISM: Influenza B virus
```

```
<400> SEQUENCE: 2160
cuacucaacu gcugcuucu                                                      19

<210> SEQ ID NO 2161
<211> LENGTH: 23
<212> TYPE: RNA
<213> ORGANISM: Influenza B virus

<400> SEQUENCE: 2161
cauccggaug cuuuccuaua aug                                                 23

<210> SEQ ID NO 2162
<211> LENGTH: 23
<212> TYPE: RNA
<213> ORGANISM: Influenza B virus

<400> SEQUENCE: 2162
aacaacaaaa cagcaacgaa ucc                                                 23

<210> SEQ ID NO 2163
<211> LENGTH: 23
<212> TYPE: RNA
<213> ORGANISM: Influenza B virus

<400> SEQUENCE: 2163
uagcuauuuu uauuguuuau aug                                                 23

<210> SEQ ID NO 2164
<211> LENGTH: 23
<212> TYPE: RNA
<213> ORGANISM: Influenza B virus

<400> SEQUENCE: 2164
ggcacuugag agaaaacuaa aga                                                 23

<210> SEQ ID NO 2165
<211> LENGTH: 21
<212> TYPE: RNA
<213> ORGANISM: Influenza B virus

<400> SEQUENCE: 2165
uggaugaacu ccauaacgaa a                                                   21

<210> SEQ ID NO 2166
<211> LENGTH: 21
<212> TYPE: RNA
<213> ORGANISM: Influenza B virus

<400> SEQUENCE: 2166
gagggaaacu augcccaacc u                                                   21

<210> SEQ ID NO 2167
<211> LENGTH: 21
<212> TYPE: RNA
<213> ORGANISM: Influenza B virus

<400> SEQUENCE: 2167
uucuugcucc aucugcuau a                                                    21

<210> SEQ ID NO 2168
<211> LENGTH: 23
<212> TYPE: RNA
<213> ORGANISM: Influenza B virus
```

```
<400> SEQUENCE: 2168
uaacaguaga aguaccacac auc                                          23

<210> SEQ ID NO 2169
<211> LENGTH: 23
<212> TYPE: RNA
<213> ORGANISM: Influenza B virus

<400> SEQUENCE: 2169
aauauagacc uccugcaaaa cua                                          23

<210> SEQ ID NO 2170
<211> LENGTH: 21
<212> TYPE: RNA
<213> ORGANISM: Influenza B virus

<400> SEQUENCE: 2170
agccauagga aauugcccaa u                                            21

<210> SEQ ID NO 2171
<211> LENGTH: 23
<212> TYPE: RNA
<213> ORGANISM: Influenza B virus

<400> SEQUENCE: 2171
caacaccaac aaaaucucau uuu                                          23

<210> SEQ ID NO 2172
<211> LENGTH: 21
<212> TYPE: RNA
<213> ORGANISM: Influenza B virus

<400> SEQUENCE: 2172
uggccuuggg cagaccaaug u                                            21

<210> SEQ ID NO 2173
<211> LENGTH: 19
<212> TYPE: RNA
<213> ORGANISM: Influenza B virus

<400> SEQUENCE: 2173 accuugaag cuugccaau                                                19

<210> SEQ ID NO 2174
<211> LENGTH: 21
<212> TYPE: RNA
<213> ORGANISM: Influenza B virus

<400> SEQUENCE: 2174 aaucuuuga gugaguuaga a                                             21

<210> SEQ ID NO 2175
<211> LENGTH: 23
<212> TYPE: RNA
<213> ORGANISM: Influenza B virus

<400> SEQUENCE: 2175
cccaaucuuc ucagaggaua uga                                          23

<210> SEQ ID NO 2176
<211> LENGTH: 21
<212> TYPE: RNA
<213> ORGANISM: Influenza B virus
```

-continued

```
<400> SEQUENCE: 2176
gaccuccugc aaaacuauua a                                              21

<210> SEQ ID NO 2177
<211> LENGTH: 21
<212> TYPE: RNA
<213> ORGANISM: Influenza B virus

<400> SEQUENCE: 2177
aauccacuaa caguagaagu a                                              21

<210> SEQ ID NO 2178
<211> LENGTH: 21
<212> TYPE: RNA
<213> ORGANISM: Influenza B virus

<400> SEQUENCE: 2178
cuugggcugu cccaagggac a                                              21

<210> SEQ ID NO 2179
<211> LENGTH: 21
<212> TYPE: RNA
<213> ORGANISM: Influenza B virus

<400> SEQUENCE: 2179
aaaugaaaaa ccucuaugga g                                              21

<210> SEQ ID NO 2180
<211> LENGTH: 21
<212> TYPE: RNA
<213> ORGANISM: Influenza B virus

<400> SEQUENCE: 2180
gauugcaggu uggcacggau a                                              21

<210> SEQ ID NO 2181
<211> LENGTH: 23
<212> TYPE: RNA
<213> ORGANISM: Influenza B virus

<400> SEQUENCE: 2181
uacagacuug gaacuucagg auc                                            23

<210> SEQ ID NO 2182
<211> LENGTH: 23
<212> TYPE: RNA
<213> ORGANISM: Influenza B virus

<400> SEQUENCE: 2182
uaauggaaua accacacauu aug                                            23

<210> SEQ ID NO 2183
<211> LENGTH: 23
<212> TYPE: RNA
<213> ORGANISM: Influenza B virus

<400> SEQUENCE: 2183
uacugcugca ucuuuaaaug aug                                            23

<210> SEQ ID NO 2184
<211> LENGTH: 23
<212> TYPE: RNA
<213> ORGANISM: Influenza B virus
```

-continued

<400> SEQUENCE: 2184
aucagacagc uacccaaucu ucu        23

<210> SEQ ID NO 2185
<211> LENGTH: 19
<212> TYPE: RNA
<213> ORGANISM: Influenza B virus

<400> SEQUENCE: 2185
gaacuugcag ucuugcuuu        19

<210> SEQ ID NO 2186
<211> LENGTH: 21
<212> TYPE: RNA
<213> ORGANISM: Influenza B virus

<400> SEQUENCE: 2186
cuccaucugu cuauaaggaa a        21

<210> SEQ ID NO 2187
<211> LENGTH: 21
<212> TYPE: RNA
<213> ORGANISM: Influenza B virus

<400> SEQUENCE: 2187
cauccggaug cuuuccuaua a        21

<210> SEQ ID NO 2188
<211> LENGTH: 21
<212> TYPE: RNA
<213> ORGANISM: Influenza B virus

<400> SEQUENCE: 2188
gaucgaaucu gcacugggau a        21

<210> SEQ ID NO 2189
<211> LENGTH: 19
<212> TYPE: RNA
<213> ORGANISM: Influenza B virus

<400> SEQUENCE: 2189
aggaaaauua agcccugua        19

<210> SEQ ID NO 2190
<211> LENGTH: 19
<212> TYPE: RNA
<213> ORGANISM: Influenza B virus

<400> SEQUENCE: 2190
ggagacucaa auccucaaa        19

<210> SEQ ID NO 2191
<211> LENGTH: 21
<212> TYPE: RNA
<213> ORGANISM: Influenza B virus

<400> SEQUENCE: 2191
aaaaaaucag auuaucaacc c        21

<210> SEQ ID NO 2192
<211> LENGTH: 23
<212> TYPE: RNA
<213> ORGANISM: Influenza B virus -continued

<400> SEQUENCE: 2192
aagaagccau aaacaagaua aca        23

<210> SEQ ID NO 2193
<211> LENGTH: 21
<212> TYPE: RNA
<213> ORGANISM: Influenza B virus

<400> SEQUENCE: 2193
uggcaguggc agcagaccuu a        21

<210> SEQ ID NO 2194
<211> LENGTH: 21
<212> TYPE: RNA
<213> ORGANISM: Influenza B virus

<400> SEQUENCE: 2194
aacauccaau gcagaucgaa u        21

<210> SEQ ID NO 2195
<211> LENGTH: 21
<212> TYPE: RNA
<213> ORGANISM: Influenza B virus

<400> SEQUENCE: 2195
uagaaguacc acacaucugu a        21

<210> SEQ ID NO 2196
<211> LENGTH: 21
<212> TYPE: RNA
<213> ORGANISM: Influenza B virus

<400> SEQUENCE: 2196
aauugucuau caaagaggga u        21

<210> SEQ ID NO 2197
<211> LENGTH: 23
<212> TYPE: RNA
<213> ORGANISM: Influenza B virus

<400> SEQUENCE: 2197
aaucagacag cuacccaauc uuc        23

<210> SEQ ID NO 2198
<211> LENGTH: 21
<212> TYPE: RNA
<213> ORGANISM: Influenza B virus

<400> SEQUENCE: 2198
aagcggauuu uucgcaacaa u        21

<210> SEQ ID NO 2199
<211> LENGTH: 19
<212> TYPE: RNA
<213> ORGANISM: Influenza B virus

<400> SEQUENCE: 2199
cggagcuauu gcugguuuc        19

<210> SEQ ID NO 2200
<211> LENGTH: 21
<212> TYPE: RNA
<213> ORGANISM: Influenza B virus -continued

```
<400> SEQUENCE: 2200
aacuauuaaa ggaaaggggu u                                              21

<210> SEQ ID NO 2201
<211> LENGTH: 23
<212> TYPE: RNA
<213> ORGANISM: Influenza B virus

<400> SEQUENCE: 2201
cggcuucccg gaccaaacag aag                                            23

<210> SEQ ID NO 2202
<211> LENGTH: 21
<212> TYPE: RNA
<213> ORGANISM: Influenza B virus

<400> SEQUENCE: 2202
cauccaaugc agaucgaauc u                                              21

<210> SEQ ID NO 2203
<211> LENGTH: 19
<212> TYPE: RNA
<213> ORGANISM: Influenza B virus

<400> SEQUENCE: 2203
guagaaguac cacacaucu                                                 19

<210> SEQ ID NO 2204
<211> LENGTH: 23
<212> TYPE: RNA
<213> ORGANISM: Influenza B virus

<400> SEQUENCE: 2204
aacugcugcu ucuaguuugg cug                                            23

<210> SEQ ID NO 2205
<211> LENGTH: 21
<212> TYPE: RNA
<213> ORGANISM: Influenza B virus

<400> SEQUENCE: 2205
gcuucgaaac caaacacaag u                                              21

<210> SEQ ID NO 2206
<211> LENGTH: 21
<212> TYPE: RNA
<213> ORGANISM: Influenza B virus

<400> SEQUENCE: 2206
aagcccugua uuuccuuua u                                               21

<210> SEQ ID NO 2207
<211> LENGTH: 23
<212> TYPE: RNA
<213> ORGANISM: Influenza B virus

<400> SEQUENCE: 2207
uugacaacaa caccaacaaa auc                                            23

<210> SEQ ID NO 2208
<211> LENGTH: 21
<212> TYPE: RNA
<213> ORGANISM: Influenza B virus
```

-continued

```
<400> SEQUENCE: 2208
ugcuccaucu gucuauaagg a                                              21

<210> SEQ ID NO 2209
<211> LENGTH: 23
<212> TYPE: RNA
<213> ORGANISM: Influenza B virus

<400> SEQUENCE: 2209
cugaugacaa aacccaaaug aaa                                            23

<210> SEQ ID NO 2210
<211> LENGTH: 21
<212> TYPE: RNA
<213> ORGANISM: Influenza B virus

<400> SEQUENCE: 2210
gguuccauuc ugaugacaaa a                                              21

<210> SEQ ID NO 2211
<211> LENGTH: 21
<212> TYPE: RNA
<213> ORGANISM: Influenza B virus

<400> SEQUENCE: 2211
gaccuuaaga guacgcaaga a                                              21

<210> SEQ ID NO 2212
<211> LENGTH: 19
<212> TYPE: RNA
<213> ORGANISM: Influenza B virus

<400> SEQUENCE: 2212
ggguuccauu cugaugaca                                                 19

<210> SEQ ID NO 2213
<211> LENGTH: 21
<212> TYPE: RNA
<213> ORGANISM: Influenza B virus

<400> SEQUENCE: 2213
aacucaccuc auguggucaa a                                              21

<210> SEQ ID NO 2214
<211> LENGTH: 21
<212> TYPE: RNA
<213> ORGANISM: Influenza B virus

<400> SEQUENCE: 2214
aacaccaaca aaaucucauu u                                              21

<210> SEQ ID NO 2215
<211> LENGTH: 19
<212> TYPE: RNA
<213> ORGANISM: Influenza B virus

<400> SEQUENCE: 2215
ggucaaaaca gcuacucaa                                                 19

<210> SEQ ID NO 2216
<211> LENGTH: 19
<212> TYPE: RNA
<213> ORGANISM: Influenza B virus
```

-continued

<400> SEQUENCE: 2216
gaaggaggau gggaaggaa                                               19

<210> SEQ ID NO 2217
<211> LENGTH: 23
<212> TYPE: RNA
<213> ORGANISM: Influenza B virus

<400> SEQUENCE: 2217
aagccauagg aaauugccca aua                                          23

<210> SEQ ID NO 2218
<211> LENGTH: 23
<212> TYPE: RNA
<213> ORGANISM: Influenza B virus

<400> SEQUENCE: 2218
cacaauaagc ucacaaauag aac                                          23

<210> SEQ ID NO 2219
<211> LENGTH: 21
<212> TYPE: RNA
<213> ORGANISM: Influenza B virus

<400> SEQUENCE: 2219
ugacuggugc gauaccauug a                                            21

<210> SEQ ID NO 2220
<211> LENGTH: 23
<212> TYPE: RNA
<213> ORGANISM: Influenza B virus

<400> SEQUENCE: 2220
uaugaucucc agagacaaug uuu                                          23

<210> SEQ ID NO 2221
<211> LENGTH: 23
<212> TYPE: RNA
<213> ORGANISM: Influenza B virus

<400> SEQUENCE: 2221
gacaacaaca ccaacaaaau cuc                                          23

<210> SEQ ID NO 2222
<211> LENGTH: 19
<212> TYPE: RNA
<213> ORGANISM: Influenza B virus

<400> SEQUENCE: 2222
gcuugccaau ggaaccaaa                                               19

<210> SEQ ID NO 2223
<211> LENGTH: 21
<212> TYPE: RNA
<213> ORGANISM: Influenza B virus

<400> SEQUENCE: 2223
aucgaaucug cacugggaua a                                            21

<210> SEQ ID NO 2224
<211> LENGTH: 23
<212> TYPE: RNA
<213> ORGANISM: Influenza B virus -continued

```
<400> SEQUENCE: 2224
gagacucaaa uccucaaaag uuc                                              23

<210> SEQ ID NO 2225
<211> LENGTH: 23
<212> TYPE: RNA
<213> ORGANISM: Influenza B virus

<400> SEQUENCE: 2225
acgaauccac uaacaguaga agu                                              23

<210> SEQ ID NO 2226
<211> LENGTH: 23
<212> TYPE: RNA
<213> ORGANISM: Influenza B virus

<400> SEQUENCE: 2226
uacaaaagaa gaagaccaaa uua                                              23

<210> SEQ ID NO 2227
<211> LENGTH: 21
<212> TYPE: RNA
<213> ORGANISM: Influenza B virus

<400> SEQUENCE: 2227
aaaguaauaa aagggaccuu g                                                21

<210> SEQ ID NO 2228
<211> LENGTH: 23
<212> TYPE: RNA
<213> ORGANISM: Influenza B virus

<400> SEQUENCE: 2228
cagacuugga acuucaggau cuu                                              23

<210> SEQ ID NO 2229
<211> LENGTH: 21
<212> TYPE: RNA
<213> ORGANISM: Influenza B virus

<400> SEQUENCE: 2229
aaacaaaagc aagccuuacu a                                                21

<210> SEQ ID NO 2230
<211> LENGTH: 23
<212> TYPE: RNA
<213> ORGANISM: Influenza B virus

<400> SEQUENCE: 2230
uagacauagg gaauggaugc uuc                                              23

<210> SEQ ID NO 2231
<211> LENGTH: 21
<212> TYPE: RNA
<213> ORGANISM: Influenza B virus

<400> SEQUENCE: 2231
accugggaaa acaggaacaa u                                                21

<210> SEQ ID NO 2232
<211> LENGTH: 19
<212> TYPE: RNA
<213> ORGANISM: Influenza B virus
```

-continued

<400> SEQUENCE: 2232
caggaacaau ugucuauca                                                19

<210> SEQ ID NO 2233
<211> LENGTH: 19
<212> TYPE: RNA
<213> ORGANISM: Influenza B virus

<400> SEQUENCE: 2233
cccaagggac aacaacaaa                                                19

<210> SEQ ID NO 2234
<211> LENGTH: 21
<212> TYPE: RNA
<213> ORGANISM: Influenza B virus

<400> SEQUENCE: 2234
aacaaaaauc agacagcuac c                                             21

<210> SEQ ID NO 2235
<211> LENGTH: 21
<212> TYPE: RNA
<213> ORGANISM: Influenza B virus

<400> SEQUENCE: 2235
aaauauagac cuccugcaaa a                                             21

<210> SEQ ID NO 2236
<211> LENGTH: 21
<212> TYPE: RNA
<213> ORGANISM: Influenza B virus

<400> SEQUENCE: 2236
gcgaguggca ggagcaaagu a                                             21

<210> SEQ ID NO 2237
<211> LENGTH: 23
<212> TYPE: RNA
<213> ORGANISM: Influenza B virus

<400> SEQUENCE: 2237
uggcagcaga ccuuaagagu acg                                           23

<210> SEQ ID NO 2238
<211> LENGTH: 23
<212> TYPE: RNA
<213> ORGANISM: Influenza B virus

<400> SEQUENCE: 2238
uuggcuguaa cauugaugau agc                                           23

<210> SEQ ID NO 2239
<211> LENGTH: 23
<212> TYPE: RNA
<213> ORGANISM: Influenza B virus

<400> SEQUENCE: 2239
uauuuuccuu uauuguagug cuu                                           23

<210> SEQ ID NO 2240
<211> LENGTH: 21
<212> TYPE: RNA
<213> ORGANISM: Influenza B virus -continued

```
<400> SEQUENCE: 2240
cacgacagaa caaaaaucag a                                              21

<210> SEQ ID NO 2241
<211> LENGTH: 21
<212> TYPE: RNA
<213> ORGANISM: Influenza B virus

<400> SEQUENCE: 2241
aaaaaccucu auggagacuc a                                              21

<210> SEQ ID NO 2242
<211> LENGTH: 23
<212> TYPE: RNA
<213> ORGANISM: Influenza B virus

<400> SEQUENCE: 2242 aggguuucu ucggagcuau ugc                                             23

<210> SEQ ID NO 2243
<211> LENGTH: 19
<212> TYPE: RNA
<213> ORGANISM: Influenza B virus

<400> SEQUENCE: 2243
cugggauaac aucgucaaa                                                 19

<210> SEQ ID NO 2244
<211> LENGTH: 21
<212> TYPE: RNA
<213> ORGANISM: Influenza B virus

<400> SEQUENCE: 2244
caugugguca aaacagcuac u                                              21

<210> SEQ ID NO 2245
<211> LENGTH: 21
<212> TYPE: RNA
<213> ORGANISM: Influenza B virus

<400> SEQUENCE: 2245
auccacaaaa ugaaggcaau a                                              21

<210> SEQ ID NO 2246
<211> LENGTH: 21
<212> TYPE: RNA
<213> ORGANISM: Influenza B virus

<400> SEQUENCE: 2246
aagaagacca aauuacuguu u                                              21

<210> SEQ ID NO 2247
<211> LENGTH: 21
<212> TYPE: RNA
<213> ORGANISM: Influenza B virus

<400> SEQUENCE: 2247
agaccuccug caaaacuauu a                                              21

<210> SEQ ID NO 2248
<211> LENGTH: 23
<212> TYPE: RNA
<213> ORGANISM: Influenza B virus
```

-continued

```
<400> SEQUENCE: 2248
aaagcggauu uucgcaaca aug                                               23

<210> SEQ ID NO 2249
<211> LENGTH: 21
<212> TYPE: RNA
<213> ORGANISM: Influenza B virus

<400> SEQUENCE: 2249
augggugaaa acaccuuuga a                                                21

<210> SEQ ID NO 2250
<211> LENGTH: 19
<212> TYPE: RNA
<213> ORGANISM: Influenza B virus

<400> SEQUENCE: 2250
caguagaagu accacacau                                                   19

<210> SEQ ID NO 2251
<211> LENGTH: 21
<212> TYPE: RNA
<213> ORGANISM: Influenza B virus

<400> SEQUENCE: 2251
uucacgaaaa auacggugga u                                                21

<210> SEQ ID NO 2252
<211> LENGTH: 23
<212> TYPE: RNA
<213> ORGANISM: Influenza B virus

<400> SEQUENCE: 2252
uucggcaaaa gcuucaauac ucc                                              23

<210> SEQ ID NO 2253
<211> LENGTH: 23
<212> TYPE: RNA
<213> ORGANISM: Influenza B virus

<400> SEQUENCE: 2253
gccuugggca gaccaaugug ugu                                              23

<210> SEQ ID NO 2254
<211> LENGTH: 21
<212> TYPE: RNA
<213> ORGANISM: Influenza B virus

<400> SEQUENCE: 2254
uacacaggag aacaugcaaa a                                                21

<210> SEQ ID NO 2255
<211> LENGTH: 19
<212> TYPE: RNA
<213> ORGANISM: Influenza B virus

<400> SEQUENCE: 2255
ccacuuuuga uucacugaa                                                   19

<210> SEQ ID NO 2256
<211> LENGTH: 23
<212> TYPE: RNA
<213> ORGANISM: Influenza B virus
```

```
<400> SEQUENCE: 2256
guggcaggag caaaguaaua aaa                                           23

<210> SEQ ID NO 2257
<211> LENGTH: 23
<212> TYPE: RNA
<213> ORGANISM: Influenza B virus

<400> SEQUENCE: 2257
aaaccucuau ggagacucaa auc                                           23

<210> SEQ ID NO 2258
<211> LENGTH: 21
<212> TYPE: RNA
<213> ORGANISM: Influenza B virus

<400> SEQUENCE: 2258
gcccuaacgc uaccaguaaa a                                             21

<210> SEQ ID NO 2259
<211> LENGTH: 23
<212> TYPE: RNA
<213> ORGANISM: Influenza B virus

<400> SEQUENCE: 2259
aauccucaaa aguucaccuc auc                                           23

<210> SEQ ID NO 2260
<211> LENGTH: 23
<212> TYPE: RNA
<213> ORGANISM: Influenza B virus

<400> SEQUENCE: 2260
aagaugagca ucuauuggca cuu                                           23

<210> SEQ ID NO 2261
<211> LENGTH: 21
<212> TYPE: RNA
<213> ORGANISM: Influenza B virus

<400> SEQUENCE: 2261
gcagauugcc uucacgaaaa a                                             21

<210> SEQ ID NO 2262
<211> LENGTH: 23
<212> TYPE: RNA
<213> ORGANISM: Influenza B virus

<400> SEQUENCE: 2262
uuggcacuug agagaaaacu aaa                                           23

<210> SEQ ID NO 2263
<211> LENGTH: 19
<212> TYPE: RNA
<213> ORGANISM: Influenza B virus

<400> SEQUENCE: 2263 cucauuugc aaaucucaa                                                 19

<210> SEQ ID NO 2264
<211> LENGTH: 21
<212> TYPE: RNA
<213> ORGANISM: Influenza B virus
```

```
<400> SEQUENCE: 2264
ggauagcugc uggcaccuuu a                                          21

<210> SEQ ID NO 2265
<211> LENGTH: 23
<212> TYPE: RNA
<213> ORGANISM: Influenza B virus

<400> SEQUENCE: 2265
aaaacuaaag aagaugcugg guc                                        23

<210> SEQ ID NO 2266
<211> LENGTH: 21
<212> TYPE: RNA
<213> ORGANISM: Influenza B virus

<400> SEQUENCE: 2266
ccuucggcaa aagcuucaau a                                          21

<210> SEQ ID NO 2267
<211> LENGTH: 19
<212> TYPE: RNA
<213> ORGANISM: Influenza B virus

<400> SEQUENCE: 2267
gugaguuaga aguaaagaa                                             19

<210> SEQ ID NO 2268
<211> LENGTH: 21
<212> TYPE: RNA
<213> ORGANISM: Influenza B virus

<400> SEQUENCE: 2268
uaccaguaaa agcggauuuu u                                          21

<210> SEQ ID NO 2269
<211> LENGTH: 21
<212> TYPE: RNA
<213> ORGANISM: Influenza B virus

<400> SEQUENCE: 2269
aacaguagaa guaccacaca u                                          21

<210> SEQ ID NO 2270
<211> LENGTH: 19
<212> TYPE: RNA
<213> ORGANISM: Influenza B virus

<400> SEQUENCE: 2270
cugcaucuuu aaaugauga                                             19

<210> SEQ ID NO 2271
<211> LENGTH: 19
<212> TYPE: RNA
<213> ORGANISM: Influenza B virus

<400> SEQUENCE: 2271
cacgaaguca gaccuguua                                             19

<210> SEQ ID NO 2272
<211> LENGTH: 19
<212> TYPE: RNA
<213> ORGANISM: Influenza B virus
```

-continued

```
<400> SEQUENCE: 2272
aacaggaaca auugucuau                                               19

<210> SEQ ID NO 2273
<211> LENGTH: 23
<212> TYPE: RNA
<213> ORGANISM: Influenza B virus

<400> SEQUENCE: 2273
caguggcagc agaccuuaag agu                                          23

<210> SEQ ID NO 2274
<211> LENGTH: 21
<212> TYPE: RNA
<213> ORGANISM: Influenza B virus

<400> SEQUENCE: 2274
aaaccucuau ggagacucaa a                                            21

<210> SEQ ID NO 2275
<211> LENGTH: 21
<212> TYPE: RNA
<213> ORGANISM: Influenza B virus

<400> SEQUENCE: 2275
cagguuggca cggauacaca u                                            21

<210> SEQ ID NO 2276
<211> LENGTH: 21
<212> TYPE: RNA
<213> ORGANISM: Influenza B virus

<400> SEQUENCE: 2276
ggcggcuucc cggaccaaac a                                            21

<210> SEQ ID NO 2277
<211> LENGTH: 19
<212> TYPE: RNA
<213> ORGANISM: Influenza B virus

<400> SEQUENCE: 2277
cgaagucaga ccuguuaca                                               19

<210> SEQ ID NO 2278
<211> LENGTH: 21
<212> TYPE: RNA
<213> ORGANISM: Influenza B virus

<400> SEQUENCE: 2278 aaaccucua uggagacuca a                                             21

<210> SEQ ID NO 2279
<211> LENGTH: 21
<212> TYPE: RNA
<213> ORGANISM: Influenza B virus

<400> SEQUENCE: 2279
uggagacuca aauccucaaa a                                            21

<210> SEQ ID NO 2280
<211> LENGTH: 21
<212> TYPE: RNA
<213> ORGANISM: Influenza B virus
```

-continued

```
<400> SEQUENCE: 2280
cggagcacac ggaguggcag u                                              21

<210> SEQ ID NO 2281
<211> LENGTH: 23
<212> TYPE: RNA
<213> ORGANISM: Influenza B virus

<400> SEQUENCE: 2281
ggguuccauu cugaugacaa aac                                            23

<210> SEQ ID NO 2282
<211> LENGTH: 19
<212> TYPE: RNA
<213> ORGANISM: Influenza B virus

<400> SEQUENCE: 2282
ccuuuauugu agugcuugu                                                 19

<210> SEQ ID NO 2283
<211> LENGTH: 23
<212> TYPE: RNA
<213> ORGANISM: Influenza B virus

<400> SEQUENCE: 2283
uccacaaaau gaaggcaaua auu                                            23

<210> SEQ ID NO 2284
<211> LENGTH: 21
<212> TYPE: RNA
<213> ORGANISM: Influenza B virus

<400> SEQUENCE: 2284
aacauugaug auagcuauuu u                                              21

<210> SEQ ID NO 2285
<211> LENGTH: 21
<212> TYPE: RNA
<213> ORGANISM: Influenza B virus

<400> SEQUENCE: 2285
cuugcuuucc aacgaaggaa u                                              21

<210> SEQ ID NO 2286
<211> LENGTH: 21
<212> TYPE: RNA
<213> ORGANISM: Influenza B virus

<400> SEQUENCE: 2286
accaggagga cccuacagac u                                              21

<210> SEQ ID NO 2287
<211> LENGTH: 21
<212> TYPE: RNA
<213> ORGANISM: Influenza B virus

<400> SEQUENCE: 2287
cccuacagac uuggaacuuc a                                              21

<210> SEQ ID NO 2288
<211> LENGTH: 21
<212> TYPE: RNA
<213> ORGANISM: Influenza B virus
```

```
<400> SEQUENCE: 2288
acgaagucag accuguuaca u                                              21

<210> SEQ ID NO 2289
<211> LENGTH: 23
<212> TYPE: RNA
<213> ORGANISM: Influenza B virus

<400> SEQUENCE: 2289
aaagaaugau cuggucccu cug                                             23

<210> SEQ ID NO 2290
<211> LENGTH: 23
<212> TYPE: RNA
<213> ORGANISM: Influenza B virus

<400> SEQUENCE: 2290
gagugaguua gaaguaaaga acc                                            23

<210> SEQ ID NO 2291
<211> LENGTH: 19
<212> TYPE: RNA
<213> ORGANISM: Influenza B virus

<400> SEQUENCE: 2291
agugaagaug agcaucuau                                                 19

<210> SEQ ID NO 2292
<211> LENGTH: 21
<212> TYPE: RNA
<213> ORGANISM: Influenza B virus

<400> SEQUENCE: 2292
aaucucaauu cuuugaguga g                                              21

<210> SEQ ID NO 2293
<211> LENGTH: 23
<212> TYPE: RNA
<213> ORGANISM: Influenza B virus

<400> SEQUENCE: 2293
aaagaaccuu caaagacuaa gug                                            23

<210> SEQ ID NO 2294
<211> LENGTH: 21
<212> TYPE: RNA
<213> ORGANISM: Influenza B virus

<400> SEQUENCE: 2294
aacaugcaaa agccauagga a                                              21

<210> SEQ ID NO 2295
<211> LENGTH: 21
<212> TYPE: RNA
<213> ORGANISM: Influenza B virus

<400> SEQUENCE: 2295
acagugaaga ugagcaucua u                                              21

<210> SEQ ID NO 2296
<211> LENGTH: 23
<212> TYPE: RNA
<213> ORGANISM: Influenza B virus
```

<400> SEQUENCE: 2296
aaccucuaug gagacucaaa ucc                                          23

<210> SEQ ID NO 2297
<211> LENGTH: 21
<212> TYPE: RNA
<213> ORGANISM: Influenza B virus

<400> SEQUENCE: 2297
aaaacaggaa caauugucua u                                            21

<210> SEQ ID NO 2298
<211> LENGTH: 19
<212> TYPE: RNA
<213> ORGANISM: Influenza B virus

<400> SEQUENCE: 2298
aagaccagag ggaaacuau                                               19

<210> SEQ ID NO 2299
<211> LENGTH: 19
<212> TYPE: RNA
<213> ORGANISM: Influenza B virus

<400> SEQUENCE: 2299
gucaaaacag cuacucaag                                               19

<210> SEQ ID NO 2300
<211> LENGTH: 23
<212> TYPE: RNA
<213> ORGANISM: Influenza B virus

<400> SEQUENCE: 2300
aucuuuaaau gaugauggau ugg                                          23

<210> SEQ ID NO 2301
<211> LENGTH: 19
<212> TYPE: RNA
<213> ORGANISM: Influenza B virus

<400> SEQUENCE: 2301
cuugggcaga ccaaugugu                                               19

<210> SEQ ID NO 2302
<211> LENGTH: 23
<212> TYPE: RNA
<213> ORGANISM: Influenza B virus

<400> SEQUENCE: 2302
uucuaguuug gcuguaacau uga                                          23

<210> SEQ ID NO 2303
<211> LENGTH: 21
<212> TYPE: RNA
<213> ORGANISM: Influenza B virus

<400> SEQUENCE: 2303
aaagcggauu uuucgcaaca a                                            21

<210> SEQ ID NO 2304
<211> LENGTH: 23
<212> TYPE: RNA
<213> ORGANISM: Influenza B virus

<400> SEQUENCE: 2304
uaaacaguga agaugagcau cua                                          23

<210> SEQ ID NO 2305
<211> LENGTH: 21
<212> TYPE: RNA
<213> ORGANISM: Influenza B virus

<400> SEQUENCE: 2305
aaggaggaug ggaaggaaug a                                            21

<210> SEQ ID NO 2306
<211> LENGTH: 23
<212> TYPE: RNA
<213> ORGANISM: Influenza B virus

<400> SEQUENCE: 2306
cagacagcua cccaaucuuc uca                                          23

<210> SEQ ID NO 2307
<211> LENGTH: 19
<212> TYPE: RNA
<213> ORGANISM: Influenza B virus

<400> SEQUENCE: 2307
accucuaugg agacucaaa                                               19

<210> SEQ ID NO 2308
<211> LENGTH: 23
<212> TYPE: RNA
<213> ORGANISM: Influenza B virus

<400> SEQUENCE: 2308
augcuggguc ccucugcuau aga                                          23

<210> SEQ ID NO 2309
<211> LENGTH: 19
<212> TYPE: RNA
<213> ORGANISM: Influenza B virus

<400> SEQUENCE: 2309
gcccuaacgc uaccaguaa                                               19

<210> SEQ ID NO 2310
<211> LENGTH: 21
<212> TYPE: RNA
<213> ORGANISM: Influenza B virus

<400> SEQUENCE: 2310
aaaaaaucuc aauucuuuga g                                            21

<210> SEQ ID NO 2311
<211> LENGTH: 23
<212> TYPE: RNA
<213> ORGANISM: Influenza B virus

<400> SEQUENCE: 2311
agcaacgaau ccacuaacag uag                                          23

<210> SEQ ID NO 2312
<211> LENGTH: 19
<212> TYPE: RNA
<213> ORGANISM: Influenza B virus -continued

```
<400> SEQUENCE: 2312
caagaagcca uaaacaaga                                                 19

<210> SEQ ID NO 2313
<211> LENGTH: 21
<212> TYPE: RNA
<213> ORGANISM: Influenza B virus

<400> SEQUENCE: 2313
aagcucacaa auagaacuug c                                              21

<210> SEQ ID NO 2314
<211> LENGTH: 21
<212> TYPE: RNA
<213> ORGANISM: Influenza B virus

<400> SEQUENCE: 2314
aagcccugua uuuccuuua u                                               21

<210> SEQ ID NO 2315
<211> LENGTH: 23
<212> TYPE: RNA
<213> ORGANISM: Influenza B virus

<400> SEQUENCE: 2315
uggcacuuga gagaaaacua aag                                            23

<210> SEQ ID NO 2316
<211> LENGTH: 19
<212> TYPE: RNA
<213> ORGANISM: Influenza B virus

<400> SEQUENCE: 2316
cgucaaacuc accucaugu                                                 19

<210> SEQ ID NO 2317
<211> LENGTH: 23
<212> TYPE: RNA
<213> ORGANISM: Influenza B virus

<400> SEQUENCE: 2317
cuggugcgau accauugaca aca                                            23

<210> SEQ ID NO 2318
<211> LENGTH: 19
<212> TYPE: RNA
<213> ORGANISM: Influenza B virus

<400> SEQUENCE: 2318
ggaaaauuaa gcccuguau                                                 19

<210> SEQ ID NO 2319
<211> LENGTH: 19
<212> TYPE: RNA
<213> ORGANISM: Influenza B virus

<400> SEQUENCE: 2319
ggcacggaua cacaucuca                                                 19

<210> SEQ ID NO 2320
<211> LENGTH: 23
<212> TYPE: RNA
<213> ORGANISM: Influenza B virus
```

-continued

<400> SEQUENCE: 2320
gucccaaggg acaacaacaa aac                                        23

<210> SEQ ID NO 2321
<211> LENGTH: 21
<212> TYPE: RNA
<213> ORGANISM: Influenza B virus

<400> SEQUENCE: 2321
ggugccaugg augaacucca u                                          21

<210> SEQ ID NO 2322
<211> LENGTH: 23
<212> TYPE: RNA
<213> ORGANISM: Influenza B virus

<400> SEQUENCE: 2322
gaggauauga aaaaaucaga uua                                        23

<210> SEQ ID NO 2323
<211> LENGTH: 21
<212> TYPE: RNA
<213> ORGANISM: Influenza B virus

<400> SEQUENCE: 2323
auguggccuu gggcagacca a                                          21

<210> SEQ ID NO 2324
<211> LENGTH: 21
<212> TYPE: RNA
<213> ORGANISM: Influenza B virus

<400> SEQUENCE: 2324
accacaaagc ggcagaauug u                                          21

<210> SEQ ID NO 2325
<211> LENGTH: 21
<212> TYPE: RNA
<213> ORGANISM: Influenza B virus

<400> SEQUENCE: 2325
aagugcaacc agaccugcuu a                                          21

<210> SEQ ID NO 2326
<211> LENGTH: 21
<212> TYPE: RNA
<213> ORGANISM: Influenza B virus

<400> SEQUENCE: 2326
auaaaagggu ccuugccuuu a                                          21

<210> SEQ ID NO 2327
<211> LENGTH: 23
<212> TYPE: RNA
<213> ORGANISM: Influenza B virus

<400> SEQUENCE: 2327
aaaaaaucuc aauucuuuga gug                                        23

<210> SEQ ID NO 2328
<211> LENGTH: 21
<212> TYPE: RNA
<213> ORGANISM: Influenza B virus -continued

```
<400> SEQUENCE: 2328
uacucaacug cugcuucuag u                                              21

<210> SEQ ID NO 2329
<211> LENGTH: 23
<212> TYPE: RNA
<213> ORGANISM: Influenza B virus

<400> SEQUENCE: 2329
gaagaugcug ggucccucug cua                                            23

<210> SEQ ID NO 2330
<211> LENGTH: 21
<212> TYPE: RNA
<213> ORGANISM: Influenza B virus

<400> SEQUENCE: 2330
auuggcacuu gagagaaaac u                                              21

<210> SEQ ID NO 2331
<211> LENGTH: 23
<212> TYPE: RNA
<213> ORGANISM: Influenza B virus

<400> SEQUENCE: 2331
caucgucaaa cucaccucau gug                                            23

<210> SEQ ID NO 2332
<211> LENGTH: 19
<212> TYPE: RNA
<213> ORGANISM: Influenza B virus

<400> SEQUENCE: 2332
ccucaucugc uaauggaau                                                 19

<210> SEQ ID NO 2333
<211> LENGTH: 23
<212> TYPE: RNA
<213> ORGANISM: Influenza B virus

<400> SEQUENCE: 2333
uccugcaaaa cuauuaaagg aaa                                            23

<210> SEQ ID NO 2334
<211> LENGTH: 19
<212> TYPE: RNA
<213> ORGANISM: Influenza B virus

<400> SEQUENCE: 2334
aggcaauaau uguacuacu                                                 19

<210> SEQ ID NO 2335
<211> LENGTH: 23
<212> TYPE: RNA
<213> ORGANISM: Influenza B virus

<400> SEQUENCE: 2335
aagcuucaau acuccacgaa guc                                            23

<210> SEQ ID NO 2336
<211> LENGTH: 23
<212> TYPE: RNA
<213> ORGANISM: Influenza B virus
```

```
<400> SEQUENCE: 2336
caauaauugu acuacucaug gua                                              23

<210> SEQ ID NO 2337
<211> LENGTH: 21
<212> TYPE: RNA
<213> ORGANISM: Influenza B virus

<400> SEQUENCE: 2337
ugcuuuccaa cgaaggaaua a                                                21

<210> SEQ ID NO 2338
<211> LENGTH: 21
<212> TYPE: RNA
<213> ORGANISM: Influenza B virus

<400> SEQUENCE: 2338
aagccauaaa caagauaaca a                                                21

<210> SEQ ID NO 2339
<211> LENGTH: 23
<212> TYPE: RNA
<213> ORGANISM: Influenza B virus

<400> SEQUENCE: 2339
accacaaagc ggcagaauug uug                                              23

<210> SEQ ID NO 2340
<211> LENGTH: 23
<212> TYPE: RNA
<213> ORGANISM: Influenza B virus

<400> SEQUENCE: 2340
agcagauugc cuucacgaaa aau                                              23

<210> SEQ ID NO 2341
<211> LENGTH: 21
<212> TYPE: RNA
<213> ORGANISM: Influenza B virus

<400> SEQUENCE: 2341
uagggaaugg augcuucgaa a                                                21

<210> SEQ ID NO 2342
<211> LENGTH: 23
<212> TYPE: RNA
<213> ORGANISM: Influenza B virus

<400> SEQUENCE: 2342
uacuguuugg ggguuccauu cug                                              23

<210> SEQ ID NO 2343
<211> LENGTH: 21
<212> TYPE: RNA
<213> ORGANISM: Influenza B virus

<400> SEQUENCE: 2343
cucaacugcu gcuucuaguu u                                                21

<210> SEQ ID NO 2344
<211> LENGTH: 21
<212> TYPE: RNA
<213> ORGANISM: Influenza B virus
```

-continued

```
<400> SEQUENCE: 2344
cacgaaguca gaccuguuac a                                           21

<210> SEQ ID NO 2345
<211> LENGTH: 19
<212> TYPE: RNA
<213> ORGANISM: Influenza B virus

<400> SEQUENCE: 2345
uggauaacca uacuauacu                                              19

<210> SEQ ID NO 2346
<211> LENGTH: 21
<212> TYPE: RNA
<213> ORGANISM: Influenza B virus

<400> SEQUENCE: 2346
ugggaaaaca ggaacaauug u                                           21

<210> SEQ ID NO 2347
<211> LENGTH: 21
<212> TYPE: RNA
<213> ORGANISM: Influenza B virus

<400> SEQUENCE: 2347
aaaacuauua aaggaaaggg g                                           21

<210> SEQ ID NO 2348
<211> LENGTH: 19
<212> TYPE: RNA
<213> ORGANISM: Influenza B virus

<400> SEQUENCE: 2348
ccaucugucu auaaggaaa                                              19

<210> SEQ ID NO 2349
<211> LENGTH: 23
<212> TYPE: RNA
<213> ORGANISM: Influenza B virus

<400> SEQUENCE: 2349
cagugaagau gagcaucuau ugg                                         23

<210> SEQ ID NO 2350
<211> LENGTH: 21
<212> TYPE: RNA
<213> ORGANISM: Influenza B virus

<400> SEQUENCE: 2350
aguggcagug gcagcagacc u                                           21

<210> SEQ ID NO 2351
<211> LENGTH: 23
<212> TYPE: RNA
<213> ORGANISM: Influenza B virus

<400> SEQUENCE: 2351
aaaacccaaa ugaaaaaccu cua                                         23

<210> SEQ ID NO 2352
<211> LENGTH: 21
<212> TYPE: RNA
<213> ORGANISM: Influenza B virus
```

```
<400> SEQUENCE: 2352
uggcacuuga gagaaaacua a                                              21

<210> SEQ ID NO 2353
<211> LENGTH: 23
<212> TYPE: RNA
<213> ORGANISM: Influenza B virus

<400> SEQUENCE: 2353
cugggauaac aucgucaaac uca                                            23

<210> SEQ ID NO 2354
<211> LENGTH: 21
<212> TYPE: RNA
<213> ORGANISM: Influenza B virus

<400> SEQUENCE: 2354
aagccauagg aaauugccca a                                              21

<210> SEQ ID NO 2355
<211> LENGTH: 21
<212> TYPE: RNA
<213> ORGANISM: Influenza B virus

<400> SEQUENCE: 2355
gugccaugga ugaacuccau a                                              21

<210> SEQ ID NO 2356
<211> LENGTH: 23
<212> TYPE: RNA
<213> ORGANISM: Influenza B virus

<400> SEQUENCE: 2356
accugggaaa acaggaacaa uug                                            23

<210> SEQ ID NO 2357
<211> LENGTH: 23
<212> TYPE: RNA
<213> ORGANISM: Influenza B virus

<400> SEQUENCE: 2357
gaguacgcaa gaagccauaa aca                                            23

<210> SEQ ID NO 2358
<211> LENGTH: 21
<212> TYPE: RNA
<213> ORGANISM: Influenza B virus

<400> SEQUENCE: 2358
aaccugucuc aacugcacag a                                              21

<210> SEQ ID NO 2359
<211> LENGTH: 19
<212> TYPE: RNA
<213> ORGANISM: Influenza B virus

<400> SEQUENCE: 2359
cuucuaguuu ggcuguaac                                                 19

<210> SEQ ID NO 2360
<211> LENGTH: 23
<212> TYPE: RNA
<213> ORGANISM: Influenza B virus
```

-continued

```
<400> SEQUENCE: 2360
uaaacaagau aacaaaaaau cuc                                            23

<210> SEQ ID NO 2361
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2361
uuuguugcuu uaauaaucga g                                              21

<210> SEQ ID NO 2362
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2362
cgauuauuaa agcaacaaat t                                              21

<210> SEQ ID NO 2363
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2363
uucauugaca gcauucuuct t                                              21

<210> SEQ ID NO 2364
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2364
gaagaaugcu gucaaugaat t                                              21

<210> SEQ ID NO 2365
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

-continued

<400> SEQUENCE: 2365
uuaauuggaa uuucaacggg a                                             21

<210> SEQ ID NO 2366
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2366
ccguugaaau uccaauuaat t                                             21

<210> SEQ ID NO 2367
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2367
uuauuuggcc agacccuccg t                                             21

<210> SEQ ID NO 2368
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2368
ggagggucug gccaaauaat t                                             21

<210> SEQ ID NO 2369
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2369
uuuaucaucu cuuaccauct t                                             21

<210> SEQ ID NO 2370
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide -continued

```
<400> SEQUENCE: 2370
gaugguaaga gaugauaaat t                                              21

<210> SEQ ID NO 2371
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2371
uugaugucuc ucaauagccc t                                              21

<210> SEQ ID NO 2372
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2372
ggcuauugag agacaucaat t                                              21

<210> SEQ ID NO 2373
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2373
uuaucaucuc uuaccaucut g                                              21

<210> SEQ ID NO 2374
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2374
agaugguaag agaugauaat t                                              21

<210> SEQ ID NO 2375
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

-continued

<400> SEQUENCE: 2375
uaaaguucca ccuccuuuga t                                              21

<210> SEQ ID NO 2376
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2376
caaaggaggu ggaacuuuat t                                              21

<210> SEQ ID NO 2377
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2377
uugcucuucc uauaaaucga a                                              21

<210> SEQ ID NO 2378
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2378
cgauuuauag gaagagcaat t                                              21

<210> SEQ ID NO 2379
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2379
uaggcuugaa uucugugcct g                                              21

<210> SEQ ID NO 2380
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 2380
ggcacagaau ucaagccuat t                                              21

<210> SEQ ID NO 2381
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2381
uuggauuagg uuucucucca t                                              21

<210> SEQ ID NO 2382
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2382
ggagagaaac cuauccaat t                                               21

<210> SEQ ID NO 2383
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2383
uuuaauaaga auaaacaccc a                                              21

<210> SEQ ID NO 2384
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2384
gguguuuauu cuuauuaaat t                                              21

<210> SEQ ID NO 2385
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

-continued

```
<400> SEQUENCE: 2385
uuaauaagaa uaaacaccca c                                              21

<210> SEQ ID NO 2386
<211> LENTGH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2386
ggguguuuau ucuuauuaat t                                              21

<210> SEQ ID NO 2387
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2387
uuuaaugcug aucuaggcut g                                              21

<210> SEQ ID NO 2388
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2388
agccuagauc agcauuaaat t                                              21

<210> SEQ ID NO 2389
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2389
uuacggauuc guuuguugct t                                              21

<210> SEQ ID NO 2390
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

-continued

```
<400> SEQUENCE: 2390
gcaacaaacg aauccguaat t                                              21

<210> SEQ ID NO 2391
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2391
uuucagacuu aauucagcct g                                              21

<210> SEQ ID NO 2392
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2392
ggcugaauua agucugaaat t                                              21

<210> SEQ ID NO 2393
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2393
uucauuugga ucuuauuugt g                                              21

<210> SEQ ID NO 2394
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2394
caaauaagau ccaaaugaat t                                              21

<210> SEQ ID NO 2395
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 2395
uaauacauuc uucuauucca g                                              21

<210> SEQ ID NO 2396
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2396
ggaauagaag aauguauuat t                                              21

<210> SEQ ID NO 2397
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2397
uuauuugugc cauucacucg g                                              21

<210> SEQ ID NO 2398
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2398
gagugaaugg cacaaauaat t                                              21

<210> SEQ ID NO 2399
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2399
uauuggguca guuugauccc g                                              21

<210> SEQ ID NO 2400
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 2400
ggaucaaacu gacccaauat t                                              21

<210> SEQ ID NO 2401
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2401
uucauuaaca aaguauuucc t                                              21

<210> SEQ ID NO 2402
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2402
gaaauacuuu guuaaugaat t                                              21

<210> SEQ ID NO 2403
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2403
uuccaugcua uuucccagct t                                              21

<210> SEQ ID NO 2404
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2404
gcugggaaau agcauggaat t                                              21

<210> SEQ ID NO 2405
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

-continued

```
<400> SEQUENCE: 2405
uucauuuacu acucuauugg t                                              21

<210> SEQ ID NO 2406
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2406
caauagagua guaaaugaat t                                              21

<210> SEQ ID NO 2407
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2407
uuaacaaagu auuccuuct t                                               21

<210> SEQ ID NO 2408
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2408
gaaggaaaua cuuuguuaat t                                              21

<210> SEQ ID NO 2409
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2409
uuguucaaca auugcuucca t                                              21

<210> SEQ ID NO 2410
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 2410
ggaagcaauu guugaacaat t                                            21

<210> SEQ ID NO 2411
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2411
uuccagaaua cauucccuct a                                            21

<210> SEQ ID NO 2412
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2412
gagggaaugu auucuggaat t                                            21

<210> SEQ ID NO 2413
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2413
ucauuuacua cucuauuggt t                                            21

<210> SEQ ID NO 2414
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2414
ccaauagagu aguaaaugat t                                            21

<210> SEQ ID NO 2415
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

-continued

<400> SEQUENCE: 2415
uuuaguauag aucuguucct t                                              21

<210> SEQ ID NO 2416
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2416
ggaacagauc uauacuaaat t                                              21

<210> SEQ ID NO 2417
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2417
uuauuggaga acaagaccgg t                                              21

<210> SEQ ID NO 2418
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2418
cggucuuguu cuccaauaat t                                              21

<210> SEQ ID NO 2419
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2419
uuuaugagga aacccuuuct g                                              21

<210> SEQ ID NO 2420
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 2420 gaaagggu uu ccucauaaat t                                              21

<210> SEQ ID NO 2421
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2421
uuuauauuca ucuuaaaggc t                                               21

<210> SEQ ID NO 2422
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2422
ccuuuaagau gaauauaaat t                                               21

<210> SEQ ID NO 2423
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2423
uagcauauua aacauuccca t                                               21

<210> SEQ ID NO 2424
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2424
gggaauguuu aauaugcuat t                                               21

<210> SEQ ID NO 2425
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

-continued

<400> SEQUENCE: 2425
uuuauuggag aacaagaccg g                                              21

<210> SEQ ID NO 2426
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2426
ggucuuguuc uccaauaaat t                                              21

<210> SEQ ID NO 2427
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2427
uuguaaauuc aaacauucca g                                              21

<210> SEQ ID NO 2428
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2428
ggaauguuug aauuuacaat t                                              21

<210> SEQ ID NO 2429
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2429
uaaugaauca augauaucut g                                              21

<210> SEQ ID NO 2430
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 2430
agauaucauu gauucauuat t                                              21

<210> SEQ ID NO 2431
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2431
uuagauacaa auccaucuct a                                              21

<210> SEQ ID NO 2432
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2432
gagauggauu uguaucuaat t                                              21

<210> SEQ ID NO 2433
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2433
uucuuuauau ucuuuacuga g                                              21

<210> SEQ ID NO 2434
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2434
caguaaagaa uauaaagaat t                                              21

<210> SEQ ID NO 2435
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

-continued

```
<400> SEQUENCE: 2435
uauuccacuc uggauauccu g                                              21

<210> SEQ ID NO 2436
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2436
ggauauccag aguggaauau t                                              21

<210> SEQ ID NO 2437
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2437
uauucuuuca gucauagcca a                                              21

<210> SEQ ID NO 2438
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2438
ggcuaugacu gaaagaauau t                                              21

<210> SEQ ID NO 2439
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2439
uaucuuucua augguaugcu a                                              21

<210> SEQ ID NO 2440
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 2440
gcauaccauu agaaagauat t                                              21

<210> SEQ ID NO 2441
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2441
uuagauugua cuucaauact a                                              21

<210> SEQ ID NO 2442
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2442
guauugaagu acaaucuaat t                                              21

<210> SEQ ID NO 2443
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2443
uuguucuuua uuauugcat t                                               21

<210> SEQ ID NO 2444
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2444
ugacaauaau aaagaacaat t                                              21

<210> SEQ ID NO 2445
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
-continued

<400> SEQUENCE: 2445
uuuauuccca auaauuuaca t                                              21

<210> SEQ ID NO 2446
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2446
guaaauuauu gggaauaaat t                                              21

<210> SEQ ID NO 2447
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2447
uuguuccuca agaaucaugt t                                              21

<210> SEQ ID NO 2448
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2448
caugauucuu gaggaacaat t                                              21

<210> SEQ ID NO 2449
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2449
uuucuuacuc uuucaacugg g                                              21

<210> SEQ ID NO 2450
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 2450
caguugaaag aguaagaaat t                                               21

<210> SEQ ID NO 2451
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2451
uauuccacca gguaacugct g                                               21

<210> SEQ ID NO 2452
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2452
gcaguuaccu gguggaauat t                                               21

<210> SEQ ID NO 2453
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2453
uuuaaguugu auucccuugt a                                               21

<210> SEQ ID NO 2454
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2454
caagggaaua caacuuaaat t                                               21

<210> SEQ ID NO 2455
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

-continued

<400> SEQUENCE: 2455
uuugaugcga cuauugauct t                                              21

<210> SEQ ID NO 2456
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2456
gaucaauagu cgcaucaaat t                                              21

<210> SEQ ID NO 2457
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2457
uucaguaucu aucacaguct t                                              21

<210> SEQ ID NO 2458
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2458
gacugugaua gauacugaat t                                              21

<210> SEQ ID NO 2459
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2459
uuuaacuacu uuaacgggct t                                              21

<210> SEQ ID NO 2460
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide -continued

<400> SEQUENCE: 2460
gcccguuaaa guaguuaaat t                                              21

<210> SEQ ID NO 2461
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2461
uuucuuauua uguuauauug a                                              21

<210> SEQ ID NO 2462
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2462
aauauaacau aauaagaaat t                                              21

<210> SEQ ID NO 2463
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2463
uuguauuccc uuguauucca a                                              21

<210> SEQ ID NO 2464
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2464
ggaauacaag ggaauacaat t                                              21

<210> SEQ ID NO 2465
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide -continued

```
<400> SEQUENCE: 2465
uaaaucuuuc augucuucct t                                              21

<210> SEQ ID NO 2466
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2466
ggaagacaug aaagauuuat t                                              21

<210> SEQ ID NO 2467
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2467
uucauuaauu cauuuauccc a                                              21

<210> SEQ ID NO 2468
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2468
ggauaaauga auuaaugaat t                                              21

<210> SEQ ID NO 2469
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2469
uaaggauuua uauucaucut a                                              21

<210> SEQ ID NO 2470
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 2470
agaugaauau aaauccuuat t                                              21

<210> SEQ ID NO 2471
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2471
uuucauuuca aucauuugut t                                              21

<210> SEQ ID NO 2472
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2472
acaaaugauu gaaaugaaat t                                              21

<210> SEQ ID NO 2473
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2473
uucaucuuaa aggcuccgct t                                              21

<210> SEQ ID NO 2474
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2474
gcggagccuu uaagaugaat t                                              21

<210> SEQ ID NO 2475
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

-continued

```
<400> SEQUENCE: 2475
cuccgaagaa auaagaucct t                                              21

<210> SEQ ID NO 2476
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2476
ggaucuuauu ucuucggagt t                                              21
```

TREATMENT OF INFLUENZA

CROSS REFERENCE TO RELATED APPLICATION

This application is a National Stage of International Application No. PCT/JP2008/062001, filed Jul. 2, 2008, which claims priority from Japanese Patent Application No. 2007-175575, filed Jul. 3, 2007, the contents of all of which are incorporated herein by reference in their entirety.

TECHNICAL FIELD

The present invention relates to a double-stranded RNA, hairpin RNA, and a vector, as well as a pharmaceutical composition, an anti-influenza virus agent, and a detection kit for influenza B viruses containing the double-stranded RNA, the hairpin RNA, and the vector.

SEQUENCE LISTING

The instant application contains a Sequence Listing which has been submitted via EFS-Web and is hereby incorporated by reference in its entirety. Said ASCII copy, created on Jun. 21, 2010, is named Q116600.txt and is 395,320 bytes in size.

BACKGROUND ART

Influenza is one of the infectious diseases most widely spread all over the world, and 250,000 to 500,000 people die of the disease annually. In Japan, 5 to 15% of the population contract influenza annually, and there are cases in which aged individuals or immunocompromised patients who have contracted influenza are complicated with pneumonia and result in death.

Influenza viruses are classified into three groups, namely type A, type B, and type C, based on differences in the antigenicity of protein which constructs a virus particle. Among them, type A and type B are mainly the ones which cause an infection in humans and circulate repeatedly every winter.

Influenza vaccines are used to prevent influenza. Attenuated live vaccines (i.e., in which attenuated viable pathogens are employed), inactivated vaccines (i.e., in which pathogens which lost infectivity after being subjected to inactivation treatment are employed), and component vaccines (i.e., in which purified specific components of pathogens are employed) are used worldwide, among which only component vaccines are practically used in Japan for prevention of influenza viruses.

A strain which is likely to prevail in a current year is predicted based on information of the influenza virus strain which circulated in the previous season, genetic information of the influenza viruses concurrently isolated in other countries, the prevalence of antibody for an influenza virus strain in the population, and the like, and influenza vaccines are produced based on the prediction.

Treatment methods of influenza include pharmacotherapy using an anti-influenza virus agent, and amantadine and a neuraminidase inhibitor (i.e., oseltamivir and zanamivir) are approved as anti-influenza virus agents in Japan (Non-Patent Document 1).

Meanwhile, RNAi (i.e., abbreviation of RNA interference) was found as a means for inhibiting expression of a specific gene in recent years. RNA interference refers to a biological phenomenon of inhibition of expression of a target gene, in which an mRNA, which is a transcription product of a target gene, is specially cleaved by a double-stranded RNA homologous with a specific region of the target gene at a site homologous with the double-stranded RNA (Patent Document 1).

In mammalian cells, introduction of a long-chain double-stranded RNA into a cell induces interferon and causes apoptosis. However, it has been elucidated that an mRNA of a target gene is specifically cleaved without causing apoptosis and thus a function of the target gene can be inhibited by introduction of a short-chain double-stranded RNA having 21 to 23 bp into a cell (Patent Document 2). Here, a short-chain double-stranded RNA which causes RNA interference in mammalian cells is called siRNA (i.e., abbreviation of small interfering RNA).

Patent Document 1: WO1999/32619
Patent Document 2: WO2001/075164
Non-Patent Document 1: Norio SUGAYA, Japanese Journal of Clinical Medicine, 2006, vol. 64, p. 1840-1844

DISCLOSURE OF THE INVENTION

Problems to be Solved by the Invention

However, accurate prediction of an epidemic strain of influenza viruses is extremely difficult, and the current situation is that when prediction of an epidemic strain is missed, an effect of an influenza vaccine is markedly reduced.

In addition, even if prediction of an epidemic strain comes true, there are cases in which side effects such as pyrexia, rash, convulsion, anaphylactic shock, and hepatic function disorder develop with administration of an influenza vaccine, and they are fatal in a worst-case scenario.

Furthermore, amantadine is an anti-influenza virus agent which targets M2 protein of influenza A viruses, therefore, it is ineffective for influenza B viruses which do not have M2 protein. Meanwhile, a neuraminidase inhibitor is subtly effective for influenza B viruses, whilst it poses a problem of serious side effects. In sum, there is no effective treatment method for influenza B viruses compared with influenza A viruses in the current situation.

In view of the foregoing, an object of the present invention is to treat and prevent an infection caused by influenza B viruses by inhibiting replication of a wide range of influenza B virus strains.

Means for Solving the Problems

In order to achieve the object, the present invention provides a double-stranded RNA which inhibits replication of influenza B viruses by RNA interference, in which the double-stranded RNA comprises an RNA having 19 to 25 nucleotides homologous with a part of an mRNA transcribed from a genomic RNA of influenza B viruses and an antisense RNA thereof.

The present inventors found that double-stranded RNA comprising RNA having 19 to 25 nucleotides homologous with a part of an mRNA transcribed from a genomic RNA of influenza B viruses and an antisense RNA thereof inhibited replication of influenza B viruses, and further found that an infection caused by influenza B viruses could be effectively treated and prevented by introducing the double-stranded RNA into mammalian cells.

The mRNA is preferably a mRNA of an NP protein gene, an RNA polymerase PA subunit gene, an RNA polymerase PB1 subunit gene, or an RNA polymerase PB2 subunit gene.

By introducing a double-stranded RNA comprising RNA having 19 to 25 nucleotides homologous with a part of an mRNA transcribed from an NP protein gene, an RNA polymerase PA subunit gene, an RNA polymerase PB1 subunit gene, or an RNA polymerase PB2 subunit gene and antisense RNA thereof into a cell, an mRNA expressed by transcription of these genes is specifically cleaved by RNA interference, thereby replication of influenza B viruses can be inhibited.

The RNA is preferably selected from the group consisting of RNA of nucleotide sequences as set forth in SEQ ID NOs: 1 to 57 or selected from the group consisting of RNA of nucleotide sequences as set forth in SEQ ID NOs: 1 to 57 in which 1 to 3 nucleotide(s) is/are substituted. Among them, it is more preferably selected from the group consisting of RNA of nucleotide sequences as set forth in SEQ ID NOs: 1 to 11 or selected from the group consisting of RNA of nucleotide sequences as set forth in SEQ ID NOs: 1 to 11 in which 1 to 3 nucleotide(s) is/are substituted.

Introduction of double-stranded RNA consisting of any one of RNA having a nucleotide sequence as set forth in SEQ ID NOs: 1 to 57 and antisense RNA thereof into a cell can inhibit replication of influenza B viruses more strongly by RNA interference. Also, introduction of double-stranded RNA consisting of any one of RNA having a nucleotide sequence as set forth in SEQ ID NOs: 1 to 11 and antisense RNA thereof into a cell can inhibit replication of a much wider range of influenza B virus strains.

The double-stranded RNA preferably has a S/N ratio of 3 or greater in screening of double-stranded RNA by a transfection microarray using B/Johannesburg/5/99 strain.

A double-stranded RNA having a S/N ratio of 3 or greater can cleave mRNA more specifically by RNA interference.

The RNA can contain one or more modified ribonucleotide(s), and a 2'-OH group of a ribose ring is preferably substituted with a fluoro group, a methyl group, a methoxyethyl group, or a propyl group in the modified ribonucleotides. Also, one or more phosphodiester bond(s) in the RNA can be substituted with phosphorothioate bond(s).

RNA introduced into a cell can be degraded by intracellular ribonucleases, however, an RNA chain modified as above gains resistance to the ribonucleases and therefore can efficiently exert an RNA interference activity.

The double-stranded RNA can form blunt ends, however, it preferably forms overhanging ends by having DNA or RNA of 1 to 4 nucleotide(s) attached to 3' ends of a sense and an antisense strands thereof.

A Double-stranded RNA forming overhanging ends has a stronger RNA interference activity so that it can inhibit replication of influenza B viruses more remarkably.

In addition, the present invention provides a hairpin RNA which forms the double-stranded RNA in a cell, in which an RNA homologous with a part of an mRNA transcribed from a genomic RNA of influenza B viruses is linked to antisense RNA thereof by a linker sequence.

It is not necessary to anneal two kinds of single-stranded RNA to form a double-stranded RNA in order to create the hairpin RNA because it can be created from one kind of RNA through chemical synthesis and the like, and thus handling of the hairpin RNA is easy. Furthermore, because the hairpin RNA forms double-stranded RNA in a cell, it exerts an RNA interference activity and can inhibit replication of influenza B viruses.

The double-stranded RNA preferably inhibits all of the following influenza B virus strains: B/Johannesburg/5/99 strain, B/Shangdong/07/97 strain, B/Hong Kong/8/73 strain, B/Shanghai/361/2002 strain, and B/Victoria/2/87 strain.

Even if influenza virus strains undergo mutation, it is highly possible that double-stranded RNA which can inhibit replication of all of the influenza virus strains described above will be still effective.

The present invention provides an expression vector for a double-stranded RNA which contains a first DNA complementary to an RNA selected from the group consisting of RNA of nucleotide sequences as set forth in SEQ ID NOs: 1 to 57 or an RNA selected from the group consisting of RNA of nucleotide sequences as set forth in SEQ ID NOs: 1 to 57 in which 1 to 3 nucleotide(s) is/are substituted and a second DNA complementary to the first DNA, as well as promoters on 5' sides of each of the first DNA and the second DNA, in which, in a cell to which the vector is introduced, the vector transcribes a first RNA complementary to the first DNA and a second RNA complementary to the second DNA, and the first RNA and the second RNA hybridize to each other to form double-stranded RNA.

Furthermore, the present invention provides an expression vector for a double-stranded RNA which contains a first DNA complementary to an RNA selected from the group consisting of RNA of nucleotide sequences as set forth in SEQ ID NOs: 1 to 57 or an RNA selected from the group consisting of RNA of nucleotide sequences as set forth in SEQ ID NOs: 1 to 57 in which 1 to 3 nucleotide(s) is/are substituted, in which the RNA has an RNA having 1 to 4 nucleotide(s) attached to a 3' end thereof, and a second DNA complementary to an RNA which is an antisense RNA of an RNA selected from the group consisting of RNA of nucleotide sequences as set forth in SEQ ID NOs: 1 to 57 or antisense RNA of RNA selected from the group consisting of RNA of nucleotide sequences as set forth in SEQ ID NOs: 1 to 57 in which 1 to 3 nucleotide(s) is/are substituted, in which the RNA has an RNA having 1 to 4 nucleotide(s) attached to a 3' end thereof, as well as promoters on 5' sides of each of the first DNA and the second DNA, in which, in a cell to which the vector is introduced, the vector transcribes a first RNA complementary to the first DNA and a second RNA complementary to the second DNA, and the first RNA and the second RNA hybridize to each other to form a double-stranded RNA.

Still further, the present invention provides an expression vector for a hairpin RNA which contains a DNA strands encoding a hairpin RNA, in which an antisense DNA complementary to an RNA selected from the group consisting of RNA of nucleotide sequences as set forth in SEQ ID NOs: 1 to 57 or an antisense DNA complementary to an RNA selected from the group consisting of RNA of nucleotide sequences as set forth in SEQ ID NOs: 1 to 57 in which 1 to 3 nucleotide(s) is/are substituted is linked to a DNA complementary to the antisense DNA by a linker sequence, as well as promoters on 5' sides of the DNA strands, in which, in a cell to which the vector is introduced, the vector transcribes the hairpin RNA, and the hairpin RNA is processed inside the cell to form a double-stranded RNA.

When the vector is introduced into a cell, a double-stranded RNA causing RNA interference is continuously transcribed within the cell, thereby replication of influenza B viruses can be inhibited for a long term.

The vector is preferably a plasmid vector or a viral vector to efficiently express a double-stranded RNA in mammalian cells.

Also, the double-stranded RNA, the hairpin RNA, or the vector can be used as a pharmaceutical composition or an anti-influenza virus agent because it can inhibit replication of influenza B viruses when introduced into mammalian cells.

The pharmaceutical compositions or the anti-influenza virus agents can contain a plurality of the double-stranded RNA, the hairpin RNA, or the vector. As shown in Examples, in some cases no effect is exerted on certain kinds of virus strains depending on a sequence of double-stranded RNA, however, there are cases in which an effect can be exerted on such strains by employing a plurality of double-stranded RNA concurrently.

Also, as shown in Examples, in some cases an effect diminishes over time when one of double-stranded RNA is used, however, there are cases in which an effect sustains for a longer period of time by employing a plurality of double-stranded RNA concurrently.

Furthermore, the double-stranded RNA or the hairpin RNA, or double-stranded RNA produced from the vector has an activity to specifically cleave an mRNA derived from influenza B viruses so that a kit containing the double-stranded RNA, the hairpin RNA, or the vector, and a transfection reagent can be used as a detection kit for influenza B viruses.

The pharmaceutical compositions or the anti-influenza virus agents can further contain a double-stranded RNA which inhibits replication of influenza A viruses by RNA interference.

The above-described pharmaceutical compositions or the anti-influenza virus agents can exert their therapeutic effects regardless of if infectious pathogens are influenza A viruses or influenza B viruses, and therefore even if superinfection due to a simultaneous infection with both strains occur, it can still be treated.

Effect of the Invention

An infectious disease caused by influenza B viruses can be effectively treated and prevented by introducing the double-stranded RNA, the hairpin RNA, and the vector of the present invention into mammalian cells. Furthermore, the double-stranded RNA of the present invention has an activity to inhibit replication of plural kinds of influenza B virus strains, therefore, in a case if influenza B viruses having mutation in a sequence targeted by the double-stranded RNA arise, mRNA derived from the viruses are still cleaved and replication of the influenza B viruses can be inhibited. For this, even when an epidemic strain of influenza B viruses is unknown, a therapeutic effect can be exerted on an infectious disease caused by influenza B viruses.

The pharmaceutical compositions and the anti-influenza virus agents of the present invention can contain two or more kinds of double-stranded RNA at the same time. For example, at least one kind of double-stranded RNA designed to target influenza A viruses and at least one kind of double-stranded RNA designed to target influenza B viruses can be used concurrently. This way of usage enables application of the pharmaceutical compositions of the present invention regardless of if infectious pathogens are influenza A viruses or influenza B viruses, and even if superinfection due to a simultaneous infection with both strains is caused, it can still be treated. For another example, at least two or more kinds of double-stranded RNA designed to target influenza B viruses can be used concurrently. This way of usage can expand and enhance an effect of double-stranded RNA in a case in which infectious pathogens are influenza B viruses.

BRIEF DESCRIPTION OF THE DRAWINGS

FIG. 2 (A) shows inhibition rates of double-stranded RNA NP-1496 alone, B-NP-1999-13 alone, as well as a combination of NP-1496 and B-NP-1999-13 for influenza virus B/Johannesburg/5/99 strain, and (B) shows inhibition rates of double-stranded RNA NP-1496 alone, B-NP-1999-13 alone, and a combination of NP-1496 and B-NP-1999-13 for influenza virus A/PR/8/34 strain;

FIG. 3 (A) shows inhibition rates of double-stranded RNA B-PB2-1997-7 alone, B-PB1-1999-1 alone, as well as a combination of B-PB2-1997-7 and B-PB1-1999-1 for influenza virus B/Shanghai/361/2002 strain, and (B) shows inhibition rates of double-stranded RNA B-PB2-1997-7 alone, B-PB1-1999-1 alone, as well as a combination of B-PB2-1997-7 and B-PB1-1999-1 for influenza virus B/Shangdong/07/97 strain.

DESCRIPTION OF SYMBOLS

Figure 1:
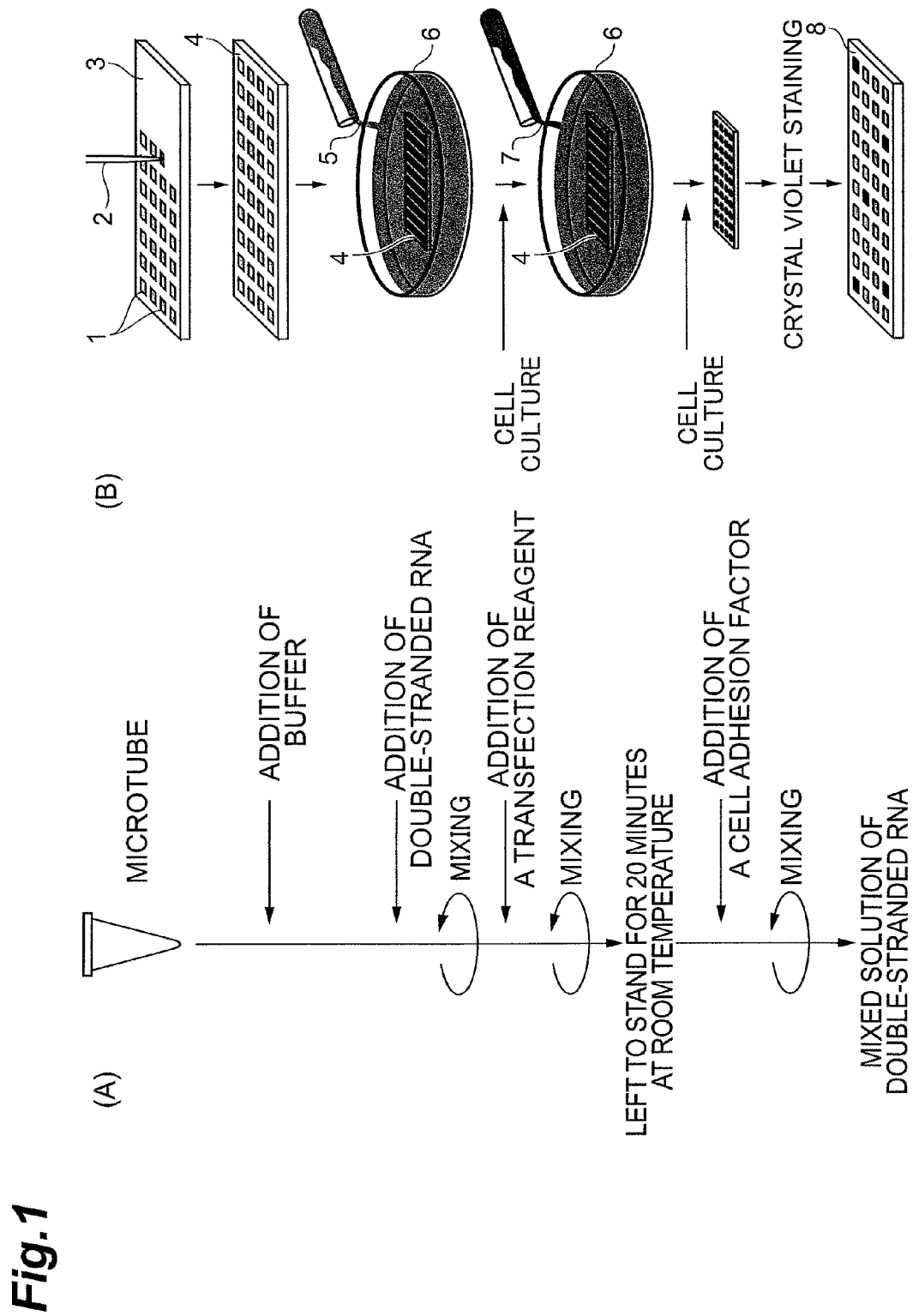
FIG. 1 shows steps of screening of double-stranded RNA which inhibits replication of influenza B viruses by a transfection microarray.

1 . . . spot position, 2 . . . spotter, 3 . . . glass slide, 4 . . . double-stranded RNA microarray, 5 . . . cell suspension, 6 . . . petri dish, 7 . . . influenza B virus solution, 8 . . . stained double-stranded RNA microarray

BEST MODES FOR CARRYING OUT THE INVENTION

Preferred embodiments of the present invention are described hereinbelow.

A double-stranded RNA of the present invention is described.

The double-stranded RNA of the present invention is characterized by being double-stranded RNA which inhibits replication of influenza B viruses by RNA interference, in which the double-stranded RNA comprises an RNA having 19 to 25 nucleotide(s) homologous with a part of an mRNA transcribed from a genomic RNA of influenza B viruses and antisense RNA thereof.

The phrase "inhibits replication of influenza B viruses by RNA interference" does not mean directly inhibiting synthesis of protein which constructs influenza viruses but it means inhibiting by cleaving an mRNA of a target viral gene sequence-specifically, and it includes transient inhibition of viral replication.

The above statement similarly applies to a case in which a double-stranded RNA "inhibits replication of influenza A viruses by RNA interference."

"RNA" is one of the nucleic acids and it refers to a polymer of ribonucleotides consisting of ribose, phosphoric acid, and bases (i.e., adenine, guanine, cytosine, or uracil). RNA can take structure of single-stranded, double-stranded, or hairpin RNA because it can form a complementary hydrogen bond similarly to DNA.

An RNA can be synthesized based on a conventional synthetic method. For example, it can be synthesized by a nucleic acid synthesizing machine or by transcribing a DNA template in vitro (i.e., in vitro transcription). At that time a mixed group of short double-stranded RNA having 19 to 25 bp can be obtained by subjecting long double-stranded RNA synthesized in advance to dicer enzyme treatment.

The term "influenza B viruses" refers to RNA viruses which belong to orthomyxoviridae and infect humans to cause influenza. Influenza B viruses have viral genes encoding hemagglutinin (HA), neuraminidase (NA), NB protein (NB), RNA polymerase PA subunit (PA), RNA polymerase PB1 subunit (PB1), RNA polymerase PB2 subunit (PB2), M1 protein (M1), BM2 protein (BM2), NP protein (nuclear protein; NP), and NS protein (nonstructural protein; NS) in RNA genome which is consisted of negative-strand, single-stranded RNA.

When influenza B viruses infect humans, mRNA of each viral gene is transcribed from a genomic RNA template by the viruses' own RNA-dependent RNA polymerases, followed by synthesis of each viral protein by ribosomes of a host cell. Then, a set of viral genome which has been replicated through a different pathway and the viral protein thus produced assembles within the cell, thereby a virus particle is replicated. As described above, the translation products of the viral gene are essential for replication of influenza B viruses, and an infection caused by influenza B viruses can be treated or prevented, if expression of the gene is inhibited.

The double-stranded RNA is produced by synthesizing RNA having 19 to 25 nucleotides which are homologous with a part of an mRNA of a hemagglutinin (HA) gene, a neuraminidase gene, a NB protein gene, an RNA polymerase PA subunit gene, an RNA polymerase PB1 subunit gene, an RNA polymerase PB2 subunit gene, a M1 protein gene, a BM2 protein gene, an NP protein gene, and a NS protein gene of influenza B viruses as well as an antisense RNA thereof each separately, and annealing the RNA thus synthesized.

In order to strongly inhibit replication of influenza B viruses, a target mRNA is preferably an mRNA of an NP protein gene, an RNA polymerase PA subunit gene, an RNA polymerase PB1 subunit gene, or an RNA polymerase PB2 subunit gene of influenza B viruses, among which it is more preferably an mRNA of an NP protein gene.

Nucleotide sequences of each influenza B viral gene is open to the public by genetic database such as GenBank, and an RNA which constructs double-stranded RNA can be designed based on such available nucleotide sequence information.

The RNA is preferably selected from the group consisting of RNA of nucleotide sequences as set forth in SEQ ID NOs: 1 to 57 or selected from the group consisting of RNA of nucleotide sequences as set forth in SEQ ID NOs: 1 to 57 in which 1 to 3 nucleotide(s) is/are substituted, and it is more preferably selected from the group consisting of RNA of nucleotide sequences as set forth in SEQ ID NOs: 1 to 11 or selected from the group consisting of RNA of nucleotide sequences as set forth in SEQ ID NOs: 1 to 11 in which 1 to 3 nucleotide(s) is/are substituted.

The nucleotide sequences shown in SEQ ID NOs: 1 to 57 are a partial sequence of an mRNA of an NP protein gene, an RNA polymerase PA subunit gene, an RNA polymerase PB1 subunit gene, and an RNA polymerase PB2 subunit gene of influenza B viruses, and RNA which constructs double-stranded RNA can be designed based on the nucleotide sequence information of the above genes.

The RNA can contain one or more modified ribonucleotide(s) to attain resistance to degradation by ribonucleases, and a ribonucleotide in which 2'-OH group of a ribose ring is substituted with a fluoro group, a methyl group, a methoxyethyl group, or a propyl group is exemplified as the modified nucleotide.

A ribose ring which is to undergo substitution can be pyrimidine, purine, or a combination thereof. Among them, pyrimidine, for example, cytosine, a cytosine derivative, uracil, a uracil derivative, or a combination thereof is preferred. Either of a sense RNA strand and an antisense RNA strand, or both RNA strands of a double-stranded RNA can contain the modified ribonucleases to protect an RNA from degradation by ribonucleases.

One or more phosphodiester bond(s) of an RNA can be substituted with phosphorothioate bond(s) to make the RNA resistant to degradation by ribonucleases.

A person skilled in the art can carry out substitution of a 2'-OH group of a ribose ring with another functional group and a phosphodiester bond with a phosphorothioate bond based on a conventional method of chemical synthesis.

An epidemic strain of influenza B viruses is broadly classified into two groups, namely B/Victoria/2/87 and B/Yamagata/16/88, according to differences in the antigenicity of hemagglutinin (HA), and a virus strain which circulates every year is a different virus strain belonging to either group. Influenza B viruses include, for example, B/Johannesburg/5/99 strain, B/Shangdong/07/97 strain, B/Hong Kong/8/73 strain, B/Shanghai/361/2002 strain, and B/Victoria/2/87 strain.

The double-stranded RNA preferably inhibits replication of two or more of the virus strains of B/Johannesburg/5/99 strain, B/Shangdong/07/97 strain, B/Hong Kong/8/73 strain, B/Shanghai/361/2002 strain, and B/Victoria/2/87 strain, all of which are influenza B viruses, more preferably inhibits replication of three or more of the virus strains, and even more preferably inhibits replication of all of the virus strains.

The double-stranded RNA has preferably 19 to 25 bp, more preferably 19 to 23 bp, and even more preferably 19 to 21 bp in order to avoid induction of interferon and subsequent apoptosis in mammalian cells.

The double-stranded RNA of the present invention preferably forms overhanging ends by having DNA or RNA having 1 to 4 nucleotide(s) attached to 3' ends of the sense and the antisense strands thereof, and it is more preferable that the overhanging ends are DNA or RNA consisting of 2 nucleotides. Also, the nucleotide sequence of the overhanging end of the antisense strand of the double-stranded RNA is preferably complementary to an mRNA of a target gene, however, that is not essential, and it is acceptable as long as DNA or RNA having an arbitrary nucleotide sequence is attached to a 3' end thereof. Furthermore, the overhanging end preferably consists of DNA.

The hairpin RNA of the present invention is characterized in that it is hairpin RNA which forms the double-stranded RNA in a cell, in which an RNA homologous with a part of an mRNA transcribed from a genomic RNA of influenza B viruses is linked to antisense RNA thereof by a linker sequence. An arbitrary sequence can be used for a linker sequence as long as it does not block formation of a hairpin structure, while the linker sequence is preferably 4 to 6 nucleotides-long, more preferably 4 nucleotides-long.

Screening of double-stranded RNA which inhibits replication of influenza B viruses can be carried out by, for example, introducing double-stranded RNA into an animal cell such as an MDCK cell and subsequently infecting the cell by influenza B viruses, and observing to see if apoptosis is induced in the cell as an indication.

That is to say, if double-stranded RNA which cleaves an mRNA derived from influenza B viruses is introduced into a cell, replication of the viruses is inhibited and apoptosis will not be induced in an animal cell, even if the cell is invaded by influenza B viruses. Therefore, if the cell survives, the double-stranded RNA introduced into the cell can be judged as double-stranded RNA which inhibits replication of influenza B viruses. On the other hand, if double-stranded RNA which does not cleave mRNA derived from influenza B viruses is introduced into a cell, viruses are replicated and eventually apoptosis will be induced in the cell. Furthermore, because cells in which apoptosis is induced will die out and detach from a culture plate, an activity of double-stranded RNA which inhibits replication of influenza B viruses, which is hereinafter described as an anti-influenza virus activity, can be determined based on a ratio of viable cells adhering to the culture plate.

The screening can be carried out using a transfection microarray. A solid phase gene transfer technology of Cyto-Pathfinder, Inc. can be employed for a system of transfection microarray, for example.

A screening using a transfection microarray starts with spotting randomly-synthesized double-stranded RNA onto a glass slide to produce a double-stranded RNA microarray. At that time a correlation between a nucleotide sequence of double-stranded RNA and a respective spot position is compiled in a database to know which double-stranded RNA is spotted on which spot position on the glass slide.

Subsequently, the double-stranded RNA microarray is placed in a petri dish and fixed thereto, to which a suspension containing MDCK cells and culture media is poured to seed the cells on the double-stranded RNA microarray. After one day of culture, the double-stranded RNA spotted on the double-stranded RNA microarray is introduced into the cells through the cell membrane. Therefore, if the cells are cultured with addition of solution containing influenza B viruses into the medium, cells which have survived without induction of apoptosis will keep adhering to specific spot positions on the double-stranded RNA microarray, while cells in which apoptosis has been induced will detach from the double-stranded RNA microarray. The double-stranded RNA having an anti-influenza virus activity can then be screened based on spot positions to which the cells are adhering as an indicator. Namely, the nucleotide sequence of double-stranded RNA having an anti-influenza virus activity can be obtained based on information of the spot position to which the cells are adhered.

The vector of the present invention is then described.

A first aspect of the vector of the present invention is characterized in that it is an expression vector for a double-stranded RNA which contains a first DNA complementary to an RNA selected from the group consisting of RNA of nucleotide sequences as set forth in SEQ ID NOs: 1 to 57 or an RNA selected from the group consisting of RNA of nucleotide sequences as set forth in SEQ ID NOs: 1 to 57 in which 1 to 3 nucleotide(s) is/are substituted and a second DNA complementary to the first DNA, as well as promoters on 5' sides of each of the first DNA and the second DNA, in which, in a cell to which the vector is introduced, the vector transcribes a first RNA complementary to the first DNA and a second RNA complementary to the second DNA, and the first RNA and the second RNA hybridize to each other to form double-stranded RNA.

For example, a vector in which a DNA which encodes a sense strand of double-stranded RNA is linked to a first promoter in a controllable way and a DNA which encodes an antisense strand of double-stranded RNA is linked to a second promoter in a controllable way can be exemplified. In that case, the sense and the antisense strands of the double-stranded RNA are transcribed each independently, and the promoters for each strand can be identical or different from each other.

The above aspect can be an expression vector for double-stranded RNA which contains a first DNA complementary to an RNA selected from the group consisting of RNA of nucleotide sequences as set forth in SEQ ID NOs: 1 to 57 or an RNA selected from the group consisting of RNA of nucleotide sequences as set forth in SEQ ID NOs: 1 to 57 in which 1 to 3 nucleotide(s) is/are substituted, in which the RNA has an RNA having 1 to 4 nucleotide(s) attached to 3' ends thereof, and a second DNA complementary to an RNA which is an antisense RNA of an RNA selected from the group consisting of RNA of nucleotide sequences as set forth in SEQ ID NOs: 1 to 57 or an antisense RNA of an RNA selected from the group consisting of RNA of nucleotide sequences as set forth in SEQ ID NOs: 1 to 57 in which 1 to 3 nucleotide(s) is/are substituted, in which the RNA has an RNA having 1 to 4 nucleotide(s) attached to 3' ends thereof, as well as promoters on 5' sides of each of the first DNA and the second DNA, and the vector transcribes a first RNA complementary to the first DNA and a second RNA complementary to the second DNA, in which the first RNA and the second RNA subsequently hybridize to each other to form double-stranded RNA in a cell to which the vector is introduced.

A second aspect of the vector of the present invention is characterized in that it is an expression vector for a hairpin RNA which contains DNA strands encoding a hairpin RNA, in which an antisense DNA complementary to an RNA selected from the group consisting of RNA of nucleotide sequences as set forth in SEQ ID NOs: 1 to 57 or an antisense DNA complementary to RNA selected from the group consisting of RNA of nucleotide sequences as set forth in SEQ ID NOs: 1 to 57 in which 1 to 3 nucleotide(s) is/are substituted is linked to a DNA complementary to the antisense DNA by a linker sequence, as well as promoters on 5' sides of the DNA strands, in which, in a cell to which the vector is introduced, the vector transcribes the hairpin RNA, and the hairpin RNA is processed inside the cell to form double-stranded RNA.

For example, a vector containing a DNA encoding a hairpin RNA, in which the DNA encoding sense and antisense strands of double-stranded RNA are linked by a linker sequence, is controllably linked to a uniform promoter can be exemplified. In that case, a single-stranded RNA, in which a sense strand and an antisense strand of double-stranded RNA are linked by a linker sequence, is produced. The sense strand part and the antisense strand part of the single-stranded RNA anneal to form hairpin RNA. An arbitrary sequence can be used for a linker sequence as long as the sequence does not block formation of a hairpin structure, while the linker sequence is preferably 4 to 6 nucleotides-long, more preferably 4 nucleotides-long.

The vector is used to create a double-stranded RNA which inhibits replication of influenza B viruses by genetic recombination technology, and it can be a vector which can transcribe a target RNA to create double-stranded RNA in a host cell. The vector can be in a form of plasmid or virus and contain an origin of replication, a terminator, a selection marker such as a neomycin resistant gene, a tetracycline resistant gene, and an ampicillin resistant gene besides a promoter, and can further contain an enhancer, a polyadenylation signal, and the like as needed.

A plasmid vector can be, for example, pcDNA3, pUC, pBR322, and pBluescript, and a viral vector can be an adenovirus, a retrovirus, a lentivirus, a baculovirus, a vaccinia virus, and the like.

A DNA to be incorporated into a vector as a template for an RNA can be synthesized by a method known in the art, and it can be inserted under control of an appropriate promoter which directs RNA transcriptional synthesis.

A promoter can be exemplified as a CMV promoter, a HSV thymidine kinase promoter, a SV40 promoter, a retroviral LTR, and a metallothionein promoter, and further, a U6 promoter or a H1 promoter, both of which are RNA polymerase III promoters. Also, the promoter can be an inducible promoter which enables alternation between "on" and "off" of expression.

A molecular biological technique necessary for construction of a vector is described in Molecular Cloning A Laboratory Manual (Sambrook, et al., Cold Spring Harbor, N.Y., 1989).

Further, the double-stranded RNA, the hairpin RNA, or the vector can be used as a pharmaceutical composition or an anti-influenza virus agent which aims to treat and prevent an infection caused by influenza B viruses.

The pharmaceutical compositions and the anti-influenza virus agents contain at least one kind of the double-stranded RNA, the hairpin RNA, or the vector as an active ingredient, and can further contain pharmaceutically acceptable additives as needed.

Also, because double-stranded RNA, the hairpin RNA, or double-stranded RNA produced from the vector can specifically cleave mRNA of a target gene of influenza B viruses, they can be used as a detection kit for influenza B viruses which exploits their such characteristic properties.

The detection kit is characterized by containing a transfection reagent in addition to the double-stranded RNA, the hairpin RNA, or the vector.

The transfection reagent can be, for example, a reagent containing lipid, in which the lipid and an objective vector form a complex, thereby the vector is introduced into a target cell. Lipid suitable for a transfection reagent can be exemplified as, for example, polyamine lipid, cationic lipid, polycationic lipid, cholesterol, neutral lipid, and cationic polyamine lipid.

The pharmaceutical composition and the anti-influenza virus agent can further contain a double-stranded RNA which inhibits replication of influenza A viruses by RNA interference. A Double-stranded RNA which inhibits replication of influenza A viruses is publicly known, and for example, ones described in the specifications of US2006/0160759 and US2006/0275265, and WO2004/028471 and WO2006/102461 can be preferably used.

EXAMPLES

The present invention is described more specifically with examples hereinbelow, however, the present invention is not limited to these examples in any way.

(Design and Synthesis of Double-Stranded RNA)

Based on nucleotide sequence information of 8 kinds of viral genes of influenza B virus B/Johannesburg/5/99 strain, which was obtained as GenBank accession nos. of CY018613 (hemagglutinin gene), CY018614 (M1 protein gene and BM2 protein gene), CY018615 (neuraminidase gene and NB protein gene), CY018616 (NP protein gene), CY018617 (NS1 protein gene and NS2 protein gene), CY018618 (RNA polymerase PA subunit gene), CY018619 (RNA polymerase PB1 subunit gene), CY018620 (RNA polymerase PB2 subunit gene), 2360 kinds of double-stranded RNA having 19 to 25 nucleotides complementary to a partial sequence of the above genes and antisense RNA thereof were designed to obtain double-stranded RNA which could cleave mRNA transcribed from the viral genes of influenza B viruses by RNA interference. Sequences of an mRNA targeted by the double-stranded RNA for RNA interference are as set forth in SEQ ID NOs: 1 to 2360.

When designing double-stranded RNA, sequences which could induce RNA interference were selected in reference to literature by Khvorova A. et al. (Cell, 2003, Vol. 115, No. 2, p. 209-216), literature by Schwarz D S. et al. (Cell, 2003, Vol. 115, No. 2, p. 199-208), literature by Hsieh A C. et al. (Nucl. Acids Res., 2004, Vol. 32, No. 3, p. 893-901), literature by Reynolds A. et al. (Nat. Biotechnol., 2004, Vol. 22, No. 3, p. 326-330) and literature by Ui-Tei K. et al. (Nucl. Acids Res., 2004, Vol. 32, No. 3, p. 936-948).

From 2360 kinds of double-stranded RNA thus designed, 80 kinds of double-stranded RNA were selected. From the selected RNA, an RNA having sequences homologous with an mRNA transcribed from viral genes of influenza B viruses, in which 2 dTTP were attached to a 3' end thereof, and an RNA which was an antisense RNA thereof, in which 2 nucleotides of DNA complementary to the mRNA were attached to a 3' end thereof based on the nucleotide sequence information, were each chemically synthesized. A set of an equal number of moles of the RNA and the antisense RNA thereof thus synthesized was mixed in annealing buffer (i.e., 100 mM KOAc, 2 mM MgOAc, 30 mM HEPES-KOH, pH 7.4), followed by denaturation treatment for 5 minutes at 90° C. Subsequently, annealing was carried out by incubation for one hour at 37° C., thereby double-stranded RNA was obtained.

(Method for Screening of Double-Stranded RNA by a Transfection Microarray)

FIG. 1 shows steps of screening of double-stranded RNA which inhibits replication of influenza B viruses by a transfection microarray.

A mixed solution of double-stranded RNA was prepared following steps shown in FIG. 1(A). Specifically, 25 μL of serum-free DMEM medium (i.e., Dulbecco's Modified Eagle's Medium) was put in a microtube, to which 1 to 10 μL of 100 μM double-stranded RNA was added and mixed. Subsequently, 1 to 5 μL of a transfection reagent (Lipofectamine 2000; Invitrogen Corporation) was added and mixed, and the resultant mixture was left to stand for 20 minutes. Thereafter, 10 to 200 μg of a cell-adhesion factor (fibronectin) was added to the solution in the microtube and mixed, thereby a mixed solution of double-stranded RNA used to make a double-stranded RNA microarray 4 was prepared.

As shown in FIG. 1(B), a spotter 2 was then filled with the mixed solution of double-stranded RNA and the solution was spotted on predetermined spot positions 1 laid out on a glass slide 3, thereby the double-stranded RNA microarray 4 was prepared. At that time, as a negative control, a mixed solution of the double-stranded RNA which does not inhibit replication of influenza B viruses (QIAGEN Cat. No. 1022076; it will be hereinafter described as control double-stranded RNA) was also spotted on the same glass slide 3.

As to the double-stranded RNA microarray 4 thus prepared, a correlation between the spot positions 1 and the respective sequence information of double-stranded RNA was compiled in a database to keep track ex-post facto of which double-stranded RNA having a certain nucleotide sequence was spotted on which spot position.

Thereafter, as shown in FIG. 1(B), the double-stranded RNA microarray 4 was set in a petri dish 6, to which a cell suspension 5 containing MDCK cells was poured to seed the cells. The cells were let to adhere to the double-stranded RNA microarray 4 and cultured for one day at 37° C. As a result, each double-stranded RNA spotted on the double-stranded RNA microarray 4 was to pass through the cell membrane of MDCK cells adhered to each spot position 1 to be introduced inside the cell.

Thereafter, 5 mL of influenza B virus solution 7 prepared to have a titer of $1.8 \times 10^7$ pfu/mL was poured into the petri dish 6 and it was cultured for 23 to 47 hours at 37° C. As a result, viral replication was to occur within the MDCK cells, and cells in which apoptosis was induced was to detach from the double-stranded RNA microarray 4.

Thereafter, the double-stranded RNA microarray 4 was taken out from the petri dish 6 and washed with PBS, and surviving viable cells on the double-stranded RNA microarray 4 were fixed with ethanol. The fixed viable cells were then stained with crystal violet. A stained double-stranded RNA microarray 8 was air dried and scanned by a DNA microarray scanner (GenePix4200) to obtain a fluorescent image used for analysis of the spot positions 1 containing surviving viable cells.

The fluorescent image thus obtained was analyzed by an image analysis software (GenePix Pro Ver.6.0) to computate a total number of pixels in each of the spot positions 1. An anti-influenza virus activity and strength thereof can be evaluated based the total number of pixels because it is a value corresponding to an area of surviving cells and a number of viable cells.

Screening of double-stranded RNA by a transfection microarray was repeatedly carried out using 6 sheets of the double-stranded RNA microarray 4 in which the spot position 1 of each double-stranded RNA was differed. Then, a statistical hypothesis testing was conducted as described below between the total number of pixels in the spot position 1 of each double-stranded RNA and the total number of pixels in the spot position 1 of the control double-stranded RNA. Double-stranded RNA for which a statistical difference was confirmed in 4 or more out of 6 sheets was judged to be double-stranded RNA having an anti-influenza virus activity.

Steps of Statistical Hypothesis Testing:

1. Normalities of the total number of pixels in the spot position of the control double-stranded RNA and the total number of pixels in the spot position of each double-stranded RNA obtained through 6 sheets of the double-stranded RNA microarray were checked (W-test, level of significance of 10%). When the values of both groups were found to be in accordance with the normal distribution, differences in mean values between 2 groups were tested (proceeding to step 2). Meanwhile, when the total number of pixels of either one of the groups was not in accordance with the normal distribution, differences in measures of central tendency between 2 groups were nonparametrically tested (proceeding to step 5).

2. Homoscedasticities of the total number of pixels in the spot position of the control double-stranded RNA and the total number of pixels in the spot position of each double-stranded RNA were tested (F-test, level of significance of 25%, two-sided test). When they were homoscedastic, a Student's t-test was conducted (step 3), and when they were non-homoscedastic, a Welch's t-test was conducted (step 4).

3. Differences in mean values between the total number of pixels in the spot position of the control double-stranded RNA and the total number of pixels in the spot position of each double-stranded RNA were tested by a Student's t-test (level of significance of 1%, one-sided test).

4. Differences in mean values between the total number of pixels in the spot position of the control double-stranded RNA and the total number of pixels in the spot position of each double-stranded RNA were tested by a Welch's t-test (level of significance of 1%, one-sided test).

5. Differences in measures of central tendency between the total number of pixels in the spot position of the control double-stranded RNA and the total number of pixels in the spot position of each double-stranded RNA were tested by a Mann-Whitney's U-test (level of significance of 1%, one-sided test).

Furthermore, among the double-stranded RNA judged to have an anti-influenza virus activity, double-stranded RNA having an average S/N ratio (Signal to Noise ratio) of 3 or greater was judged to be a double-stranded RNA having a remarkable anti-influenza virus activity.

A S/N ratio described here refers to a ratio between a signal intensity obtained from a negative control (N) and a signal intensity obtained from a sample to be evaluated (S) in a screening system using a microarray, and it is used as an indication to represent strength of RNA interference effect in a screening of double-stranded RNA by a transfection microarray. Specifically, a S/N ratio is a value defined by the following formula using a mean value of the total number of pixels in the spot position of each double-stranded RNA which has been verified to have an anti-influenza virus activity by the statistical hypothesis testing (i.e., $\mu_{sample}$), a mean value of the total number of pixels in the spot position of the control double-stranded RNA (i.e., $\mu_{neg}$), and unbiased standard deviation (i.e., $\delta_{neg}$).

$$S/N \text{ ratio} = \mu_{sample} - \mu_{neg}/\delta_{neg}$$

The number of surviving cells in each spot position represents strength of RNA interference effect in the present screening method, therefore, how much the total number of pixels in the spot position of each double-stranded RNA which has been confirmed to have a significant difference by the statistical hypothesis testing exceeds the total number of pixels in the spot position of the control double-stranded RNA can be evaluated by a S/N ratio.

When a distribution of the total number of pixels in the spot position of the control double-stranded RNA conforms with the normal distribution, the unbiased standard deviation ($\delta_{neg}$) corresponds to a flexion point of a normal distribution curve and 99.73% of data will be included within a range of $\mu_{neg} \pm 3\delta_{neg}$. In that case, when a detection limit of the S/N ratio is set as 3 or greater, the differences between the mean values will be $3\delta_{neg}$ or greater according to the above formula. Therefore, it is assured that the mean value of the total number of pixels in the spot positions of the double-stranded RNA will not be included within the range of 99.73% of the distribution of the total number of pixels in the spot position of the control double-stranded RNA.

A S/N ratio was calculated after normalizing (or standardizing) the total number of pixels in the spot positions of the double-stranded RNA following the below-described steps considering that 6 sheets of the double-stranded RNA microarray were employed for investigation of the anti-influenza virus activity in the present screening method.

1. For each double-stranded RNA microarray, the total number of pixels in the spot position of each double-stranded RNA was normalized using the mean value of the total number of pixels in the spot position of the control double-stranded RNA (i.e., $\mu_{neg}$) and the unbiased standard deviation (i.e., $\delta_{neg}$).

2. A S/N ratio was calculated using the normalized total number of pixels in the spot position of each double-stranded RNA.

3. Double-stranded RNA of mean S/N ratio of 3 or greater was judged as double-stranded RNA having a remarkable anti-influenza virus activity.

In the above screening method, if double-stranded RNA which cleaves mRNA derived from influenza B viruses is introduced into MDCK cells, replication of the viruses is inhibited within the cells in a case when the MDCK cells is invaded by influenza B viruses, and consequently apoptosis will not be induced. Therefore, if the cells are viable and keep adhering to the spot positions 1, the double-stranded RNA introduced into the cells are judged as double-stranded RNA which inhibits replication of influenza B viruses, and it will be judged that the greater the total number of pixels in the spot position 1, the stronger the activity of inhibiting replication of influenza B viruses. On the other hand, if double-stranded RNA which does not cleave mRNA derived from influenza B viruses is introduced into MDCK cells, replication of the viruses proceeds within the cells and eventually apoptosis will be induced. Because cells in which apoptosis has been induced detach from the double-stranded RNA microarray 4, when cells detach from a spot position 1, double-stranded RNA introduced into the cells will be judged as double-stranded RNA which is not capable of inhibiting replication of influenza B viruses.

Accordingly, as long as spot positions 1 to which surviving cells are adhered are known, nucleotide sequences of double-stranded RNA having an anti-influenza virus activity is revealed by searching through the database constructed in advance.

For screening using the transfection microarray, Transfection MicroArray (trademark) of CytoPathfinder, Inc. was employed.

Example 1

Screening of Double-Stranded RNA which Inhibits Replication of Influenza B Virus B/Johannesburg/5/99 Strain Double-stranded RNA which inhibits replication of influenza B virus B/Johannesburg/5/99 strain was screened out from 80 kinds of synthesized double-stranded RNA according to the screening method of double-stranded RNA by the transfection microarray. At that time culture time after addition of the virus strain was set as 34 hours.

Table 1 shows nucleotide sequences of antisense and sense strands of double-stranded RNA which inhibited viral replication caused by an infection with influenza B virus B/Johannesburg/5/99 strain and blocked induction of apoptosis. Double-stranded RNA which has a circle in the column titled "S/N ratio≧3" means double-stranded RNA which has an average S/N ratio of 3 or greater and a remarkable anti-influenza virus activity against viral replication.

TABLE 1

| Double-stranded RNA ID | Nucleotide sequence of an antisense strand | SEQ ID No | Nucleotide sequence of a sense strand | SEQ ID No | S/N ≧ 3 |
|---|---|---|---|---|---|
| B-NP-1999-2 | UUUGUUGCUUUAAUAAUCGag | 2361 | CGAUUAUUAAAGCAACAAAtt | 2362 | ○ |
| B-NP-1999-3 | UUCAUUGACAGCAUUCUUCtt | 2363 | GAAGAAUGCUGUCAAUGAAtt | 2364 | ○ |
| B-NP-1999-4 | UUAAUUGGAAUUUCAACGGga | 2365 | CCGUUGAAAUUCCAAUUAAtt | 2366 | ○ |
| B-NP-1999-5 | UUAUUUGGCCAGACCCUCCgt | 2367 | GGAGGGUCUGGCCAAAUAAtt | 2368 | ○ |
| B-NP-1999-6 | UUUAUCAUCUCUUACCAUCtt | 2369 | GAUGGUAAGAGAUGAUAAAtt | 2370 | ○ |
| B-NP-1999-8 | UUGAUGUCUCUCAAUAGCCct | 2371 | GGCUAUUGAGAGACAUCAAtt | 2372 | ○ |
| B-NP-1999-10 | UUAUCAUCUCUUACCAUCUtg | 2373 | AGAUGGUAAGAGAUGAUAAtt | 2374 | ○ |
| B-NP-1999-11 | UAAAGUUCCACCUCCUUUGat | 2375 | CAAAGGAGGUGGAACUUUAtt | 2376 | ○ |
| B-NP-1999-12 | UUGCUCUUCCUAUAAAUCGaa | 2377 | CGAUUUAUAGGAAGAGCAAtt | 2378 | ○ |
| B-NP-1999-13 | UAGGCUUGAAUUCUGUGCCtg | 2379 | GGCACAGAAUUCAAGCCUAtt | 2380 | ○ |
| B-NP-1999-14 | UUGGAUUAGGUUUCUCUCCat | 2381 | GGAGAGAAACCUAAUCCAAtt | 2382 | ○ |
| B-NP-1999-1 | UUUAAUAAGAAUAAACACCca | 2383 | GGUGUUUAUUCUUAUUAAAtt | 2384 | ○ |
| B-NP-1999-7 | UUAAUAAGAAUAAACACCCac | 2385 | GGGUGUUUAUUCUUAUUAAtt | 2386 | ○ |
| B-NP-1999-9 | UUUAAUGGUGAUCUAGGCUtg | 2387 | AGCCUAGAUCAGCAUUAAAtt | 2388 | ○ |
| B-NP-1999-15 | UUACGGAUUCGUUUGUUGCtt | 2389 | GCAACAAACGAAUCCGUAAtt | 2390 | ○ |
| B-PA-1999-1 | UUUCAGACUUAAUUCAGCCtg | 2391 | GGCUGAAUUAAGUCUGAAAtt | 2392 | |
| B-PA-1999-2 | UUCAUUUGGAUCUUAUUUGtg | 2393 | CAAAUAAGAUCCAAAUGAAtt | 2394 | |
| B-PA-1999-3 | UAAUACAUUCUUCUAUUCCag | 2395 | GGAAUAGAAGAAUGUAUUAtt | 2396 | |
| B-PA-1999-4 | UUAUUUGUGCCAUUCACUCgg | 2397 | GAGUGAAUGGCACAAAUAAtt | 2398 | ○ |
| B-PA-1999-6 | UAUUGGGUCAGUUUGAUCCcg | 2399 | GGAUCAAACUGACCCAAUAtt | 2400 | |
| B-PA-1999-7 | UUCAUUAACAAAGUAUUUCct | 2401 | GAAAUACUUUGUUAAUGAAtt | 2402 | |
| B-PA-1999-8 | UUCCAUGCUAUUUCCCAGCtt | 2403 | GCUGGGAAAUAGCAUGGAAtt | 2404 | |
| B-PA-1999-9 | UUCAUUACUACUCUAUUGgt | 2405 | CAAUAGAGUAGUAAAUGAAtt | 2406 | ○ |

TABLE 1-continued

| Double-stranded RNA ID | Nucleotide sequence of an antisense strand | SEQ ID No | Nucleotide sequence of a sense strand | SEQ ID No | S/N ≥ 3 |
|---|---|---|---|---|---|
| B-PA-1999-10 | UUAACAAAGUAUUCCUUCtt | 2407 | GAAGGAAAUACUUUGUUAAtt | 2408 | |
| B-PA-1999-11 | UUGUUCAACAAUUGCUUCCat | 2409 | GGAAGCAAUUGUUGAACAAtt | 2410 | |
| B-PA-1999-15 | UUCCAGAAUACAUUCCCUCta | 2411 | GAGGGAAUGUAUUCUGGAAtt | 2412 | ○ |
| B-PA-1999-16 | UCAUUUACUACUCUAUUGGtt | 2413 | CCAAUAGAGUAGUAAAUGAtt | 2414 | |
| B-PB1-1999-1 | UUUAGUAUAGAUCUGUUCCtt | 2415 | GGAACAGAUCUAUACUAAAtt | 2416 | ○ |
| B-PB1-1999-3 | UUAUUGGAGAACAAGACCGgt | 2417 | CGGUCUUGUUCUCCAAUAAtt | 2418 | |
| B-PB1-1999-5 | UUUAUGAGGAAACCCUUUCtg | 2419 | GAAAGGGUUUCCUCAUAAAtt | 2420 | |
| B-PB1-1999-6 | UUUAUAUUCAUCUUAAAGGct | 2421 | CCUUUAAGAUGAAUAUAAAtt | 2422 | |
| B-PB1-1999-7 | UAGCAUAUUAAACAUUCCCat | 2423 | GGGAAUGUUUAAUAUCCUAtt | 2424 | |
| B-PB1-1999-8 | UUUAUUGGAGAACAAGACCgg | 2425 | GGUCUUGUUCUCCAAUAAAtt | 2426 | ○ |
| B-PB1-1999-9 | UUGUAAAUUCAAACAUUCCag | 2427 | GGAAUGUUUGAAUUUACAAtt | 2428 | ○ |
| B-PB1-1999-10 | UAAUGAAUCAAUGAUAUCUgt | 2429 | AGAUAUCAUUGAUUCAUUAtt | 2430 | |
| B-PB1-1999-11 | UUAGAUACAAAUCCAUCUCta | 2431 | GAGAUGGAUUUGUAUCUAAtt | 2432 | ○ |
| B-PB1-1999-13 | UUCUUUAUAUUCUUUACUGag | 2433 | CAGUAAAGAAUAUAAAGAAtt | 2434 | |
| B-PB1-1999-15 | UAUUCCACUCUGGAUAUCCtg | 2435 | GGAUAUCCAGAGUGGAAUAtt | 2436 | ○ |
| B-PB1-1999-18 | UAUUCUUUCAGUCAUAGCCaa | 2437 | GGCUAUGACUGAAAGAAUAtt | 2438 | |
| B-PB1-1999-19 | UAUCUUUCUAAUGGUAUGCta | 2439 | GCAUACCAUUAGAAAGAUAtt | 2440 | |
| B-PB1-1999-22 | UUAGAUUGUACUUCAAUACta | 2441 | GUAUUGAAGUACAAUCUAAtt | 2442 | |
| B-PB1-1999-23 | UUGUUCUUUAUUAUUGUCAtt | 2443 | UGACAAUAAUAAAGAACAAtt | 2444 | |
| B-PB1-1999-27 | UUUAUUCCCAAUAAUUUACat | 2445 | GUAAAUUAUUGGGAAUAAAtt | 2446 | |
| B-PB1-1999-28 | UUGUUCCUCAAGAAUCAUGtt | 2447 | CAUGAUUCUUGAGGAACAAtt | 2448 | |
| B-PB2-1999-5 | UUUCUUACUCUUUCAACUGgg | 2449 | CAGUUGAAAGAGUAAGAAAtt | 2450 | |
| B-PB2-1999-7 | UAUUCCACCAGGUAACUGCtg | 2451 | GCAGUUACCUGGUGGAAUAtt | 2452 | ○ |
| B-PB2-1999-10 | UUUAAGUUGUAUUCCCUUGta | 2453 | CAAGGGAAUACAACUUAAAtt | 2454 | |
| B-PB2-1999-11 | UUUGAUGCGACUAUUGAUCtt | 2455 | GAUCAAUAGUCGCAUCAAAtt | 2456 | ○ |
| B-PB2-1999-12 | UUCAGUAUCUAUCACAGUCtt | 2457 | GACUGUGAUAGAUACUGAAtt | 2458 | ○ |
| B-PB2-1999-15 | UUUAACUACUUUAACGGGCtt | 2459 | GCCCGUUAAAGUAGUUAAAtt | 2460 | |
| B-PB2-1999-16 | UUUCUUAUUAUGUUAUAUUga | 2461 | AAUAUAACAUAAUAAGAAAtt | 2462 | |
| B-PB2-1999-18 | UUGUAUUCCCUUGUAUUCCaa | 2463 | GGAAUACAAGGGAAUACAAtt | 2464 | |

As a result, a statistical difference was confirmed between 52 double-stranded RNA and the control double-stranded RNA, of which 26 double-stranded RNA had an average S/N ratio of 3 or greater.

Example 2

Screening of Double-Stranded RNA which Inhibits Replication of Influenza B Virus Strains Other than B/Johannesburg/5/99 Strain Among the 80 kinds of synthesized double-stranded RNA, 28 double-stranded RNA which did not exhibit an anti-influenza activity for B/Johannesburg/5/99 strain were studied to find out if any of them had an anti-influenza activity for other influenza B virus strains.

As influenza B viruses, B/Shangdong/07/97, B/Hong Kong/8/73, B/Shanghai/361/2002, and B/Victoria/2/87 strains were employed, and a test was carried out according to the method for screening of double-stranded RNA by the transfection microarray in a similar manner to Example 1.

However, because culture time needed for cell detachment to occur after addition of virus strains to a petri dish differed depending on the virus strain, the culture time after addition of virus strains was set as follows: 23 hours for B/Shangdon/07/97 strain, 36 hours for B/Hong Kong/8/73 strain, 26 hours for B/Shanghai/361/2002 strain, and 47 hours for B/Victoria/2/87 strain.

Table 2 shows nucleotide sequences of antisense and sense strands of double-stranded RNA which inhibited viral replication caused by an infection with influenza B virus B/Shangdong/07/97, B/Hong Kong/8/73, B/Shanghai/361/2002, or B/Victoria/2/87 strains and blocked induction of apoptosis. Double-stranded RNA which has a circle in the column titled "S/N ratio≧3" means double-stranded RNA which has an average S/N ratio of 3 or greater for one of the above virus strains and a remarkable anti-influenza virus activity against viral replication.

TABLE 2

| Double-stranded RNA ID | Nucleotide sequence of an antisense strand | SEQ ID No | Nucleotide sequence of a sense strand | SEQ ID No | S/NL ≧ 3 |
|---|---|---|---|---|---|
| B-PB2-1999-2 | UAAAUCUUUCAUGUCUUCCtt | 2465 | GGAAGACAUGAAAGAUUUAtt | 2466 | ○ |
| B-PB2-1999-6 | UUCAUUAAUUCAUUUAUCCca | 2467 | GGAUAAAUGAAUUAAUGAAtt | 2468 | |
| B-PB1-1999-17 | UAAGGAUUUAUAUUCAUCUta | 2469 | AGAUGAAUAUAAAUCCUUAtt | 2470 | |
| B-PB1-1999-24 | UUUCAUUUCAAUCAUUUGUtt | 2471 | ACAAAUGAUUGAAAUGAAAtt | 2472 | |
| B-PB1-1999-26 | UUCAUCUUAAAGGCUCCGCtt | 2473 | GCGGAGCCUUUAAGAUGAAtt | 2474 | |

As a result, a statistical difference was confirmed between 3 double-stranded RNA (B-PB2-1999-02, B-PB1-1999-17, and B-PB1-1999-26) and the control double-stranded RNA against an infection caused by B/Shangdong/07/97 strain, of which 1 double-stranded RNA (B-PB2-1999-2) had an average S/N ratio of 3 or greater. A statistical difference was confirmed between 2 double-stranded RNA (B-PB2-1999-2 and B-PB1-1999-24) and the control double-stranded RNA against an infection caused by B/Hong Kong/8/73 strain, however, neither of them had a mean S/N ratio of 3 or greater. A statistical difference was confirmed between 1 double-stranded RNA (B-PB2-1999-6) and the control double-stranded RNA against an infection caused by B/Shanghai/361/2002 strain, however, it did not have a mean S/N ratio of 3 or greater. Meanwhile, a statistical difference was not observed between any double-stranded RNA and the control double-stranded RNA against infection caused by B/Victoria/2/87 strain.

Combined with the results obtained from Example 1, 57 double-stranded RNA exhibited an anti-influenza virus activity for one of the 5 strains of influenza B viruses. Furthermore, 39 out of the 57 double-stranded RNA had a remarkable anti-influenza virus activity with a mean S/N ratio of 3 or greater for one of the virus strains. Accordingly, it was presumed that one of the 57 double-stranded RNA could inhibit viral replication and exert efficacy in treatment of influenza B viruses, even if an influenza B virus strain which is to circulate from now forward undergoes various mutations.

Example 3

Screening of Double-Stranded RNA which Inhibits Replication of a Plurality of Influenza B Virus Strains Simultaneously Prediction of an influenza B virus strain to circulate is difficult, and even if prediction comes true, the virus is highly prone to mutation, therefore, it is presumed that if one kind of double-stranded RNA can inhibit replication of a plurality of influenza B virus strains, treatment and prevention of an infection caused by influenza B viruses are realizable. In view of the above, among the 52 double-stranded RNA which exhibited an anti-influenza virus activity for influenza B virus B/Johannesburg/5/99 strain in Example 1, double-stranded RNA further having an anti-influenza virus activity for all virus strains of B/Shangdong/07/97, B/Hong Kong/8/73, B/Shanghai/361/2002, and B/Victoria/2/87 strains was screened.

Screening was carried out according to the above-described method for screening of double-stranded RNA by the transfection microarray in a similar manner to Examples 1 and 2. In this screening, a double-stranded RNA microarray was used in which double-stranded RNA which has been reported to inhibit replication of influenza B viruses (PB1-POS and PB2-POS) was spotted to a slide as a positive control in addition to the 52 double-stranded RNA which exhibited an anti-influenza activity in Example 1. Both of PB1-POS and PB2-POS are double-stranded RNA comprising nucleotide sequences identical to PB1-2196 and PB2-1999 described in Antiviral Therapy (2006, Vol. 11, p. 431-438), and each of them was reported to cleave mRNA of an RNA polymerase PB1 subunit (PB1) gene and an RNA polymerase PB2 subunit (PB2) gene by RNA interference.

Table 3 shows double-stranded RNA IDs which inhibited viral replication caused by an infection with influenza B virus B/Johannesburg/5/99 strain, B/Shangdong/07/97 strain, B/Hong Kong/8/73 strain, B/Shanghai/361/2002 strain, and B/Victoria/2/87 strain and blocked induction of apoptosis as well as values of S/N ratio thereof.

TABLE 3

| | Values of S/N ratio | | | | |
|---|---|---|---|---|---|
| Double-stranded RNA ID | B/Jonannesburg/ 5/99 strain | B/Shangdong/ 07/97 strain | B/HongKong/ 8/73 strain | B/Shanghai/ 361/2002 strain | B/Victoria/ 2/87 strain |
| PB1_POS | 1.2 | 10.8 | ND | 3.0 | ND |
| PB2_POS | 1.0 | 1.9 | ND | 1.3 | ND |
| B-NP-1999-02 | 11.5 | 29.2 | 9.8 | 19.9 | 8.2 |
| B-NP-1999-03 | 23.6 | 68.0 | 13.9 | 30.4 | 16.5 |
| B-NP-1999-04 | 32.1 | 82.6 | 8.5 | 30.8 | 7.3 |

TABLE 3-continued

| Double-stranded RNA ID | Values of S/N ratio | | | | |
|---|---|---|---|---|---|
| | B/Jonannesburg/ 5/99 strain | B/Shangdong/ 07/97 strain | B/HongKong/ 8/73 strain | B/Shanghai/ 361/2002 strain | B/Victoria/ 2/87 strain |
| B-NP-1999-05 | 11.4 | 37.0 | 4.1 | 17.9 | 6.1 |
| B-NP-1999-06 | 27.5 | 78.1 | 16.2 | 37.7 | 16.2 |
| B-NP-1999-08 | 7.5 | 36.7 | 6.8 | 19.4 | 7.5 |
| B-NP-1999-10 | 20.8 | 61.2 | 12.7 | 31.3 | 14.5 |
| B-NP-1999-11 | 5.9 | 36.0 | 6.1 | 18.4 | 8.7 |
| B-NP-1999-12 | 9.7 | 42.2 | 7.5 | 21.4 | 3.5 |
| B-NP-1999-13 | 32.2 | 85.2 | 12.2 | 37.8 | 17.5 |
| B-NP-1999-14 | 14.9 | 56.6 | 8.0 | 5.2 | 8.5 |

As a result, out of the 52 double-stranded RNAs, a statistical difference was confirmed between 11 double-stranded RNA and the control double-stranded RNA against an infection of all virus strains of the above 5 strains, and those 11 double-stranded RNAs exhibited a remarkable anti-influenza virus activity for any of the virus strains with a mean S/N ratio of 3 or greater.

On the other hand, PB1-POS, a positive control, exhibited an anti-influenza virus activity for B/Shangdong/07/97 strain and B/Shanghai/361/2002 strain, while it hardly exhibited an anti-influenza virus activity for other virus strains.

Also, PB2-POS, another positive control, exhibited a very weak anti-influenza virus activity for B/Johannesburg/5/99 strain and B/Shangdong/07/97 strain, and it did not exhibit an anti-influenza virus activity for other virus strains.

Interestingly, it is to be noted that any one of the antisense strands of the above 11 double-stranded RNA was RNA having a sequence complementary to mRNA of NP protein.

Example 4

An Anti-Influenza Virus Activity of Double-Stranded RNA Having Mutation in a Target Sequence Among the double-stranded RNA which has a remarkable anti-influenza virus activity for the 5 strains of influenza B viruses found in Example 3, homology between B-NP-1999-13 (sequence No. 10) and the nucleotide sequence of mRNA of the 5 virus strains were compared.

The nucleotide sequences registered in GenBank were referred to for the 4 strains other than B/Johannesburg/5/99 strain, in which an accession number for each strain was as follows: AY0441698 for B/Shangdong/7/97 strain, EF456777 for B/Hong Kong/8/73 strain, AJ784078 for B/Shanghai/361/2002 strain, and AF100359 for B/Victoria/2/87 strain.

As a result, although B-NP-1999-13 had 3 mismatched nucleotides with respect to B/Hong Kong/8/73, it exhibited a remarkable anti-influenza virus activity. Also, although it had a mismatch in a second nucleotide counting from a 5' end of an antisense strand with respect to B/Victoria/2/87 strain, it similarly exhibited a remarkable anti-influenza virus activity.

Generally, it is said that an RNA interference activity of double-stranded RNA becomes weaker as a mismatch occurs closer to the center of a strand from the end and a number of mismatched nucleotide increases. However, B-NP-1999-13 especially had an RNA interference activity and exhibited a remarkable anti-influenza virus activity regardless of the presence of 3 mismatched nucleotides.

Based on the above results, it was suggested that even a mismatch is present, double-stranded RNA having a remarkable anti-influenza virus activity still exists depending on its nucleotide sequence. Such double-stranded RNA has an anti-influenza virus activity not only for one kind but also for plural kinds of influenza B virus strains, therefore, it was suggested that even in a case when an influenza virus strain having mutation in a sequence targeted by double-stranded RNA becomes an epidemic strain, such double-stranded RNA could fully exert a therapeutic effect for an infection caused by the strain.

Example 5

A Combinational Use of Double-Stranded RNA Designed to Target Influenza a Viruses and Influenza B Viruses An effect for influenza viruses brought by simultaneous use of a plurality of double-stranded RNA was studied. NP-1496, which was siRNA described in WO2004/028471, was chemically synthesized as double-stranded RNA for influenza A viruses. The nucleotide sequence of NP-1496 is shown in Table 4 with the direction from a 5' end toward a 3' end. The 3' ends of sense and antisense strands of NP-1496 have 2 deoxythymidine nucleotides attached thereto, and they were denoted in lowercase letters in Table 4. A set of an equal number of moles of the RNA thus synthesized and the antisense RNA thereof was mixed in annealing buffer (i.e., 100 mM KOAc, 2 mM MgOAc, 30 mM HEPES-KOH, pH 7.4), followed by denaturation treatment for 5 minutes at 90° C. Subsequently, annealing was carried out by incubation for one hour at 37° C., thereby double-stranded RNA was obtained. The above-described B-NP-1999-13 was used as double-stranded RNA for influenza B viruses.

TABLE 4

| Double-stranded RNA ID | Nucleotide sequence of an antisense strand | SEQ ID No | Nucleotide sequence of a sense strand | SEQ ID No |
|---|---|---|---|---|
| NP-1496 | CUCCGAAGAAAUAAGAUCCtt | 2475 | GGAUCUUAUUUCUUCGGAGtt | 2476 |

MDCK cells were suspended in RPMI1640 medium and the suspension was prepared to have $1\times10^7$ cells/mL, to which NP-1496 and B-NP-1999-13 were mixed. To an electroporation cuvette having an interelectrode distance of 4 mm (product of Shimadzu Corporation), 800 μL of a mixture of the MDCK cells and the double-stranded RNA was transferred. An electrical pulse was applied with voltage of 400 V and a capacitor having capacitance of 800 μF by Shimadzu Electro Gene Transfer Equipment (GTE-10), after which the suspension was left to stand for 5 minutes on ice. The suspension thus obtained was diluted by RPMI1640 medium to be at $1\times10^6$ cells/mL, and FCS was added to make a final concentration of 10%. The suspension thus obtained was seeded in a 96-well plate at 0.1 mL/well, and cultured for one day at 37° C. in the presence of 5% $CO_2$.

A/PR/8/34 and B/Johannesburg/5/99 were used as influenza A viruses and influenza B viruses, respectively. Each of the viruses was prepared at a concentration of $1\times10^4$ pfu/mL and added at 50 μL/well to the MDCK cells into which siRNA had been introduced for virus infection. After culturing for 24 hours, the infected cells were fixed with ethanol. In order to quantitate viral protein expressed in the infected cells by ELISA, the fixed cells were blocked with 10% skim milk, after which an anti-influenza A virus nucleoprotein antibody (product of AbD serotec, MCA400) or an anti-influenza B virus nucleoprotein antibody (product of AbD serotec, MCA403) was added as a primary antibody. Subsequently, a rabbit anti-mouse IgG labeled with HRP (horse radish peroxidase) was added as a secondary antibody for recognition of the primary antibody. Then, TMB (i.e., 3,3',5,5'-tetramethyl-benzidene), which was a substrate for HRP, was added for color development, and absorbance at a wavelength of 450 nm was measured. An inhibition rate in the wells to which siRNA was introduced was calculated by the following formula based on values obtained from a negative-control well which was not infected with viruses and a positive-control well which was infected with viruses without addition of siRNA.

Inhibition rate=(absorbance of a positive-control well−absorbance of a sample well)×100/(absorbance of a positive-control well−absorbance of a negative-control well)

The results are shown in FIG. 2. As shown in FIG. 2(A), when B-NP-1999-13 was solely used at 0.1 nmol/mL, approximately 100% of an inhibitory activity was observed for B/Johannesburg/5/99 viruses. Also, as shown in FIG. 2(B), when NP-1496, which was double-stranded RNA, was solely used at 1 nmol/mL, approximately 90% of an inhibitory activity was observed for A/PR/8/34. When a mixture of these double-stranded RNA was used, an anti-virus activity was exhibited for an infection with either of the viruses, and the activity level was observed as approximately the same as when each of the double-stranded RNA was used solely.

Example 6

A Combinational Use of Double-Stranded RNA Designed to Target Influenza B Viruses and Expansion of Spectrum B-PB2-1999-7 and B-PB1-1999-1, both of which were double-stranded RNA, were used in this test. As for viruses, B/Shanghai/361/2002 and B/Shangdong/07/97 were used. MDCK cells were mixed with the double-stranded RNA in a similar manner to Example 5, and introduction into cell was conducted by electroporation. Each of the influenza B viruses was allowed to infect after one-day culture, and a combinational effect of the double-stranded RNA was measured by quantitating viral protein present after 18 hours by ELISA using an influenza B virus antibody.

The results were shown in FIG. 3. Although B-PB2-1999-7 exhibited approximately 100% of an inhibitory activity for B/Shanghai/361/2002 when used at 0.25 nmol/mL as shown in FIG. 3(A), it exhibited as low as approximately 30% of an inhibitory activity for B/Shangdong/07/97 as shown in FIG. 3(B). Also, although B-PB1-1999-1 exhibited only approximately 20% of an inhibitory activity for B/Shanghai/361/2002 when used at 0.25 nmol/mL as shown in FIG. 3(A), it exhibited approximately 90% of an inhibitory activity for B/Shangdong/07/97 as shown in FIG. 3(B). An inhibitory activity as strong as approximately 90% or more was confirmed for either of the virus strains, when a mixture of these two kinds of double-stranded RNA was used. As shown above, it was demonstrated that there were cases in which no effect was exerted on a certain virus strain depending on a nucleotide sequence of double-stranded RNA, while an effect could be exerted on such a viral strain by combinational use of a plurality of double-stranded RNA.

Example 7

Combinational Effect of Double-Stranded RNA Designed to Target Influenza B Viruses B-NP-1999-3 and B-NP-1999-13, both of which were double-stranded RNA, were used in this test. As for viruses, B/Shanghai/361/2002 and B/Shangdong/07/97 were used. MDCK cells were mixed with the double-stranded RNA in a similar manner to Example 5, and introduction into cell was conducted by electroporation. Each of the influenza B virus strains was allowed to infect after one-day culture, and a combinational effect of double-stranded RNA was measured by quantitating viral protein present after 18 to 30 hours by ELISA using an influenza B virus antibody.

Figure 4:
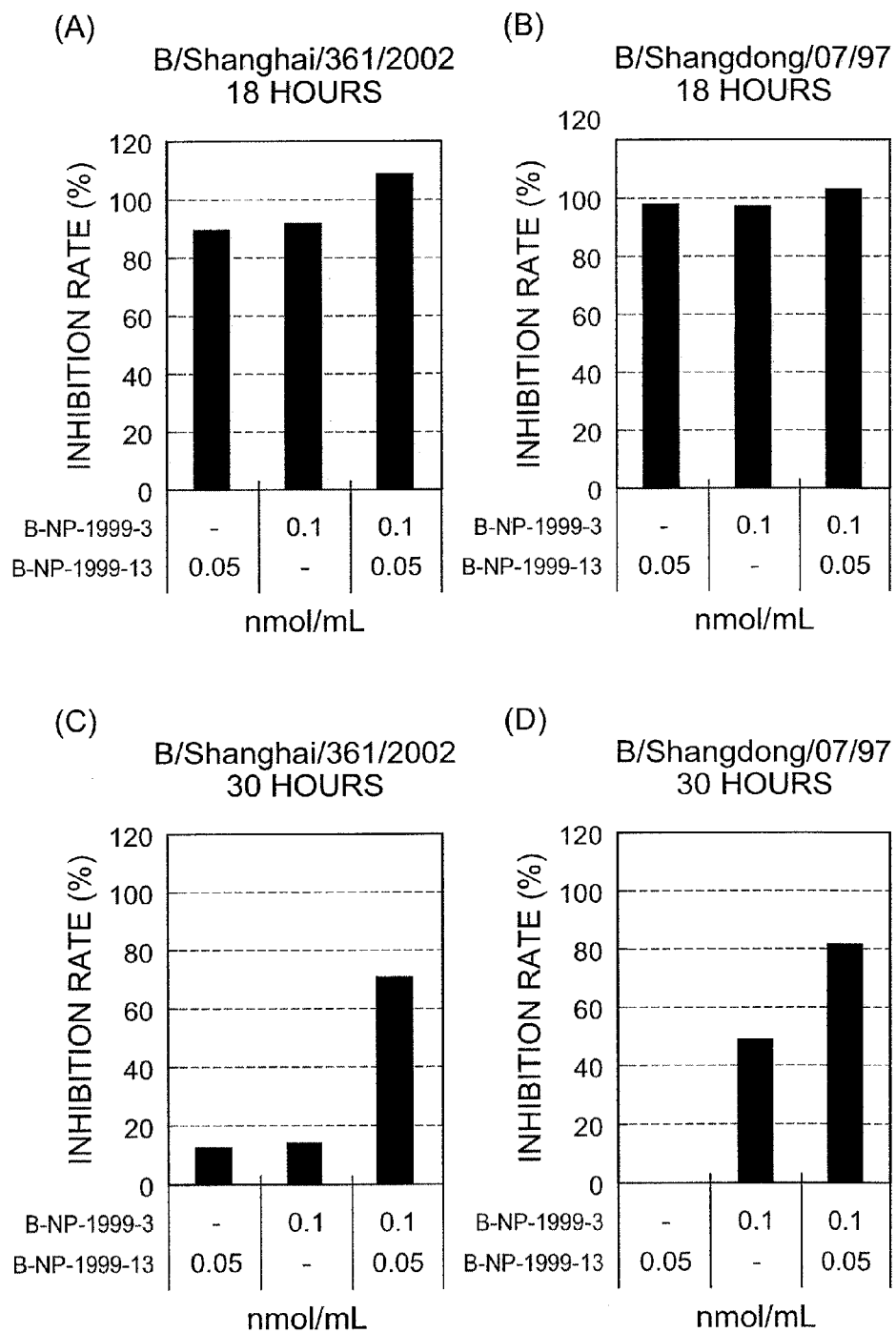
FIG. 4 (A) shows inhibition rates of double-stranded RNA B-NP-1999-3 alone, B-NP-1999-13 alone, as well as a combination of B-NP-1999-3 and B-NP-1999-13 for influenza virus B/Shanghai/361/2002 strain in 18-hour culture, and (B) shows inhibition rates of double-stranded RNA B-NP-1999-3 alone, B-NP-1999-13 alone, as well as a combination of B-NP-1999-3 and B-NP-1999-13 for influenza virus B/Shangdong/07/97 strain in 18-hour culture, and (C) shows inhibition rates of double-stranded RNA B-NP-1999-3 alone, B-NP-1999-13 alone, as well as a combination of B-NP-1999-3 and B-NP-1999-13 for influenza virus B/Shanghai/361/2002 strain in 30-hour culture, and (D) shows inhibition rates of double-stranded RNA B-NP-1999-3 alone, B-NP-1999-13 alone, as well as a combination of B-NP-1999-3 and B-NP-1999-13 for influenza virus B/Shangdong/07/97 strain in 30-hour culture.

The results were shown in FIG. 4. As shown in FIGS. 4(A) and 4(B), the two kinds of double-stranded RNA exhibited 80% or more of an inhibitory activity for both virus strains either solely or in combination in an 18-hour culture. On the other hand, as shown in FIG. 4(C), when B-NP-1999-3 and B-NP-1999-13 were each used solely at 0.1 nmol/mL and 0.05 nmol/mL, respectively, each of them exhibited only approximately 10% of an effect for B/Shanghai/361/2002 in 30-hour culture. When a mixture of these two kinds of double-stranded RNA was used, approximately 70% of an inhibitory activity was confirmed for B/Shanghai/361/2002. Also, as similarly shown in FIG. 4(D), when B-NP-1999-3 and B-NP-1999-13 were each used solely at 0.1 nmol/mL and 0.05 nmom/mL, respectively, each exhibited 50% and 0% of an inhibitory effect for B/Shangdong/07/97, respectively. Meanwhile, when a mixture of them was used, 80% of an inhibitory activity was confirmed for B/Shangdong/07/97. As shown above, it was demonstrated that there were cases in which an effect was diminished as culture time of the virus was extended with use of one kind of double-stranded RNA, however, even in such a case, the effect was sustained by using a plurality of double-stranded RNA concurrently.

The invention claimed is:

1. A double-stranded RNA which inhibits replication of influenza B viruses by RNA interference, wherein the double-stranded RNA comprises an RNA and an antisense RNA thereof, wherein the RNA is selected from the group consisting of RNA of nucleotide sequences as set forth in SEQ ID NOs: 4 and 5 or selected from the group consisting of RNA of nucleotide sequences as set forth in SEQ ID NOs: 4 and 5 in which 1 to 3 nucleotide(s) is/are substituted.

2. The double-stranded RNA according to claim 1, which has a S/N ratio of 3 or greater in screening of double-stranded RNA by a transfection microarray using B/Johannesburg/5/99 strain.

3. The double-stranded RNA according to claim 1, wherein the RNA optionally contains one or more modified ribonucleotide(s).

4. The double-stranded RNA according to claim 1, wherein one or more phosphodiester bond(s) in the RNA is/are optionally substituted with phosphorothioate bond(s).

5. The double-stranded RNA according to claim 1, which forms blunt ends.

6. The double-stranded RNA according to claim 1, wherein the RNA is the RNA of nucleotide sequence as set forth in SEQ ID NO:4 or the RNA of nucleotide sequence as set forth in SEQ ID NO:4 in which 1 to 3 nucleotide(s) is/are substituted.

7. A double-stranded RNA having DNA or RNA of 1 to 4 nucleotide(s) attached to 3' ends of the sense and the antisense strands of a double-stranded RNA according to claim 6 to form overhanging ends.

8. The double-stranded RNA according to claim 1, wherein the RNA is the RNA of nucleotide sequence as set forth in SEQ ID NO:5 or the RNA of nucleotide sequence as set forth in SEQ ID NO:5 in which 1 to 3 nucleotide(s) is/are substituted.

9. A double-stranded RNA having DNA or RNA of 1 to 4 nucleotide(s) attached to 3' ends of the sense and the antisense strands of a double-stranded RNA according to claim 8 to form overhanging ends.

10. A double-stranded RNA having DNA or RNA of 1 to 4 nucleotide(s) attached to 3' ends of the sense and the antisense strands of a double-stranded RNA according to claim 1 to form overhanging ends.

11. A hairpin RNA which forms the double-stranded RNA according to claim 1 in a cell, wherein the RNA is linked to the antisense RNA thereof by a linker sequence.

12. An expression vector for a double-stranded RNA which comprises a first DNA complementary to an RNA selected from the group consisting of RNA of nucleotide sequences as set forth in SEQ ID NOs: 4 and 5 or an RNA selected from the group consisting of RNA of nucleotide sequences as set forth in SEQ ID NOs: 4 and 5 in which 1 to 3 nucleotide(s) is/are substituted and a second DNA complementary to the first DNA, as well as promoters on 5' sides of each of the first DNA and the second DNA, wherein, in a cell to which the vector is introduced, the vector transcribes a first RNA complementary to the first DNA and a second RNA complementary to the second DNA, and the first RNA and the second RNA hybridize to each other to form a double-stranded RNA.

13. An expression vector for a double-stranded RNA which comprises a first DNA complementary to an RNA selected from the group consisting of RNA of nucleotide sequences as set forth in SEQ ID NOs: 4 and 5 or an RNA selected from the group consisting of RNA of nucleotide sequences as set forth in SEQ ID NOs: 4 and 5 in which 1 to 3 nucleotide(s) is/are substituted, wherein the RNA has an RNA having 1 to 4 nucleotide(s) attached to 3' ends thereof, and a second DNA complementary to an RNA which is antisense RNA of an RNA selected from the group consisting of RNA of nucleotide sequences as set forth in SEQ ID NOs: 4 and 5 or an antisense RNA of an RNA selected from the group consisting of RNA of nucleotide sequences as set forth in SEQ ID NOs: 4 and 5 in which 1 to 3 nucleotide(s) is/are substituted, wherein the RNA has an RNA having 1 to 4 nucleotide(s) attached to 3' ends thereof, as well as promoters on 5' sides of each of the first DNA and the second DNA, wherein, in a cell to which the vector is introduced, the vector transcribes a first RNA complementary to the first DNA and a second RNA complementary to the second DNA, and the first RNA and the second RNA hybridize to each other to form a double-stranded RNA.

14. An expression vector for a hairpin RNA which comprises DNA strands encoding a hairpin RNA, in which an antisense DNA complementary to an RNA selected from the group consisting of RNA of nucleotide sequences as set forth in SEQ ID NOs: 4 and 5 or an antisense DNA complementary to an RNA selected from the group consisting of RNA of nucleotide sequences as set forth in SEQ ID NOs: 4 and 5 in which 1 to 3 nucleotide(s) is/are substituted is linked to a DNA complementary to the antisense DNA by a linker sequence, as well as promoters on 5' sides of the DNA strands, wherein, inside the cell to which the vector is introduced, the vector transcribes the hairpin RNA, and the hairpin RNA is processed in a cell to form a double-stranded RNA.

15. A pharmaceutical composition which comprises at least one kind of a double-stranded RNA according to claim 1 as an active ingredient and one or more pharmaceutical additives.

16. The pharmaceutical composition according to claim 15, which further comprises a double-stranded RNA which inhibits replication of influenza A viruses by RNA interference.

17. A detection kit for influenza B viruses which comprises at least one of a double-stranded RNA according to claim 1 and a transfection reagent.

18. A method for treatment of an infectious disease caused by influenza comprising administering to a patient in need thereof at least one kind of a double-stranded RNA according to claim 1 as an active ingredient.

19. The method for treatment of an infectious disease caused by influenza according to claim 18, which further comprises administering to the patient a double-stranded RNA which inhibits replication of influenza A viruses by RNA interference.

* * * * *